(12) United States Patent
Hass et al.

(10) Patent No.: US 10,654,932 B2
(45) Date of Patent: May 19, 2020

(54) ANTI-FACTOR D ANTIBODY VARIANT CONJUGATES AND USES THEREOF

(71) Applicant: Genentech, Inc., South San Francisco, CA (US)

(72) Inventors: Philip E. Hass, South San Francisco, CA (US); Robert F. Kelley, South San Francisco, CA (US); Justin M. Scheer, South San Francisco, CA (US); Whitney Shatz, South San Francisco, CA (US); Devin Tesar, South San Francisco, CA (US); Menno van Lookeren Campagne, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 171 days.

(21) Appl. No.: 15/336,522

(22) Filed: Oct. 27, 2016

(65) Prior Publication Data
US 2017/0143843 A1 May 25, 2017

Related U.S. Application Data

(60) Provisional application No. 62/250,965, filed on Nov. 4, 2015, provisional application No. 62/249,020, filed on Oct. 30, 2015.

(51) Int. Cl.
| | | |
|---|---|---|
| A61K 45/06 | (2006.01) | |
| A61K 9/00 | (2006.01) | |
| A61K 47/60 | (2017.01) | |
| C07K 16/18 | (2006.01) | |
| C07K 16/22 | (2006.01) | |
| C07K 16/28 | (2006.01) | |
| A61K 39/00 | (2006.01) | |

(52) U.S. Cl.
CPC ........ *C07K 16/2863* (2013.01); *A61K 9/0048* (2013.01); *A61K 45/06* (2013.01); *A61K 47/60* (2017.08); *C07K 16/18* (2013.01); *C07K 16/22* (2013.01); *A61K 2039/505* (2013.01); *C07K 2317/55* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,179,337 A | 12/1979 | Davis et al. |
| 4,741,900 A | 5/1988 | Alvarez et al. |
| 4,816,567 A | 3/1989 | Cabilly et al. |
| 4,935,465 A | 6/1990 | Garman |
| 4,946,778 A | 8/1990 | Ladner et al. |
| 5,166,322 A | 11/1992 | Shaw et al. |
| 5,206,344 A | 4/1993 | Katre et al. |
| 5,225,539 A | 7/1993 | Winter |
| 5,244,800 A | 9/1993 | Delucas et al. |
| 5,456,909 A | 10/1995 | Marsh, Jr. et al. |
| 5,530,101 A | 6/1996 | Queen et al. |
| 5,534,615 A | 7/1996 | Baker et al. |
| 5,571,894 A | 11/1996 | Wels et al. |
| 5,587,458 A | 12/1996 | King et al. |
| 5,624,837 A | 4/1997 | Fodor et al. |
| 5,627,264 A | 5/1997 | Fodor et al. |
| 5,679,345 A | 10/1997 | Sanfilippo et al. |
| 5,679,354 A | 10/1997 | Morein et al. |
| 5,679,546 A | 10/1997 | Ko et al. |
| 5,679,564 A | 10/1997 | Pace et al. |
| 5,849,535 A | 12/1998 | Cunningham et al. |
| 5,851,528 A | 12/1998 | Ko et al. |
| 5,853,722 A | 12/1998 | Rollins et al. |
| 5,856,297 A | 1/1999 | Fearon et al. |
| 5,856,300 A | 1/1999 | Rittershaus et al. |
| 5,858,969 A | 1/1999 | Marsh, Jr. et al. |
| 5,861,156 A | 1/1999 | George et al. |
| 5,869,046 A | 2/1999 | Presta et al. |
| 5,919,623 A | 7/1999 | Taylor |
| 6,267,958 B1 | 7/2001 | Andya et al. |
| 6,333,034 B1 | 12/2001 | Gupta-Bansal et al. |
| 6,376,653 B1 | 4/2002 | Holmes et al. |
| 6,407,213 B1 | 6/2002 | Carter et al. |
| 6,410,708 B1 | 6/2002 | Ashkenazi et al. |
| 6,472,520 B2 | 10/2002 | Fisher |
| 6,534,058 B2 | 3/2003 | Fung et al. |
| 6,569,992 B1 | 5/2003 | Lafleur et al. |
| 6,642,353 B1 | 11/2003 | Lund et al. |
| 6,828,401 B2 | 12/2004 | Nho et al. |

(Continued)

FOREIGN PATENT DOCUMENTS

| | | |
|---|---|---|
| EP | 0245993 A2 | 11/1987 |
| EP | 0239400 B1 | 8/1994 |

(Continued)

OTHER PUBLICATIONS

Jevsevar et al Biotechnol. J. 2010, 5, 113-128.*
Igawa et al 2011 (mAbs 3:3: 243-252).*
Vlasak et al 2011 (mAbs 3:3, 253-263).*
1000 Genomes Project Consortium, "A map of human genome variation from population-scale sequencing," Nature 467(7319): 1061-1073 (2010).
European Bioinformatics Institute, Accession No. UNIPROT: P00746, "Complement Factor D," Jul. 21, 1986 (5 pages).
NCBI Reference Sequence: NM-001928/ "*Homo sapiens* Complement Factor D (adipsin) (cFD), mRNA" Nucleotide Result, Mar. 12, 2011 (7 pages).

(Continued)

*Primary Examiner* — Padmavathi Baskar
(74) *Attorney, Agent, or Firm* — Armstrong Teasdale LLP

(57) ABSTRACT

The disclosure relates to antibody-polymer conjugates comprising one or more anti-Factor D antibody variants, their production and their use in the preparation of compositions and medicaments for treatment of diseases and disorders associated with excessive or uncontrolled complement activation.

41 Claims, 62 Drawing Sheets
Specification includes a Sequence Listing.

(56) References Cited

U.S. PATENT DOCUMENTS

| | | |
|---|---|---|
| 6,838,554 B2 | 1/2005 | Ashkenazi et al. |
| 6,867,189 B2 | 3/2005 | Lucas et al. |
| 6,884,879 B1 | 4/2005 | Baca et al. |
| 6,956,107 B2 | 10/2005 | Fung et al. |
| 7,005,504 B2 | 2/2006 | Hsei et al. |
| 7,112,327 B2 | 9/2006 | Fung et al. |
| 7,122,636 B1 | 10/2006 | Hsei et al. |
| 7,192,589 B2 | 3/2007 | Ashkenazi et al. |
| 7,211,400 B2 | 5/2007 | Ashkenazi et al. |
| 7,282,565 B2 | 10/2007 | Ashkenazi et al. |
| 7,351,524 B2 | 4/2008 | Hageman et al. |
| 7,419,663 B2 | 9/2008 | Ashkenazi et al. |
| 7,432,356 B2 | 10/2008 | Fung et al. |
| 7,439,331 B2 | 10/2008 | Fung et al. |
| 7,807,164 B2 | 10/2010 | Furfine et al. |
| 7,816,497 B2 | 10/2010 | Ambati |
| 7,943,135 B2 | 5/2011 | Fung et al. |
| 8,007,791 B2 | 8/2011 | Hass et al. |
| 8,007,798 B2 | 8/2011 | Ashkenazi et al. |
| 8,067,002 B2 | 11/2011 | An et al. |
| 8,124,090 B2 | 2/2012 | Fung et al. |
| 8,142,776 B2 | 3/2012 | Liu et al. |
| 8,187,604 B2 | 5/2012 | An et al. |
| 8,193,329 B2 | 6/2012 | An et al. |
| 8,236,317 B2 | 8/2012 | Fung et al. |
| 8,268,310 B2 | 9/2012 | Hass et al. |
| 8,273,352 B2 * | 9/2012 | Huang ............... C07K 16/18 424/133.1 |
| 8,277,830 B2 | 10/2012 | de Juan, Jr. et al. |
| 8,372,403 B2 | 2/2013 | An et al. |
| 8,383,802 B2 | 2/2013 | Fung et al. |
| 8,399,003 B2 | 3/2013 | Krall et al. |
| 8,399,006 B2 | 3/2013 | De Juan, Jr. et al. |
| 8,481,046 B2 | 7/2013 | Furfine et al. |
| 8,497,094 B2 | 7/2013 | Hass et al. |
| 8,614,306 B2 | 12/2013 | Huang et al. |
| 8,753,625 B2 | 6/2014 | Fung et al. |
| 8,753,826 B2 | 6/2014 | An et al. |
| 8,765,131 B2 | 7/2014 | Fung et al. |
| 8,795,712 B2 | 8/2014 | de Juan, Jr. et al. |
| 9,676,868 B2 | 6/2017 | Huang et al. |
| 2002/0081293 A1 | 6/2002 | Fung |
| 2002/0136719 A1 | 9/2002 | Shenoy et al. |
| 2003/0021790 A1 | 1/2003 | Hsei et al. |
| 2003/0129187 A1 | 7/2003 | Fung et al. |
| 2003/0207309 A1 | 11/2003 | Hageman et al. |
| 2004/0152105 A1 | 8/2004 | Vogt et al. |
| 2004/0177387 A1 | 9/2004 | Jayakrishna |
| 2005/0036991 A1 | 2/2005 | Fodor |
| 2005/0191298 A1 | 9/2005 | Bell et al. |
| 2005/0196394 A1 | 9/2005 | Fung |
| 2005/0197285 A1 | 9/2005 | Rosen et al. |
| 2005/0222027 A1 | 10/2005 | Chiang et al. |
| 2005/0232920 A1 | 10/2005 | Fung et al. |
| 2006/0067935 A1 | 3/2006 | Ambati |
| 2006/0233803 A1 | 10/2006 | Ashkenazi et al. |
| 2006/0240020 A1 | 10/2006 | Fung et al. |
| 2006/0281120 A1 | 12/2006 | Gorin et al. |
| 2007/0020647 A1 | 1/2007 | Hageman et al. |
| 2007/0077233 A1 | 4/2007 | Giordano |
| 2007/0092940 A1 | 4/2007 | Eigenbrot et al. |
| 2007/0098692 A1 | 5/2007 | Kovesdi et al. |
| 2007/0190054 A1 | 8/2007 | Ashkenazi et al. |
| 2008/0118506 A1 | 5/2008 | An et al. |
| 2008/0146501 A1 | 6/2008 | Hageman et al. |
| 2008/0193442 A1 | 8/2008 | Fung et al. |
| 2008/0280825 A1 | 11/2008 | Hageman et al. |
| 2009/0111708 A1 | 4/2009 | Seddon et al. |
| 2009/0124542 A1 | 5/2009 | Hageman et al. |
| 2009/0181017 A1 | 7/2009 | Hass et al. |
| 2009/0214538 A1 | 8/2009 | Fung et al. |
| 2009/0233277 A1 | 9/2009 | Murakami |
| 2009/0253689 A1 | 10/2009 | Baeschlin et al. |
| 2009/0269338 A1 | 10/2009 | Huang et al. |
| 2009/0304694 A1 | 12/2009 | Oliner et al. |
| 2010/0104568 A1 * | 4/2010 | Beirnaert ............ A61K 47/6849 424/133.1 |
| 2010/0129379 A1 * | 5/2010 | Carpenter ............ A61K 9/0019 424/158.1 |
| 2010/0174272 A1 | 7/2010 | Weiner |
| 2011/0014716 A1 | 1/2011 | Swaroop et al. |
| 2011/0123528 A1 | 5/2011 | An et al. |
| 2011/0165622 A1 | 7/2011 | An et al. |
| 2011/0165648 A1 | 7/2011 | Campagne et al. |
| 2011/0195069 A1 | 8/2011 | Fung et al. |
| 2011/0212433 A1 | 9/2011 | Barker et al. |
| 2011/0282034 A1 | 11/2011 | Hass et al. |
| 2011/0286956 A1 | 11/2011 | Xhao et al. |
| 2012/0107315 A1 | 5/2012 | Behrens et al. |
| 2012/0141480 A1 | 6/2012 | Fung et al. |
| 2012/0190578 A1 | 7/2012 | Seddon et al. |
| 2012/0230985 A1 | 9/2012 | An et al. |
| 2012/0230990 A1 * | 9/2012 | Beckmann ......... C07K 16/2866 424/133.1 |
| 2012/0322975 A1 | 12/2012 | Fung et al. |
| 2012/0328613 A1 | 12/2012 | Huang et al. |
| 2013/0171070 A1 | 7/2013 | An et al. |
| 2013/0171155 A1 | 7/2013 | Fung et al. |
| 2013/0302333 A1 | 11/2013 | Hass et al. |
| 2014/0065137 A1 | 3/2014 | Huang et al. |
| 2014/0135486 A1 | 5/2014 | Zhao et al. |
| 2014/0212433 A1 | 7/2014 | Huang et al. |
| 2014/0286947 A1 | 9/2014 | Behrens et al. |
| 2014/0303355 A1 | 10/2014 | An et al. |
| 2014/0335078 A1 | 11/2014 | Fung et al. |
| 2015/0010569 A1 | 1/2015 | Fung et al. |
| 2015/0044205 A1 | 2/2015 | Yaspan et al. |
| 2015/0073155 A1 | 3/2015 | Yoshioka et al. |
| 2015/0376295 A1 | 12/2015 | An et al. |
| 2016/0002352 A1 | 1/2016 | An et al. |
| 2016/0002353 A1 | 1/2016 | An et al. |
| 2016/0017052 A1 * | 1/2016 | Kelley ............... C07K 16/40 424/133.1 |
| 2016/0145349 A1 | 5/2016 | Huang et al. |
| 2016/0264682 A1 | 9/2016 | Fung et al. |
| 2016/0272726 A1 | 9/2016 | Hass et al. |
| 2017/0122944 A1 | 5/2017 | Orren et al. |
| 2017/0137535 A1 | 5/2017 | Petry et al. |
| 2017/0143843 A1 | 5/2017 | Hass et al. |
| 2017/0145112 A1 | 5/2017 | Kelley et al. |

FOREIGN PATENT DOCUMENTS

| | | |
|---|---|---|
| EP | 1287364 B1 | 10/2008 |
| EP | 2267028 A2 | 12/2010 |
| RU | 2232991 C1 | 7/2004 |
| WO | 199300109 A1 | 1/1993 |
| WO | 1993016185 A2 | 8/1993 |
| WO | 199404188 A1 | 3/1994 |
| WO | 199412219 A2 | 6/1994 |
| WO | 199422466 A1 | 10/1994 |
| WO | 1995029697 A1 | 11/1995 |
| WO | 199845331 A2 | 10/1998 |
| WO | 199901556 A2 | 1/1999 |
| WO | 199903887 A1 | 1/1999 |
| WO | 1999027098 A2 | 6/1999 |
| WO | 1999040100 A1 | 8/1999 |
| WO | 1999042133 A1 | 8/1999 |
| WO | 1999046281 A2 | 9/1999 |
| WO | 2000012703 A2 | 3/2000 |
| WO | 2000036102 A2 | 6/2000 |
| WO | 2000037638 A2 | 6/2000 |
| WO | 2000042072 A2 | 7/2000 |
| WO | 2000053749 A2 | 9/2000 |
| WO | 2000053758 A2 | 9/2000 |
| WO | 2001004311 A1 | 1/2001 |
| WO | 2001036432 A2 | 5/2001 |
| WO | 2001040466 A2 | 6/2001 |
| WO | 2001084149 A2 | 11/2001 |
| WO | 2002000690 A2 | 1/2002 |
| WO | 2002008284 A2 | 1/2002 |
| WO | 2002030985 A2 | 4/2002 |
| WO | 2002030986 A2 | 4/2002 |

(56) References Cited

FOREIGN PATENT DOCUMENTS

| | | |
|---|---|---|
| WO | 2003029420 A2 | 4/2003 |
| WO | 2004001009 A2 | 12/2003 |
| WO | 2004014953 A2 | 2/2004 |
| WO | 2004022594 A2 | 3/2004 |
| WO | 2004032828 A2 | 4/2004 |
| WO | 2004075837 A2 | 9/2004 |
| WO | 2005012359 A2 | 2/2005 |
| WO | 2005025509 A2 | 3/2005 |
| WO | 2005044853 A2 | 5/2005 |
| WO | 2005086770 A2 | 9/2005 |
| WO | 2005102387 A2 | 11/2005 |
| WO | 2006042329 A2 | 4/2006 |
| WO | 2006062716 A2 | 6/2006 |
| WO | 2006071856 A2 | 7/2006 |
| WO | 2006088950 A2 | 8/2006 |
| WO | 2006133295 A2 | 12/2006 |
| WO | 2007044668 A2 | 4/2007 |
| WO | 2007053447 A2 | 5/2007 |
| WO | 2007056227 A2 | 5/2007 |
| WO | 2007087384 A2 | 8/2007 |
| WO | 2008055206 A2 | 5/2008 |
| WO | 2008147883 A1 | 12/2008 |
| WO | 2009029587 A2 | 3/2009 |
| WO | 2009042686 A1 | 4/2009 |
| WO | 2009134709 A2 | 11/2009 |
| WO | 2009134711 A1 | 11/2009 |
| WO | 2009146204 A1 | 12/2009 |
| WO | 2010054110 A2 | 5/2010 |
| WO | 2010075519 A2 | 7/2010 |
| WO | 2010085542 A2 | 7/2010 |
| WO | 2010132459 A2 | 11/2010 |
| WO | 2011006161 A2 | 1/2011 |
| WO | 2011017229 A2 | 2/2011 |
| WO | 2011057014 A1 | 5/2011 |
| WO | 2011069104 A2 | 6/2011 |
| WO | 2012061421 A1 | 5/2012 |
| WO | 2013055998 A1 | 4/2013 |
| WO | 2015023596 A1 | 2/2015 |
| WO | 2015032776 A1 | 3/2015 |
| WO | 2015168468 A1 | 11/2015 |

OTHER PUBLICATIONS

Aderem et al., "Mechanisms of phagocytosis in macrophages," Annual Review of Immunology, 17: 593-623 (1999).

Ahamed et al., "Phase Behavior of an Intact Monoclonal Antibody," Biophysical Journal, 93(2): 610-619 (2007).

Altshuler et al., "Genetic Mapping in Human Disease," Science, 322(5093): 881-888 (2008).

Ambati et al., "An animal model of age-related macular degeneration in senescent Ccl-2- or Ccr-2-deficient mice," Nature Medicine, 9(11):1390-1397 (2003).

Amin et al., "Genetic Scoring Analysis: a way forward in Genome Wide Association Studies?" European J. Epidemiol, 24(10): 585-587 (2009).

Amsterdam et al., "Limitation of reperfusion injury by a monoclonal antibody to C5a during myocardial infarction in pigs," American Journal of Physiology-Heart and Circulatory Physiology, 268(1): H448-H457 (1995).

Anderson et al., "A Role for Local Inflammation in the Formation of Drusen in the Aging Eye," American Journal of Ophthalmology, 134(3): 411-431 (2002).

Anderson et al., "The pivotal role of the complement system in aging and age-related macular degeneration: Hypothesis re-visited," Progress in Retinal and Eye Research, 29(2): 95-112 (2010).

Arrate et al., "Cloning of Human Junctional Adhesion Molecule 3 (JAM3) and its Identification as the JAM2 Counter-receptor," J. Biological Chemistry, 276(49): 45826-45832 (2001).

Attwood, Theresa K. "The Babel of Bioinformatics," Science, 290(5491): 471-473 (2000).

Benvenuti et al., "Crystallization of soluble proteins in vapor diffusion for x-ray crystallography," Nature Protocols, 2(7): 1633-1651 (2007).

Bertozzi et al., "An ELISA for selectins based on binding to a physiological ligand," J. Immunological Methods, 203(2) :157-165 (1997).

Bielefeld-Sevigny, Martina "AlphaLISA Immunoassay Platform—The "No-Wash" High-Throughput Alternative to ELISA," Assay and Drug Development Technologies, 7(1): 90-92 (2009).

Biomarkers Definitions Working Group, "Biomarkers and surrogate endpoints: Preferred definitions and conceptual framework," Clinical Pharmacology & Therapeutics, 69(3): 89-95 (2001).

Bok, Dean "Evidence for an inflammatory process in age-related macular degeneration gains new support," PNAS, 102(20): 7053-7054 (2005).

Bora et al., "Role of Complement and Complement Membrane Attack Complex in Laser-Induced Choroidal Neovascularization," J. Immunology, 174(1): 491-497 (2005).

Bora et al., "Complement Activation via Alternative Pathway is Critical in the Development of Laser-Induced Choroidal Neovascularization: Role of Factor B and Factor H," J. Immunology, 177(3): 1872-1878 (2006).

Bora et al., "The role of complement in ocular pathology," Semin Immunopathol., 30(2): 85-95 (2008).

Brown, Eric J. "Complement Receptors, Adhesion, and Phagocytosis," Infectious Agents and Disease, 1(2): 63-70 (1992).

Brown et al., "Mechanisms of Disease: the complement system in renal injury—new ways of looking at an old foe," Nature, 3(5): 277-286 (2007).

Cancer Genome Atlas Research Network, "Comprehensive genomic characterization defines human glioblastoma genes and core pathways," Nature 455(7216): 1061-1068 (2008); correctecd at Corrigendum, Nature 494: 506 (2013).

Carroll, Michael C. "The complement system in regulation of adaptive immunity," Nature Immunology, 5(10): 981-986 (2004).

Carroll, Michael "Immunology: Exposure of an Executioner," Nature, 444(7116): 159-160 (2006).

Casset et al., "A peptide mimetic of an anti-CD4 monoclonal antibody by rational design," Biochemical & Biophysical Research Communications, 307(1): 198-205 (2003).

Chen et al., "Enhancement and destruction of antibody function by somatic mutation: unequal occurrence is controlled by V gene combinatorial associations," EMBO J., 14(12): 2784-2794 (1995).

Chen et al., Selection and Analysis of an Optimized Anti-VEGF Antibody: Crystal Structure of an Affinity-matured Fab in Complex with Antigen, J. Molecular Biology, 293(4): 865-881 (1999).

Chen et al., "Genetic variants new TIMP3 and high-density lipoprotein-associated loci influence susceptibility to age-related macular degeneration," PNAS, 107(16): 740-7406 (2010).

Chen et al., "Association between Variant Y402H in Age-Related Macular Degeneration (AMD) Susceptibility Gene CFH and Treatment Response of AMD: A Meta-Analysis," PLoS One, 7(8): 1-7, e42464 (2012).

Collins et al., "Mapping the Cancer Genome," Scientific American, Nature, 296(3): 50-57 (2007).

Colman, P.M. "Effects of amino acid sequence changes on antibody-antigen interactions," Research in Immunology, 145(1): 33-36 (1994).

Cudney, Bob "Protein Crystallization and Dumb Luck," The Rigaku Journal, 16(1): 1-7 (1999).

Cui et al., "Noncoding Variant in the Complement Factor H Gene and Risk of Exudative Age-Related Macular Degeneration in a Chinese Population," Investigative Ophthalmology & Visual Science, 51(2): 1116-1120 (2010).

Damico et al., "New approaches and potential treatments for dry age-related macular degeneration," Arq Bras Oftalmol, 75(1): 71-75 (2012).

Davies et al., "Affinity improvement of single antibody VH domains: residues in all three hypervariable regions affect antigen binding," Immunotechnology, 2(3): 169-179 (1996).

de Cordoba et al., "The human complement factor H: functional roles, genetic variations and disease associations," Molecular Immunology, 41(4): 355-367 (2004).

Demirkan et al., "Genetic risk profiles for depression and anxiety in adult and elderly cohorts," Molecular Psychiatry, 16(7): 773-783 (2011).

(56) References Cited

OTHER PUBLICATIONS

Diamond et al., "Somatic mutation of the T15 heavy chain gives rise to an antibody with autoantibody specificity," PNAS, 81(18): 5841-5844 (1984).
Do et al., "A Phase IA Dose-Escalation Study of the Anti-Factor D Monoclonal Antibody Fragment FCFD4514S in Patients with Geographic Atrophy," Retina 34(2): 313-320 (2014).
Drenth J. "Crystallizing a Protein," In: Principles of Protein X-ray Crystallography. Springer Advanced Texts in Chemistry. Springer, New York, NY, pp. 1-20, 1999.
Duddu et al., "The Relationship Between Protein Aggregation and Molecular MObility Below the Glass Transition Temperature of Lyophilized Formulations Containing a Monoclonal Antibody," Pharmaceutical Research, 14(5): 596-600 (1997).
Durairaj et al., "Prediction of Vitreal Half-Life Based on Drug Physicochemical Properties: Quantitative Structure—Pharmacokinetic Relationships (QSPKR)," Pharmaceutical Research, 26(5): 1236-1260 (2009).
Duvvuri et al., "Drug delivery to the retina: challenges and opportunities," Expert Opinion on Biological Therapy, 3(1): 45-56 (2003).
Edwards et al., "Complement Factor H Polymorphism and Age-Related Macular Degeneration," Science, 308(5720): 421-424 (2005).
Esparza-Gordillo et al., "Genetic and environmental factors influencing the human factor H plasma levels," Immunogenetics, 56(2): 77-82 (2004).
Evans et al., "Rapid expression of an anti-human C5 chimeric Fab utilizing a vector that replicates in COSS and 293 cells," J. Immunological Methods, 184(1): 123-138 (1995).
Evans et al., "Harnessing the information contained within genome-wide association studies to improve individual prediction of complex disease risk," Human Molecular Genetics, 18(18): 3525-3531 (2009).
Faelber et al., "The 1.85 A Resolution Crystal Structures of Tissue Factor in Complex with Humanized Fab D3h44 and of Free Humanized Fab D3h44: Revisiting the Solvation of Antigen Combining Sites," J. Molecular Biology, 313(1): 83-97 (2001).
Vajdos et al., "Comprehensive Functional Maps of the Antigen-binding Site of an Anti-ErbB2 Antibody Obtained with Shotgun Scanning Mutagenesis," J. Molecular Biology, 320(2): 415-428 (2002).
Van De Ven et al., "A functional variant in the CFI gene confers a high risk of age-related macular degeneration," Nature Genetics, 45(7): 813-817 (2013).
Van Lookeren Campagne et al., "Mechanisms of age-related macular degeneration and therapeutic opportunities," J. Pathology, 232(2): 151-164 (2014).
Vlasak et al., "Fragmentation of monoclonal antibodies," mAbs, 3(3): 253-263 (2011).
Volanakis et al., "Complement factor D, a novel serine protease," Protein Science, 5(4): 553-564 (1996).
Volanakis et al., "Complement Enzymes," in Human Complement System in Health and Disease, JE Volanakis and MM Frank (Editors), Marcel Dekker, NY, pp. 49-81 (1998).
Vugmeyster et al., "Pharmacokinetic, Biodistribution, and Biophysical Profiles of TNF Nanobodies Conjugated to Linear or Branched Poly(ethylene glycol)," Bioconjugate Chemistry, 23(7): 1452-1462 (2012).
Walker, M. G. "Z39Ig is co-expressed with activated macrophage genes," Biochimica et Biophysica Acta (BBA)—Gene Structure and Expression, 1574(3): 387-390 (2002).
Walport, M.J. "Complement," New England Journal of Medicine, 344(14): 1058-1066 (2001).
Wang et al., "Anti-C5 monoclonal antibody therapy prevents collagen-induced arthritis and ameliorates established disease," PNAS, 92(19): 8955-8959 (1995).
Wang et al., "Amelioration of lupus-like autoimmune disease in NZB/WF1 mice after treatment with a blocking monoclonal antibody specific for complement component C5," PNAS, 93(16): 8563-8568 (1996).
Wang et al., "Age-related Macular Degeneration Susceptibility Genes in an Older Australian Population: Comparison of Distributions and Clinical Significance of Two Major Genes with Other Known Genes," Investigative Ophthalmology & Visual Science, 53(14): 1322 (2012).
Wang et al., "Effect of Ionic Strength and pH on the Physical and Chemical Stability of a Monoclonal Antibody Antigen-Binding Fragment," J Pharmaceutical Sciences, 102(8): 2520-2537 (2013).
Weber, P.C. "[2] Overview of protein crystallization methods," Methods in Enzymology, 276: 13-22 (1997).
Weber et al., "The Role of the Complement System in Age-Related Macular Degeneration," Deutsches Arzteblatt International, 111(8): 133-138 (2014).
Wei et al., "From Disease Association to Risk Assessment: An Optimistic View from Genome-Wide Association Studies on Type 1 Diabetes," PLoS Genetics, 5(10): e1000678 (11 pages) (2009).
Weisman et al., "Soluble Human Complement Receptor Type 1: In Vivo Inhibitor of Complement Suppressing Post-Ischemic Myocardial Inflammation and Necrosis," 249(4965): 146-151 (1990).
White et al., "Human Adipsin is Identical to Complement Factor D and is Expressed at High Levels in Adipose Tissue," J. Biological Chemistry, 267(13): 9210-9213 (1992).
Wilson et al., "A competitive inhibition ELISA for the quantification of human interferon-γ," J. Immunological Methods, 162(2): 247-255 (1993).
Wong et al., "Global prevalence of age-related macular degeneration and disease burden projection for 2020 and 2040: a systematic review and meta-analysis," Lancet Global Health, 2(2): e106-e116 (2014).
Wu et al., "Humanization of a murine monoclonal antibody by simultaneous optimization of framework and CDR residues," J. Molecular Biology, 294(1): 151-162 (1999).
Wu et al., "BioGPS: an extensible and customizable portal for querying and organizing gene annotation resources," Genome Biology, 10(11): R130, 8 pages (2009).
Wu et al., "Fast and SNP-tolerant detection of complex variants and splicing in short reads," Bioinformatics, 26(7): 873-881 (2010).
Yates et al., "Complement C3 variant and the risk of age-related macular degeneration," New England J. Medicine, 357(6): 553-561 (2007).
Yi et al., "Isomerization of Asp—Asp motif in model peptides and a Monoclonal Antibody Fab Fragment," J. Pharmaceutical Sciences, 102(3): 947-959 (2013).
Yu et al., "Prospective Assessment of Genetic Effects on Progression to Different Stages of Age-Related Macular Degeneration Using Multistate Markov Models," Investigative Ophthalmology & Visual Science, 53(3): 1548-1556 (2012).
Zareparsi et al., "Strong Association of the Y402H Variant in Complement Factor H at 1q32 with Susceptibility to Age-Related Macular Degeneration," American Journal of Human Genetics, 77(1): 149-153 (2005).
Zeng et al., "Lack of association of CFD polymorphisms with advanced age-related macular degeneration," Molecular Vision, 16: 2273-2278 (2010).
Zhang et al., "Identification of isomerization and racemization of aspartate in the Asp—Asp motifs of a therapeutic protein," Analytical Biochemistry, 410(2): 234-243 (2011).
Extended European Search Report issued for Application No. EP06836941.2 dated Mar. 2, 2011 (16 pages).
Extended European Search Report issued for Application No. EP12172001.5 dated Oct. 24, 2012 (6 pages).
International Preliminary Report on Patentability issued for PCT/US2006/043103 dated May 6, 2008 (6 pages).
International Preliminary Report on Patentability issued for PCT/US2007/083172 dated May 5, 2009 (8 pages).
International Preliminary Report on Patentability issued for PCT/US2008/064526 dated Nov. 24, 2009 (10 pages).
International Preliminary Report on Patentability issued for PCT/US2009/041785 dated Nov. 2, 2010 (6 pages).
International Preliminary Report on Patentability issued for PCT/US2011/058829 dated May 7, 2013 (8 pages).
International Preliminary Report on Patentability issued for PCT/US2015/028641 dated Nov. 1, 2016 (8 pages).

(56) References Cited

OTHER PUBLICATIONS

International Search Report issued for PCT/US1999/003566 dated Jun. 2, 1999 (1 page).
International Search Report issued for PCT/US2006/043103 dated Aug. 10, 2007 (1 page).
International Search Report issued for PCT/US2007/083172 dated Jun. 26, 2008 (2 page).
International Search Report issued for PCT/US2008/064526 dated Aug. 14, 2008 (4 pages).
International Search Report issued for PCT/US2009/041785 dated Sep. 15, 2009 (3 pages).
International Search Report issued for PCT/US2011/058829 dated Apr. 1, 2012 (6 pages).
International Search Report issued for PCT/US2014/050579 dated Nov. 28, 2014 (6 pages).
International Search Report issued for PCT/US2015/028641 dated Oct. 8, 2015 (4 pages).
Written Opinion of the International Searching Authority issued for PCT/US2006/043103 dated Aug. 10, 2007 (5 pages).
Written Opinion of the International Searching Authority issued for PCT/US2007/083172 dated May 2, 2009 (7 pages).
Written Opinion of the International Searching Authority issued for PCT/US2008/064526 dated Nov. 23, 2009 (9 pages).
Written Opinion of the International Searching Authority issued for PCT/US2009/041785 dated Oct. 28, 2010 (5 pages).
Written Opinion of the International Searching Authority issued for PCT/US2011/058829 dated May 1, 2013 (7 pages).
Written Opinion of the International Searching Authority issued for PCT/US2014/050579 dated Feb. 19, 2015 (9 pages).
Written Opinion of the International Searching Authority issued for PCT/US2015/028641 dated Nov. 5, 2015 (7 pages).
Database No. NLM20510150: Leveziel et al., 2010, "Genetic factors associated with age-related macular degeneration". Med Sci (Paris). 26(5):509-15 (Abstract from PubMed).
Dictionary: Webster New American Webster Handy College Dictionary Fourth Edition (2006) p. 566-567 and 694 (definitions for "product" and "sum").
NCBI Blast Report: Q80WA3, Jun. 1, 2003, National Center for Biotechnology Information, National Library of Medicine, Bethesda, MD (2 page).
NCBI dbSNP Database: ss70817155, rs4698775, Apr. 20, 2007, National Center for Biotechnology Information, National Library of Medicine, Bethesda, MD (1 page).
NCBI dbSNP Database: ss66926822, rs11206973, Nov. 14, 2006, National Center for Biotechnology Information, National Library of Medicine, Bethesda, MD (2 pages).
NCBI dbSNP Database: ss6697713, rs 4848063 Feb. 12, 2003, National Center for Biotechnology Information, gational Library of Medicine, Md (2 pp.).
NCBI dbSNP Database: ss67486158, rs6697258, Nov. 14, 2006, National Center for Biotechnology Information, National Library of Medicine, Bethesda, MD (2 pages).
NCBI dbSNP Database: rs1329428 Cluster Report, National Center for Biotechnology Information, National Library of Medicine, Bethesda, MD, retrieved May 18, 2017 (6 pages).
NCBI dbSNP Database: rs429608 Cluster Report, National Center for Biotechnology Information, National Library of Medicine, Bethesda, MD, retrieved May 18, 2017 (4 pages).
Genbank Database Accession No. AAB80272, "Human Pro1868 Protein," (2 pages) dated Apr. 24, 2001 (revised Jun. 15, 2007).
Undar et al., "Novel Anti-Factor D Monoclonal Antibody Inhibits Complement, Neutrophil, and Platelet Activation in a Simulated Pediatric Cardiopulmonary Bypass Circuit," Presented in the 46th Annual Conference of the American Society for Artificial Internal Organs, New York, NY, Jun. 28-Jul. 1, 2000 (Abstract only).
U.S. Appl. No. 09/253,689, filed Feb. 20, 1999, entitled Inhibitors of Complement Activation.
Fagerness et al., "Variation Near Complement Factor I is Associated with Risk of Advanced AMD," European Journal of Human Genetics, 17(1): 100-104 (2009).
Farries et al., "The Mechanism of Activation of the Alternative Pathway of Complement by Cell-Bound C4b," Molecular Immunology, 27(11): 1155-1161 (1990).
Foote et al., "Antibody Framework Residues Affecting the Conformation of the Hypervariable Loops," J. Molecular Biology, 224(2): 487-499 (1992).
Francis et al., "Polymorphisms in C2, CFB and C3 are associated with progression to advanced age related macular degeneration associated with visual loss," Journal of Medical Genetics, 46(5): 300-307 (2009).
Friedman et al., "Prevalence of Age Related Macular Degeneration in the United States," The Eye Diseases Prevalence Research Group, Archives of Ophthalmology, 122(4): 564-572 (2004).
Fritsche et al., "Seven new loci associated with age-related macular degeneration," The AMD Gene Consortium, Nature Genetics, 45(4): -438 (2013).
Fung et al., Inhibition of Complement, Neutrophil, and Platelet Activation by an Anti-factor D Antibody During Extracorporeal Circulation, 25 Cardiovascular Research II, Houston Society for Engineering in Medicine and Biology, 18th Annual Meeting, Feb. 10-11, 2000, Houston, Texas, (p. 162).
Fung et al., "Inhibition of Complement, Neutrophil, and Platelet Activation by an Anti-factor D Monoclonal Antibody in Simulated Cardiopulmonary Bypass Circuits," J. Thoracic and Cardiovascular Surgery, 122(1): 113-122 (2001).
Fung et al., "Pre-neutralization of C5a-mediated effects by the monoclonal antibody 137-26 reacting with the C5a moiety of native C5 without preventing C5 cleavage," Clinical & Experimental Immunology, 133(2): 160-169 (2003).
Gagneux et al., "Genetic Differences Between Humans and Great Apes," Molecular Phylogenetics and Evolution, 18(1): 2-13 (2001).
Gao et al., "An enzyme-linked immunosorbent assay to identify inhibitors of activation of platelet integrin alpha IIb Beta 3," J. Immunological Methods, 181(1): 55-64 (1995).
Gaudreault et al., "Pharmacokinetics and retinal distribution of ranibizumab, a humanized antibody fragment directed against VEGF-A, following intravitreal administration in rabbits," Retina, 27(9): 1260-1266 (2007).
Ghate et al., "Ocular Drug Delivery," Expert Opinion on Drug Delivery, 3(2): 275-287 (2006).
Glickman et al., "A Comparison of ALPHAScreen, TR-FRET, and TRF as Assay Methods for FXR Nuclear Receptors," J. Biomolecular Screening, 7(1): 3-10 (2002).
Gold et al., "Variation in factor B (BF) and complement component 2 (C2) genes is associated with age-related macular degeneration," Nature Genetics, 38(4): 458-462 (2006).
Gorin, M. B. "Genetic insights into age-related macular degeneration: Controversies addressing Risk, Causality, and Therapeutics," Molecular Aspects of Medicine, 33(4): 467-486 (2012).
Gullberg et al., "Cytokine detection by antibody-based proximity ligation," PNAS, 101(22): 8420-8424 (2004).
Hageman et al., "An Integrated Hypothesis That Considers Drusen as Biomarkers of Immune-Mediated Processes at the RPE-Bruch's Membrane Interface in Aging and Age-Related Macular Degeneration," Process in Retinal and Eye Research, 20(6): 705-732 (2001).
Hageman et al., "A common haplotype in the complement regulatory gene factor H (HF1/CFH) predisposes Individuals to age-related macular degeneration," 102(20): 7227-7232 (2005).
Haines et al., "Complement Factor H Variant Increases the Risk of Age-Related Macular Degeneration," Science, 308: 419-421 (2005).
Halushka et al., "Patterns of single-nucleotide polymorphisms in candidate genes for blood-pressure homeostasis," Nature Genetics, 22: 239-247 (1999).
Harboe et al., "The quantitative role of alternative pathway amplification in classical pathway induced terminal complement activation," Clinical & Experimental Immunology, 138(3): 439-446 (2004).
Hattersley et al., "What makes a good genetic association study?" Lancet, 366(9493): 1315-1323 (2005).
Haubenwallner et al., "A Novel Missense Mutation in the Gene for Lipoprotein Lipase Resulting in a Highly Conservative Amino Acid Substitution (Asp180→Glu) Causes Familial Chylomicronemia (Type I Hyperlipoproteinemia)," Genomics, 18(2): 392-396 (1993).

(56) References Cited

OTHER PUBLICATIONS

Heurich et al., "Common polymorphisms in C3, factor B, and factor H collaborate to determine systemic complement activity and disease risk," PNAS, 108(21): 8761-8766 (2011).
Hirschhorn et al., "A comprehensive review of genetic association studies," Genetics in Medicine, 4(2): 45-61 (2002).
Hoffman et al., "Rare Complement Factor H Variant Associated with Age-Related Macular Degeneration in the Amish," Investigative Ophthalmology & Visual Science, 55(7): 4455-4460 (2014).
Holers et al., "The evolution of mouse and human complement C3-binding proteins: divergence of form but conservation of function," Immunology Today, 13(6): 231-236 (1992).
Holers, V.M., "The spectrum of complement alternative pathway-mediated diseases," Immunological Reviews, 223(1): 300-316 (2008).
Holland et al., "Detection of specific polymerase chain reaction product by utilizing the 5'13 3' exonuclease activity of Thermus aquaticus DNA polymerase," PNAS, 88(16): 7276-7280 (1991).
Holm et al., "Functional mapping and single chain construction of the anti-cytokeratin 8 monoclonal antibody TS1," Molecular Immunology, 44(6): 1075-1084 (2007).
Holt et al., "Domain antibodies: proteins for therapy," Trends in Biotechnology, 21(11): 484-490 (2003).
Holz et al., "Geographic Atrophy: Clinical Features and Potential Therapeutic Approaches," Ophthalmology, 121(5): 1079-1091 (2014).
Holz et al., "Recent developments in the treatment of age-related macular degeneration," J. Clinical Investigation, 124(4): 1430-1438 (2014).
Homeister et al., "Soluble complement receptor type 1 prevents human complement-mediated damage of the rabbit isolated heart," J. Immunology, 150(3): 1055-1064 (1993).
Houghten et al., "The use of synthetic peptide combinatorial libraries for the identification of bioactive peptides," BioTechniques, 13(3): 412-421 (1992).
Howie et al, "A Flexible and Accurate Genotype Imputation Method for the Next Generation of Genome-Wide Association Studies," PLOS Genetics, 5(6): e1000529 (2009).
Huber-Lang et al., "Role of C5a in Multiorgan Failure During Sepsis," J. Immunology, 166(2): 1193-1199 (2001).
Igawa et al., "Engineering the Variable Region of Therapeutic IgG antibodies," mAbs 3(3) 243-252 (2011).
Inagi et al., "Decreased Activity of Complement-Mediated Immune Complex Clearance in Hemodialysis Patients," Clinical Immunology & Immunopathology, 68(3): 333-339 (1993).
Ioannidis et al., "Replication validity of genetic association studies," Nature Genetics, 29(3): 306-309 (2001).
Janeway, Jr. et al. (Editors), "Immunobiology," 3rd Edition, Current Biology Ltd./Garland Publishing Inc., pp. 13:5 to 13:9 (1997).
Janssen et al., "Structural Insights into the Central Complement Component C3," Molecular Immunology 44(1-3): 3-10 (2007).
Jevsevar et al., "PEGylation of Antibody Fragments for Half-Life Extension," Antibody Methods and Protocols, Methods in Molecular Biology, G. Proetzel & H. Ebersbach, Editors, Chapter 15, 901: 233-246 (2012).
Jing et al., "Structures of Native and Complexed Complement Factor D: Implications of the Atypical His57 Conformation and Self-Inhibitory Loop in the Regulation of Specific Serine Protease Activity," J. Molecular Biology, 282(5): 1061-1081 (1998).
Jing et al., "Structural basis of profactor D activation: from a highly flexible zymogen to a novel self-inhibited serine protease, complement factor D," EMBO Journal, 18(4): 804-814 (1999).
Johnson et al., "Complement activation and inflammatory processes in Drusen formation and age related macular degeneration," Experimental Eye Research, 73(6): 887-896 (2001).
Kathiresan et al., "Polymorphisms Associated with Cholesterol and Risk of Cardiovascular Events," Journal of Vascular Surgery, 47(6): 1372 (2008).
Katschke et al., "A novel inhibitor of the alternative pathway of complement reverses inflammation and bone destruction in experimental arthritis," J. Experimental Medicine, 204(6): 1319-1325 (2007).
Kelley et al., "Methods to engineer and identify IgG1 variants with improved FcRn binding or effector function," Antibody Methods and Protocols, Methods in Molecular Biology, G. Proetzel & H. Ebersbach, Editors, Chapter 18, 301: 277-293 (2012).
Khalili et al., "Fab-PEG-Fab as a Potential Antibody Mimetic," Bioconjugate Chemistry, 24(11): 1870-1882 (2013).
Kim et al., "Crystal Structure of a Complement Factor D Mutant Expressing Enhanced Catalytic Activity," J. Biological Chemistry, 270(41): 24399-24405 (1995).
Kim et al., "Characterization of monoclonal antibody specific to the Z39Ig protein, a member of immunoglobulin superfamily," Immunology Letters, 99(2): 153-161 (2005).
Klein et al., "Complement Factor H Polymorphism in Age-Related Macular Degeneration," Science, 308(5720): 385-389 (2005).
Kloeckener-Gruissem et al., "Genetic Association with Response to Intravitreal Ranibizumab in Patients with Neovascular AMD," Investigative Ophthalmology & Visual Science, 52(7): 4694-4702 (2011).
Klohs et al., "Inhibitors of Tyrosine Kinase," Current Opinion in Oncology, 9(6): 562-568 (1997).
Kozlov, et al., "Isotyping of component C4 of human complement using differences in the functional activity of Isotypes C4A and C4B," Russian J. Bioorganic Chemistry, 26(7): 482-489 (2000).
Kroshus et al., "Complement Inhibition with an Anti-05 Monoclonal Antibody Prevents Acute Cardiac Tissue Injury In an ex vivo Model of Pig-to-Human Xenotransplantation," Transplantation, 60(11): 1194-1202 (1995).
Krzystolik et al., "Prevention of Experimental Choroidal Neovascularization With Intravitreal Anti-Vascular Endothelial Growth Factor Antibody Fragment," Archives of Ophthalmology, 120(3): 338-346 (2002).
Kumagai et al., "Generation of Novel Functional Antibody Molecules by in vitro Selection System," Tanpakushitu Kakusan Koso, 43(2): 159-167 (1998) with English Abstract.
Kundrot, C.E. "Which strategy for a protein crystallization project?" Cellular and Molecular Life Sciences, 61(5): 525-536 (2004).
Kussie et al., "A single engineered amino acid substitution changes antibody tine specificity," J. Immunology, 152(1): 146-152(1994).
Lam, K. S. "Application of combination library methods in cancer research and drug discovery," Anti-Cancer Drug Design, 12(3): 145-167 (1997).
Langnaese et al., "Cloning of Z39Ig, a novel gene with immunoglobulin-like domains located on human chromosome X," Biochimica et Biophysica Acta, 1492(2-3): 522-525 (2000).
Lee et al., Z39Ig is expressed on macrophages and may mediate inflammatory reactions in arthritis and atherosclerosis, J. Leukocyte Biology, 80(4): 922-928 (2006).
Lettre et al., "Autoimmune Diseases: Insights from Genome-Wide Association Studies," Human Molecular Genetics, 17(R2): R116-R121 (2008).
Loubser et al., "Inhibition of Complement, Neutrophil and Platelet Activation by an Anti-Factor D Antibody during Extracorporeal Circulation," American Society of Anesthesiologists, Abstract A-657: 1 page (2000).
loyet et al., "Anti-Factor D Fab Specifically Inhibits the Alternative Complement Pathway: In vitro Characterization and in vivo Effects Following Administration to Cynomolgus Monkeys," Investigative Ophthalmology & Visual Science, 51(13): 2980 (2010).
Lucentini, J. "Gene association studies typically wrong: reproducible gene-disease associations are few and far between," The Scientist, 18(24): 20 (2004).
Makrides, S. C., "Therapeutic Inhibition of the Complement System," Pharmacological Reviews, 50(1): 59-87 (1998).
Matson et al., "Evolving concepts of therapy for sepsis and septic shock and the use of hyperpermeable membranes," Current Opinion in Critical Care, 6(6): 431-436 (2000).
Maynard et al., "Antibody Engineering," Annual Review of Biomedical Engineering, 2: 339-376 (2000).
McPherson, A. "Review, Current approaches to macromolecular crystallization," European J. Biochemistry Reviews, 189: 1-23 (1990).

(56) References Cited

OTHER PUBLICATIONS

Mohlke et al., "Metabolic and cardiovascular traits: an abundance of recently identified common genetic variants," Human Molecular Genetics, 17(R2): R102-R108 (2008).
Moon et al., "A synergistic approach to protein crystallization: Combination of a fixed-arm carrier with surface entropy reduction," Protein Science, 19(5): 901-913 (2010).
Morgan, B.P. "Clinical complementology: recent progress and future trends," European J. Clinical Investigation, 24(4): 219-228 (1994).
Morrison, L. E., "Time-Resolved Detection of Energy Transfer: Theory and Application to Immunoassays," Analytical Biochemistry, 174(1): 101-120 (1988).
Mulligan et al., "Protective Effects of Soluble CR1 in Complement- and Neutrophil-Mediated Tissue Injury," J. Immunology, 148(5): 1479-1485 (1992).
Mullins et al., "Drusen associated with aging and age-related macular degeneration contain proteins common to extracellular deposits associated with atherosclerosis, elastosis, amyloidosis, and dense deposit disease," FASEB J., 14(7): 835-846 (2000).
Narayana et al., "Structure of Human Factor D: A Complement System Protein at 2.0 Å Resolution," J Molecular Thology, 235(2): 695-708 (1994).
Neale et al., "Genome-wide association study of advanced age-related macular degeneration identifies a role of the hepatic lipase gene (LIPC)," PNAS, 107(16): 7395-7400 (2010).
Niemann et al., "The Use of Monoclonal Antibodies as Probes of the Three-Dimensional Structure of Human Complement Factor D," J. Immunology, 132(2): 809-815 (1984).
Nozaki et al., "Drusen complement components C3a and C5a promote choroidal neovascularization," PNAS, 103(7): 2328-2333 (2006).
Ohno et al., "Antigen-binding specificities of antibodies are primarily determined by seven residues of VH," PNAS, 82 (9): 2945-2949 (1985).
Oliphant et al., "BeadArray Technology: Enabling an Accurate, Cost-Effective Approach to High-Throughput Genotyping," Product & Technology Report, BioTechniques 32(6): S56-S61 (2002).
Omer et al., "CA1A2X-competitive inhibitors of farnesyltransferase as anti-cancer agents," Trends in Pharmacological Sciences, 18(4): 437-445 (1997).
Padlan et al., "Structure of an antibody-antigen complex: Crystal structure of the HyHEL-10 Fab-lysozyme complex," PNAS, 86(15): 5938-5942 (1989).
Pascual et al., "A monoclonal antibody which blocks the function of factor D of human complement," J Immunological Methods, 127(2): 263-269 (1990).
Pascual et al., "Inhibition of complement alternative pathway in mice with Fab antibody to recombinant adipsin/factor D." European J. Immunology, 23(6): 1389-1392 (1993).
Patterson et al., "Improving the Serum Stability of Site-Specific Antibody Conjugates with Sulfone Linkers," Bioconjugate Chemistry, 25(2): 1402-1407 (2014).
Paul, W. E (Editor) "Structure and Function of Immunoglobins," Fundamental Immunology, Chapter 9, 3rd Edition, Raven Press, NY, pp. 292-295 (1993).
Petrukhin, K. "New therapeutic targets in atrophic age-related macular degeneration," Expert Opinion Therapeutic Targets, 11(5): 625-639 (2007).
Pikal et al., "Solid State Chemistry of Proteins: II. The Correlation of Storage Stability of Freeze-Dried Human Growth Hormone (hGH) with Structure and Dynamics in the Glassy Solid," J. Pharmaceutical Sciences, 97(12): 5106-5121 (2008).
Pini et al., "Design and Use of a Phage Display Library," J. Biological Chemistry, 273(34): 21769-21776 (1998).
Plackett, R. L. "Studies in the History of Probability and Statistics. XXIX: The discovery of the method of least squares," Biometrika, 59(2): 239-251 (1972).
Prosser et al., "Structural basis for complement factor H-linked age-related macular degeneration," J. Experimental Medicine, 204(10): 2277-2283 (2007).
Purcell et al., "Common polygenic variation contributes to risk of schizophrenia and bipolar disorder," Nature, 460 (7256): 748-752 (2009).
Pyz et al., "C-type lectin-like receptors on myeloid cells," Annals of Medicine, 38(4): 242-251 (2006).
Rabinovici et al., "Role of Complement in Endotoxin/Platelet-Activating Factor-Induced Lung Injury," J. Immunology, 149(5): 1744-1750 (1992).
Rattner et al., "Macular degeneration: recent advances and therapeutic opportunities," Nature Reviews, Neuroscience, 7(11): 860-872 (2006).
Almagro et al., "Humanization of antibodies," Frontiers in Bioscience, 13: 1619-1633 (2008).
Amit et al., "Three-Dimensional Structure of an Antigen-Antibody Complex at 2.8 A Resolution," Science, 233(4765): 747-753 (1986).
Avery et al., "Systemic pharmacokinetics following intravitreal injections of ranibizumab, bevacizumab or aflibercept in patients with neovascular AMD," Br. J. Ophthalmol., 98(12):1636-1641 (2014).
Badescu et al., "A New Reagent for Stable Thiol-Specific Conjugation," Bioconjugate Chemistry, 25(3): 460-469 (2014).
Barnum et al., "Quantitation of Complement Factor D in Human Serum by a Solid-Phase Radioimmunoassay," J. Immunol. Methods, 67(2): 303-309 (1984).
Buckmann et al., "Functionalization of Poly(ethylene glycol) and Monomethoxy-Poly(ethylene glycol)," Makromol. Chem., 182(5):1379-1384 (1981).
Cacia et al., "Isomerization of an Aspartic Acid Residue in the Complementarity-Determining Regions of a Recombinant Antibody to Human IgE: Identification and Effect on Binding Affinity," Biochemistry, 35(6): 1897-1903 (1996).
Carter et al., "Humanization of an anti-p185HER2 antibody for human cancer therapy," PNAS, 89(10): 4285-4289 (1992).
Champe et al., "Monoclonal Antibodies That Block the Activity of Leukocyte Function-associated Antigen 1 Recognize Three Discrete Epitopes in the Inserted Domain of CD11a," J. Biological Chemistry, 270(3): 1388-1394 (1995).
Chen et al., "Modulating antibody pharmacokinetics using hydrophilic polymers," Expert Opinion on Drug Delivery, 8 (9): 1221-1236 (2011).
Chothia et al., "Canonical Structures for the Hypervariable Regions of Immunoglobulins," Reprinted from J. Mol. Biol., 196(4): 901-917 (1987).
Clackson et al., "Making Antibody Fragments Using Phage Display Libraries," Nature, 352(6336): 624-628 (1991).
Cunningham et al., "High-Resolution Epitope Mapping of hGH-Receptor Interactions by Alanine-Scanning Mutagenesis," Science, 244(4908): 1081-1085 (1989).
Davis et al., "Soluble, Nonantigenic Polyethylene Gylcol-Bound Enzymes," Biomedical Polymers: Polymeric Materials and Pharmaceuticals for Biomedical Use, Editors E. P. Goldberg et al., Academic Press, NY, pp. 441-452 (1980).
De Jong, "Age-Related Macular Degeneration," New England Journal of Medicine, 355(14): 1474-1485 (2006).
Ellman et al., "[15] Biosynthetic Method for Introducing Unnatural Amino Acids Site-Specifically into Proteins," Methods in Enzymology, 202: 301-336 (1991).
Ferris et al., "A Simplified Severity Scale for Age-Related Macular Degeneration: AREDS Report No. 18," Arch Ophthalmol., 123(11): 1570-1574 (2005).
Fitch et al., "Optimal Sequence Alignments," Proc. Natl. Acad. Sci. USA, 80: 1382-1386 (1983).
Gaudreault et al., "Preclinical Pharmacokinetics of Ranibizumab (rhuFabV2) after a Single Intravitreal Administration," Invest. Ophthalmol. Vis. Sci., 46(2): 726-733 (2005).
Geiger et al., "Deamidation, Isomerization, and Racemization at Asparaginyl and Aspartyl Residues in Peptides," J. Biol. Chem., 262(2): 785-794 (1987).
Green, A. "Studies in the Physical Chemistry of the Proteins: IX. The Effect of Electrolytes on the Solubility of Hemoglobin in Solutions of Varying Hydrogen Ion Activity with a Note on the Comparable Behavior of Casein," J. Biol. Chem., 93:517-542 (1931).

(56) References Cited

OTHER PUBLICATIONS

Hakimi et al., "Reduced Immunogenicity and Improved Pharmacokinetics of Humanized Anti-Tac in Cynomolgus Monkeys;" J. Immunol. 147(4):1352-1359 (1991).
Harboe et al., "The alternative complement pathway revisited," J. Cell. Mol. Med., 12(4): 1074-1084 (2008).
Harlow et al., "Antibiodies: A Laboratory Manual," Ed Harlow and David Lane Editors, Cold Spring Harbor Laboratory, N.Y., pp. 55-137 and 141-142 (1988).
Holers, V.M., "Complement," In Clinical Immunology: Principles and Practice, Chapter 24, pp. 363-391, Editor R.R. Rich et al., Mosby Press (1996).
Humphreys et al., "Alternative antibody Fab' fragment PEGylation strategies: combination of strong reducing agents, disruption of the interchain disulphide bond and disulphide engineering," Protein Engineering, Design & Selection, 20(5): 227-234 (2007).
Hutanu et al., "Recent Applications of Polyethylene Glycols (PEGs) and PEG Derivatives," Mod. Chem. Appl., 2(2): 6 pages (2014).
Jaffers et al., "Monoclonal Antibody Therapy. Anti-Idiotypic and Non-Anti-Idiotypic Antibodies to OKT3 Arising Despite Intense Immunosuppression," Transplantation, 41(5): 572-578 (1986).
Jager et al., "Age-Related Macular Degeneration," New Engl. J. Med., 358(24): 2606-2617 (2008); and Erratum in N. Engl. J. Med. 359(16): 1735 (2008).
Jevsevar et al., "PEGylation of therapeutic proteins," Biotech. J., 5(1): 113-128 (2010).
Johnson et al., "The Kabat Database and a Bioinformatics Example," in Methods in Molecular Biology, 248: 11-25, Antibody Engineering: Methods and Protocols, Edited by Benny Lo, Humana Press Inc., Totowa NJ. (2004).
Jones et al. "Replacing the complementarity-determining regions in a human antibody with those from a mouse," Nature, 321(6069): 522-525 (1986).
Jones, A. "Analysis of polypeptides and proteins," Advanced Drug Delivery Reviews, 10(1): 29-90 (1993).
Joubert et al., Classification and Characterization of Therapeutic Antibody Aggregates, J. Biol. Chem., 286(28): 25118-25133 (2011).
Joubert et al., "Highly Aggregated Antibody Therapeutics Can Enhance the in vitro Innate and Late-stage T-cell Immune Responses," J. Biol. Chem., 287(30): 25266-25279 (2012).
Junghans et al., "Anti-Tac-H, a Humanized Antibody to the Interleukin 2 Receptor with New Features for Immunotherapy in Malignant and Immune Disorders," Cancer Res., 50(5): 1495-1502 (1990).
Junutula et al., "Rapid identification of reactive cysteine residues for site-specific labeling of antibody-Fabs," J. Immunol. Methods, 332(1-2): 41-52 (2008).
Kabat et al., "Sequences of Proteins of Immunological Interest," 5th Ed. Public Health Service, National Institutes of Health, Bethesda, Md., 11 pages (1991).
Katre, N.V. "The conjugation of proteins with polyethylene glycol and other polymers: Altering properties of proteins to enhance their therapeutic potential," Advanced Drug Delivery Reviews, 10(1): 91-114 (1993).
Katschke Jr. et al., "Structural and Functional Analysis of a C3b-specific Antibody That Selectively Inhibits the Alternative Pathway of Complement," J. Biol. Chem., 284(16): 10473-10479 (2009).
Katschke Jr. et al., "Inhibiting Alternative Pathway Complement Activation by Targeting the Factor D Exosite", J. Biol. Chem., 287(16): 12886-12892 (2012).
Khazaeli et al., "Phase I Trial of Multiple Large Doses of Murine Monoclonal Antibody CO17-1A. II. Pharmacokinetics and Immune Response," J Natl. Cancer Inst., 80(12): 937-942 (1988).
Kindt et al., "Antigens and Antibodies," Kuby Immunology, Chapter 4, p. 91, 6th Edition, Editors, T. J. Kindt et al., W.H. Freeman and Co., N.Y. (2007).
Kontermann, R.E "Strategies to extend plasma half-lives of recombinant antibodies," BioDrugs, 23(2): 93-109 (2009).
Kostavasili et al., "Mechanism of complement inactivation by glycoprotein C of herpes simplex virus," J. Immunol., 158(4): 1763-1771 (1997).
Kunkel, T.A. "Rapid and efficient site-specific mutagenesis without phenotypic selection," PNAS, 82(2): 488-492 (1985).
Le et al., "A Mechanistic Pharmacokinetic/Pharmacodynamic Model of Factor D Inhibition in Cynomolgus Monkeys by Lampalizumab for the Treatment of Geographic Atrophy," J. Pharmacol. Exp. Ther., 355(2): 288-296 (2015).
Lesavre et al., "Mechanism of Action of Factor D of the Alternative Complement Pathway," J. Exp. Med., 148(6): 1498-509 (1978).
Ray et al., "Thrombin Receptor: A Novel Target for Antiplatelet Drug Development," Thrombosis Research, 87(1): 37-50 (1997).
Reynolds et al., "Plasma Complement Components and Activation Fragments: Associations with Age-Related Macular Degeneration Genotypes and Phenotypes," Investigative Ophthalmology & Visual Science, 50(12): 5818-5827 (2009).
Ricklin et al., "Complement-targeted therapeutics," Nature Biotechnology, 25(11): 1265-1275 (2007).
Ricklin et al., "Complement: a key system for immune surveillance and homeostasis," Nature Immunology, 11(9): 785-797 (2010).
Rinder et al., "Blockade of C5a and C5b-9 generation inhibits leukocyte and platelet activation during extracorporeal circulation," J Clinical Investigation, 96(3): 1564-1572 (1995).
Rohrer et al., "Eliminating Complement Factor D Reduces Photoreceptor Susceptibility to Light-Induced Damage," Investigative Ophthalmology & Visual Science, 48(11): 5282-5289 (2007).
Rohrer et al., "A Targeted Inhibitor of the Alternative Complement Pathway Reduces Angiogenesis in a Mouse Model of Age-Related Macular Degeneration," Investigative Ophthalmology & Visual Science, 50(7): 3056-3064 (2009).
Roitt et al., (Editors), Immunology, 5th Edition, Mosby International Ltd., pp. 110-113 (10 pgs) (1998).
Ross et al., "Membrane complement receptors specific for bound fragments of C3," Advances in Immunology, 37: 217-267 (1985).
Roversi et al., "Structural basis for complement factor I control and its disease-associated sequence polymorphisms," PNAS, 108(31): 12839-12844 (2011).
Rudikoff et al., "Single amino acid substitution altering antigen-binding specificity," PNAS, 79(6): 1979-1983 (1982).
The International SNP Map Working Group, "A map of human genome sequence variation containing 1.42 million single nucleotide polymorphisms," Nature 409(6822): 928-934 (2001).
Sahu et al., "Identification of multiple sites of interaction between heparin and the complement system," Molecular Immunology, 30(7): 679-684 (1993).
Sambrook et al., (Editors) "Chapter 5, Gel Electrophoresis of DNA and Pulsed-Field Agarose Gel Electrophoresis," Molecular Cloning: A Laboratory Manual, 3rd Ed., vol. 1: 5.1 to 5.90 (2001).
Sambrook et al., (Editors) "Chapter 9, Preparation of Radiolabeled DNA and RNA Probes," Molecular Cloning: A Laboratory Manual, 3rd Ed., vol. 2: 9.1 to 9.102 (2001).
Sato et al., "A new method for studying the binding of human IgE to CD23 and the inhibition of this binding," J Immunological Methods, 209(1): 59-66 (1997).
Scheffe, H. (Editor) "Section 1.2 Mathematical Models," The Analysis of Variance, John Wiley & Sons, pp. 4-8 (1999).
Scholl et al., "Systemic Complement Activation in Age-Related Macular Degeneration," PloS One, 3(7): e2593 (7 pages) (2008).
Schweitzer et al., "Combining nucleic acid amplification and detection," Current Opinion in Biotechnology, 12(1): 21-27 (2001).
Seddon et al., "Association of CFH Y402H and LOC387715 A695 With Progression of Age-Related Macular Degeneration," JAMA, 297(16): 1793-1800 (2007).
Seddon et al., "Prediction Model for Prevalence and Incidence of Advanced Age-Related Macular Degeneration Based on Genetic, Demographic, and Environmental Variables," Investigative Ophthalmology & Visual Science, 50(5): 2044-2053 (2009).
Seddon et al., "Risk Models for Progression to Advanced Age-Related Macular Degeneration Using Demographic, Environmental, Genetic, and Ocular Factors," Ophthalmology, 118(11): 2203-2211 (2011).
Seddon et al., "Rare variants in CFI, C3 and C9 are associated with high risk of advanced age-related macular degeneration," Nature Genetics, 45(11): 1366-1370 (2013).

(56) References Cited

OTHER PUBLICATIONS

Selvin, P. R. "Fluorescence resonance energy transfer," Methods in Enzymology, 246: 300-334 (1995).
Sim et al., "Innate Immunity," Biochemical Society Transactions, 28(5): 545-550 (2000).
Sivakumaran et al., "A 32 kb Critical Region Excluding Y402H in CFH Mediates Risk for Age-Related Macular Degeneration," PLoS One, 6(10): 1-13, e25598 (2011).
Skolnick et al., "From genes to protein structure and function: novel applications of computational approaches in the genomic era," Trends in Biotechnology, 18(1): 34-39 (2000).
Stadel et al., "Orphan G protein-coupled receptors: a neglected opportunity for pioneer drug discovery," Trends in Pharmacological Sciences, 18(11): 430-437 (1997).
Stanton et al., "Complement factor D in age-related macular degeneration," Investigative Ophthalmology & Visual Science, 52(12): 8828-8834 (2011).
Strasberg et al., "Generation and initial analysis of more than 15,000 full-length human and mouse cDNA sequences," PNAS, 99(26): 16899-16903 (2002).
Strawn et al., "Flk-1 as a Target for Tumor Growth Inhibition," Cancer Research, 56(15): 3540-3545 (1996).
Streiner, D. L. "Last Observation Carried Forward," In Encyclopedia of Research Design, N. Salkind Editor, SAGE Publications, 6 pages (2010).
Stryer, L. "Fluorescence Energy Transfer as a Spectroscopic Ruler," Annual Review of Biochemistry, 47: 819-846 (1978).
Stuart et al., "Phagocytosis: Elegant Complexity," Immunity, 22(5): 539-550 (2005).
Sunness et al., "Visual Function Abnormalities and Prognosis in Eyes with Age-related Geographic Atrophy of the Macula and Good Visual Acuity," Ophthalmology, 104(10): 1677-1691 (1997).
Sunness et al., "Designing Clinical Trials for Age-Related Geographic Atrophy of The Macula: Enrollment Data From the Geographic Atrophy Natural History Study," Retina, 27(2): 204-210 (2007).
Tamura et al., "Structural correlates of an anticarcinoma antibody: identification of specificity-determining residues (SDRs) and development of a minimally immunogenic antibody variant by retention of SDRs only," J. Immunology, 164(3): 1432-1441 (2000).
Tanhehco et al., "The Anti-Factor D Antibody, MAb 166-32, Inhibits the Alternative Pathway of the Human Complement System," Transplantation Proceedings, 31(5): 2168-2171 (1999).
Taylor et al., "Pattern recognition receptors and differentiation antigens define murine myeloid cell heterogeneity ex vivo," European J. Immunology, 33(8): 2090-2097 (2003).
Taylor et al., "Macrophage Receptors and Immune Recognition," Annual Review of Immunology, 23: 901-944 (2005).
Teo et al., "A genotype calling algorithm for the Illumina BeadArray platform," Bioinformatics, 23(20): 2741-2746 (2007).
Thurman et al., "The Central Role of the Alternative Complement Pathway in Human Disease," J. Immunology, 176(3): 1305-1310 (2006).
Tedeschi-Blok et al., "Population-Based Study of Early Age-Related Macular Degeneration: Role of the Complement Factor H Y402H Polymorphism in Bilateral but not Unilateral Disease," Ophthalmology, 114(1): 99-103 (2007).
Tsuchihashi et al., "Complement Factor H and High-Temperature Requirement A-1 Genotypes and Treatment Response of Age-related Macular Degeneration," Ophthalmology, 118(1): 93-100 (2011).
Tsukita et al., "Multifunctional Strands in Tight Junctions," Nature Reviews, Molecular Cell Biology, 2(4): 285-293 (2001).
Ullman et al., "Luminescent oxygen channeling immunoassay: Measurement of particle binding kinetics by chemiluminescence," PNAS, 91(12): 5426-5430 (1994).
Ullman et al., "Luminescent oxygen channeling assay (LOCI): sensitive, broadly applicable homogeneous Immunoassay method," Clinical Chemistry, 42(9): 1518-1526 (1996).
Undar et al., "Novel anti-factor D monoclonal antibody inhibits complement and leukocyte activation in a baboon model of cardiopulmonary bypass," The Annals of Thoracic Surgery, 74(2): 355-362 (2002).
Underhill et al., "Phagocytosis of Microbes: Complexity in Action," Annual Review of Immunology, 20(1): 825-852 (2002).
Urtti, A. "Challenges and obstacles of ocular pharmacokinetics and drug delivery," Advanced Drug Delivery Reviews, 58(11): 1131-1135 (2006).
Lewis et al., "Maleimidocysteineamido-DOTA Derivatives: New Reagents for Radiometal Chelate Conjugation to Antibody Sulfhydryl Groups Undergo pH-Dependent Cleavage Reactions," Bioconjug Chem., 9(1): 72-86 (1998).
Lim et al. "Age-related Macular Degeneration," Lancet 379(9827):1728-1738 (2012).
Lowe et al., "Aggregation, Stability, and Formulation of Human Antibody Therapeutics," Adv. Protein Chem. Struct. Biol., 84:41-61 (2011).
Loyet et al., "Activation of the Alternative Complement Pathway in Vitreous is Controlled by Genetics in Age-Related Macular Degeneration," Invest. Ophthalmol. Vis. Sci., 53(10): 6628-6637 (2012).
Loyet et al., "Complement Inhibition in Cynomolgus Monkeys by Anti-Factor D Antigen-Binding Fragment for the Treatment of an Advanced Form of Dry Age-Related Macular Degeneration," J. Pharmacol. Exp. Ther., 351(3): 527-537 (2014).
MacCallum et al., "Antibody-antigen Interactions: Contact Analysis and Binding Site Topography," J Mol. Biol., 262 (5): 732-745 (1996).
Meredith, T.A. "Intravitreal Antimicrobials," Intraocular Drug Delivery, Chapter 6, pp. 85-95, Editor Jaffe et al., Taylor & Francis, NY (Mar. 2006).
Michels et al., "Fluorescent Derivatization Method of Proteins for Characterization by Capillary Electrophoresis-Sodium Dodecyl Sulfate with Laser-Induced Fluorescence Detection," Anal. Chem., 79(15): 5963-5971 (2007).
Michels et al., "Quantitative impurity analysis of monoclonal antibody size heterogeneity by CE-LIF: Example of development and validation through a quality-by-design framework," Electrophoresis, 33(5): 815-826 (2012).
Miller et al., "Monoclonal Antibody Therapeutic Trials in Seven Patients with T-Cell Lymphoma," Blood, 62(5): 988-995 (1983).
Moore et al. "Role of Aggregated Human Growth Hormone (hGH) in Development of Antibodies to hGH," J. Clin. Endocrnnol. Metab., 51(4): 691-697 (1980).
Needleman et al., "A General Method Applicable to the Search for Similarities in the Amino Acid Sequence of Two Proteins," J. Mol. Biol., 48(3): 443-453 (1970).
Noren et al., "A General Method for Site-Specific Incorporation of Unnatural Amino Acids into Proteins," Science, 244 (4901): 182-188 (1989).
Pangburn, M.K. "Alternative Pathway of Complement," Methods Enzymol., 162: 639-653 (1988).
Pascual et al., "Metabolism of complement factor D in renal failure," Kidney International, 34(4): 529-536 (1988).
Patel et al., "Ocular drug delivery systems: An overview," World J. Pharmacol., 2(2): 47-64 (2013).
Pearlman et al., "Analysis of Protein Drugs," in Peptide and Protein Drug Delivery, Chapter 6, pp. 247-301 (V. Lee Editor, Marcel Dekker, Inc., New York, NY, 1991).
Pedley et al., "The potential for enhanced tumour localisation by poly(ethylene glycol) modification of anti-CEA antibody," Br. J. Cancer, 70(6): 1126-1130 (1994).
Portolano et al., Lack of Promiscuity in Autoantigen-Specific H and L Chain Combinations as Revealed by Human H and L Chain "Roulette", J. Immunol., 150(3): 880-887 (1993).
Powell et al., "A Compendium and Hydropathy/Flexibility Analysis of Common Reactive Sites in Proteins: Reactivity at Asn, Asp, Gln, and Met Motifs in Neutral pH Solution," Formulation, Characterization and Stability of Protein Drugs, Chapter 1, pp. 1-140, Editor R. Pearlman et al., Plenum Press, NY (1996).
Presta et al., "Humanization of an Antibody Directed Against IgE," J. Immunol., 151(5): 2623-2632 (1993).

(56) References Cited

OTHER PUBLICATIONS

Remington's Pharmaceutical Sciences, 16th ed., Mack Publishing Company, Easton, PA, 1980 (Table of Contents, 4 pages).
Riechmann et al., "Reshaping human antibodies for therapy," Nature 332(24): 323-327 (1988).
Rosenberg et al., "Effects of Protein Aggregates: An Immunologic Perspective," AAPS J., 8(3): E501-E507 (2006).
Ryan et al., "Advances in PEGylation of important biotech molecules: Delivery aspects," Expert Opinion on Drug Delivery, 5(4): 371-383 (2008).
Salas-Solano et al., "Robustness of iCIEF Methodology for the Analysis of Monoclonal Antibodies: An Interlaboratory Study," J. Sep. Sci., 35(22): 3124-3129 (2012).
Sallo et al., "The International Classification System and the Progression of Age-Related Macular Degeneration," Curr. Eye Res., 34(3): 238-240 (2009).
Schifferli et al. "Factor D: C3 Convertase Activator, Adipsin, EC 3.4.21A6," The Complement Facts Book, pp. 69-72, Editor B. Morley et al., Academic Press (2000).
Seards et al., "Effects of Monoclonal Antibody Immunotherapy on Patients with Gastrointestinal Adenocarcinoma," J. Biol. Response Mod., 3(2): 138-150 (1984).
Shawler et al. "Human Immune Response to Multiple Injections of Murine Monoclonal IgG," J. Immunol., 135(2): 1530-1535 (1985).
Sims et al., "A Humanized CD18 Antibody can Block Function without Cell Destruction," J. Immunol., 151(4): 2296-2308 (1993).
Verhoeyen et al., "Reshaping Human Antibodies: Grafting an Antilysozyme Activity," Science, 239(4847): 1534-1536 (1988).
Volanakis et al., "Renal Filtration and Catabolism of Complement Protein D," N. Engl. J. Med., 312(7): 395-399 (1985).
Walsh, G., "Biopharmaceutical Benchmarks," Nature Biotech., 18(8): 831-833 (2000).
Wang et al., "Antibody Structure, Instability, and Formulation," J. Pharm. Sci., 96(1): 1-26 (2007).
Wiesmann et al., "Structure of C3b in complex with CRIg gives insights into regulation of complement activation," Nature, 444(7116): 217-220 (2006).
Xie et al., "Secondary Structure and Protein Deamidation," J. Pharm. Sci., 88(1): 8-13 (1999).
Xu et al., "Diversity in the CDR3 Region of VH Is Sufficient for Most Antibody Specificities," Immunity, 13(1): 37-45 (2000).
International Search Report issued for PCT/US2016/059179, dated Jan. 31, 2017 (18 pages).

\* cited by examiner

WT Light Chain

```
DIQVTQSPSS LSASVGDRVT ITCIISTDID DDMNWYQQKP GKVPKLLISG GNTLRPGVPS    60
RFSGSGSGTD FTLTISSLQP EDVATYYCLQ SDSLPYTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC   (SEQ ID NO:1)               214
```

WT Heavy Chain

```
EVQLVQSGPE LKKPGASVKV SCKASGYTFT NYGMNWVRQA PGQGLEWMGW INTYTGETTY    60
ADDFKGRFVF SLDTSVSTAY LQISSLKAED TAVYYCEREG GVNNWGQGTL VTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KKVEPKSCDK THT   (SEQ ID NO:2)     223
```

FIG. 1A

VL Domain

| | |
|---|---|
| WT | DIQVTQSPSSLSASVGDRVTITCTITSTDIDDDMNWYQQKPGKVPKLLISGGNTLRPGVPSRFSGSGSGTDFTLTISSLQP |
| TM | DIQVTQSPSSLSASVGDRVTITCTITSTDIESDMNWYQQKPGKVPKLLISGGNTLRPGVPSRFSGSGSGTDFTLTISSLQP |
| TM.D92E | DIQVTQSPSSLSASVGDRVTITCTITSTDIESDMNWYQQKPGKVPKLLISGGNTLRPGVPSRFSGSGSGTDFTLTISSLQP |
| SIESD | DIQVTQSPSSLSASVGDRVTITCTITCISTSISIESDMNWYQQKPGKVPKLLISGGNTLRPGVPSRFSGSGSGTDFTLTISSLQP |
| SIESD.N103S | DIQVTQSPSSLSASVGDRVTITCTITCISTSISIESDMNWYQQKPGKVPKLLISGGNTLRPGVPSRFSGSGSGTDFTLTISSLQP |

| | | |
|---|---|---|
| WT | EDVATYYCLQSDSLPYTFGQGTKVEIK | (SEQ ID NO:3) |
| TM | EDVATYYCLQSDSLPYTFGQGTKVEIK | (SEQ ID NO:16) |
| TM.D92E | EDVATYYCLQSESLPYTFGQGTKVEIK | (SEQ ID NO:18) |
| SIESD | EDVATYYCLQSDSLPYTFGQGTKVEIK | (SEQ ID NO:19) |
| SIESD.N103S | EDVATYYCLQSDSLPYTFGQGTKVEIK | (SEQ ID NO:19) |

VH Domain

| | |
|---|---|
| WT | EVQLVQSGPELKKPGASVKVSCKASGYTFTNYGMNWVRQAPGQGLEWMGWINTYTGETTYADDFKGRFVFSLDTSVSTAY |
| TM | EVQLVQSGPELKKPGASVKVSCKASGYTFTNYGMNWVRQAPGQGLEWMGWINTYTGETTYAEDFKGRFVFSLDTSVSTAY |
| TM.D92E | EVQLVQSGPELKKPGASVKVSCKASGYTFTNYGMNWVRQAPGQGLEWMGWINTYTGETTYAEDFKGRFVFSLDTSVSTAY |
| SIESD | EVQLVQSGPELKKPGASVKVSCKASGYTFTNYGMNWVRQAPGQGLEWMGWINTYTGETTYAEDFKGRFVFSLDTSVSTAY |
| SIESD.N103S | EVQLVQSGPELKKPGASVKVSCKASGYTFTNYGMNWVRQAPGQGLEWMGWINTYTGETTYAEDFKGRFVFSLDTSVSTAY |

| | | |
|---|---|---|
| WT | LQISSLKAEDTAVYYCEREGGVNNWGQGTLVTVSS | (SEQ ID NO:4) |
| TM | LQISSLKAEDTAVYYCEREGGVNNWGQGTLVTVSS | (SEQ ID NO:17) |
| TM.D92E | LQISSLKAEDTAVYYCEREGGVNNWGQGTLVTVSS | (SEQ ID NO:17) |
| SIESD | LQISSLKAEDTAVYYCEREGGVNNWGQGTLVTVSS | (SEQ ID NO:17) |
| SIESD.N103S | LQISSLKAEDTAVYYCEREGGVSNWGQGTLVTVSS | (SEQ ID NO:20) |

FIG. 1B

SIESD (AFD.v8) Light Chain

```
DIQVTQSPSS LSASVGDRVT ITCITSTSIE SDMNWYQQKP GKVPKLLISG  60
RFSGSGSGTD FTLTISSLQP EDVATYYCLQ SDSLPYIFGQ GTKVEIKRTV  120
SDEQLKSGTA SVVCLLNNFY PREAKVQWKV DNALQSGNSQ ESVTEQDSKD  180
LSKADYEKHK VYACEVTHQG LSSPVTKSFN RGEC  (SEQ ID NO:26)  214
```
Underlined: ITSTSIE, SDMNWYQQKP, SDSLPYIFGQ, GNTLRPGVPS, AAPSVFIFPP, STYSLSSTLT

SIESD (AFD.v8) Heavy Chain

```
EVQLVQSGPE LKKPGASVKV SCKASGYTFT NYGMNWVRQA PGQGLEWMGW  60
AEDFKGRFVF SLDTSVSTAY LQISSLKAED TAVYYCEREG GVNNWGQGTL  120
PSVFPLAPSS KSTSGGTAAL GCLVKDYFPE PVTVSWNSGA LTSGVHTFPA  180
SSVVTVPSSS LGTQTYICNV NHKPSNTKVD KKVEPKSCDK THT         223
```
(SEQ ID NO:27)

Cys-Modified SIESD (AFD.v8) Heavy Chain

```
EVQLVQSGPE LKKPGASVKV SCKASGYTFT NYGMNWVRQA PGQGLEWMGW  60
AEDFKGRFVF SLDTSVSTAY LQISSLKAED TAVYYCEREG GVNNWGQGTL  120
PSVFPLAPSS KSTSGGTAAL GCLVKDYFPE PVTVSWNSGA LTSGVHTFPA  180
SSVVTVPSSS LGTQTYICNV NHKPSNTKVD KKVEPKSCDK THTC        223
```
(SEQ ID NO:30)

Cys-Pro-Pro-Cys-Modified SIESD (AFD.v8) Heavy Chain

```
EVQLVQSGPE LKKPGASVKV SCKASGYTFT NYGMNWVRQA PGQGLEWMGW  60
AEDFKGRFVF SLDTSVSTAY LQISSLKAED TAVYYCEREG GVNNWGQGTL  120
PSVFPLAPSS KSTSGGTAAL GCLVKDYFPE PVTVSWNSGA LTSGVHTFPA  180
SSVVTVPSSS LGTQTYICNV NHKPSNTKVD KKVEPKSCDK THT*CPPC*   223
```
(SEQ ID NO:31)

FIG. 1C

SIESD.N103S (AFD.v14) Light Chain

```
DIQVTQSPSS LSASVGDRVT ITCITSTSIE SDMNWYQQKP GKVPKLLISG GNTLRPGVPS   60
RFSGSGSGTD FTLTISSLQP EDVATYYCLQ SDSLPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC  (SEQ ID NO:28)              214
```

SIESD.N103S (AFD.v14) Heavy Chain

```
EVQLVQSGPE LKKPGASVKV SCKASGYTFT NYGMNWVRQA PGQGLEWMGW INIYTGETTY   60
AEDFKGRFVF SLDTSVSTAY LQISSLKAED TAVYYCEREG GVSNWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THT  (SEQ ID NO:29)    223
```

Cys-Modified SIESD.N103S (AFD.v14) Heavy Chain

```
EVQLVQSGPE LKKPGASVKV SCKASGYTFT NYGMNWVRQA PGQGLEWMGW INIYTGETTY   60
AEDFKGRFVF SLDTSVSTAY LQISSLKAED TAVYYCEREG GVSNWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTC  (SEQ ID NO:32)   223
```

Cys-Pro-Pro-Cys-Modified SIESD.N103S (AFD.v14) Heavy Chain

```
EVQLVQSGPE LKKPGASVKV SCKASGYTFT NYGMNWVRQA PGQGLEWMGW INIYTGETTY   60
AEDFKGRFVF SLDTSVSTAY LQISSLKAED TAVYYCEREG GVSNWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THT*CPPC*  (SEQ ID NO:33)  223
```

FIG. 1D

Solutions after dialysis versus 20mM His-HCl pH 6.0 (top) and subsequent dialysis versus PBS (bottom)

Concentration Dependence of Viscosity for AFD Variants in pH 5.5 Buffer

△ aFD WT
● SIESD (AFD.v8)
■ SIESD.N103S (AFD.v14)

FIG. 12

SEQUENCE LISTING

```
<160> NUMBER OF SEQ ID NOS: 118

<210> SEQ ID NO 1
<211> LENGTH: 214
<212> TYPE: PRT
<213> ORGANISM: Homo sapiens

<400> SEQUENCE: 1
```

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 223
<212> TYPE: PRT
<213> ORGANISM: Homo sapiens

<400> SEQUENCE: 2

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala

```
                145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Gln Thr Tyr Ile Cys Asn Val Asn His Lys Pro Ser Asn Thr Lys
                195                 200                 205
Val Asp Lys Lys Val Glu Pro Lys Ser Cys Asp Lys Thr His Thr
    210                 215                 220

<210> SEQ ID NO 3
<211> LENGTH: 107
<212> TYPE: PRT
<213> ORGANISM: Homo sapiens

<400> SEQUENCE: 3

Asp Ile Gln Val Thr Gln Ser Pro Ser Ser Leu Ser Ala Ser Val Gly
1               5                   10                  15
Asp Arg Val Thr Ile Thr Cys Ile Thr Ser Thr Asp Ile Asp Asp Asp
                20                  25                  30
Met Asn Trp Tyr Gln Gln Lys Pro Gly Lys Val Pro Lys Leu Leu Ile
                35                  40                  45
Ser Gly Gly Asn Thr Leu Arg Pro Gly Val Pro Ser Arg Phe Ser Gly
            50                  55                  60
Ser Gly Ser Gly Thr Asp Phe Thr Leu Thr Ile Ser Ser Leu Gln Pro
65              70                  75                  80
Glu Asp Val Ala Thr Tyr Tyr Cys Leu Gln Ser Asp Ser Leu Pro Tyr
                85                  90                  95
Thr Phe Gly Gln Gly Thr Lys Val Glu Ile Lys
                100                 105

<210> SEQ ID NO 4
<211> LENGTH: 115
<212> TYPE: PRT
<213> ORGANISM: Homo sapiens

<400> SEQUENCE: 4

Glu Val Gln Leu Val Gln Ser Gly Pro Glu Leu Lys Lys Pro Gly Ala
1               5                   10                  15
Ser Val Lys Val Ser Cys Lys Ala Ser Gly Tyr Thr Phe Thr Asn Tyr
                20                  25                  30
Gly Met Asn Trp Val Arg Gln Ala Pro Gly Gln Gly Leu Glu Trp Met
                35                  40                  45
Gly Trp Ile Asn Thr Tyr Thr Gly Glu Thr Thr Tyr Ala Asp Asp Phe
            50                  55                  60
Lys Gly Arg Phe Val Phe Ser Leu Asp Thr Ser Val Ser Thr Ala Tyr
65              70                  75                  80
Leu Gln Ile Ser Ser Leu Lys Ala Glu Asp Thr Ala Val Tyr Tyr Cys
                85                  90                  95
Glu Arg Glu Gly Gly Val Asn Asn Trp Gly Gln Gly Thr Leu Val Thr
                100                 105                 110
Val Ser Ser
        115

<210> SEQ ID NO 5
<211> LENGTH: 11
<212> TYPE: PRT
```

<213> ORGANISM: Homo sapiens

<400> SEQUENCE: 5

Ile Thr Ser Thr Asp Ile Asp Asp Met Asn
1               5                   10

<210> SEQ ID NO 6
<211> LENGTH: 7
<212> TYPE: PRT
<213> ORGANISM: Homo sapiens

<400> SEQUENCE: 6

Gly Gly Asn Thr Leu Arg Pro
1               5

<210> SEQ ID NO 7
<211> LENGTH: 9
<212> TYPE: PRT
<213> ORGANISM: Homo sapiens

<400> SEQUENCE: 7

Leu Gln Ser Asp Ser Leu Pro Tyr Thr
1               5

<210> SEQ ID NO 8
<211> LENGTH: 10
<212> TYPE: PRT
<213> ORGANISM: Homo sapiens

<400> SEQUENCE: 8

Gly Tyr Thr Phe Thr Asn Tyr Gly Met Asn
1               5                   10

<210> SEQ ID NO 9
<211> LENGTH: 17
<212> TYPE: PRT
<213> ORGANISM: Homo sapiens

<400> SEQUENCE: 9

Trp Ile Asn Thr Tyr Thr Gly Glu Thr Thr Tyr Ala Asp Asp Phe Lys
1               5                   10                  15

Gly

<210> SEQ ID NO 10
<211> LENGTH: 6
<212> TYPE: PRT
<213> ORGANISM: Homo sapiens

<400> SEQUENCE: 10

Glu Gly Gly Val Asn Asn
1               5

<210> SEQ ID NO 11
<211> LENGTH: 11
<212> TYPE: PRT
<213> ORGANISM: Homo sapiens

<400> SEQUENCE: 11

Ile Thr Ser Thr Asp Ile Glu Ser Asp Met Asn
1               5                   10

<210> SEQ ID NO 12
<211> LENGTH: 17
<212> TYPE: PRT

<213> ORGANISM: Homo sapiens

<400> SEQUENCE: 12

Trp Ile Asn Thr Tyr Thr Gly Glu Thr Thr Tyr Ala Glu Asp Phe Lys
1               5                   10                  15

Gly

<210> SEQ ID NO 13
<211> LENGTH: 9
<212> TYPE: PRT
<213> ORGANISM: Homo sapiens

<400> SEQUENCE: 13

Leu Gln Ser Glu Ser Leu Pro Tyr Thr
1               5

<210> SEQ ID NO 14
<211> LENGTH: 11
<212> TYPE: PRT
<213> ORGANISM: Homo sapiens

<400> SEQUENCE: 14

Ile Thr Ser Thr Ser Ile Glu Ser Asp Met Asn
1               5                   10

<210> SEQ ID NO 15
<211> LENGTH: 6
<212> TYPE: PRT
<213> ORGANISM: Homo sapiens

<400> SEQUENCE: 15

Glu Gly Gly Val Ser Asn
1               5

<210> SEQ ID NO 16
<211> LENGTH: 107
<212> TYPE: PRT
<213> ORGANISM: Homo sapiens

<400> SEQUENCE: 16

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Glu Ser Asp
                20                  25                  30

Met Asn Trp Tyr Gln Gln Lys Pro Gly Lys Val Pro Lys Leu Leu Ile
            35                  40                  45

Ser Gly Gly Asn Thr Leu Arg Pro Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys
            100                 105

<210> SEQ ID NO 17
<211> LENGTH: 115
<212> TYPE: PRT
<213> ORGANISM: Homo sapiens

<400> SEQUENCE: 17

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
                100                 105                 110

Val Ser Ser
        115
```

```
<210> SEQ ID NO 18
<211> LENGTH: 107
<212> TYPE: PRT
<213> ORGANISM: Homo sapiens

<400> SEQUENCE: 18

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Glu Ser Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Glu Ser Leu Pro Tyr
                85                  90                  95

Thr Phe Gly Gln Gly Thr Lys Val Glu Ile Lys
                100                 105
```

```
<210> SEQ ID NO 19
<211> LENGTH: 107
<212> TYPE: PRT
<213> ORGANISM: Homo sapiens

<400> SEQUENCE: 19

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Ser Ile Glu Ser Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95
```

```
Thr Phe Gly Gln Gly Thr Lys Val Glu Ile Lys
            100                 105

<210> SEQ ID NO 20
<211> LENGTH: 115
<212> TYPE: PRT
<213> ORGANISM: Homo sapiens

<400> SEQUENCE: 20

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser
        115

<210> SEQ ID NO 21
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 21

Cys Pro Pro Cys
1

<210> SEQ ID NO 22
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: Asp or Ser
<220> FEATURE:
<221> NAME/KEY: MOD_RES
<222> LOCATION: (7)..(7)
<223> OTHER INFORMATION: Asp or Glu
<220> FEATURE:
<221> NAME/KEY: MOD_RES
<222> LOCATION: (8)..(8)
<223> OTHER INFORMATION: Asp or Ser

<400> SEQUENCE: 22

Ile Thr Ser Thr Xaa Ile Xaa Xaa Asp Met Asn
1               5                   10

<210> SEQ ID NO 23
<211> LENGTH: 17
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MOD_RES
<222> LOCATION: (13)..(13)
<223> OTHER INFORMATION: Asp or Glu

<400> SEQUENCE: 23

Trp Ile Asn Thr Tyr Thr Gly Glu Thr Thr Tyr Ala Xaa Asp Phe Lys
1               5                   10                  15

Gly

<210> SEQ ID NO 24
<211> LENGTH: 9
<212> TYPE: PRT
<213> ORGANISM: Artificial Sequence
<220> FEATURE:
<223> OTHER INFORMATION: Sythetic peptide
<220> FEATURE:
<221> NAME/KEY: MOD_RES
<222> LOCATION: (4)..(4)
<223> OTHER INFORMATION: Asp or Glu

<400> SEQUENCE: 24

Leu Gln Ser Xaa Ser Leu Pro Tyr Thr
1               5

<210> SEQ ID NO 25
<211> LENGTH: 6
<212> TYPE: PRT
<213> ORGANISM: Artificial Sequence
<220> FEATURE:
<223> OTHER INFORMATION: Sythetic Peptide
<220> FEATURE:
<221> NAME/KEY: MOD_RES
<222> LOCATION: (5)..(5)
<223> OTHER INFORMATION: Asn or Ser

<400> SEQUENCE: 25

Glu Gly Gly Val Xaa Asn
1               5

<210> SEQ ID NO 26
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 26

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Ser Ile Glu Ser Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
                    115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
                195                 200                 205
Phe Asn Arg Gly Glu Cys
    210

<210> SEQ ID NO 27
<211> LENGTH: 223
<212> TYPE: PRT
<213> ORGANISM: Artificial Sequence
<220> FEATURE:
<223> OTHER INFORMATION: Synthetic polypeptide

<400> SEQUENCE: 27

Glu Val Gln Leu Val Gln Ser Gly Pro Glu Leu Lys Lys Pro Gly Ala
1               5                   10                  15
Ser Val Lys Val Ser Cys Lys Ala Ser Gly Tyr Thr Phe Thr Asn Tyr
                20                  25                  30
Gly Met Asn Trp Val Arg Gln Ala Pro Gly Gln Gly Leu Glu Trp Met
            35                  40                  45
Gly Trp Ile Asn Thr Tyr Thr Gly Glu Thr Thr Tyr Ala Glu Asp Phe
        50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Glu Arg Glu Gly Gly Val Asn Asn Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr
    210                 215                 220

<210> SEQ ID NO 28
<211> LENGTH: 214
<212> TYPE: PRT
<213> ORGANISM: Artificial Sequence
<220> FEATURE:
<223> OTHER INFORMATION: Sythetic polypeptide
```

<400> SEQUENCE: 28

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Ser Ile Glu Ser Asp
            20                  25                  30

Met Asn Trp Tyr Gln Gln Lys Pro Gly Lys Val Pro Lys Leu Leu Ile
        35                  40                  45

Ser Gly Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Ser Asp Ser Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 29
<211> LENGTH: 223
<212> TYPE: PRT
<213> ORGANISM: Artificial Sequence
<220> FEATURE:
<223> OTHER INFORMATION: Sythetic polypeptide

<400> SEQUENCE: 29

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

```
Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr
210                 215                 220
```

<210> SEQ ID NO 30
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 30

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220
```

<210> SEQ ID NO 31
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 31

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys
225

<210> SEQ ID NO 32
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 32

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

<210> SEQ ID NO 33
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 33

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys
225

<210> SEQ ID NO 34
<211> LENGTH: 223
<212> TYPE: PRT
<213> ORGANISM: Artificial Sequence
<220> FEATURE:
<223> OTHER INFORMATION: Synthetic Polypeptide

<400> SEQUENCE: 34

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Leu
    210                 215                 220
```

<210> SEQ ID NO 35
<211> LENGTH: 222
<212> TYPE: PRT
<213> ORGANISM: Artificial Sequence
<220> FEATURE:
<223> OTHER INFORMATION: Synthetic Polypeptide

<400> SEQUENCE: 35

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
```

```
            115                 120                 125
Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His
    210                 215                 220
```

<210> SEQ ID NO 36
<211> LENGTH: 221
<212> TYPE: PRT
<213> ORGANISM: Artificial Sequence
<220> FEATURE:
<223> OTHER INFORMATION: Synthetic Polypeptide

<400> SEQUENCE: 36

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr
    210                 215                 220
```

<210> SEQ ID NO 37
<211> LENGTH: 220
<212> TYPE: PRT
<213> ORGANISM: Artificial Sequence
<220> FEATURE:
<223> OTHER INFORMATION: Synthetic Polypeptide

<400> SEQUENCE: 37

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys
    210                 215                 220

<210> SEQ ID NO 38
<211> LENGTH: 219
<212> TYPE: PRT
<213> ORGANISM: Artificial Sequence
<220> FEATURE:
<223> OTHER INFORMATION: Synthetic Polypeptide

<400> SEQUENCE: 38

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

```
Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp
    210                 215
```

<210> SEQ ID NO 39
<211> LENGTH: 224
<212> TYPE: PRT
<213> ORGANISM: Artificial Sequence
<220> FEATURE:
<223> OTHER INFORMATION: Synthetic Polypeptide

<400> SEQUENCE: 39

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
    210                 215                 220
```

<210> SEQ ID NO 40
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 40

Glu Val Gln Leu Val Gln Ser Gly Pro Glu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys
225

<210> SEQ ID NO 41
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 41

Glu Val Gln Leu Val Gln Ser Gly Pro Glu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
                100                 105                 110

Val Ser Ser Ala Ser Thr Lys Gly Pro Ser Val Phe Pro Leu Ala Pro
            115                 120                 125

```
Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Ser
225

<210> SEQ ID NO 42
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 42

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Ser
    210                 215                 220

Pro Pro Cys
225

<210> SEQ ID NO 43
```

<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 43

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Ala
    210                 215                 220

Pro Pro Cys
225
```

<210> SEQ ID NO 44
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 44

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
```

```
                      85                  90                  95
Glu Arg Glu Gly Gly Val Asn Asn Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Ser
210                 215                 220

Gly Gly Cys
225

<210> SEQ ID NO 45
<211> LENGTH: 223
<212> TYPE: PRT
<213> ORGANISM: Artificial Sequence
<220> FEATURE:
<223> OTHER INFORMATION: Synthetic Polypeptide

<400> SEQUENCE: 45

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Tyr Gly Pro Pro Cys
```

210            215            220

<210> SEQ ID NO 46
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 46

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys
    210                 215

<210> SEQ ID NO 47
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 47

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                    85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys
    210                 215

<210> SEQ ID NO 48
<211> LENGTH: 220
<212> TYPE: PRT
<213> ORGANISM: Artificial Sequence
<220> FEATURE:
<223> OTHER INFORMATION: Synthetic Polypeptide

<400> SEQUENCE: 48

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro
    210                 215                 220

<210> SEQ ID NO 49
<211> LENGTH: 219
<212> TYPE: PRT
<213> ORGANISM: Artificial Sequence
<220> FEATURE:
<223> OTHER INFORMATION: Synthetic Polypeptide

<400> SEQUENCE: 49

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro
    210                 215
```

<210> SEQ ID NO 50
<211> LENGTH: 218
<212> TYPE: PRT
<213> ORGANISM: Artificial Sequence
<220> FEATURE:
<223> OTHER INFORMATION: Synthetic Polypeptide

<400> SEQUENCE: 50

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95
```

```
Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                    165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
            195                 200                 205

Val Asp Lys Arg Val Glu Ser Lys Tyr Gly
210                 215
```

<210> SEQ ID NO 51
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 51

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Asp Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                    165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
            195                 200                 205

Val Asp Lys Arg Val Glu Ser Lys Tyr
210                 215
```

<210> SEQ ID NO 52

<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 52

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys
    210                 215

<210> SEQ ID NO 53
<211> LENGTH: 221
<212> TYPE: PRT
<213> ORGANISM: Artificial Sequence
<220> FEATURE:
<223> OTHER INFORMATION: Synthetic Polypeptide

<400> SEQUENCE: 53

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr

```
                 100                 105                 110
Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys
    210                 215                 220

<210> SEQ ID NO 54
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr
            100                 105

<210> SEQ ID NO 55
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

-continued

Tyr Ile Cys Asn Val Asn His Lys Pro Ser Asn Thr Lys Val Asp Lys
                85                  90                  95

Lys Val Glu Pro Lys Ser Cys Asp Lys Thr His Leu
            100                 105

<210> SEQ ID NO 56
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys
            100                 105

<210> SEQ ID NO 57
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

<210> SEQ ID NO 58
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 58

Ala Ser Thr Lys Gly Pro Ser Val Phe Pro Leu Ala Pro Ser Ser Lys

```
                1               5                   10                  15
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Ser
            100                 105                 110

<210> SEQ ID NO 59
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 59

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Ser Pro Pro Cys
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Val Glu Pro Lys Ser Cys Asp Lys Thr His Thr Ala Pro Pro Cys
            100                 105                 110

<210> SEQ ID NO 61
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Ser Gly Gly Cys
            100                 105                 110

<210> SEQ ID NO 62
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Tyr Gly Pro Pro Cys
            100                 105

<210> SEQ ID NO 63
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr 20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105

<210> SEQ ID NO 64
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr
            100                 105

<210> SEQ ID NO 65
<211> LENGTH: 105
<212> TYPE: PRT
<213> ORGANISM: Artificial Sequence
<220> FEATURE:
<223> OTHER INFORMATION: Synthetic Polypeptide

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys
            100                 105

```
<210> SEQ ID NO 66
<211> LENGTH: 104
<212> TYPE: PRT
<213> ORGANISM: Artificial Sequence
<220> FEATURE:
<223> OTHER INFORMATION: Synthetic Polypeptide

<400> SEQUENCE: 66

Ala Ser Thr Lys Gly Pro Ser Val Phe Pro Leu Ala Pro Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp
            100

<210> SEQ ID NO 67
<211> LENGTH: 101
<212> TYPE: PRT
<213> ORGANISM: Artificial Sequence
<220> FEATURE:
<223> OTHER INFORMATION: Synthetic Polypeptide

<400> SEQUENCE: 67

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys
            100

<210> SEQ ID NO 68
<211> LENGTH: 102
<212> TYPE: PRT
<213> ORGANISM: Artificial Sequence
<220> FEATURE:
<223> OTHER INFORMATION: Synthetic Polypeptide

<400> SEQUENCE: 68

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys
            100

<210> SEQ ID NO 69
<211> LENGTH: 105
<212> TYPE: PRT
<213> ORGANISM: Artificial Sequence
<220> FEATURE:
<223> OTHER INFORMATION: Synthetic Polypeptide

<400> SEQUENCE: 69

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro
            100                 105

<210> SEQ ID NO 70
<211> LENGTH: 104
<212> TYPE: PRT
<213> ORGANISM: Artificial Sequence
<220> FEATURE:
<223> OTHER INFORMATION: Synthetic Polypeptide

<400> SEQUENCE: 70

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro
            100

<210> SEQ ID NO 71
<211> LENGTH: 103
```

<212> TYPE: PRT
<213> ORGANISM: Artificial Sequence
<220> FEATURE:
<223> OTHER INFORMATION: Synthetic Polypeptide

<400> SEQUENCE: 71

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly
            100

<210> SEQ ID NO 72
<211> LENGTH: 102
<212> TYPE: PRT
<213> ORGANISM: Artificial Sequence
<220> FEATURE:
<223> OTHER INFORMATION: Synthetic Polypeptide

<400> SEQUENCE: 72

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr
            100

<210> SEQ ID NO 73
<211> LENGTH: 101
<212> TYPE: PRT
<213> ORGANISM: Artificial Sequence
<220> FEATURE:
<223> OTHER INFORMATION: Synthetic Polypeptide

<400> SEQUENCE: 73

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser

```
                    50                  55                  60
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys
            100

<210> SEQ ID NO 74
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 74

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys
            100                 105

<210> SEQ ID NO 75
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 75

Glu Val Gln Leu Val Gln Ser Gly Pro Glu Leu Lys Lys Pro Gly Ala
 1               5                  10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
             35                  40                  45

Gly Trp Ile Asn Thr Tyr Thr Gly Glu Thr Thr Tyr Ala Glu Asp Phe
         50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140
```

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Ser
        210                 215                 220

Pro Pro Cys
225

<210> SEQ ID NO 76
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 76

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
        210                 215                 220

Pro Pro Ser
225

<210> SEQ ID NO 77
<211> LENGTH: 227
<212> TYPE: PRT
<213> ORGANISM: Artificial Sequence
<220> FEATURE:
```

<223> OTHER INFORMATION: Synthetic Polypeptide

<400> SEQUENCE: 77

```
Glu Val Gln Leu Val Gln Ser Gly Pro Glu Leu Lys Lys Pro Gly Ala
1               5                   10                  15
Ser Val Lys Val Ser Cys Lys Ala Ser Gly Tyr Thr Phe Thr Asn Tyr
            20                  25                  30
Gly Met Asn Trp Val Arg Gln Ala Pro Gly Gln Gly Leu Glu Trp Met
        35                  40                  45
Gly Trp Ile Asn Thr Tyr Thr Gly Glu Thr Thr Tyr Ala Glu Asp Phe
    50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Glu Arg Glu Gly Gly Val Asn Asn Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Ala
    210                 215                 220
Pro Pro Cys
225
```

<210> SEQ ID NO 78
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 78

```
Glu Val Gln Leu Val Gln Ser Gly Pro Glu Leu Lys Lys Pro Gly Ala
1               5                   10                  15
Ser Val Lys Val Ser Cys Lys Ala Ser Gly Tyr Thr Phe Thr Asn Tyr
            20                  25                  30
Gly Met Asn Trp Val Arg Gln Ala Pro Gly Gln Gly Leu Glu Trp Met
        35                  40                  45
Gly Trp Ile Asn Thr Tyr Thr Gly Glu Thr Thr Tyr Ala Glu Asp Phe
    50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Glu Arg Glu Gly Gly Val Asn Asn Trp Gly Gln Gly Thr Leu Val Thr
            100                 105                 110
```

```
Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Ser
210                 215                 220

Gly Gly Cys
225

<210> SEQ ID NO 79
<211> LENGTH: 223
<212> TYPE: PRT
<213> ORGANISM: Artificial Sequence
<220> FEATURE:
<223> OTHER INFORMATION: Synthetic Polypeptide

<400> SEQUENCE: 79

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Tyr Gly Pro Pro Cys
210                 215                 220

<210> SEQ ID NO 80
```

<211> LENGTH: 223
<212> TYPE: PRT
<213> ORGANISM: Artificial Sequence
<220> FEATURE:
<223> OTHER INFORMATION: Synthetic Polypeptide

<400> SEQUENCE: 80

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Leu
    210                 215                 220

<210> SEQ ID NO 81
<211> LENGTH: 222
<212> TYPE: PRT
<213> ORGANISM: Artificial Sequence
<220> FEATURE:
<223> OTHER INFORMATION: Synthetic Polypeptide

<400> SEQUENCE: 81

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr

```
                100             105             110
Val Ser Ser Ala Ser Thr Lys Gly Pro Ser Val Phe Pro Leu Ala Pro
            115                 120             125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His
            210                 215                 220
```

<210> SEQ ID NO 82
<211> LENGTH: 221
<212> TYPE: PRT
<213> ORGANISM: Artificial Sequence
<220> FEATURE:
<223> OTHER INFORMATION: Synthetic Polypeptide

<400> SEQUENCE: 82

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr
            210                 215                 220
```

<210> SEQ ID NO 83
<211> LENGTH: 220
<212> TYPE: PRT

<213> ORGANISM: Artificial Sequence
<220> FEATURE:
<223> OTHER INFORMATION: Synthetic Polypeptide

<400> SEQUENCE: 83

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys
    210                 215                 220
```

<210> SEQ ID NO 84
<211> LENGTH: 219
<212> TYPE: PRT
<213> ORGANISM: Artificial Sequence
<220> FEATURE:
<223> OTHER INFORMATION: Synthetic Polypeptide

<400> SEQUENCE: 84

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110
```

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp
    210                 215

<210> SEQ ID NO 85
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 85

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys
    210                 215

<210> SEQ ID NO 86
<211> LENGTH: 217
<212> TYPE: PRT
<213> ORGANISM: Artificial Sequence
<220> FEATURE:

<223> OTHER INFORMATION: Synthetic Polypeptide

<400> SEQUENCE: 86

```
Glu Val Gln Leu Val Gln Ser Gly Pro Glu Leu Lys Lys Pro Gly Ala
1               5                   10                  15
Ser Val Lys Val Ser Cys Lys Ala Ser Gly Tyr Thr Phe Thr Asn Tyr
            20                  25                  30
Gly Met Asn Trp Val Arg Gln Ala Pro Gly Gln Gly Leu Glu Trp Met
        35                  40                  45
Gly Trp Ile Asn Thr Tyr Thr Gly Glu Thr Thr Tyr Ala Glu Asp Phe
    50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Glu Arg Glu Gly Gly Val Asn Asn Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Cys Ser Arg Ser Thr Ser Glu Ser Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Asn Phe Gly
            180                 185                 190
Thr Gln Thr Tyr Thr Cys Asn Val Asp His Lys Pro Ser Asn Thr Lys
        195                 200                 205
Val Asp Lys Thr Val Glu Arg Lys Cys
    210                 215
```

<210> SEQ ID NO 87
<211> LENGTH: 220
<212> TYPE: PRT
<213> ORGANISM: Artificial Sequence
<220> FEATURE:
<223> OTHER INFORMATION: Synthetic Polypeptide

<400> SEQUENCE: 87

```
Glu Val Gln Leu Val Gln Ser Gly Pro Glu Leu Lys Lys Pro Gly Ala
1               5                   10                  15
Ser Val Lys Val Ser Cys Lys Ala Ser Gly Tyr Thr Phe Thr Asn Tyr
            20                  25                  30
Gly Met Asn Trp Val Arg Gln Ala Pro Gly Gln Gly Leu Glu Trp Met
        35                  40                  45
Gly Trp Ile Asn Thr Tyr Thr Gly Glu Thr Thr Tyr Ala Glu Asp Phe
    50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Glu Arg Glu Gly Gly Val Asn Asn Trp Gly Gln Gly Thr Leu Val Thr
            100                 105                 110
Val Ser Ser Ala Ser Thr Lys Gly Pro Ser Val Phe Pro Leu Ala Pro
        115                 120                 125
```

Cys Ser Arg Ser Thr Ser Glu Ser Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
                195                 200                 205

Val Asp Lys Arg Val Glu Ser Lys Tyr Gly Pro Pro
            210                 215                 220

<210> SEQ ID NO 88
<211> LENGTH: 219
<212> TYPE: PRT
<213> ORGANISM: Artificial Sequence
<220> FEATURE:
<223> OTHER INFORMATION: Synthetic Polypeptide

<400> SEQUENCE: 88

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
                195                 200                 205

Val Asp Lys Arg Val Glu Ser Lys Tyr Gly Pro
            210                 215

<210> SEQ ID NO 89
<211> LENGTH: 218
<212> TYPE: PRT
<213> ORGANISM: Artificial Sequence
<220> FEATURE:
<223> OTHER INFORMATION: Synthetic Polypeptide

<400> SEQUENCE: 89

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly
    210                 215
```

<210> SEQ ID NO 90
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 90

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
```

-continued

```
            130                 135                 140
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
                195                 200                 205

Val Asp Lys Arg Val Glu Ser Lys Tyr
    210                 215
```

<210> SEQ ID NO 91
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 91

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
                195                 200                 205

Val Asp Lys Arg Val Glu Ser Lys
    210                 215
```

<210> SEQ ID NO 92
<211> LENGTH: 221
<212> TYPE: PRT
<213> ORGANISM: Artificial Sequence
<220> FEATURE:
<223> OTHER INFORMATION: Synthetic Polypeptide

<400> SEQUENCE: 92

Glu Val Gln Leu Val Gln Ser Gly Pro Glu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
            195                 200                 205

Val Asp Lys Arg Val Glu Ser Lys Tyr Gly Pro Pro Cys
210                 215                 220

<210> SEQ ID NO 93
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 93

Glu Val Gln Leu Val Gln Ser Gly Pro Glu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Ser
    210                 215                 220

Pro Pro Cys
225

<210> SEQ ID NO 94
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 94

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Ser
225

<210> SEQ ID NO 95
<211> LENGTH: 227
<212> TYPE: PRT
<213> ORGANISM: Artificial Sequence
<220> FEATURE:
```

<223> OTHER INFORMATION: Synthetic Polypeptide

<400> SEQUENCE: 95

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Ala
    210                 215                 220

Pro Pro Cys
225

<210> SEQ ID NO 96
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 96

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Ser
210                 215                 220

Gly Gly Cys
225

<210> SEQ ID NO 97
<211> LENGTH: 223
<212> TYPE: PRT
<213> ORGANISM: Artificial Sequence
<220> FEATURE:
<223> OTHER INFORMATION: Synthetic Polypeptide

<400> SEQUENCE: 97

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Tyr Gly Pro Pro Cys
210                 215                 220

<210> SEQ ID NO 98

<211> LENGTH: 223
<212> TYPE: PRT
<213> ORGANISM: Artificial Sequence
<220> FEATURE:
<223> OTHER INFORMATION: Synthetic Polypeptide

<400> SEQUENCE: 98

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Leu
    210                 215                 220
```

<210> SEQ ID NO 99
<211> LENGTH: 222
<212> TYPE: PRT
<213> ORGANISM: Artificial Sequence
<220> FEATURE:
<223> OTHER INFORMATION: Synthetic Polypeptide

<400> SEQUENCE: 99

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
```

```
            100                 105                 110
Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His
    210                 215                 220
```

<210> SEQ ID NO 100
<211> LENGTH: 221
<212> TYPE: PRT
<213> ORGANISM: Artificial Sequence
<220> FEATURE:
<223> OTHER INFORMATION: Synthetic Polypeptide

<400> SEQUENCE: 100

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr
    210                 215                 220
```

<210> SEQ ID NO 101
<211> LENGTH: 220
<212> TYPE: PRT

<213> ORGANISM: Artificial Sequence
<220> FEATURE:
<223> OTHER INFORMATION: Synthetic Polypeptide

<400> SEQUENCE: 101

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys
    210                 215                 220

<210> SEQ ID NO 102
<211> LENGTH: 219
<212> TYPE: PRT
<213> ORGANISM: Artificial Sequence
<220> FEATURE:
<223> OTHER INFORMATION: Synthetic Polypeptide

<400> SEQUENCE: 102

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp
    210                 215

<210> SEQ ID NO 103
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 103

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys
    210                 215

<210> SEQ ID NO 104
<211> LENGTH: 217
<212> TYPE: PRT
<213> ORGANISM: Artificial Sequence
<220> FEATURE:

<223> OTHER INFORMATION: Synthetic Polypeptide

<400> SEQUENCE: 104

```
Glu Val Gln Leu Val Gln Ser Gly Pro Glu Leu Lys Lys Pro Gly Ala
1               5                   10                  15
Ser Val Lys Val Ser Cys Lys Ala Ser Gly Tyr Thr Phe Thr Asn Tyr
            20                  25                  30
Gly Met Asn Trp Val Arg Gln Ala Pro Gly Gln Gly Leu Glu Trp Met
        35                  40                  45
Gly Trp Ile Asn Thr Tyr Thr Gly Glu Thr Thr Tyr Ala Glu Asp Phe
    50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Glu Arg Glu Gly Gly Val Ser Asn Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Cys Ser Arg Ser Thr Ser Glu Ser Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Asn Phe Gly
            180                 185                 190
Thr Gln Thr Tyr Thr Cys Asn Val Asp His Lys Pro Ser Asn Thr Lys
        195                 200                 205
Val Asp Lys Thr Val Glu Arg Lys Cys
    210                 215
```

<210> SEQ ID NO 105
<211> LENGTH: 220
<212> TYPE: PRT
<213> ORGANISM: Artificial Sequence
<220> FEATURE:
<223> OTHER INFORMATION: Synthetic Polypeptide

<400> SEQUENCE: 105

```
Glu Val Gln Leu Val Gln Ser Gly Pro Glu Leu Lys Lys Pro Gly Ala
1               5                   10                  15
Ser Val Lys Val Ser Cys Lys Ala Ser Gly Tyr Thr Phe Thr Asn Tyr
            20                  25                  30
Gly Met Asn Trp Val Arg Gln Ala Pro Gly Gln Gly Leu Glu Trp Met
        35                  40                  45
Gly Trp Ile Asn Thr Tyr Thr Gly Glu Thr Thr Tyr Ala Glu Asp Phe
    50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Glu Arg Glu Gly Gly Val Ser Asn Trp Gly Gln Gly Thr Leu Val Thr
            100                 105                 110
Val Ser Ser Ala Ser Thr Lys Gly Pro Ser Val Phe Pro Leu Ala Pro
        115                 120                 125
```

Cys Ser Arg Ser Thr Ser Glu Ser Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
                195                 200                 205

Val Asp Lys Arg Val Glu Ser Lys Tyr Gly Pro Pro
        210                 215                 220

<210> SEQ ID NO 106
<211> LENGTH: 219
<212> TYPE: PRT
<213> ORGANISM: Artificial Sequence
<220> FEATURE:
<223> OTHER INFORMATION: Synthetic Polypeptide

<400> SEQUENCE: 106

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
                195                 200                 205

Val Asp Lys Arg Val Glu Ser Lys Tyr Gly Pro
        210                 215

<210> SEQ ID NO 107
<211> LENGTH: 218
<212> TYPE: PRT
<213> ORGANISM: Artificial Sequence
<220> FEATURE:
<223> OTHER INFORMATION: Synthetic Polypeptide -continued

<400> SEQUENCE: 107

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly
    210                 215

<210> SEQ ID NO 108
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 108

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val 130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
                195                 200                 205

Val Asp Lys Arg Val Glu Ser Lys Tyr
    210                 215

<210> SEQ ID NO 109
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 109

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
                195                 200                 205

Val Asp Lys Arg Val Glu Ser Lys
    210                 215

<210> SEQ ID NO 110
<211> LENGTH: 221
<212> TYPE: PRT
<213> ORGANISM: Artificial Sequence
<220> FEATURE:
<223> OTHER INFORMATION: Synthetic Polypeptide

<400> SEQUENCE: 110

```
Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
                195                 200                 205

Val Asp Lys Arg Val Glu Ser Lys Tyr Gly Pro Pro Cys
210                 215                 220

<210> SEQ ID NO 111
<211> LENGTH: 4
<212> TYPE: PRT
<213> ORGANISM: Artificial Sequence
<220> FEATURE:
<223> OTHER INFORMATION: Synthetic peptide

<400> SEQUENCE: 111

Ser Pro Pro Cys
1

<210> SEQ ID NO 112
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 112

Cys Pro Pro Ser
1

<210> SEQ ID NO 113
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 113

Ala Pro Pro Cys
```

<210> SEQ ID NO 114
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 114

Ser Gly Gly Cys
1

<210> SEQ ID NO 115
<211> LENGTH: 223
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (223)..(223)
<223> OTHER INFORMATION: Xaa can be any amino acid other than Thr

<400> SEQUENCE: 115

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Asn Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Xaa
    210                 215                 220

<210> SEQ ID NO 116
<211> LENGTH: 108
<212> TYPE: PRT
<213> ORGANISM: Artificial Sequence
<220> FEATURE:
<223> OTHER INFORMATION: Synthetic Polypeptide
<220> FEATURE:

<221> NAME/KEY: MOD_RES
<222> LOCATION: (108)..(108)
<223> OTHER INFORMATION: Xaa can be any amino acid other than Thr

<400> SEQUENCE: 116

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Xaa
            100                 105

<210> SEQ ID NO 117
<211> LENGTH: 223
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (223)..(223)
<223> OTHER INFORMATION: Xaa can be any amino acid other than Thr

<400> SEQUENCE: 117

Glu Val Gln Leu Val Gln Ser Gly Pro Glu Leu Lys Lys Pro Gly Ala
1               5                   10                  15
Ser Val Lys Val Ser Cys Lys Ala Ser Gly Tyr Thr Phe Thr Asn Tyr
            20                  25                  30
Gly Met Asn Trp Val Arg Gln Ala Pro Gly Gln Gly Leu Glu Trp Met
        35                  40                  45
Gly Trp Ile Asn Thr Tyr Thr Gly Glu Thr Thr Tyr Ala Glu Asp Phe
    50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Glu Arg Glu Gly Gly Val Asn Asn Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Xaa
        210                 215                 220

<210> SEQ ID NO 118
<211> LENGTH: 223
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (223)..(223)
<223> OTHER INFORMATION: Xaa can be any amino acid other than Thr

<400> SEQUENCE: 118

Glu Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Thr Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Glu Arg Glu Gly Gly Val Ser Asn Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Xaa
    210                 215                 220

ANTI-FACTOR D ANTIBODY VARIANT CONJUGATES AND USES THEREOF

CROSS-REFERENCE TO RELATED APPLICATIONS

The instant application claims the benefit of priority to U.S. Provisional Application No. 62/249,020, which was filed on Oct. 30, 2015, and to U.S. Provisional Application No. 62/250,965, which was filed on Nov. 4, 2015, both of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Oct. 27, 2016, is named P33044-US-02.txt and is 172,135 bytes in size.

BACKGROUND OF THE DISCLOSURE

The development of therapeutic antibodies represents a revolutionary era in the long history of human medicine. More than 30 antibodies have been approved for human therapy, and over 250 antibodies are in clinical development worldwide for a wide range of major diseases, including cancer, autoimmunity, inflammation, cardiovascular disease, infectious diseases and ocular disease. Over the past decade, the market for monoclonal antibody products has grown exponentially, propelled by the success of such blockbuster drugs as trastuzumab, bevacizumab, rituximab, infliximab and adalimumab. While these first-generation antibody therapeutics have benefited numerous patients, advances in antibody technology and a deeper understanding of the mechanism of action have paved the way for improved versions of antibodies with even better efficacy and fewer side effects.

Successful development and viable use of antibody therapeutics pose many unique challenges compared to traditional medicines that are small organic and inorganic molecules. The biophysical properties of antibodies, like all proteins, are important determinants of their behavior and have significant impacts for development of therapeutics relating to expression, purification, formulation, storage, delivery, pharmacokinetics, immunogenicity and dosing regimens. Among the many characteristics, protein stability is a main feature defining the quality of a candidate antibody and its desirability as a successful therapeutic.

Protein therapy often requires delivering high dose of the protein to patients in order to achieve the desired efficacy. Meanwhile, certain routes of administration are associated with limitations such as delivery time, volume and physical force that require the high dose protein to be in a high-concentration formulation (e.g., at least 100 mg/ml). However, highly concentrated protein formulations pose particular challenges with respect to stability, solubility, viscosity and other protein properties.

Proteins can be unstable and become degraded via multiple physical and chemical degradation pathways. Physical instability occurs mainly via two pathways—denaturation and aggregation, whereas chemical instability can occur via many pathways, such as deamidation, isomerization, cross-linking, oxidation, and fragmentation. Antibody instability is undesirable for drug development, as it can lead to decreased amount of active drug and lower in vivo efficacy, increased variability among batches of the therapeutics, and perhaps most importantly, immunogenicity in patients against aggregates and degradants. Wang et al (2007) *J. Pharm. Sci.* 96:1-26; Moore et al (1980) *J Clin Endocrinology & Metabolism* 51: 691-697; Rosenberg et al (2006) AAPSJ 8:E501-7; Joubert et al (2011) *J Biol Chem* 286: 25118-25133; Joubert et al (2012) *J Biol Chem* (2012) 286:25266-79).

Antibodies are large multidomain proteins, and factors contributing to their stability and propensity to aggregate are complex, including many extrinsic conditions such as temperature, pH, concentration, ionic strength and physical stress. Equally critical is the protein's own primary sequence. Although by nature the Fc region is largely identical between antibodies of a particular isotype, the Fab region differs greatly. Thus, there are significant variations in stability and aggregation propensity between antibodies, largely due to Fab sequence differences and the particular antigen specificity of the antibody. Lowe et al. (2011) *Adv. Protein Chem. Struct Biol.* 84:41-61.

The complement system plays a central role in the clearance of immune complexes and the immune response to infectious agents, foreign antigens, virus-infected cells and tumor cells. However, complement is also involved in pathological inflammation and in autoimmune diseases. Therefore, inhibition of excessive or uncontrolled activation of the complement cascade could provide clinical benefit to patients with such diseases and conditions.

The complement system encompasses three distinct activation pathways, designated the classical, mannose-binding lectin, and the alternative pathways. V. M. Holers In *Clinical Immunology: Principles and Practice*, ed. R. R. Rich, Mosby Press; 1996, 363-391. The classical pathway is a calcium/magnesium-dependent cascade which is normally activated by the formation of antigen-antibody complexes. The mannose-binding lectin (MBL) pathway is initiated by the binding of MBL to carbohydrate structures on pathogens, resulting in the activation of MBL protease (MASP) that cleaves C2 and C4 to form active C2a, C2b, C4a and C4b. The alternative pathway is a magnesium-dependent cascade which is activated by deposition and activation of C3 on certain susceptible surfaces (e.g., cell wall polysaccharides of yeast and bacteria, and certain biopolymer materials). Activation of the complement pathway generates biologically active fragments of complement proteins, e.g., C3a, C4a and C5a anaphylatoxins and C5b-9 membrane attack complexes (MAC), which mediate inflammatory activities involving leukocyte chemotaxis, activation of macrophages, neutrophils, platelets, mast cells and endothelial cells, vascular permeability, cytolysis, and tissue injury.

Factor D is a highly specific serine protease essential for activation of the alternative complement pathway. It cleaves factor B bound to C3b, generating the C3b/Bb enzyme which is the active component of the alternative pathway C3/C5 convertases. Factor D may be a suitable target for inhibition, since its plasma concentration in humans is very low (1.8 μg/ml), and it has been shown to be the limiting enzyme for activation of the alternative complement pathway. P. H. Lesavre and H. J. Müller-Eberhard. (1978) *J. Exp. Med.* 148: 1498-1510; J. E. Volanakis et al. (1985) *New Eng. J. Med.* 312: 395-401.

The down-regulation of complement activation has been demonstrated to be effective in treating several disease indications in animal models and in ex vivo studies, e.g., systemic lupus erythematosus and glomerulonephritis, rheumatoid arthritis, cardiopulmonary bypass and hemodialysis, hyperacute rejection in organ transplantation, myocardial infarction, reperfusion injury, and adult respiratory distress syndrome. In addition, other inflammatory conditions and autoimmune/immune complex diseases are also closely associated with complement activation, including thermal injury, severe asthma, anaphylactic shock, bowel inflammation, urticaria, angioedema, vasculitis, multiple sclerosis, myasthenia gravis, membranoproliferative glomerulonephritis, and Sjögren's syndrome.

Age-related macular degeneration (AMD) is a progressive chronic disease of the central retina with significant consequences for visual acuity. Lim et al. (2012) *Lancet* 379:1728. Late forms of the disease are the leading cause of vision loss in industrialized countries. For the Caucasian population ≥40 years of age the prevalence of early AMD is estimated at 6.8% and advanced AMD at 1.5%. de Jong (2006) *N. Engl. J. Med.* 355: 1474. The prevalence of late AMD increases dramatically with age rising to 11.8% after 80 years of age. Two types of AMD exist, non-exudative (dry) and exudative (wet) AMD. The more common dry form AMD involves atrophic and hypertrophic changes in the retinal pigment epithelium (RPE) underlying the central retina (macula) as well as deposits (drusen) on the RPE. Advanced dry AMD can result in significant retinal damage, including geographic atrophy (GA), with irreversible vision loss. Moreover, patients with dry AMD can progress to the wet form, in which abnormal blood vessels called choroidal neovascular membranes (CNVMs) develop under the retina, leak fluid and blood, and ultimately cause a blinding disciform scar in and under the retina.

Drugs targeting new blood vessel formation (neovasculazation) have been the mainstay for treating wet AMD. Ranibizumab, which is an anti-VEGFA antibody fragment, has proven to be highly effective in improving vision for patients afflicted with wet AMD. Recent studies have implicated an association between AMD and key proteins in the complement cascade and a number of therapies targeting specific complement components are being developed to treat dry AMD. A humanized anti-Factor D Fab fragment (aFD, lampalizumab; FCFD4514S) that potently inhibits Factor D and the alternative complement pathway, through binding to an exosite on factor D is currently in clinical development for the treatment of GA associated with dry AMD. Katschke et al. (2012) *J Biol. Chem.* 287:12886. A recent phase II clinical trial has shown that monthly intravitreal injection of lampalizumab effectively slowed the progression of GA lesions in patients with advanced dry AMD.

Eyes have many unique biophysical and anatomic features that make the ocular drug delivery more challenging. For example, blood-ocular barriers are defense mechanisms to protect the eye from infection, but at the same time make it hard for drug to penetrate, especially for diseases in the posterior segments of the eye. Consequently, high-dose administration is often desired to achieve and maintain drug's onsite bioavailability (e.g., ocular residence time) in order to improve efficacy. Meanwhile, the limited space in the back of the eye restrains the drug volume to be delivered, which in turn demands drugs to be delivered in a high concentration formulation.

Patients with ocular diseases can also benefit from long acting/slow released delivery of therapeutics. Less frequent dosing would provide improved convenience to the patient, have potential benefits of decreased infection rate and increased clinical efficacy. Controlled release of high dose drugs could also minimize drug side effects. Two promising systems for long-acting delivery are PLGA-based solid implants and an implantable port delivery system (PDS). Both systems have the potential to provide near zero-order release kinetics for an extended period of time. For PLGA implants the protein drug is encapsulated in a hydrophobic polymer matrix and drug release is accomplished via slow hydrolysis of the polymer. The rate of release can be controlled by changing the drug loading, polymer hydrophobicity, or polymer molecular weight. The PDS is a refillable device where release into the vitreous is controlled by a porous metal membrane comprising a titanium frit. Since the reservoir has a low volume, a high protein concentration is required for effective delivery with the PDS.

The conditions that a drug is exposed to vary depending on the delivery system used. For incorporation into solid PLGA implants, lyophilized or spray-dried drug is used. Implants are produced using a hot-melt extrusion process such that the drug is briefly exposed to temperatures approaching 90° C. Although the drug remains in solid state for the duration of release, degradation of PLGA may expose the drug to a low pH environment. In contrast, drug delivered with the PDS is maintained at high concentration in liquid state and exposed to vitreous which is characterized as a reducing environment at physiological ionic strength and pH.

In addition to or in lieu of high concentration and long acting delivery, increased bioavailability (e.g., ocular residence time) of the drug can be achieved, or facilitated, by post-translational modifications, wherein the protein drug is covalently conjugated with natural or synthetic polymers such as polysialylation, HESylation (conjugation with hydroxyethyl starch) and PEGylation. Chen et al (2011) *Expert. Opin. Drug Deliv.* 8:1221-36; Kontermann (2009) *BioDrugs* 23:93-109. PEGylation, the covalent attachment of polymer polyethylene glycol (PEG) to a protein, is a well-established technology especially useful for extending the half-life of antibody fragment therapeutics. Jevsevar et al. (2010) *Biotech. J.* 5:113-128.

Thus, there exists a great need for anti-factor D antibodies, as well as conjugates thereof, having improved stabilities, and that in some embodiments, are suitable for high concentration formulation and/or long acting delivery.

SUMMARY OF THE INVENTION

The present disclosure is based in part on the discovery that targeted amino acid substitutions of identified hot spots in an antibody can effectively improve the antibody's stability and overall potency as a therapeutic. Conjugation of such antibodies to multi-armed polymers, such as multi-armed polyols, can improve the vitreous humour half-life, the aqueous humour half-life, and/or the retinal half-life, as compared to the unconjugated antibodies.

In some aspects, the present disclosure relates to conjugates comprising one or more anti-Factor D antibodies or anti-Factor D antibody variants covalently linked to one or more multi-armed polyols. In certain embodiments, the polyol is an eight-armed polyol (i.e., an octamer). In some embodiments, the polyol is a polyethylene glycol (PEG). In certain embodiments, the PEG may have the structure of any of general formulas (Ia), (Ib), (IIa), (IIIa), or (IVa), as set forth hereinafter.

The anti-factor D antibody variants used in the conjugates of the present disclosure have improved stability. The anti-factor D antibody variants comprise substitution of at least one target aspartic acid (D or Asp) residue within a hypervariable region (HVR) of a reference anti-Factor D antibody, wherein the target Asp residue is identified as prone to isomerization and the substitution is Asp to Glutamic acid (E or Glu), and wherein the anti-Factor D antibody variant exhibits improved stability without significant loss of Factor D binding affinity when compared to the reference anti-Factor D antibody. In some aspects, the target Asp residue subject to substitution is within an Asp-Xaa motif, wherein Xaa is Asp, Gly, His, Ser or Thr. In some aspects, the target Asp residue is the first Asp of an Asp-Asp (DD) motif. In some aspects, the anti-factor D antibody variants comprise one or more substitutions at additional Asp sites within a HVR of a reference anti-Factor D antibody, wherein the substitution is Asp to Serine (S or Ser) in order to reduce the overall charges of the antibody, thereby improving the solubility of the antibody. In some aspects, the anti-factor D antibody variants comprise one or more substitutions at asparagine (N or Asn) sites identified as prone to deamidation, wherein the substitution is Asn to Ser in order to reduce or eliminate the antibody's deamidation.

In some embodiments, the anti-Factor D antibody variant is a Fab fragment, wherein the C-terminus of the heavy chain of the Fab fragment ends in the amino acids "CDKTHT," "CDKTHL," "CDKTH," "CDKT," "CDK," or "CD." In some embodiments, the C-terminus of the heavy chain of the Fab fragment ends in the sequence "CDKTHX," wherein X is any amino acid except T. Truncations and/or mutations at the C terminus may be able to reduce or eliminate AHA-reactivity against the Fab, without compromising thermostability or expression. In some embodiments, the C-terminus of the heavy chain of a Fab fragment ends in the amino acids "CDKTHTC," "CDKTHTCPPC," "CDKTHTCPPS," "CDKTHTSPPC", "CDKTHTAPPC", "CDKTHTSGGC" or "CYGPPC". In some such embodiments, a free cysteine in the C-terminal amino acids may be amenable to conjugation, for example, to a polymer such as PEG. In some embodiments, a Fab fragment comprises a heavy chain constant domain amino acid sequence selected from the group consisting of SEQ ID NOs: 54 (ending in "CDKTHT"), 55-66 (ending in "CDKTHL," "CDKTHC," "CPPC," "CPPS," "SPPC," "APPC," "SGGC," "CYGPPC," "CDKTH," "CDKT," "CDK," or "CD"), and 116 (ending in "CDKTHX"). In some embodiments, a Fab is an IgG2 Fab fragment comprising a heavy chain constant domain amino acid sequence of SEQ ID NOs: 67 (ending in "VERK") or an IgG2 Fab-C fragment comprising a heavy chain constant domain amino acid sequence of SEQ ID NO: 68 (ending in "VERKC"). In some embodiments, a Fab is an IgG4 Fab fragment comprising a heavy chain constant domain amino acid sequence selected from the group consisting of SEQ ID NOs: 69-73 (ending in "KYGPP", "KYGP", "KYG", "KY", or "K") or an IgG4 Fab-C fragment comprising a heavy chain constant domain amino acid sequence of SEQ ID NO: 74 (ending in "KYGPPC"). As an alternative to truncating and/or mutation at the C terminus, to avoid pre-existing anti-hinge antibody (PE-AHA) responses, IgG2 or IgG4 Fab fragments may be used, since these do not show PE-AHA response.

In some aspects, the reference anti-factor D antibody used to generate the antibody variants used in the conjugates of the disclosure comprises the light chain variable domain sequence of SEQ ID NO:3, the heavy chain variable domain sequence of SEQ ID NO:4, or both. Subsequently, the resulting antibody variants may comprise a light chain HVR1 (HVR-L1) sequence of SEQ ID NO:11 and a heavy chain HVR2 (HVR-H2) sequence of SEQ ID NO:12, or may comprise a light chain HVR3 (HVR-L3) sequence of SEQ ID NO:13, or may comprise a light chain HVR1 (HVR-L1) sequence of SEQ ID NO:14 and a heavy chain HVR2 (HVR-H2) sequence of SEQ ID NO:12, or may comprise a heavy chain HVR3 (HVR-H3) sequence of SEQ ID NO:15.

In some aspects, the anti-factor D antibody variant used in the conjugates of the disclosure is a variant of a reference anti-factor D antibody, wherein the reference anti-factor D antibody comprises the light chain sequence of SEQ ID NO:1 and the heavy chain sequence of SEQ ID NO:2, and wherein the variant comprises the following sequence modifications over the reference anti-factor D antibody: a light chain HVR1 (HVR-L1) sequence of SEQ ID NO:11 and a heavy chain HVR2 (HVR-H2) sequence of SEQ ID NO:12. Such variant is referred to as the "TM" variant (AFD.v6) in the Examples herein below (see, e.g., Table 1).

In some aspects, the anti-factor D antibody variant used in the conjugates of the disclosure is a variant of a reference anti-factor D antibody, wherein the reference anti-factor D antibody comprises the light chain sequence of SEQ ID NO:1 and a heavy chain sequence selected from the group consisting of SEQ ID NOs: 34-53 and 115, and wherein the variant comprises the following sequence modifications over the reference anti-factor D antibody: a light chain HVR1 (HVR-L1) sequence of SEQ ID NO:11 and a heavy chain HVR2 (HVR-H2) sequence of SEQ ID NO:12. Such variants are referred to as "modified TM" variants. These modified TM variants comprise a heavy chain constant domain that differs from that of the TM variant, and which is selected from the group consisting of SEQ ID NOs: 55-74 and 116.

In some aspects, the anti-factor D antibody variant used in the conjugates of the disclosure is a variant of a reference anti-factor D antibody, wherein the reference anti-factor D antibody comprises the light chain sequence of SEQ ID NO:1 and the heavy chain sequence of SEQ ID NO:2, and wherein the variant comprises the following sequence modifications over the reference anti-factor D antibody: a light chain HVR1 (HVR-L1) sequence of SEQ ID NO:11, a heavy chain HVR2 (HVR-H2) sequence of SEQ ID NO:12 and a light chain HVR3 (HVR-L3) sequence of SEQ ID NO:13. Such variant is referred to as the "TM.D92E" variant (AFD.v7) in Examples herein below (see, e.g., Table 1).

In some aspects, the anti-factor D antibody variant used in the conjugates of the disclosure is a variant of a reference anti-factor D antibody, wherein the reference anti-factor D antibody comprises the light chain sequence of SEQ ID NO:1 and a heavy chain sequence selected from the group consisting of SEQ ID NOs: 34-53 and 115, and wherein the variant comprises the following sequence modifications over the reference anti-factor D antibody: a light chain HVR1 (HVR-L1) sequence of SEQ ID NO:11, a heavy chain HVR2 (HVR-H2) sequence of SEQ ID NO:12 and a light chain HVR3 (HVR-L3) sequence of SEQ ID NO:13. Such variants are referred to as "modified TM.D92E" variants. These modified TM.D92E variants comprise a heavy chain constant domain that differs from that of the TM.D92E variant, and which is selected from the group consisting of SEQ ID NOs: 55-74 and 116.

In some aspects, the anti-factor D antibody variant used in the conjugates of the disclosure is a variant of a reference anti-factor D antibody, wherein the reference anti-factor D antibody comprises the light chain sequence of SEQ ID NO:1 and the heavy chain sequence of SEQ ID NO:2, and wherein the variant comprises the following sequence modifications over the reference anti-factor D antibody: a light chain HVR1 (HVR-L1) sequence of SEQ ID NO:14 and a heavy chain HVR2 (HVR-H2) sequence of SEQ ID NO:12. Such variant is referred to as the "SIESD" variant (AFD.v8) in Examples herein below (see, e.g., Table 1). In some embodiments, the "SIESD" variant (AFD.v8) comprises the light chain sequence of SEQ ID NO: 26 and the heavy chain sequence of SEQ ID NO: 27. In some embodiments, a Cys-modified version of the "SIESD" variant comprises the light chain sequence of SEQ ID NO: 26 and the heavy chain sequence of SEQ ID NO: 30. In some embodiments, a Cys-Pro-Pro-Cys-modified version of the "SIESD" variant comprises the light chain sequence of SEQ ID NO: 26 and the heavy chain sequence of SEQ ID NO: 31. In some embodiments, a modified version of the "SIESD" variant comprises the light chain sequence of SEQ ID NO: 26 and the heavy chain sequence selected from the group consisting of SEQ ID NOs: 75-92 and 117.

In some aspects, the anti-factor D antibody variant used in the conjugates of the disclosure is a variant of a reference anti-factor D antibody, wherein the reference anti-factor D antibody comprises the light chain sequence of SEQ ID NO:1 and a heavy chain sequence selected from the group consisting of SEQ ID NOs: 34-53 and 115, and wherein the variant comprises the following sequence modifications over the reference anti-factor D antibody: a light chain HVR1 (HVR-L1) sequence of SEQ ID NO:14 and a heavy chain HVR2 (HVR-H2) sequence of SEQ ID NO:12. Such variants are referred to as "modified SIESD" variants. These modified SIESD variants comprise a heavy chain constant domain that differs from that of the SIESD variant, and which is selected from the group consisting of SEQ ID NOs: 55-74 and 116.

In some aspects, the anti-factor D antibody variant used in the conjugates of the disclosure is a variant of a reference anti-factor D antibody, wherein the reference anti-factor D antibody comprises the light chain sequence of SEQ ID NO:1 and the heavy chain sequence of SEQ ID NO:2, and wherein the variant comprises the following sequence modifications over the reference anti-factor D antibody: a light chain HVR1 (HVR-L1) sequence of SEQ ID NO:14, a heavy chain HVR2 (HVR-H2) sequence of SEQ ID NO:12 and a heavy chain HVR3 (HVR-H3) sequence of SEQ ID NO:15. Such variant is referred to as the "SIESD.N103S" variant (AFD.v14) in Examples herein below (see, e.g., Table 1). In some embodiments, the "SIESD.N103S" variant (AFD.v14) comprises the light chain sequence of SEQ ID NO: 28 and the heavy chain sequence of SEQ ID NO: 29. In some embodiments, a Cys-modified version of the "SIESD.N103S" variant comprises the light chain sequence of SEQ ID NO: 28 and the heavy chain sequence of SEQ ID NO: 32. In some embodiments, a Cys-Pro-Pro-Cys-modified version of the "SIESD.N103S" variant comprises the light chain sequence of SEQ ID NO: 28 and the heavy chain sequence of SEQ ID NO: 33. In some embodiments, a modified version of the "SIESD.N103S" variant comprises the light chain sequence of SEQ ID NO: 28 and a heavy chain sequence selected from the group consisting of SEQ ID NOs: 93-110 and 118.

In some aspects, the anti-factor D antibody variant used in the conjugates of the disclosure is a variant of a reference anti-factor D antibody, wherein the reference anti-factor D antibody comprises the light chain sequence of SEQ ID NO:1 and a heavy chain sequence selected from the group consisting of SEQ ID NOs: 34-53 and 115, and wherein the variant comprises the following sequence modifications over the reference anti-factor D antibody: a light chain HVR1 (HVR-L1) sequence of SEQ ID NO:14, a heavy chain HVR2 (HVR-H2) sequence of SEQ ID NO:12 and a heavy chain HVR3 (HVR-H3) sequence of SEQ ID NO:15. Such variants are referred to as "modified SIESD.N103S" variants. These modified SIESD.N103S variants comprise a heavy chain constant domain that differs from that of the SIESD.N103S variant, and which is selected from the group consisting of SEQ ID NOs: 55-74 and 116.

In some aspects, the present disclosure relates to conjugates comprising one or more anti-Factor D antibody variants comprising one or more substitutions within the HVRs of a reference anti-Factor D antibody. In some aspects, the reference anti-Factor D antibody comprises the following HVR sequences:

```
HVR-L1:
                                           (SEQ ID NO: 5)
ITSTDIDDDMN;

HVR-L2:
                                           (SEQ ID NO: 6)
GGNTLRP;

HVR-L3:
                                           (SEQ ID NO: 7)
LQSDSLPYT;

HVR-H1:
                                           (SEQ ID NO: 8)
GYTFTNYGMN;

HVR-H2:
                                           (SEQ ID NO: 9)
WINTYTGETTYADDFKG;
and

HVR-H3:
                                          (SEQ ID NO: 10)
EGGVNN.
```

The corresponding variants comprise one or more of the following substitutions:
(a) D5S in SEQ ID NO: 5;
(b) D7E in SEQ ID NO: 5;
(c) D8S in SEQ ID NO: 5 (a, b, and c disclosed in SEQ ID NO: 22);
(d) D13E in SEQ ID NO: 9 (SEQ ID NO: 23);
(e) D4E in SEQ ID NO: 7 (SEQ ID NO: 24); or
(f) N5S in SEQ ID NO: 10 (SEQ ID NO: 25).

In some embodiments, the reference anti-Factor D antibody comprises a heavy chain constant domain amino acid sequence selected from the group consisting of SEQ ID NOs: 54-74 and 116.

In some aspects, the variant combines the substitutions (b)-(d) above. In another aspect, the variant combines the substitutions (b)-(e) above. In another aspect, the variant combines the substitutions (a)-(d) above. In another aspect, the variant combines the substitutions (a)-(d) and (f) above. In another aspect, the variant comprises one or more of substitution (a), (b), (c), (d), (e), or (f) above, and further comprises a heavy chain constant domain amino acid sequence selected from the group consisting of SEQ ID NOs: 54-74 and 116. In another aspect the variant comprises substitutions selected from the group consisting of: the substitutions (b)-(d) above, the substitutions (b)-(e) above, the substitutions (a)-(d) above, and the substitutions (a)-(d) and (f) above, wherein the variant further comprises a heavy chain constant domain amino acid sequence selected from the group consisting of SEQ ID NOs: 54-74 and 116.

In some aspects, the present disclosure relates to a conjugate comprising one or more anti-Factor D antibody comprising a light chain variable domain amino acid sequence of SEQ ID NO:16, 18 or 19. In another aspect, the present disclosure relates to a conjugate comprising an anti-Factor D antibody comprising a heavy chain variable domain amino acid sequence of SEQ ID NO:17 or 20. In another aspect, the anti-Factor D antibody may comprise a heavy chain constant domain amino acid sequence selected from the group consisting of SEQ ID NOs: 54-74 and 116. In another aspect, the anti-Factor D antibody comprises a light chain variable domain amino acid sequence of SEQ ID NO:16, 18 or 19 and a heavy chain variable domain amino acid sequence of SEQ ID NO:17 or 20. For example, the anti-Factor D antibody can be the "TM" variant (AFD.v6) that comprises the light chain variable domain amino acid sequence of SEQ ID NO:16 and the heavy chain variable domain amino acid sequence of SEQ ID NO:17; the "TM.D92E" variant (AFD.v7) that comprises the light chain variable domain amino acid sequence of SEQ ID NO:18 and the heavy chain variable domain amino acid sequence of SEQ ID NO:17; the "SIESD" variant (AFD.v8) that comprises the light chain variable domain amino acid sequence of SEQ ID NO:19 and the heavy chain variable domain amino acid sequence of SEQ ID NO:17; or the "SIESD.N103S" variant (AFD.v14) that comprises the light chain variable domain amino acid sequence of SEQ ID NO:19 and the heavy chain variable domain amino acid sequence of SEQ ID NO:20.

In another aspect, the anti-Factor D antibody comprises a light chain variable domain amino acid sequence of SEQ ID NO:16, 18 or 19, a heavy chain variable domain amino acid sequence of SEQ ID NO:17 or 20, and a heavy chain constant domain amino acid sequence selected from the group consisting of SEQ ID NOs: 54-74 and 116. For example, the anti-Factor D antibody can be a modified version of the "TM" variant (AFD.v6) that comprises the light chain variable domain amino acid sequence of SEQ ID NO:16, the heavy chain variable domain amino acid sequence of SEQ ID NO:17, and a heavy chain constant domain amino acid sequence selected from the group consisting of SEQ ID NOs: 55-74 and 116; a modified version of the "TM.D92E" variant (AFD.v7) that comprises the light chain variable domain amino acid sequence of SEQ ID NO:18, the heavy chain variable domain amino acid sequence of SEQ ID NO:17, and a heavy chain constant domain amino acid sequence selected from the group consisting of SEQ ID NOs: 55-74 and 116; a modified version of the "SIESD" variant (AFD.v8) that comprises the light chain variable domain amino acid sequence of SEQ ID NO:19, the heavy chain variable domain amino acid sequence of SEQ ID NO:17, and a heavy chain constant domain amino acid sequence selected from the group consisting of SEQ ID NOs: 55-74 and 116; or a modified version of the "SIESD.N103S" variant (AFD.v14) that comprises the light chain variable domain amino acid sequence of SEQ ID NO:19, the heavy chain variable domain amino acid sequence of SEQ ID NO:20, and a heavy chain constant domain amino acid sequence selected from the group consisting of SEQ ID NOs: 55-74 and 116.

In some embodiments, the anti-Factor D antibody is a modified version of the "SIESD" variant (AFD.v8) that comprises the light chain variable domain amino acid sequence of SEQ ID NO:19, and a heavy chain sequence selected from the group consisting of SEQ ID NOs: 30, 31, 75-92, and 117. In some embodiments, the anti-Factor D antibody is a modified version of the "SIESD" variant (AFD.v8) that comprises the light chain sequence of SEQ ID NO: 26, and a heavy chain having an amino acid sequence selected from the group consisting of SEQ ID NOs: 30, 31, 75-92, and 117. In another embodiment, the anti-Factor D antibody is a modified version of the "SIESD.N103S" variant (AFD.v14) that comprises the light chain variable domain amino acid sequence of SEQ ID NO:19 and a heavy chain having an amino acid sequence selected from the group consisting of SEQ ID NOs: 32, 33, 93-110, and 118. In some embodiments, the anti-Factor D antibody is a modified version of the "SIESD.N103S" variant (AFD.v14) that comprises the light chain sequence of SEQ ID NO: 28, and a heavy chain sequence selected from the group consisting of SEQ ID NOs: 32, 33, 93-110, and 118.

In some aspects, the present disclosure relates to conjugates comprising one or more anti-Factor D antibody having a variable light chain comprising a HVR-L1 having the sequence of SEQ ID NO:11 or 14, a HVR-L2 having the sequence of SEQ ID NO:6, and a HVR-L3 having the sequence of SEQ ID NO:7 or 13; and a variable heavy chain comprising a HVR-H1 having the sequence of SEQ ID NO:8, a HVR-H2 having the sequence of SEQ ID NO:9 or 12, and a HVR-H3 having the sequence of SEQ ID NO:10 or 15. In another embodiment, the anti-Factor D antibody may further comprise a heavy chain constant domain amino acid sequence selected from the group consisting of SEQ ID NOs: 54-74 and 116. For example, the anti-Factor D antibody can be the "SIESD" variant (AFD.v8) comprising the following six HVR sequences: HVR-L1 (SEQ ID NO:14), HVR-L2 (SEQ ID NO:6), HVR-L3 (SEQ ID NO:7), HVR-H1 (SEQ ID NO:8), HVR-H2 (SEQ ID NO:12), and HVR-H3 (SEQ ID NO:10); or the "SIESD.N103S" variant (AFD.v14) comprising the following six HVR sequences: HVR-L1 (SEQ ID NO:14), HVR-L2 (SEQ ID NO:6), HVR-L3 (SEQ ID NO:7), HVR-H1 (SEQ ID NO:8), HVR-H2 (SEQ ID NO:12), and HVR-H3 (SEQ ID NO:15). In some embodiments, the anti-Factor D antibody can be a modified version of the "SIESD" variant (AFD.v8) comprising the following six HVR sequences: HVR-L1 (SEQ ID NO:14), HVR-L2 (SEQ ID NO:6), HVR-L3 (SEQ ID NO:7), HVR-H1 (SEQ ID NO:8), HVR-H2 (SEQ ID NO:12), and HVR-H3 (SEQ ID NO:10), and further comprising a heavy chain constant domain amino acid sequence selected from the group consisting of SEQ ID NOs: 55-74 and 116. In another embodiment, the anti-Factor D antibody can be a modified version of the "SIESD.N103S" variant (AFD.v14) comprising the following six HVR sequences: HVR-L1 (SEQ ID NO:14), HVR-L2 (SEQ ID NO:6), HVR-L3 (SEQ ID NO:7), HVR-H1 (SEQ ID NO:8), HVR-H2 (SEQ ID NO:12), and HVR-H3 (SEQ ID NO:15), and further comprising a heavy chain constant domain amino acid sequence selected from the group consisting of SEQ ID NOs: 55-74 and 116.

In some aspects, the present disclosure relates to conjugates comprising one or more anti-Factor D antibody variants with no detectable Asp isomerization, wherein the variants are made by a method for removing or reducing isomerization, comprising: (a) identifying one or more Asp residues prone to Asp isomerization within HVRs of a reference anti-Factor D antibody; (b) substituting Glu for the Asp residue identified in step (a); (c) screening the resulting candidate variants for Asp isomerization; and (d) selecting those variants that have no detectable Asp isomerization. In some aspects, the method above is combined with a method for removing or reducing deamidation, comprising (a) identifying one or more Asn residues prone to deamidation within HVRs of the reference anti-Factor D antibody; (b) substituting Ser for the Asn residue identified in step (a); (c) screening the resulting candidate variants for deamidation; and (d) selecting those variants having reduced or eliminated deamidation. In another aspect, the method for removing or reducing isomerization is combined with a method for reducing overall charge of the antibody by: (a) selecting one or more negatively charged amino acid residues D or E within HVRs of the reference anti-Factor D antibody; (b)

substituting Ser for the residue selected in step (a); (c) screening the resulting candidate variants for solubility; and (d) selecting those variants having improved solubility when compared to the reference anti-Factor D antibody.

In some aspects, the present disclosure is directed to a conjugate comprising one or more anti-Factor D antibody or antibody variant disclosed herein and one or more multi-armed polyol, wherein the conjugate is prepared by covalently linking at least one of the anti-Factor D antibodies or antibody variants disclosed herein to the polyol. In some embodiments, the multi-armed polyol is a PEG. In some embodiments, the PEG is an octamer. In some embodiments, the PEG has the structure of general formula (Ia), (Ib), (IIa), (IIIa), or (IVa), as set forth herein.

In some aspects, the conjugates of the present disclosure comprise anti-factor D antibody variants that have improved stability while maintaining the factor D binding affinity when compared to the reference anti-factor D antibody. In some aspects, the antibodies bind to Factor D with a binding affinity of at least about 10-9 to 10-12M. In some aspects, the antibodies used in the conjugates of the present disclosure include human, humanized or chimeric antibodies.

In some aspects, the antibodies used in the conjugates of the present disclosure are antibody fragments (e.g., antigen-binding fragments). The antibody fragments may, for example, be Fab, Fab', F(ab')2, scFv, (scFv)2, dAb, complementarity determining region (CDR) fragments, linear antibodies, single-chain antibody molecules, minibodies, diabodies, or multispecific antibodies formed from antibody fragments.

In other aspects of the disclosure, the present disclosure includes compositions comprising a conjugate of the disclosure. In another aspect, the disclosure concerns a composition of matter comprising a conjugate of the disclosure, as described herein, in combination with a carrier. Optionally, the carrier is a pharmaceutically acceptable carrier.

In some aspects, the present disclosure includes pharmaceutical formulations comprising the conjugates described herein, at therapeutically effective concentrations. In some aspects, the pharmaceutical formulation comprises the antibody or antibody variant at a concentration of at least about 100 mg/mL, from about 100 to about 150 mg/mL, from about 100 to about 200 mg/mL, from about 100 to about 300 mg/mL, from about 100 to about 400 mg/mL, from about 100 to about 500 mg/ml; at least about 200 mg/mL, at least about 300 mg/mL, at least about 400 mg/mL or at least about 500 mg/mL. In some aspects, the concentration of the antibody or antibody variant in the formulation is about 200, 250, 300, 350, 400, 450 or 500 mg/mL. In some aspects, the concentration of the antibody or antibody variant in the formulation is less than about 450 mg/mL.

Another aspect of the present disclosure is the use of the conjugate or pharmaceutical formulation of the disclosure for treatment of disorders associated with excessive or uncontrolled complement activation. In one embodiment, the disclosure is directed to a method of treating a complement-associated disorder in a subject, the method comprising administering to the subject a conjugate or pharmaceutical formulation of the disclosure. The disorders include complement activation during cardiopulmonary bypass operations; complement activation due to ischemia-reperfusion following acute myocardial infarction, aneurysm, stroke, hemorrhagic shock, crush injury, multiple organ failure, hypobolemic shock, intestinal ischemia or other events causing ischemia. Complement activation has also been shown to be associated with inflammatory conditions such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. In one embodiment, the complement-associated disorder is systemic. It may also include autoimmune disease such as systemic lupus erythematosus, myasthenia gravis, rheumatoid arthritis, Alzheimer's disease and multiple sclerosis. In another embodiment, complement activation is also associated with transplant rejection. In another embodiment, complement activation is also associated with ocular diseases (all ocular conditions and diseases the pathology of which involve complement, including the classical and the alternative pathway of complement) or complement-associated eye conditions, such as, for example, without limitation, macular degenerative disease, such as all stages of age-related macular degeneration (AMD), including dry and wet (non-exudative and exudative) forms, diabetic retinopathy and other ischemia-related retinopathies, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization. In one example, complement-associated eye conditions include age-related macular degeneration (AMD), including non-exudative (e.g., intermediate dry AMD or geographic atrophy (GA)) and exudative (e.g., wet AMD (choroidal neovascularization (CNV)) AMD, diabetic retinopathy (DR), endophthalmitis and uveitis. In a further example, nonexudative AMD may include the presence of hard drusen, soft drusen, geographic atrophy and/or pigment clumping. In another example, complement-associated eye conditions include age-related macular degeneration (AMD), including early AMD (e.g., includes multiple small to one or more non-extensive medium sized drusen), intermediate AMD (e.g., includes extensive medium drusen to one or more large drusen) and advanced AMD (e.g., includes geographic atrophy or advanced wet AMD (CNV). In a further example, intermediate dry AMD may include large confluent drusen. In a further example, geographic atrophy may include photoreceptor and/or Retinal Pigmented Epithelial (RPE) loss. In a further example, the area of geographic atrophy may be small or large and/or may be in the macula area or in the peripheral retina. In one example, the complement-associated eye condition is intermediate dry AMD. In one example, the complement-associated eye condition is geographic atrophy. In one example, the complement-associated eye condition is wet AMD (choroidal neovascularization (CNV)). In one embodiment, the conjugate or pharmaceutical formulation is administered using an implantable port-delivery system. In one embodiment, the conjugate or pharmaceutical formulation is administered by intravitreal administration. In one embodiment, the method or use further comprises administering to the subject an additional therapeutic agent, such as a HTRA1 antagonist, an ANG2 antagonist, a TIE2 antagonist, a VEGF antagonist, or an antagonist of one or more of the C1, C2, C3, C4, C5, C6, C7, C8, or C9 complement components.

In another aspect, the disclosure provides a kit, comprising a conjugate of the disclosure. In some embodiments, the disclosure provides a kit, comprising a conjugate of the disclosure and instructions for use. In some embodiments, the disclosure concerns a kit comprising a conjugate of the disclosure and instructions for administering said conjugate, to treat a complement-associated disorder. In some embodiments, the disclosure provides a kit comprising a first container comprising a composition comprising one or more one or more conjugate of the disclosure; and a second container comprising a buffer. In some embodiments, the buffer is pharmaceutically acceptable. In some embodiments, a composition comprising a conjugate of the disclosure further comprises a carrier, which in some embodiments is pharmaceutically acceptable. In some embodiments, a kit further comprises instructions for administering the composition (e.g., the conjugate comprising one or more antibody, or antibody fragment thereof (e.g., antigen-binding fragment) to a subject. In some embodiments, a kit further comprises instructions for use of the kit.

In some aspects, the disclosure concerns an article of manufacture containing materials useful for the treatment, prevention and/or diagnosis of complement-associated disorders. In some embodiments, the disclosure concerns an article of manufacture, comprising: (a) a container; (b) a label on the container; and (c) a composition of matter comprising a conjugate of the present disclosure, contained with the container, wherein the label on said container indicates that the composition can be used for treatment, prevention and/or diagnosis of complement-associated disorders.

In some aspects, the disclosure provides use of a conjugate of the disclosure in the preparation of a medicament for the therapeutic and/or prophylactic treatment of a disease, such as a complement-associated eye condition. In one embodiment, the disclosure is directed to a method of treating a complement-associated disorder, such as a complement-associated eye condition, in a subject, the method comprising administering to the subject a conjugate or pharmaceutical formulation of the disclosure. In some embodiments, the complement-associated eye condition is selected from age-related macular degeneration (AMD), including non-exudative (e.g intermediate dry AMD or geographic atrophy (GA)) and exudative (e.g., wet AMD (choroidal neovascularization (CNV)) AMD, diabetic retinopathy (DR), endophthalmitis and uveitis. In one example, the complement-associated eye condition is intermediate dry AMD. In one example, the complement-associated eye condition is geographic atrophy. In one example, the complement-associated eye condition is wet AMD (choroidal neovascularization (CNV)).

In some aspects, the disclosure provides use of an article of manufacture of the disclosure in the preparation of a medicament for the therapeutic and/or prophylactic treatment of a disease, such as a complement-associated eye condition. In some embodiments, the complement-associated eye condition is selected from age-related macular degeneration (AMD), including non-exudative (e.g intermediate dry AMD or geographic atrophy (GA)) and exudative (e.g., wet AMD (choroidal neovascularization (CNV)) AMD, diabetic retinopathy (DR), endophthalmitis and uveitis. In one example, the complement-associated eye condition is intermediate dry AMD. In one example, the complement-associated eye condition is geographic atrophy. In one example, the complement-associated eye condition is wet AMD (choroidal neovascularization (CNV)).

In some aspects, the disclosure provides use of a kit of the disclosure in the preparation of a medicament for the therapeutic and/or prophylactic treatment of a disease, such as a complement-associated eye condition. In some embodiments, the complement-associated eye condition is selected from age-related macular degeneration (AMD), including non-exudative (e.g intermediate dry AMD or geographic atrophy (GA)) and exudative (e.g., wet AMD (choroidal neovascularization (CNV)) AMD, diabetic retinopathy (DR), endophthalmitis and uveitis. In one example, the complement-associated eye condition is intermediate dry AMD. In one example, the complement-associated eye condition is geographic atrophy. In one example, the complement-associated eye condition is wet AMD (choroidal neovascularization (CNV)).

In some aspects, the disclosure provides a formulation comprising a conjugate comprising one or more Factor D antagonist, and further comprises a HTRA1 antagonist, an ANG2 antagonist, a TIE2 antagonist, a VEGF antagonist, or an antagonist of one or more of the C1, C2, C3, C4, C5, C6, C7, C8, and C9 complement components. In some embodiments, the Factor D antagonist is an anti-Factor D antibody. In a further embodiment, the anti-Factor D antibody is an anti-Factor D antibody variant described herein. In some embodiments the HTRA1 antagonist is an anti-HTRA1 antibody. In another embodiment the ANG2 antagonist is an anti-ANG2 antibody. In another embodiment, the TIE2 antagonist is an anti-TIE2 antibody. In another embodiment, the VEGF antagonist is an anti-VEGF antibody. In another embodiment, the antagonist of the C2 and/or C4 and/or C5 complement components is an anti-C2 and/or anti-C4 and/or anti-C5 antibody.

In some aspects, the treatment of disorders associated with excessive or uncontrolled complement activation in a human subject with a disorder associated with excessive or uncontrolled complement activation comprises administering to the subject an effective amount of a therapeutic compound, such as conjugate comprising one or more Factor D antagonist, and further comprises administering to the subject an effective amount of a second therapeutic compound, such as a HTRA1 antagonist, an ANG2 antagonist, a TIE2 antagonist, a VEGF antagonist, or an antagonist of one or more of the C1, C2, C3, C4, C5, C6, C7, C8, and C9 complement components. In some embodiments, the Factor D antagonist is an anti-Factor D antibody. In some embodiments, the anti-Factor D antibody is an anti-Factor D antibody variant described herein. In some embodiments, the HTRA1 antagonist is an anti-HTRA1 antibody. In another embodiment the ANG2 antagonist is an anti-ANG2 antibody. In another embodiment, the TIE2 antagonist is an anti-TIE2 antibody. In another embodiment, the VEGF antagonist is an anti-VEGF antibody. In another embodiment, the antagonist of the C2 and/or C4 and/or C5 complement components is an anti-C2 and/or anti-C4 and/or anti-C5 antibody.

In some aspects, the administration of the conjugate comprising the Factor D antagonist and any second therapeutic compound can be done simultaneously, e.g., as a single composition or as two or more distinct compositions using the same or different administration routes. Alternatively, or additionally the administration can be done sequentially, in any order.

BRIEF DESCRIPTION OF THE FIGURES

FIGS. 1A-1D shows amino acid sequences of a reference anti-factor D antibody WT (aFD.WT) and its select variants (1A: light and heavy chain sequences of WT; 1B: alignment of light and heavy chain variable domains; 1C: light and heavy chain sequences of SIESD (AFD.v8) and heavy chain sequences of Cys-modified SIESD (AFD.v8) and Cys-Pro-Pro-Cys-modified SIESD (AFD.v8); 1D: light and heavy chain sequences of SIESD.N103S (AFD.v14) and heavy chain sequences of Cys-modified SIESD.N103S (AFD.v14) and Cys-Pro-Pro-Cys-modified SIESD.N103S (AFD.v14)).

HVRs within the variable domains are underlined. Residue substitutions in the variants are shown in bold. Cys and Cys-Pro-Pro-Cys (SEQ ID NO: 21) modifications are shown in italics in FIGS. 1C and 1D.

Figure 2A:
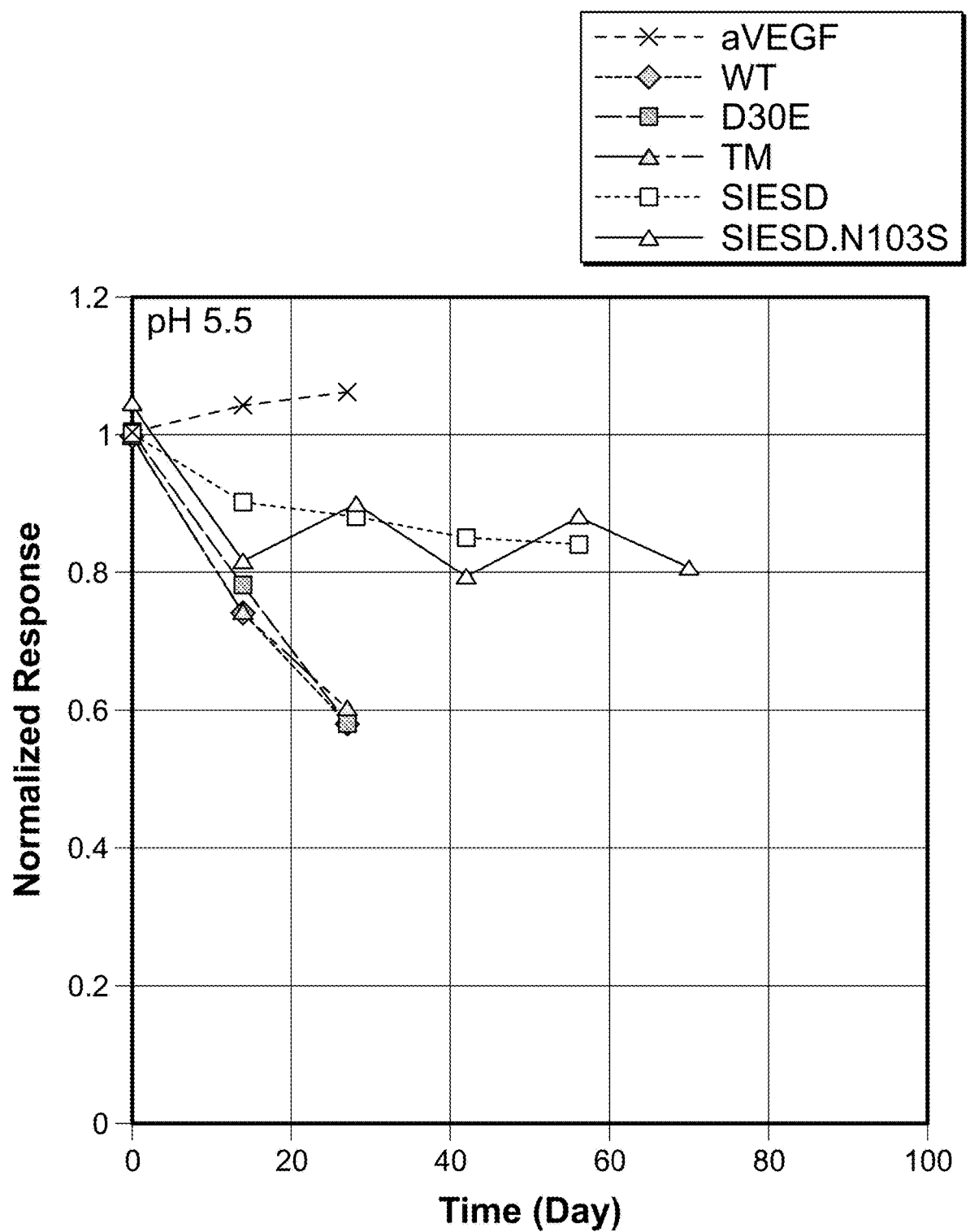
Figure 2B:
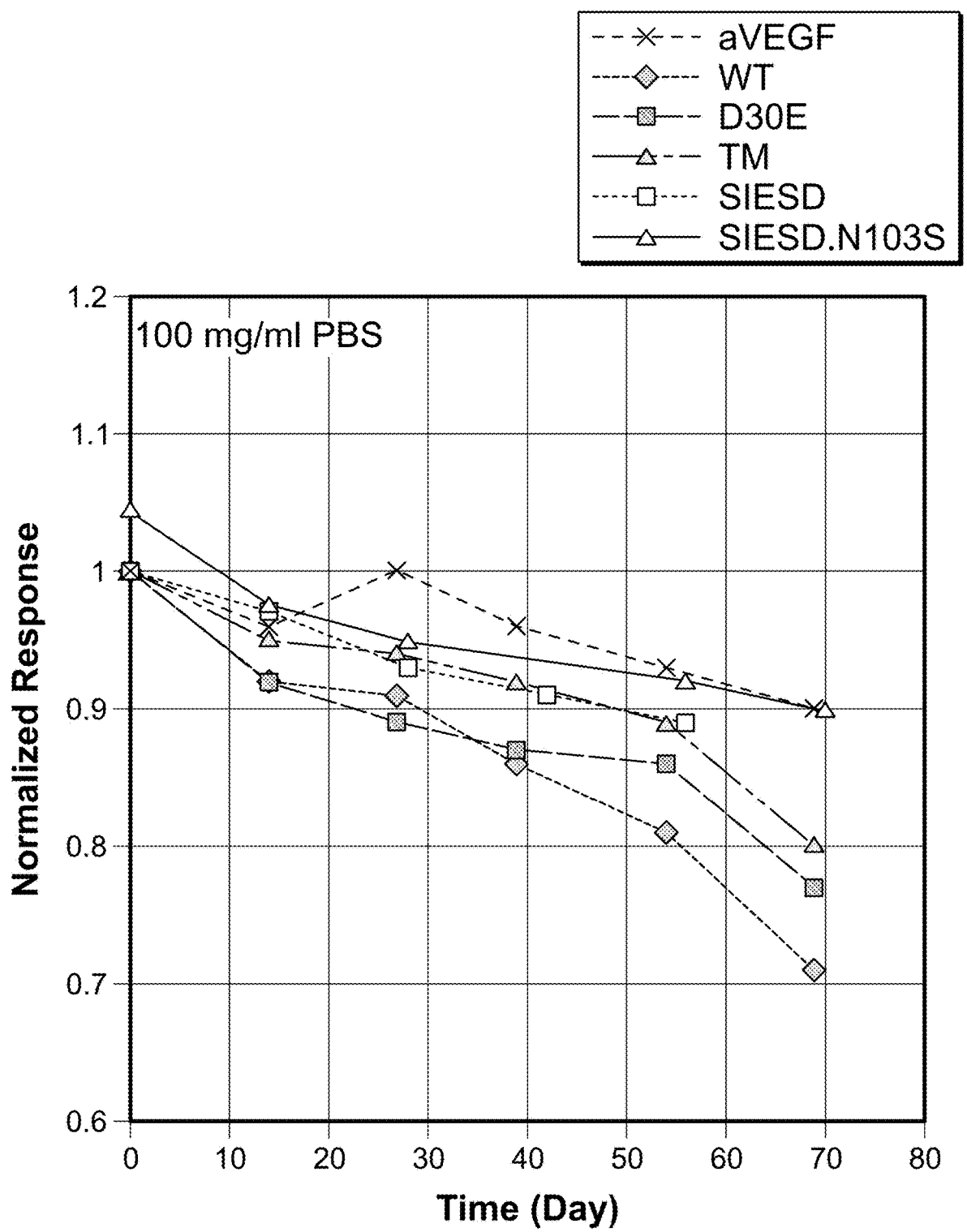
Figure 2C:
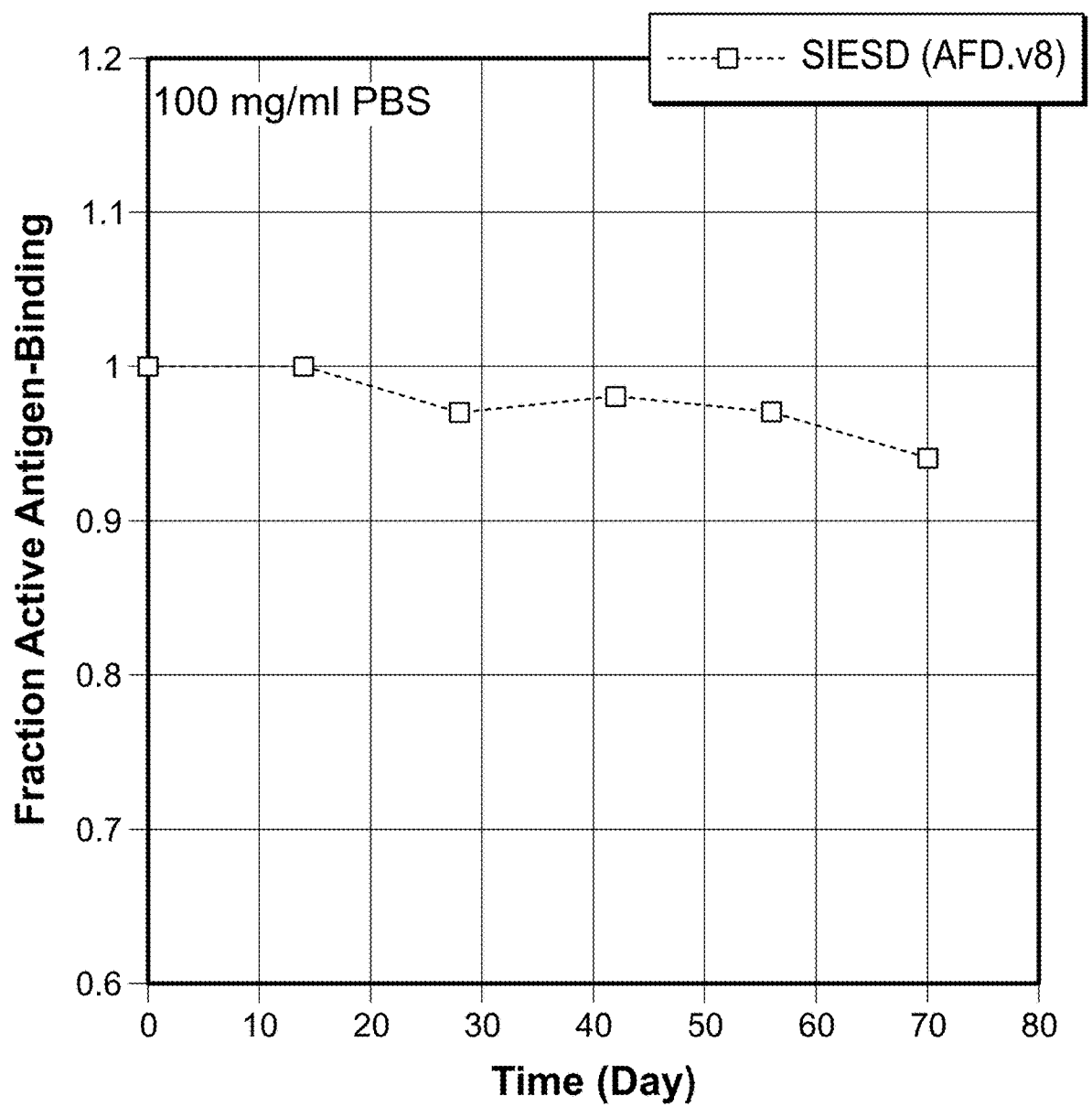

FIGS. 2A-2C illustrates antigen binding capacity of various antibody Fab fragments over prolonged time under defined conditions (2A: Fab protein concentration of 10 mg/mL in pH 5.5 buffer; 2B: Fab protein concentration of 100 mg/ml in PBS; 2C: Fab protein concentration of 100 mg/ml in PBS).

Figure 3A:
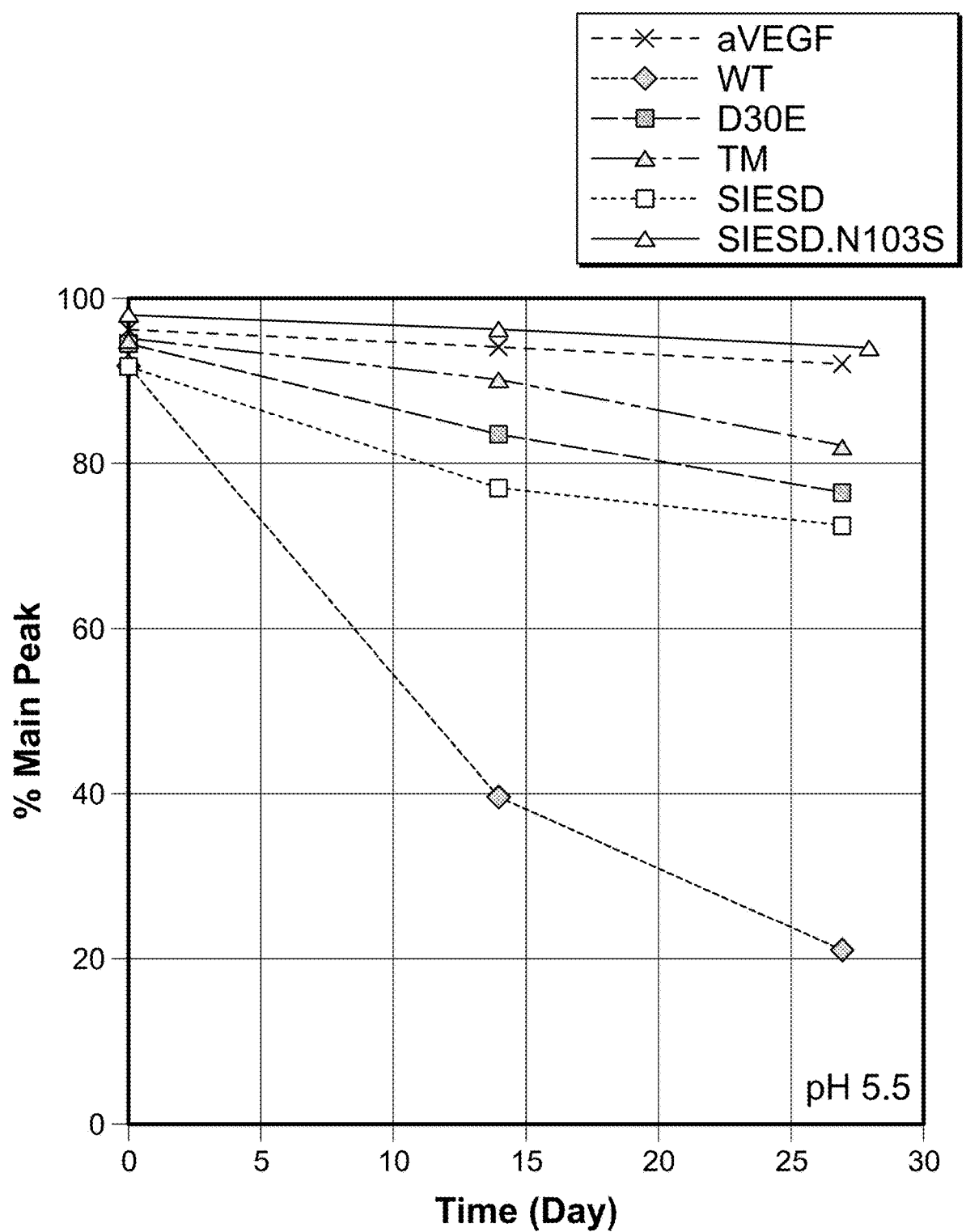
Figure 3B:
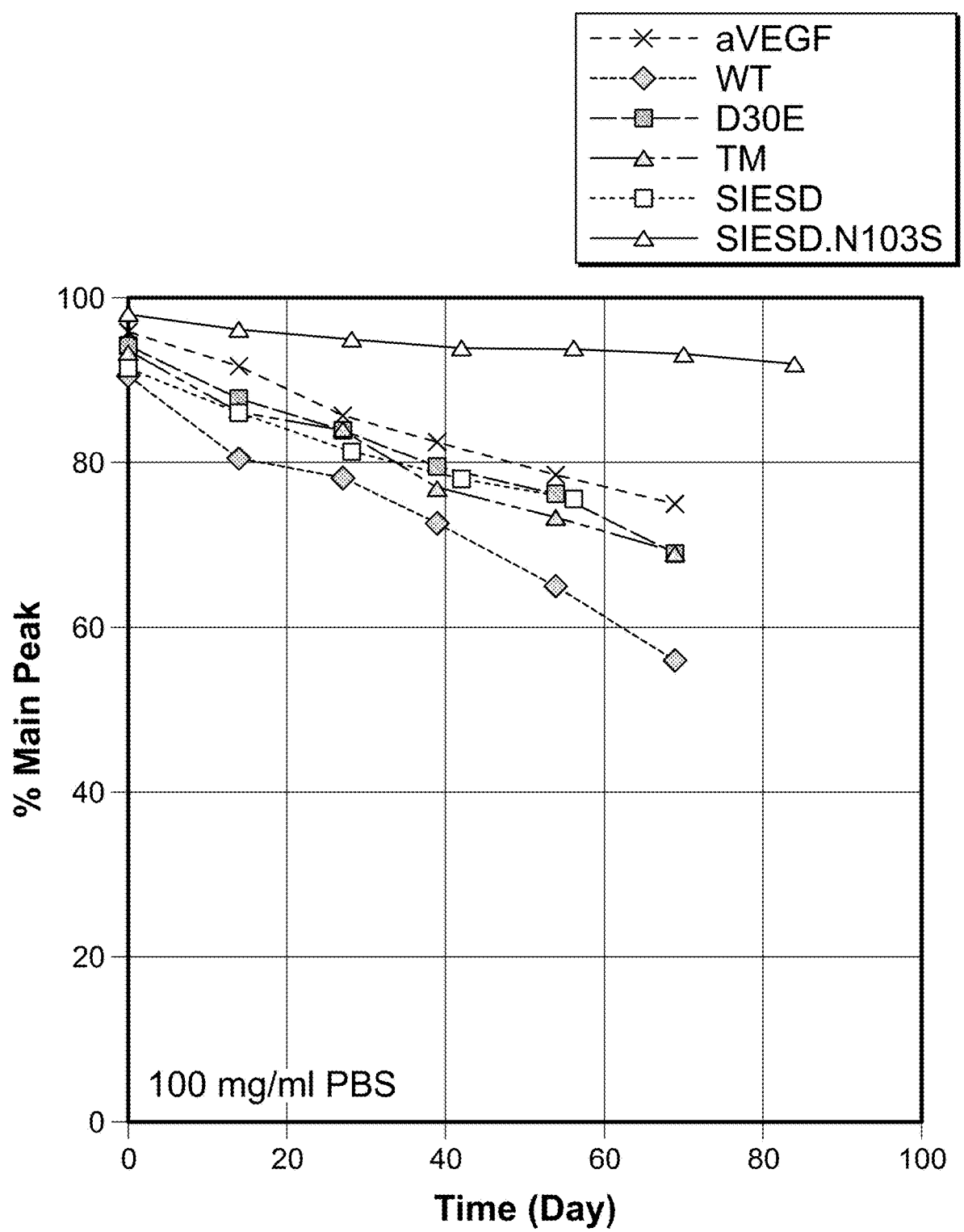

FIGS. 3A-3B illustrates degradations of various antibody Fab fragments over time under defined conditions whereby main peak is determined by ion-exchange chromatography (IEC) (3A: Fab protein concentration of 10 mg/mL in pH 5.5 buffer; 3B: Fab protein concentration of 100 mg/ml in PBS).

Figure 4A:
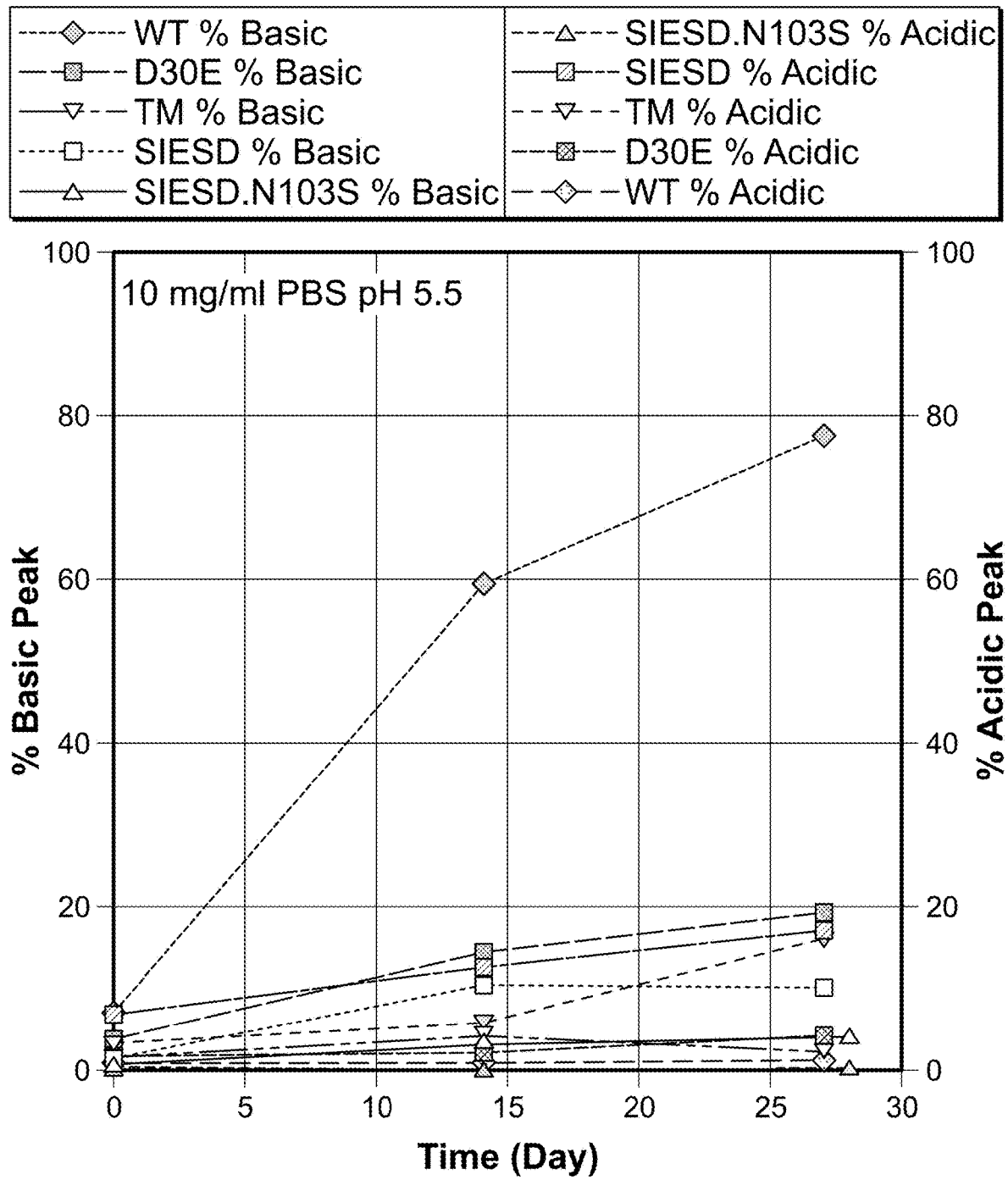
Figure 4B:
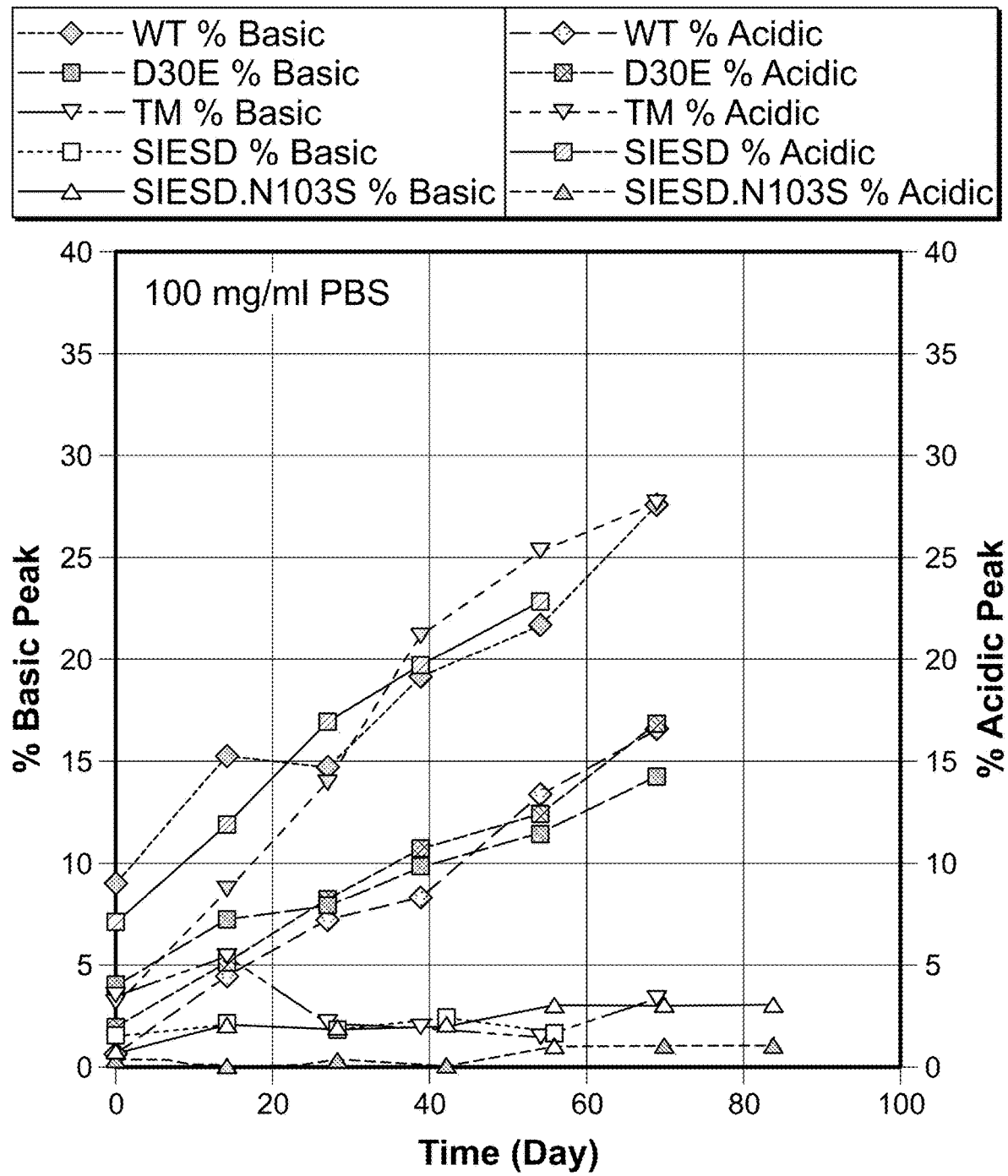

FIGS. 4A-4B illustrates isomerization and deamidation of various antibody Fab fragments over time under defined conditions (4A: Fab protein concentration of 10 mg/mL in pH 5.5 buffer; 4B: Fab protein concentration of 100 mg/ml in PBS).

Figure 5:
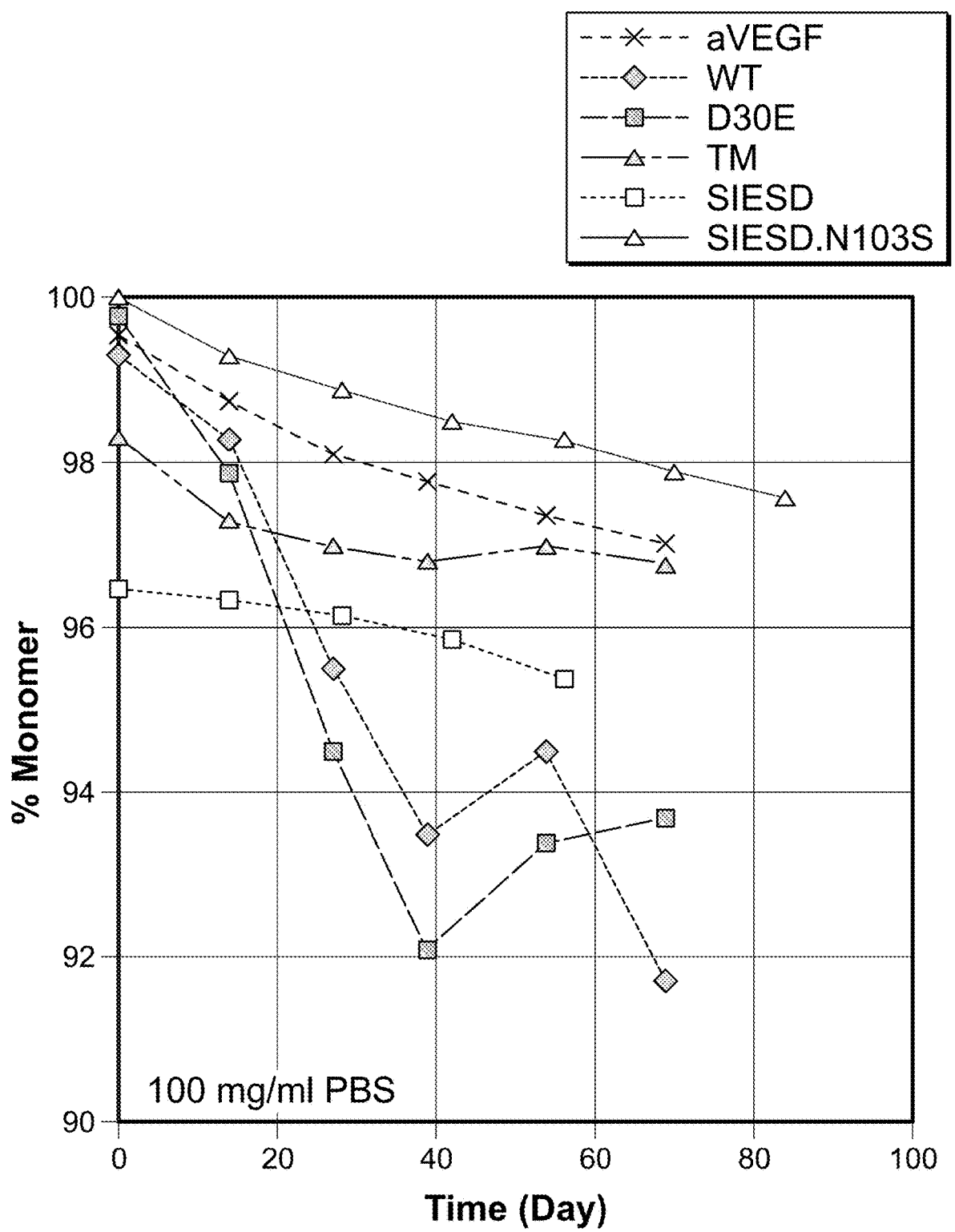

FIG. 5 illustrates aggregation of various antibody Fab fragments over prolonged time under defined condition (Fab protein concentration of 100 mg/ml in PBS) as determined by measurements of monomer peak by size-exclusion chromatography (SEC).

Figure 6:
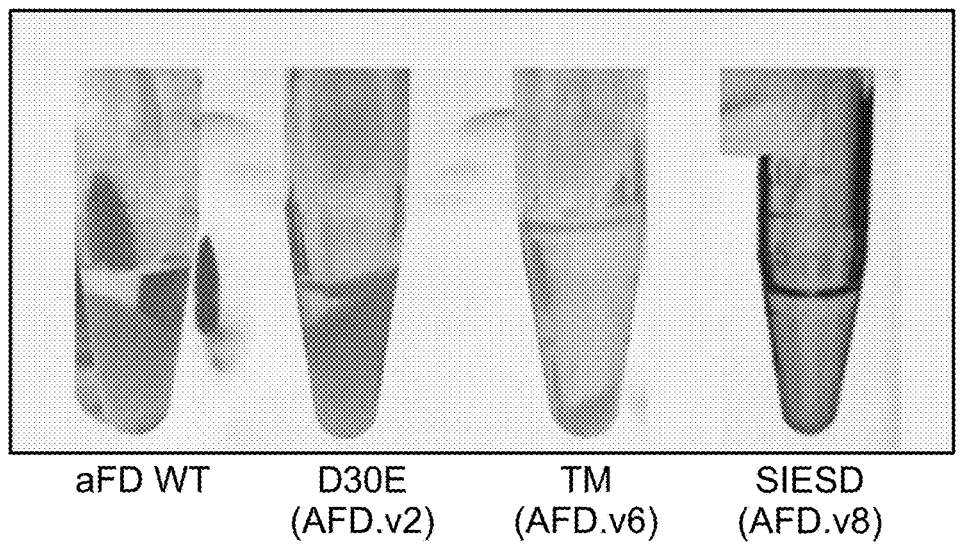

FIG. 6 illustrates solubility of aFD.WT, AFD.v2, AFD.v6 and AFD.v8 at pH 6 and low ionic strength (~100 mg/ml in 20 mM His-HCl, pH 6).

Figure 7:
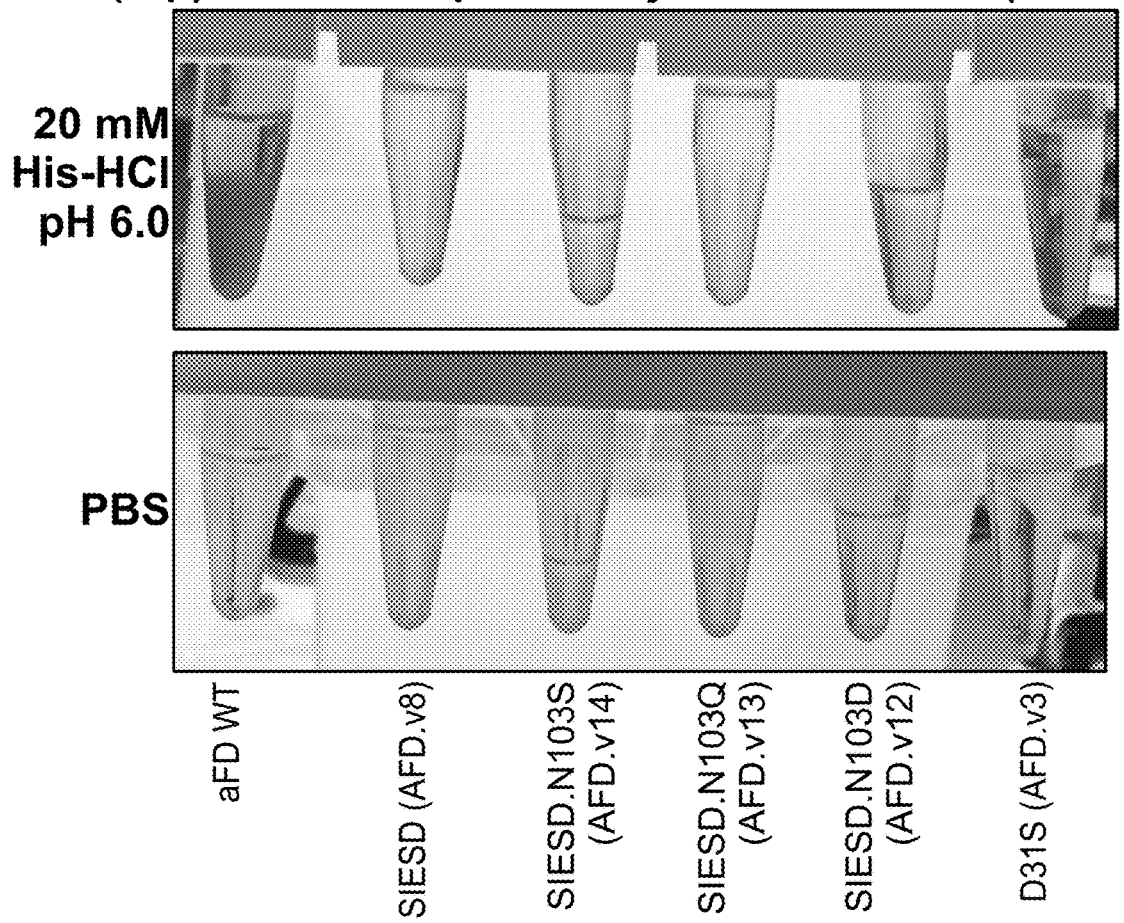

FIG. 7 illustrates solubility of antibody Fab fragments at pH 6 and low ionic strength (~100 mg/ml in 20 mM His-HCl, pH 6). The insolubility of aFD.WT is reversed by the exchange into PBS, a salt (NaCl) containing buffer, via dialysis.

Figure 8:
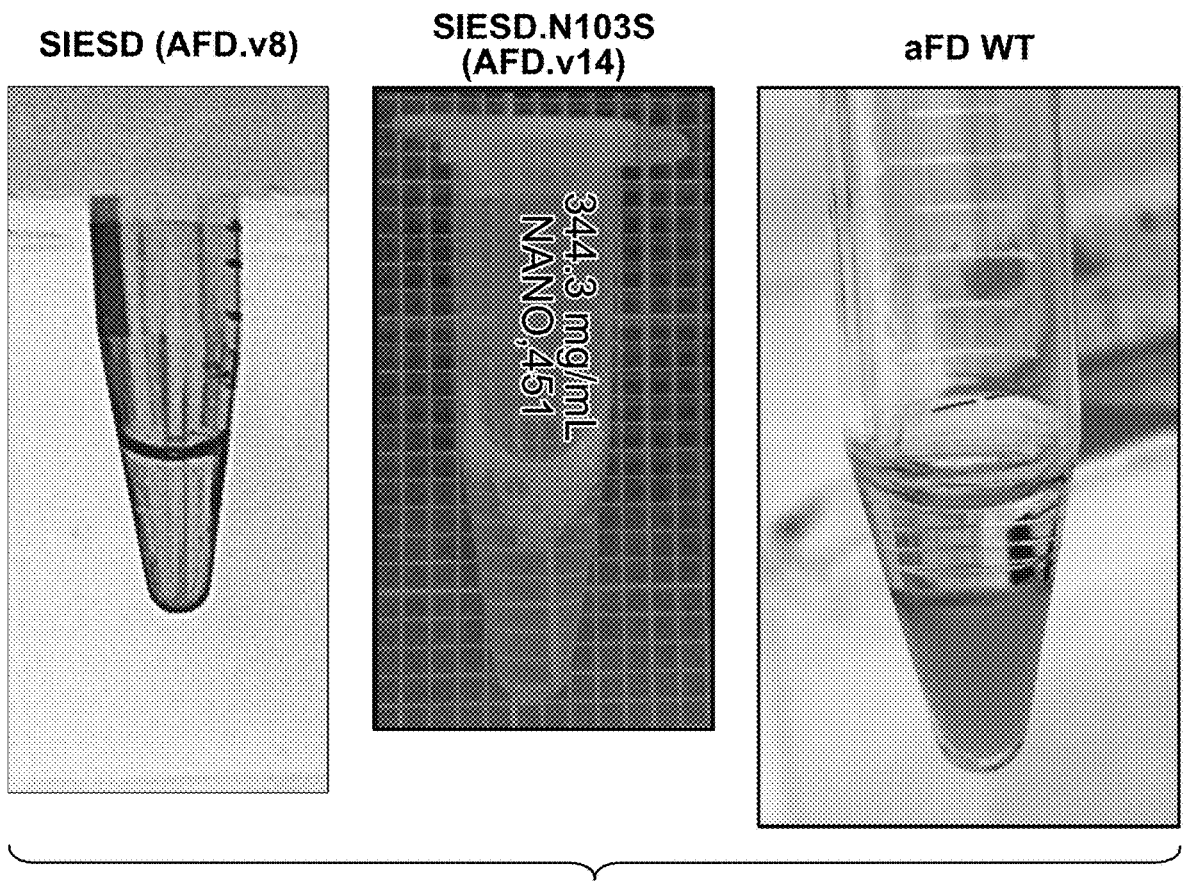

FIG. 8 illustrates solubility of antibody Fab fragments in PBS (pH 7.3) at 227 mg/ml for aFD.WT, 269 mg/ml for AFD.v8 and 344 mg/ml for AFD.v14.

Figure 9:
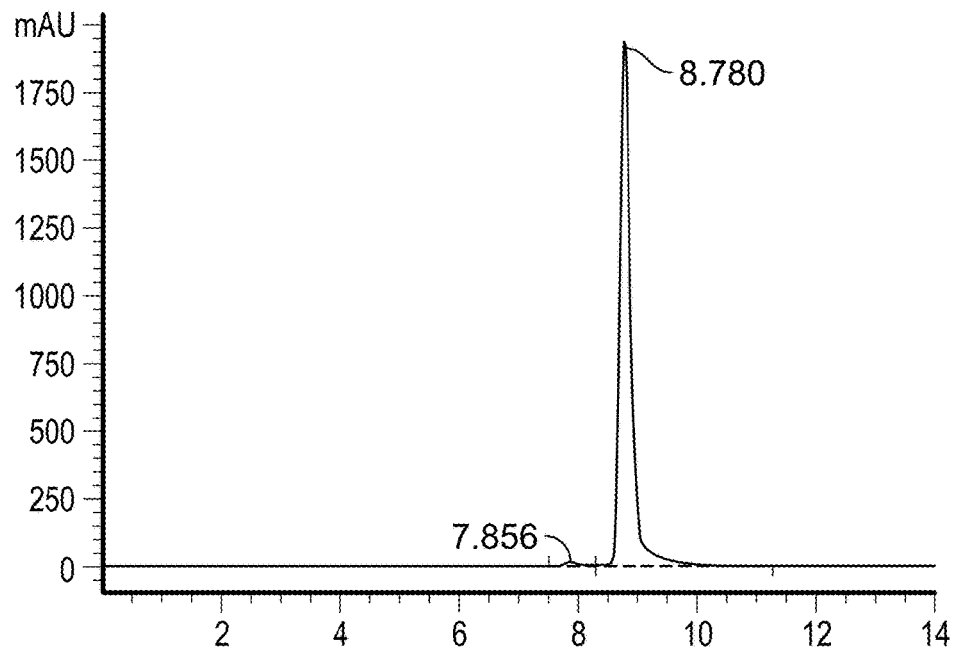

FIG. 9 illustrates % aggregate as measured by size-exclusion chromatography (SEC) of SIESD.N103S (AFD.v14) in PBS prior to 3 week incubation at 2-8° C.

Figure 10A:
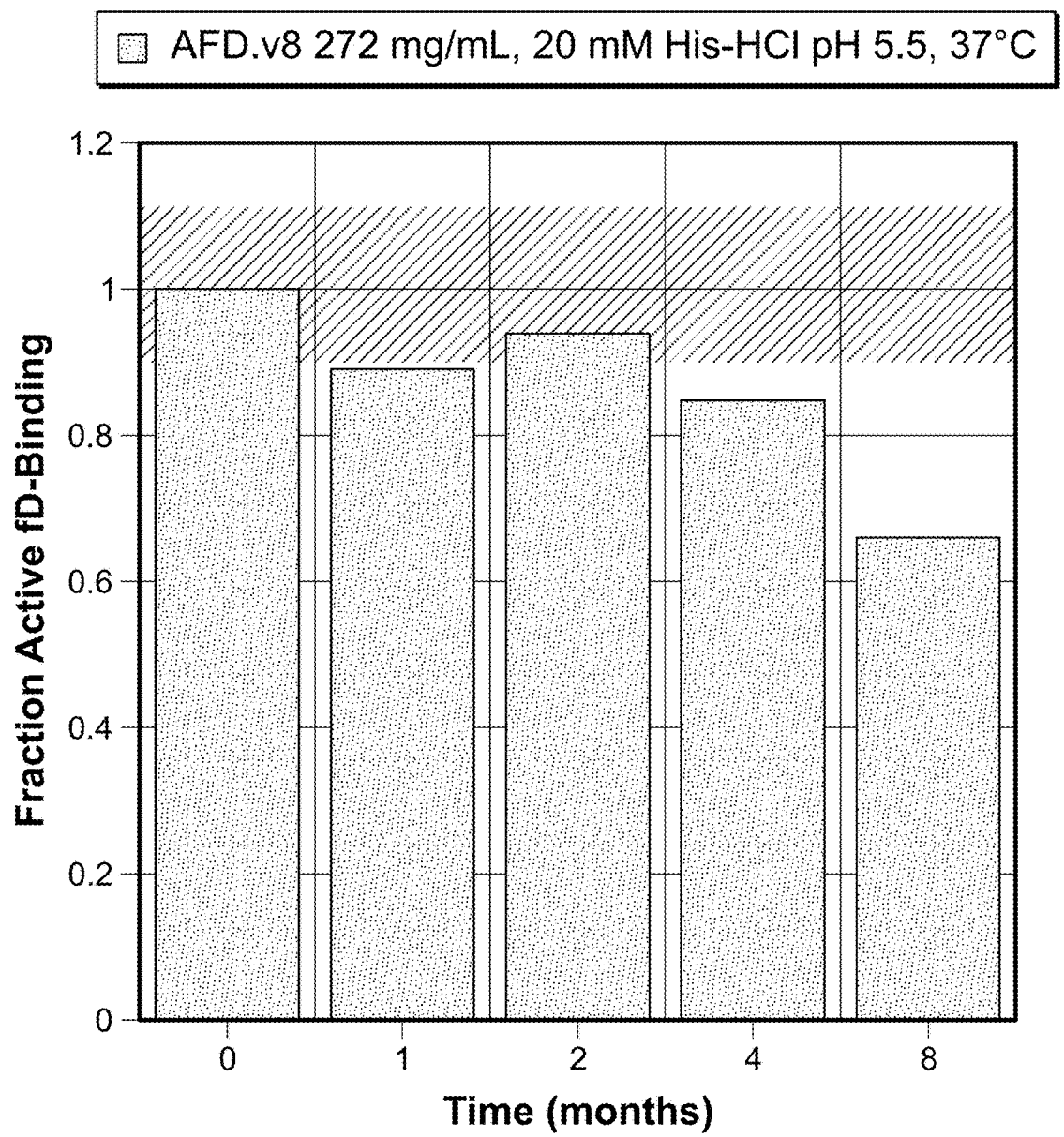

FIG. 10A illustrates the antigen binding capacity for a high concentration (272 mg/mL) AFD.v8 formulation (20 mM His-HCl, pH 5.5) over prolonged time under thermal stress at 37° C. The hatched area denotes the ±10% standard error in the measurements.

Figure 10B:
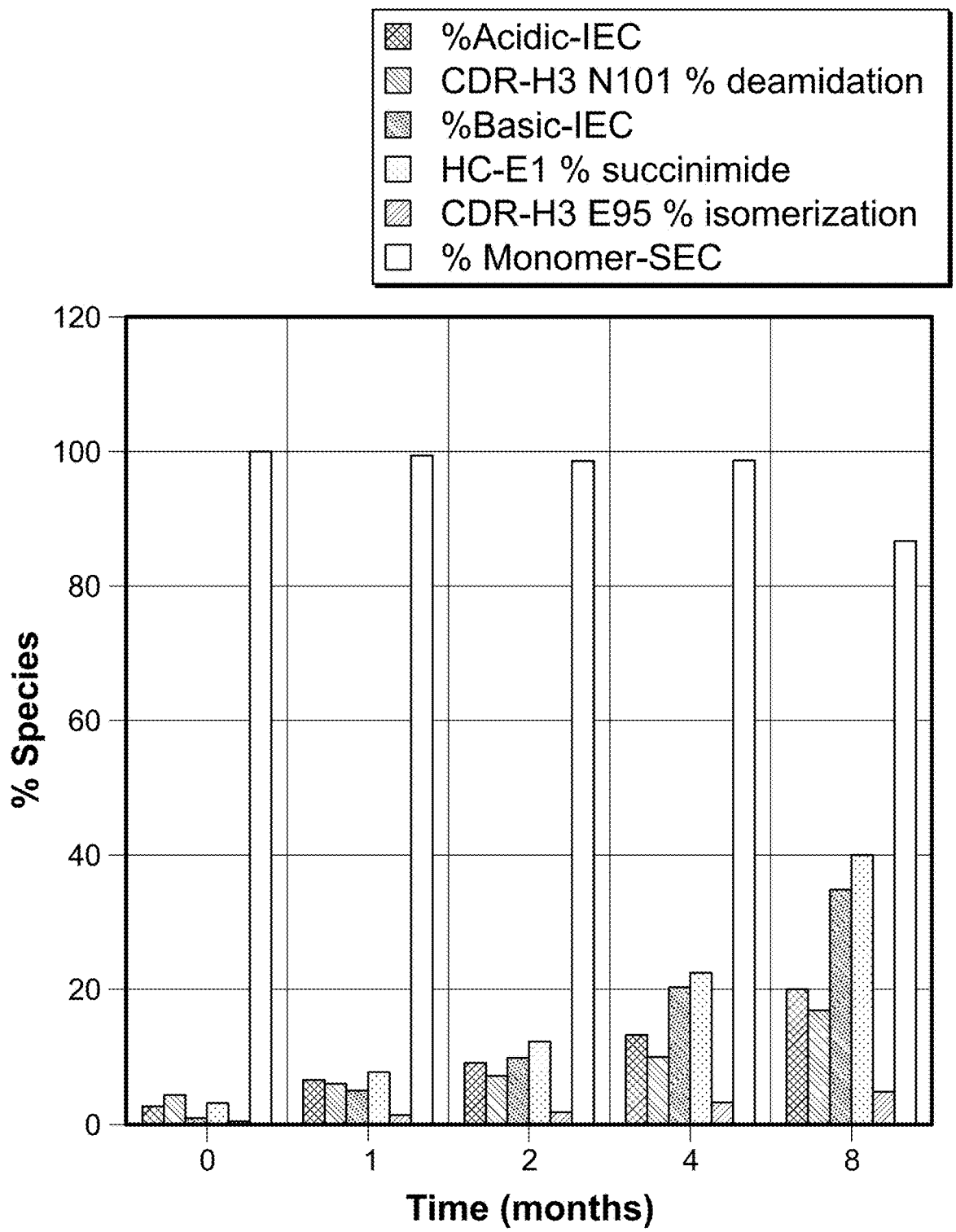

FIG. 10B illustrates the chemical and physical stability for a high concentration (272 mg/mL) AFD.v8 formulation (20 mM His-HCl, pH 5.5) over prolonged time under thermal stress at 37° C. The N101 and E95 are according to Kabat numbering.

Figure 11:
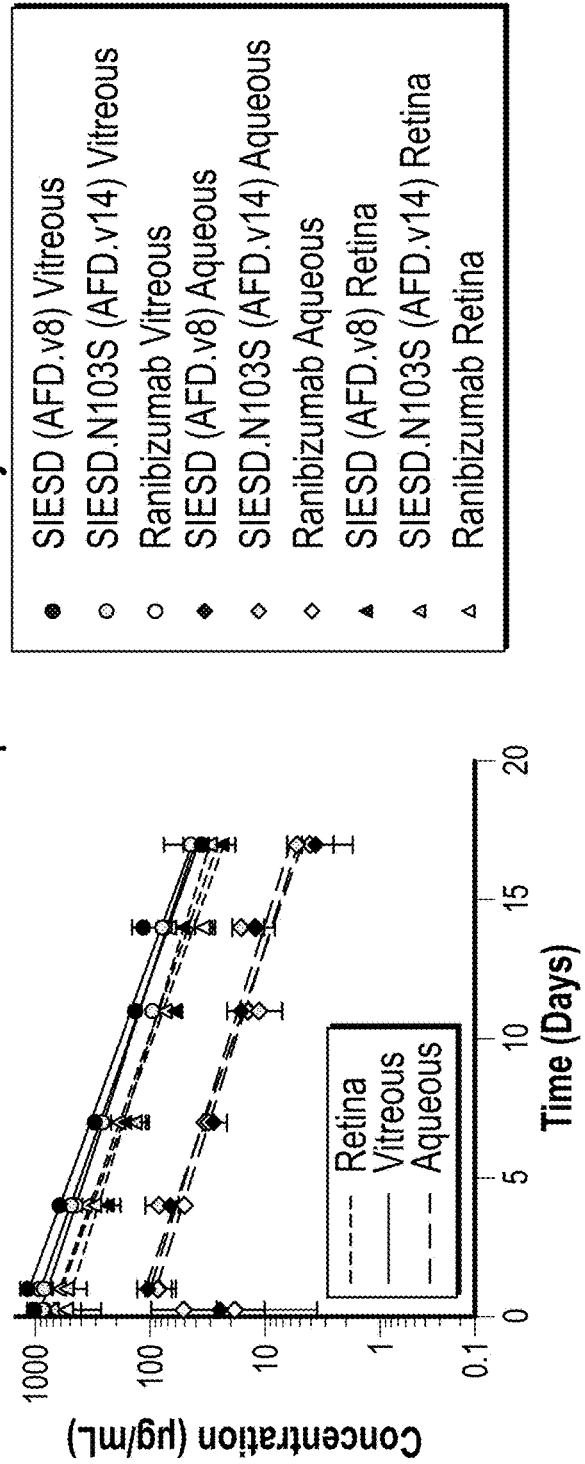

FIG. 11 illustrates pharmacokinetics of antibody Fab fragments upon intravitreal injection in rabbits.

FIG. 12 illustrates protein concentration dependence of viscosity for antibody Fab fragments in pH 5.5 buffer.

Figure 13A:
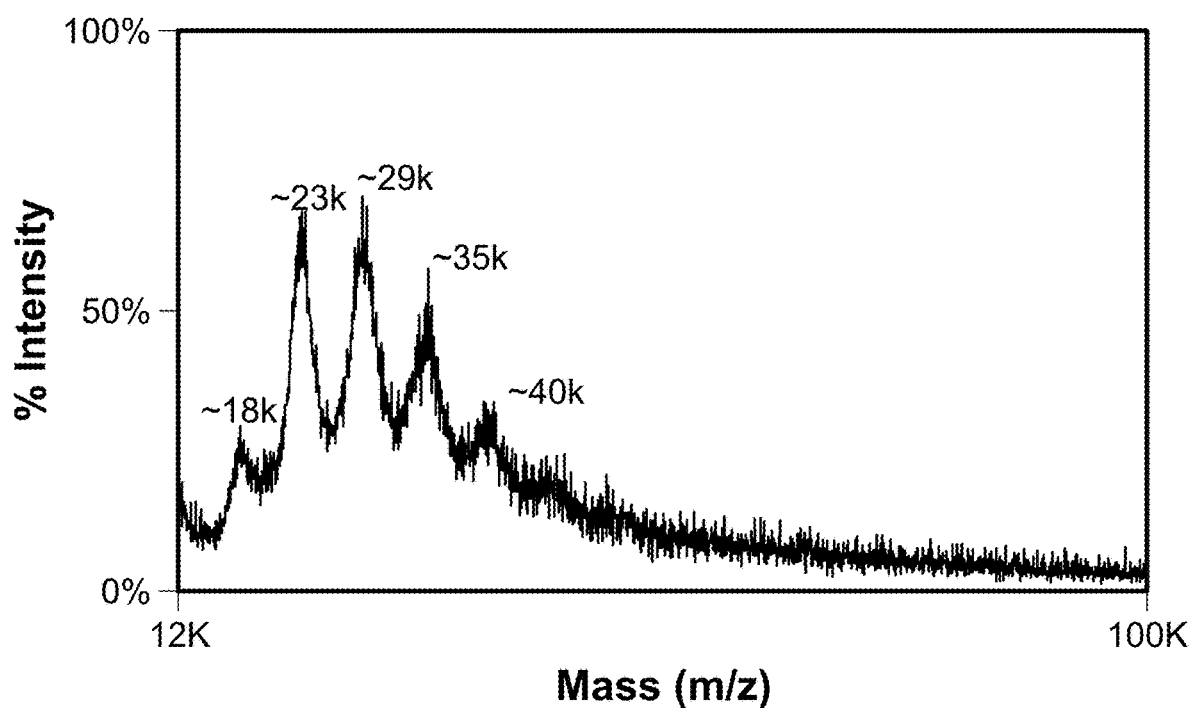
Figure 13B:
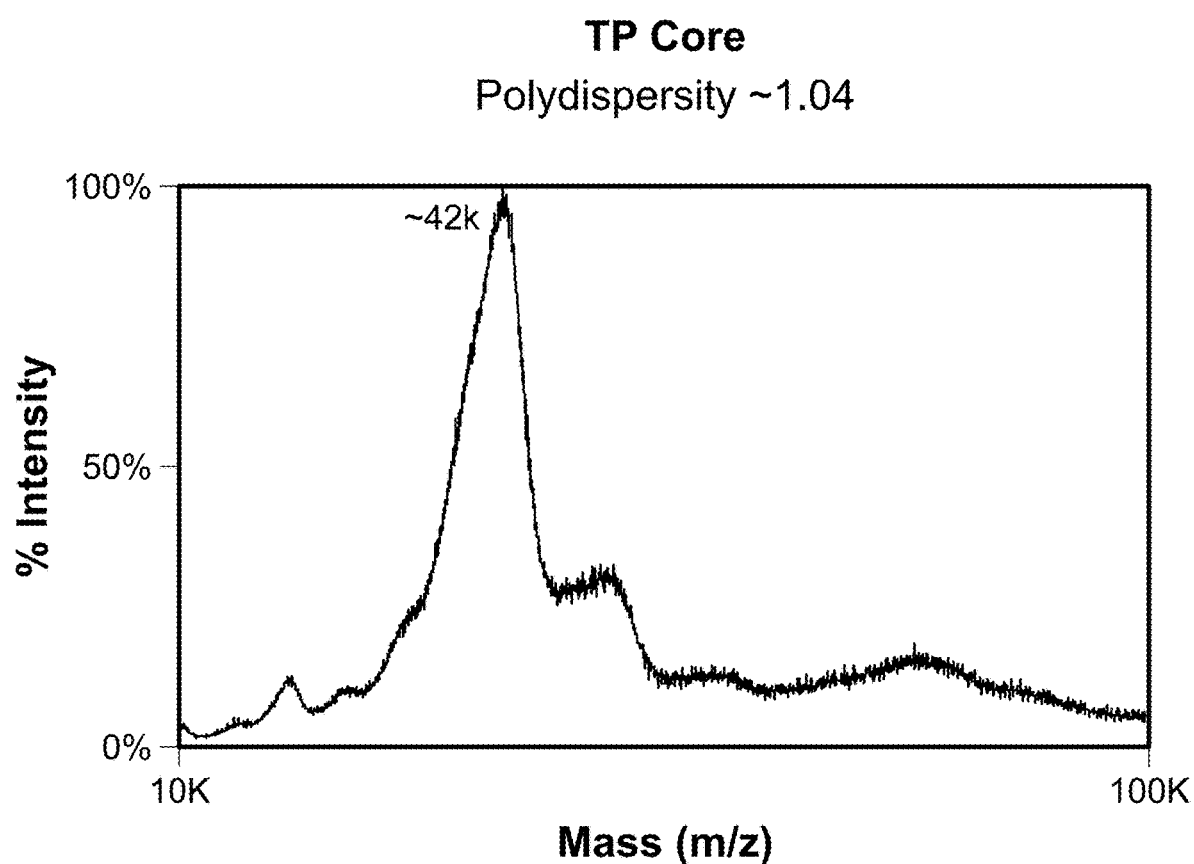

FIGS. 13A and 13B show the MALDI analysis of a multi-armed PEG comprising a hexaglycerol (HGEO) core (Sunbright® HGEO-400MA, NOF America, Corp.) and a tripentaerythritol (TP) core (8ARM (TP)-PEG-MAL, Jen-Kem Technology, USA) (13A: HGEO core; 13B: TP core).

Figure 14A:
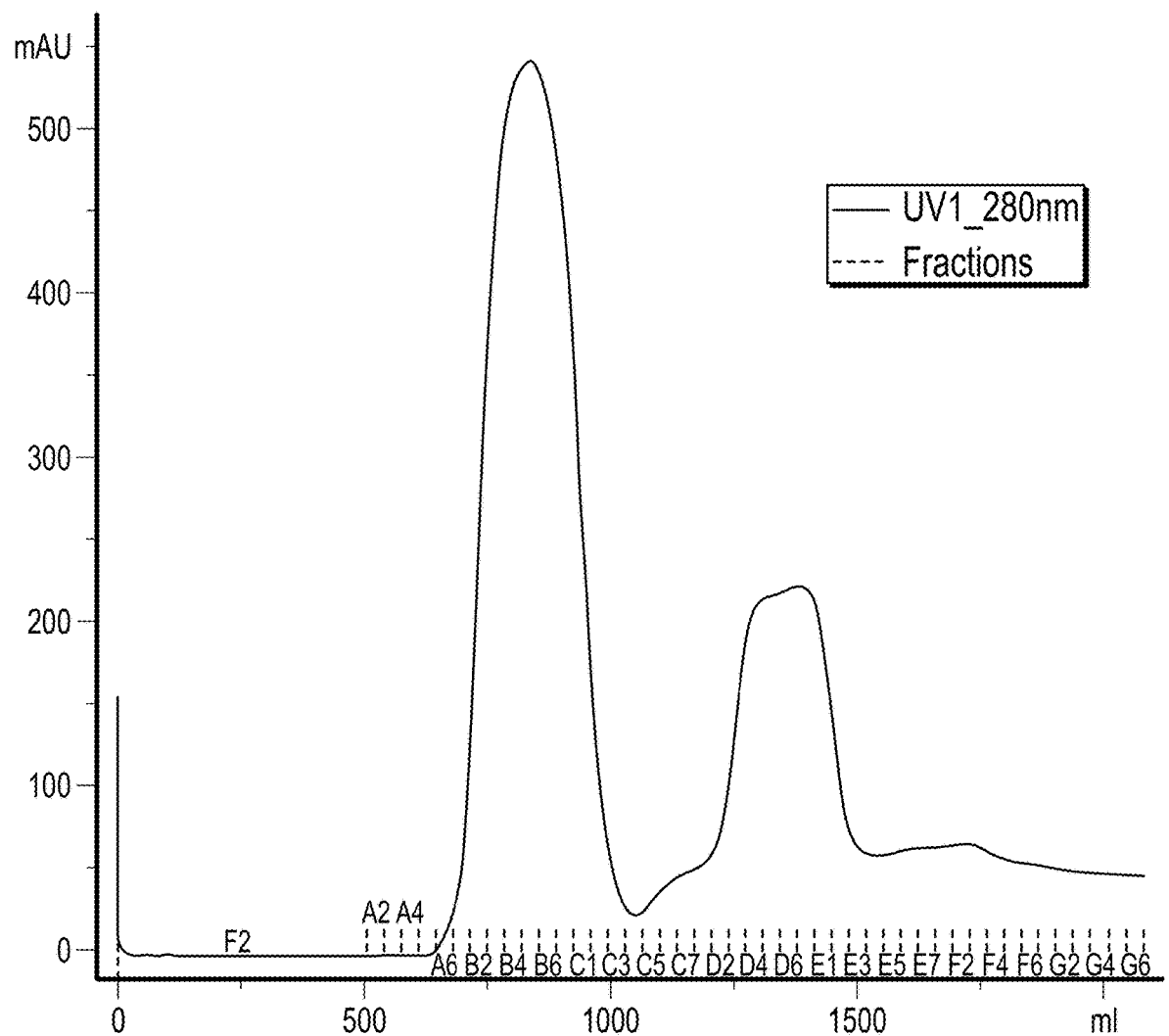
Figure 14B:
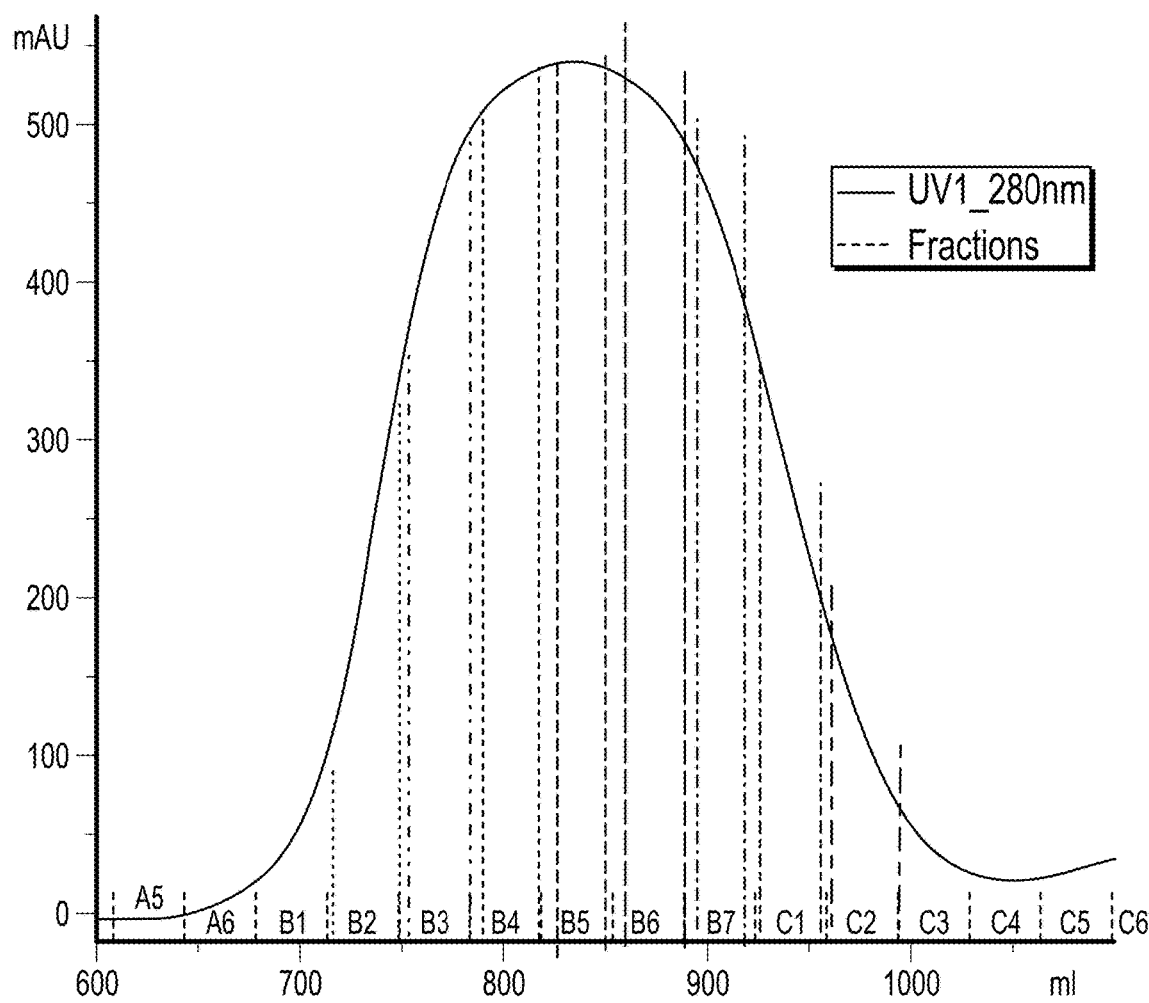
Figure 14C:
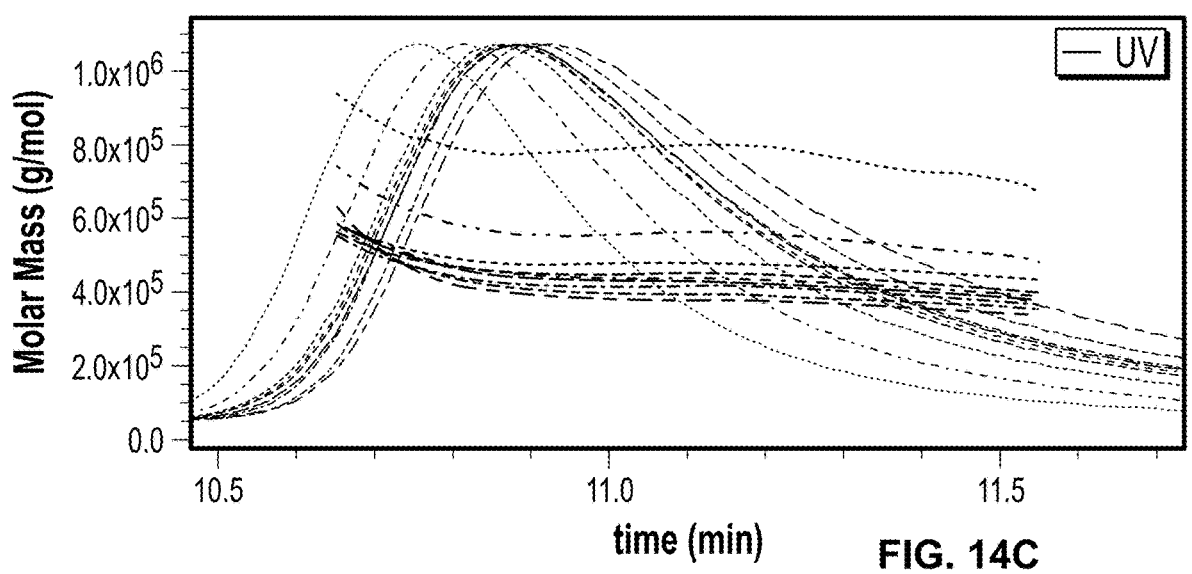

FIGS. 14A-14C show the results of a purification of the AFD.v14.C+TP octamer by Size Exclusion Chromatography (SEC) on a Sephacryl S-300 HR (GE Healthcare) column in 20 mM His-acetate, pH 5.5, 50 mM NaCl (isocratic gradient) (14A: initial chromatogram of the SEC column; 14B: an expansion of the peak from 600 mL to 1100 mL; 14C: MALS profile of the chromatogram fractions collected during the purification shown in 14B).

Figure 15A:
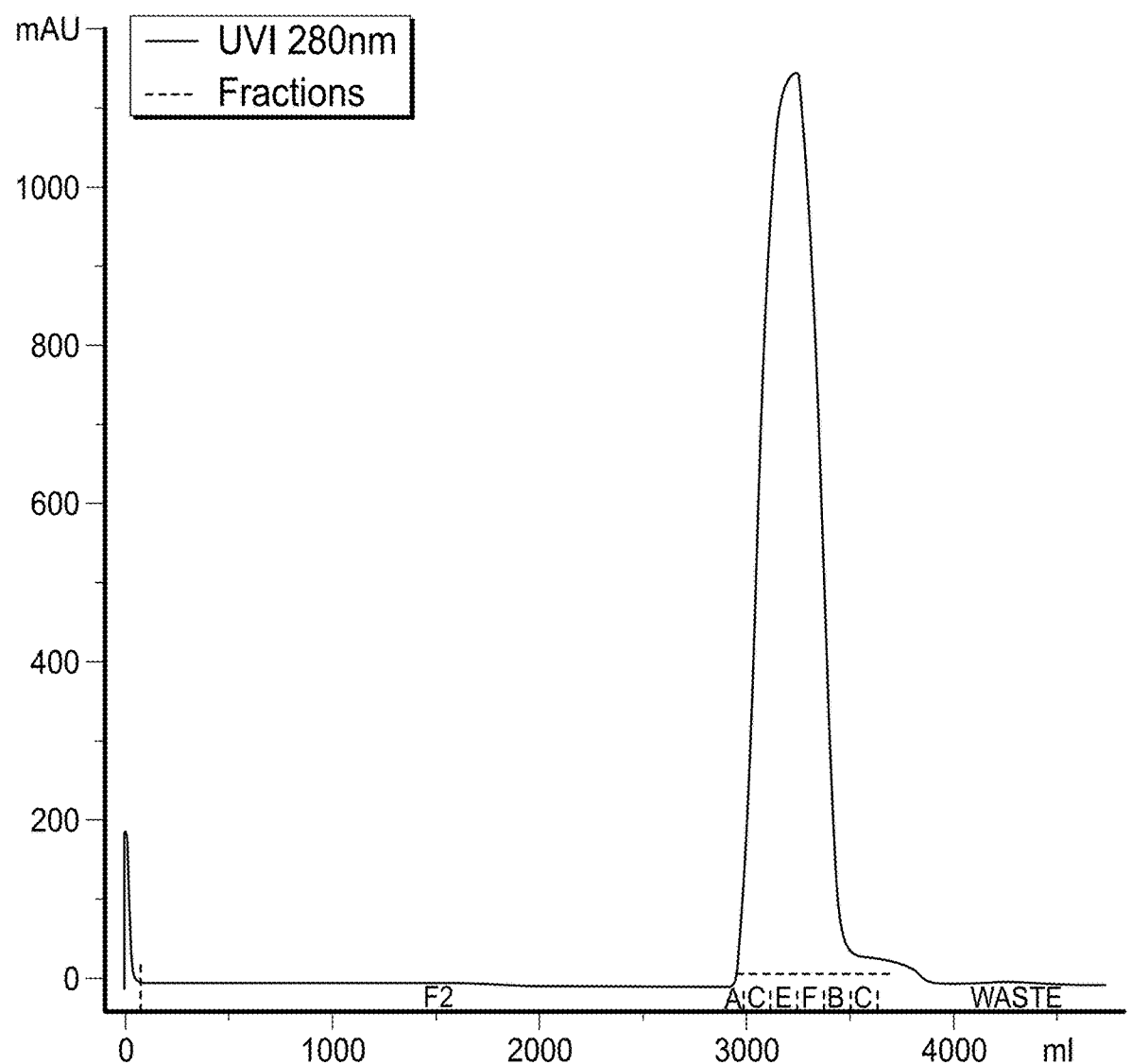
Figure 15B:
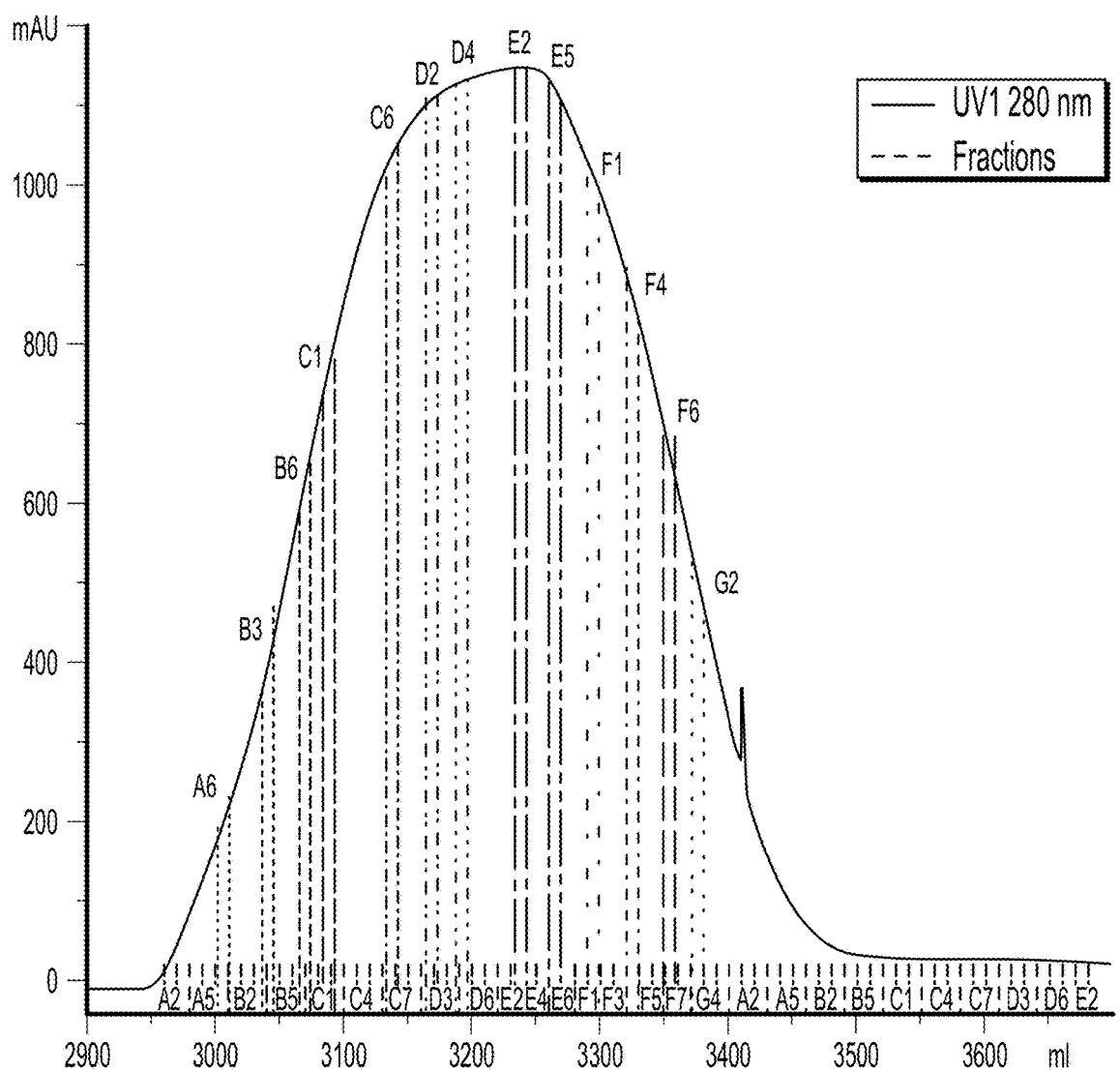
Figure 15C:
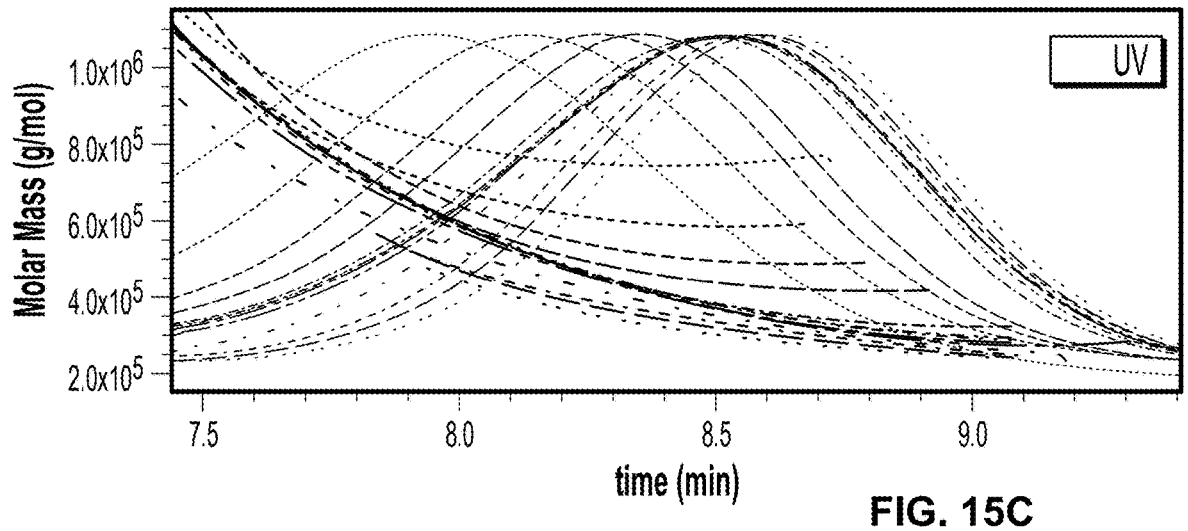

FIGS. 15A-15C show the results of a purification of the AFD.v14.C+HG octamer by SEC on a Sephacryl S-300 HR (GE Healthcare) column in 20 mM His-acetate, pH 5.5, 50 mM NaCl (isocratic gradient) (15A: initial chromatogram of the SEC column; 15B: enlargement of the chromatogram of 15A from 2900-3600 mL; 15C: MALS profile of the chromatogram fractions collected during the purification shown in FIG. 15B).

Figure 16A:
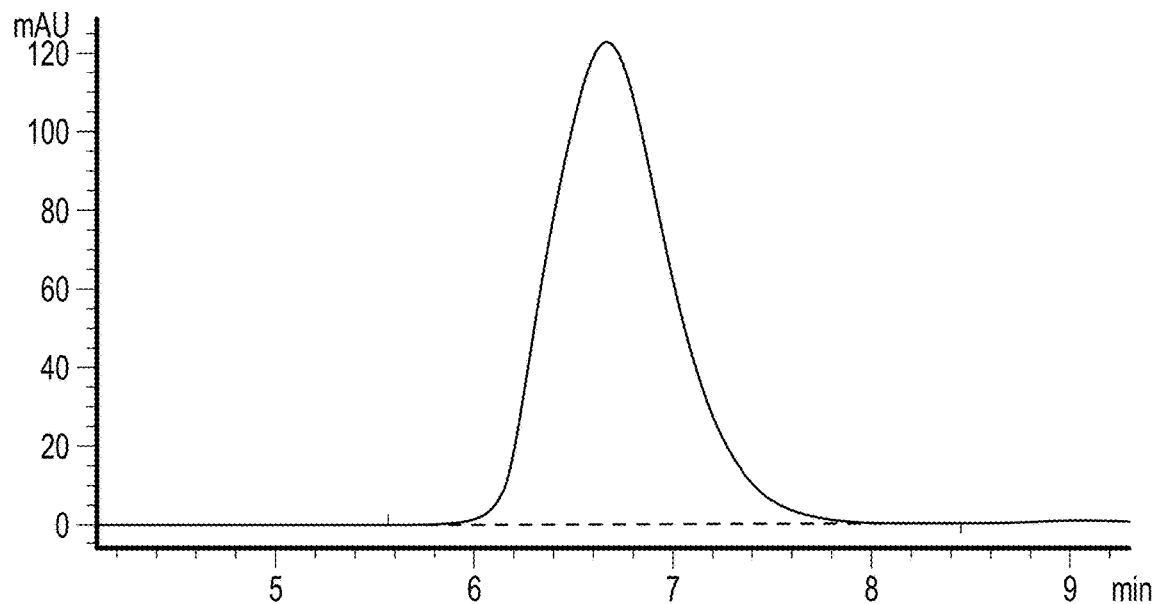
Figure 16B:
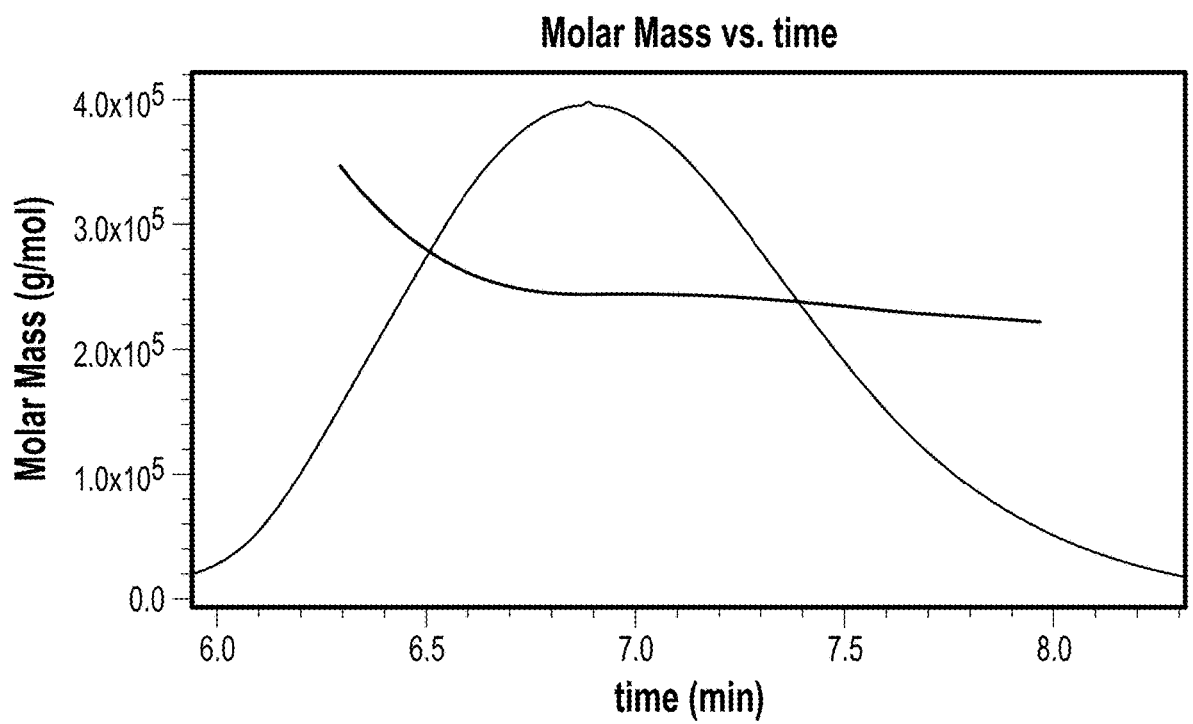

FIGS. 16A-16B show the results of an analysis of the AFD.v14.C+HG octamer using a Sephacryl S-400 HR (GE Healthcare) column in PBS, pH 7.4 (16A: initial chromatogram of the column; 16B: MALS profile of the chromatogram in FIG. 16A).

Figure 17A:
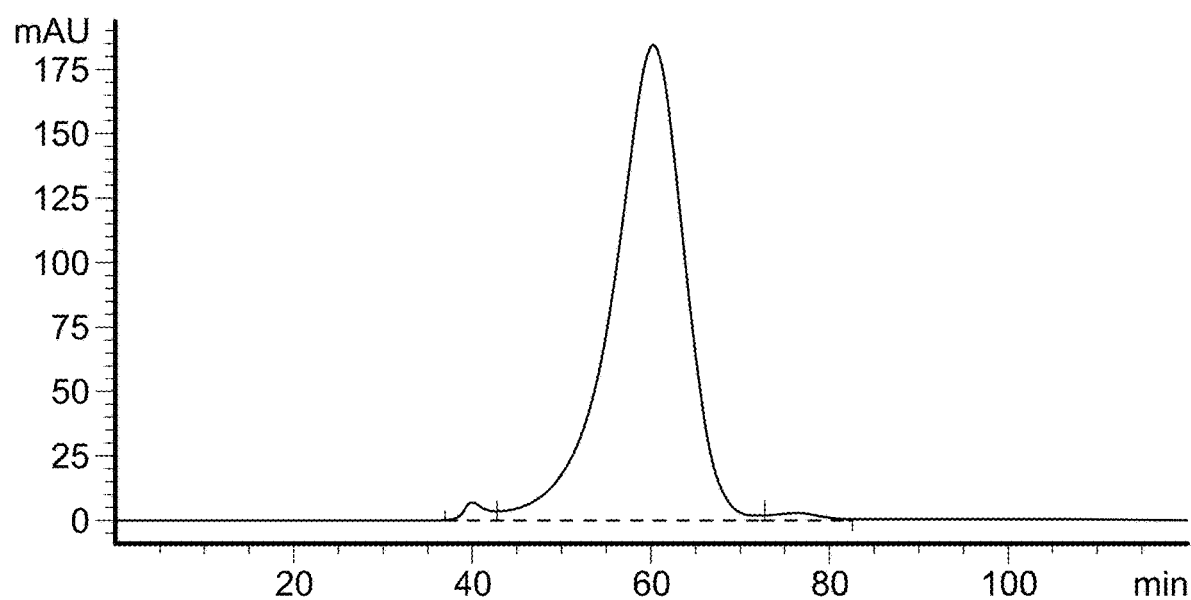
Figure 17B:
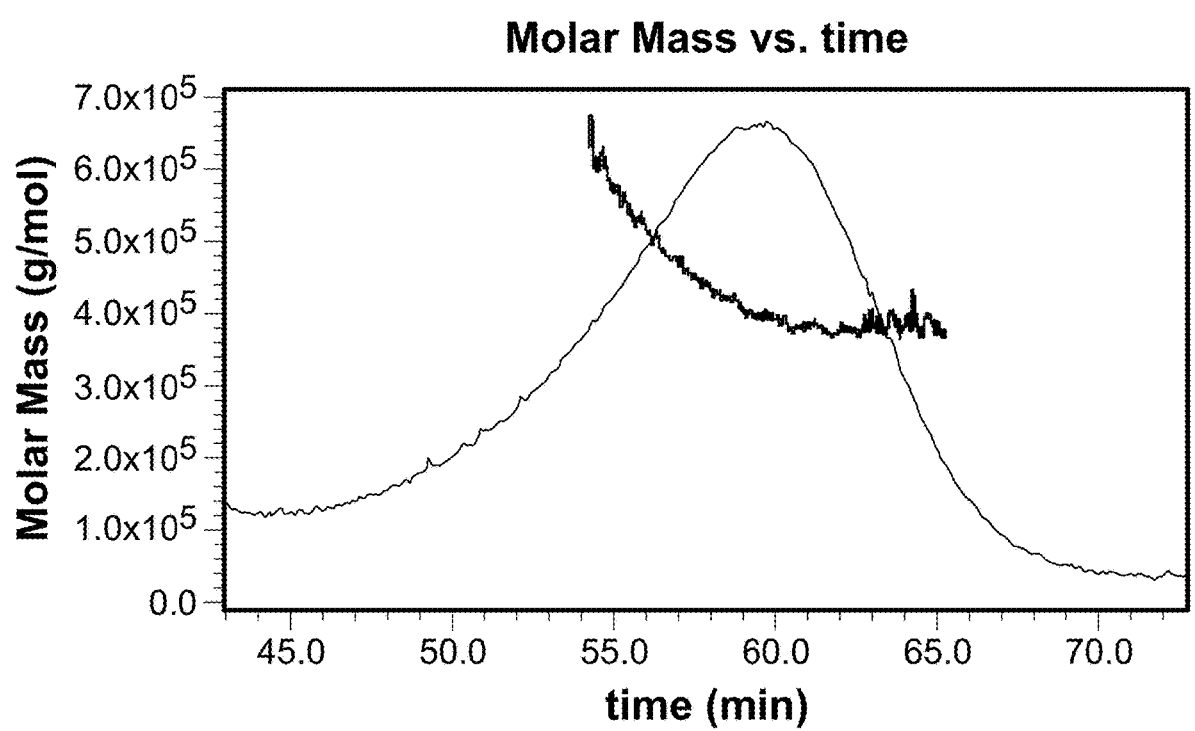

FIGS. 17A-17B show the results of a purification of the AFD.v14.C+HGEO octamer by SEC on a Sephacryl S-300 HR (GE Healthcare) column in 20 mM His-acetate, pH 5.5, 50 mM NaCl (isocratic gradient), followed by SEC-MALS characterization on Sephacryl S-400 HR at 0.25 mL/minute in PBS, pH 7.4 (17A: initial chromatogram of the SEC S-400 column; 17B: MALS profile of the chromatogram fractions in FIG. 17A).

Figure 18A:
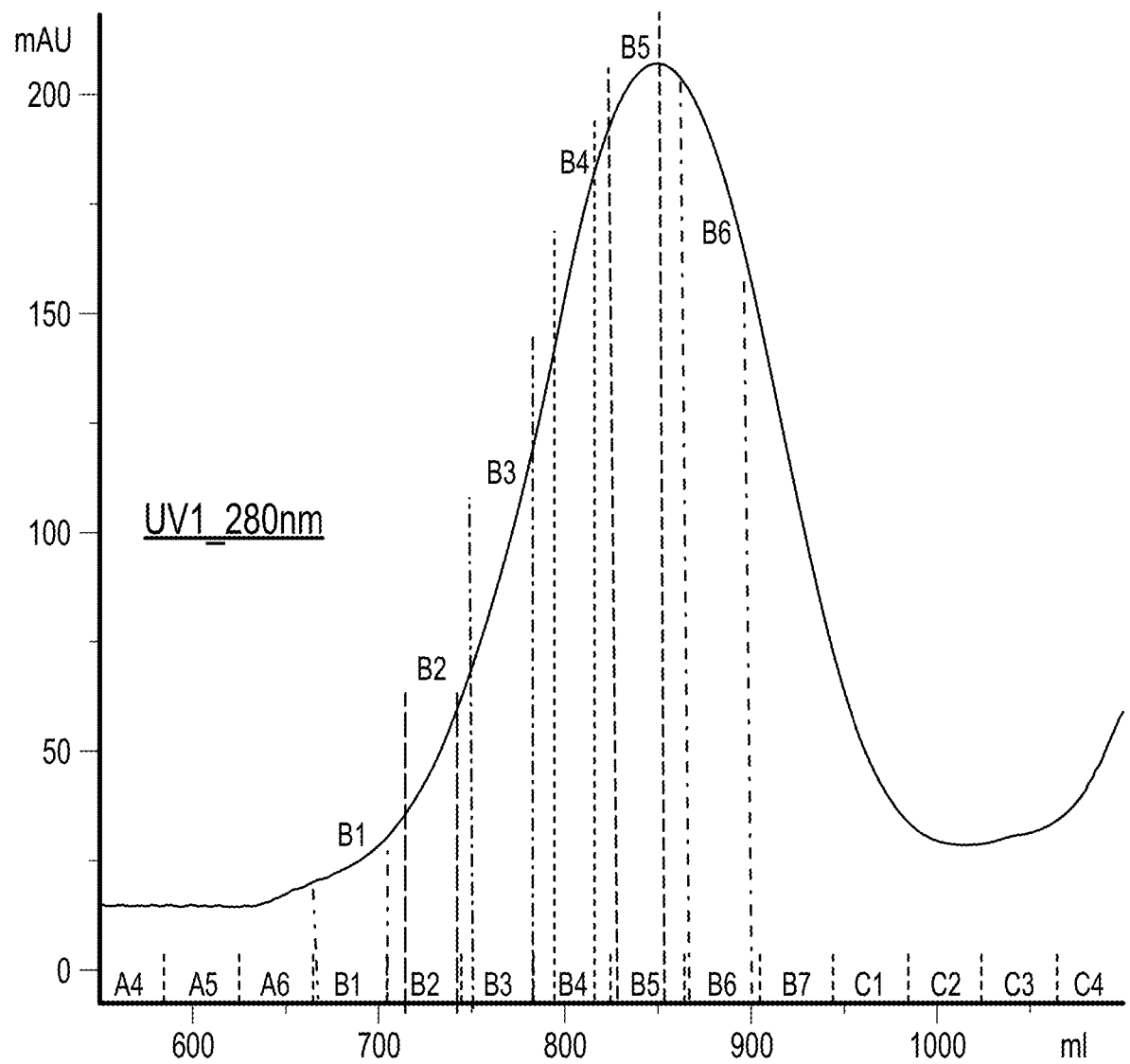
Figure 18B:
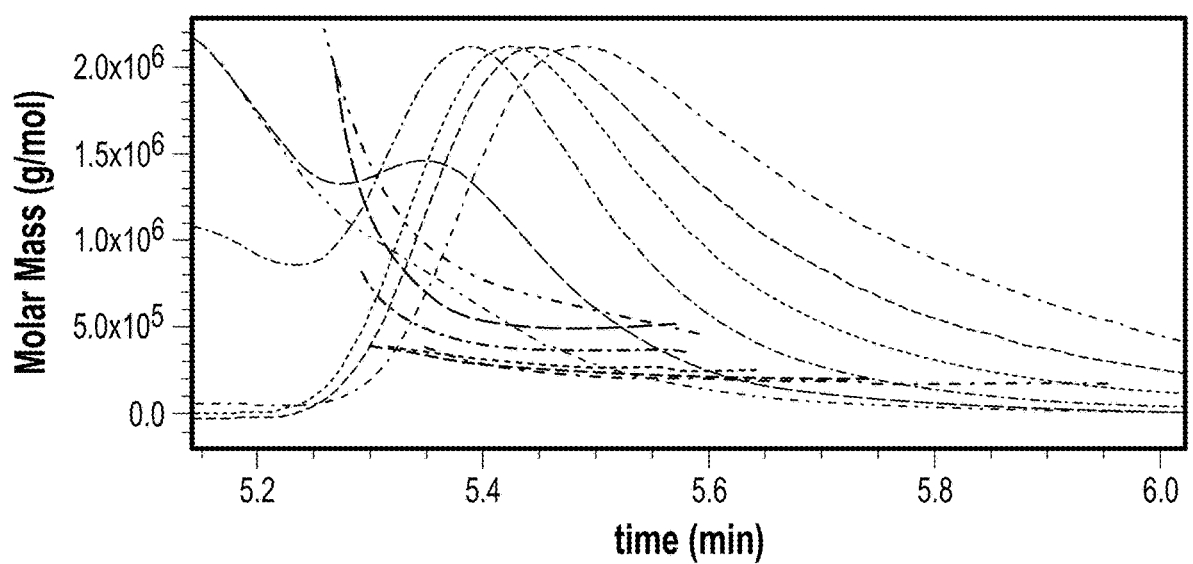

FIGS. 18A-18B show the results of a purification of the AFD.v14.C+HGEO octamer by SEC on a Sephacryl S-300 HR (GE Healthcare) column in 20 mM His-acetate, pH 5.5, 50 mM NaCl (isocratic gradient), followed by SEC-MALS characterization on a Tosoh G3000PW column (18A: initial chromatogram of the SEC S-300 column; 18B: overlay of laser intensity for S-300 fractions from 18A using SEC-MALS with G3000PW column).

Figure 19A:
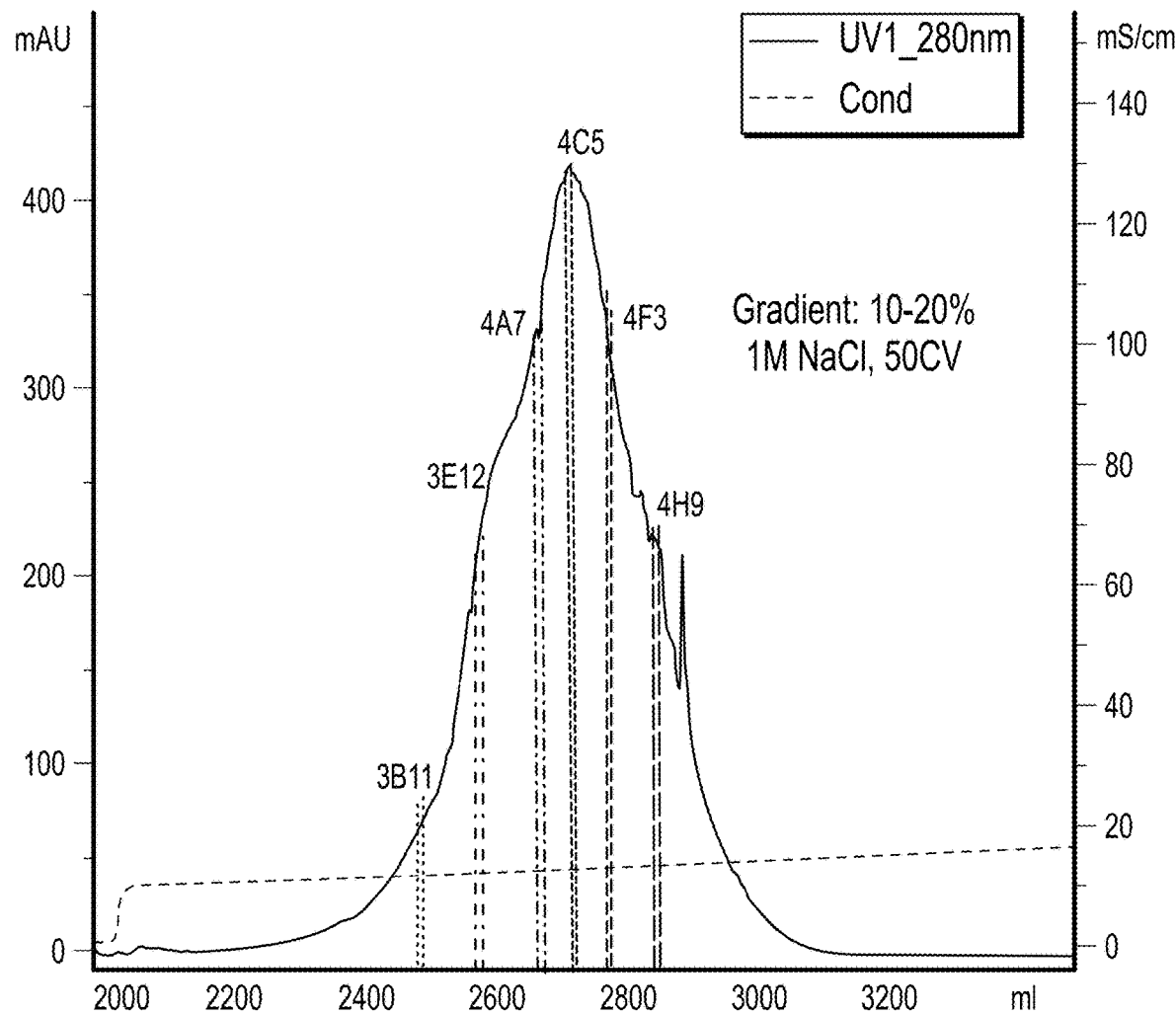
Figure 19B:
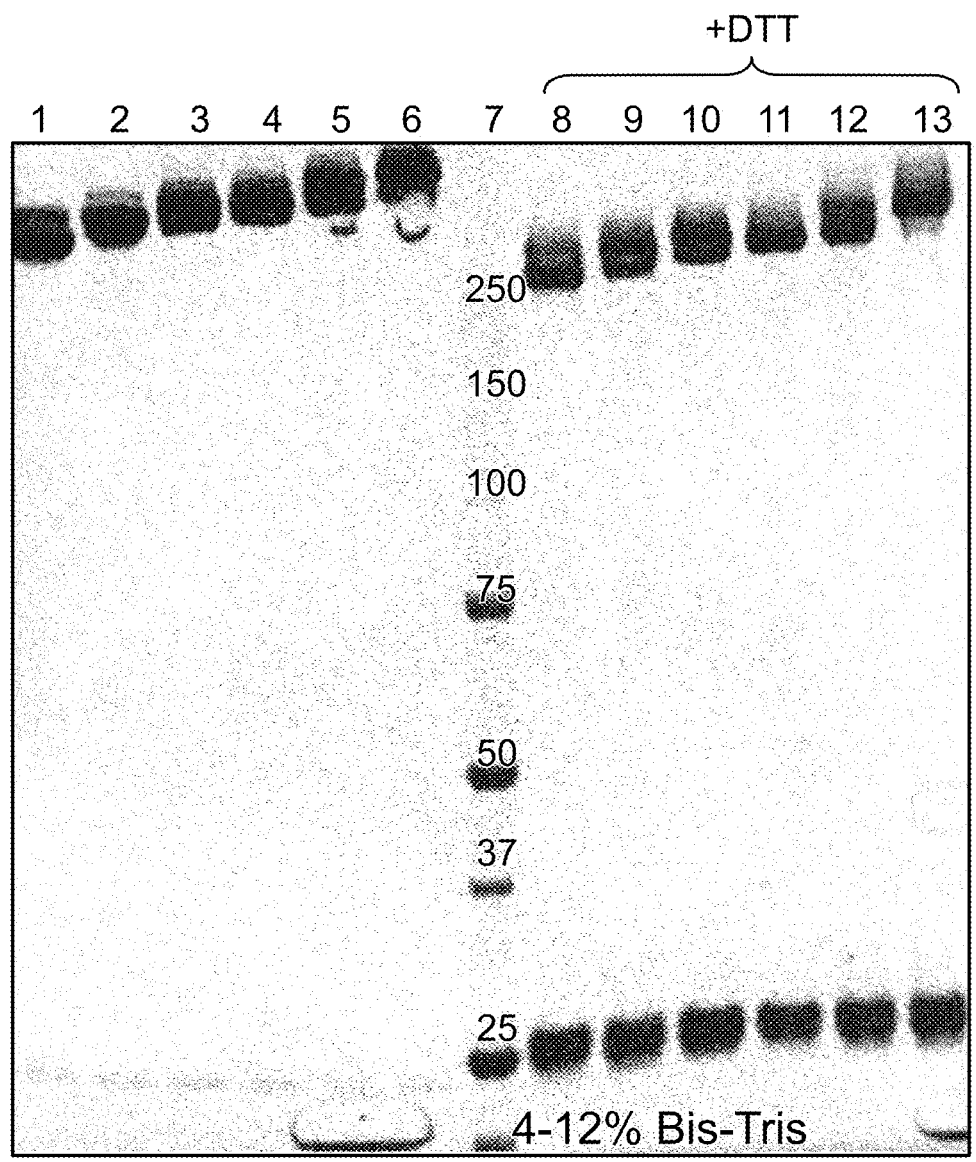
Figure 19C:
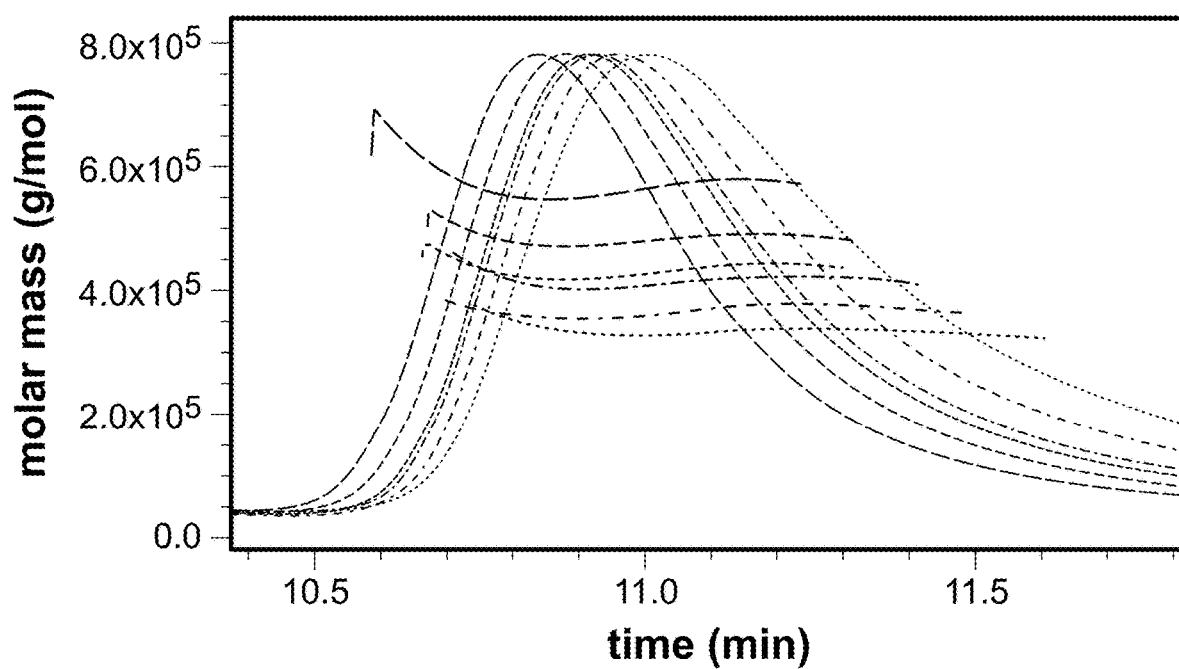

FIGS. 19A-19C show further purification of select fractions in Example 9a (shown in FIG. 14) by cation exchange chromatography (CEX) in Triton wash, 10-20% 1M NaCl gradient over 50CV (19A: initial chromatogram of the CEX column; 19B: SEC gel of the fractions from the CEX column; 19C: MALS profile of the chromatogram fractions in FIG. 19A).

Figure 20:
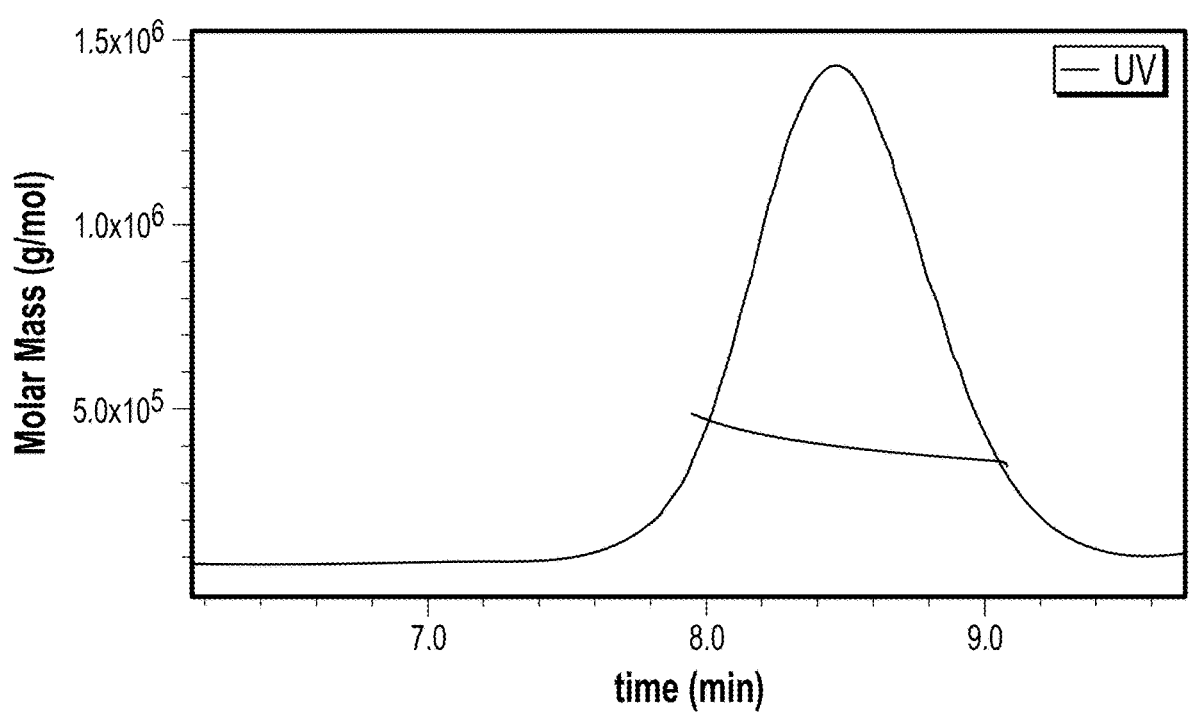

FIG. 20 shows the final analytical run of the AFD.v14.C+TP octamer after CEX purification.

Figure 21A:
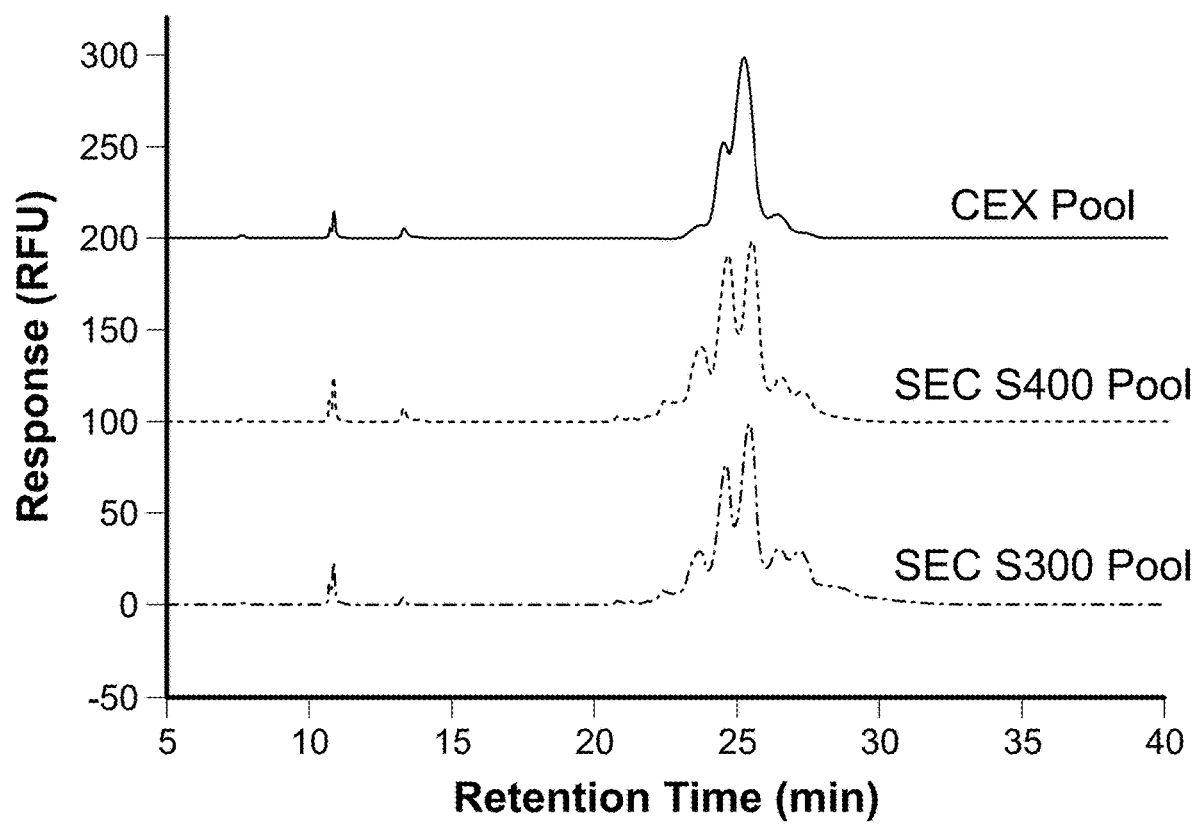
Figure 21B:
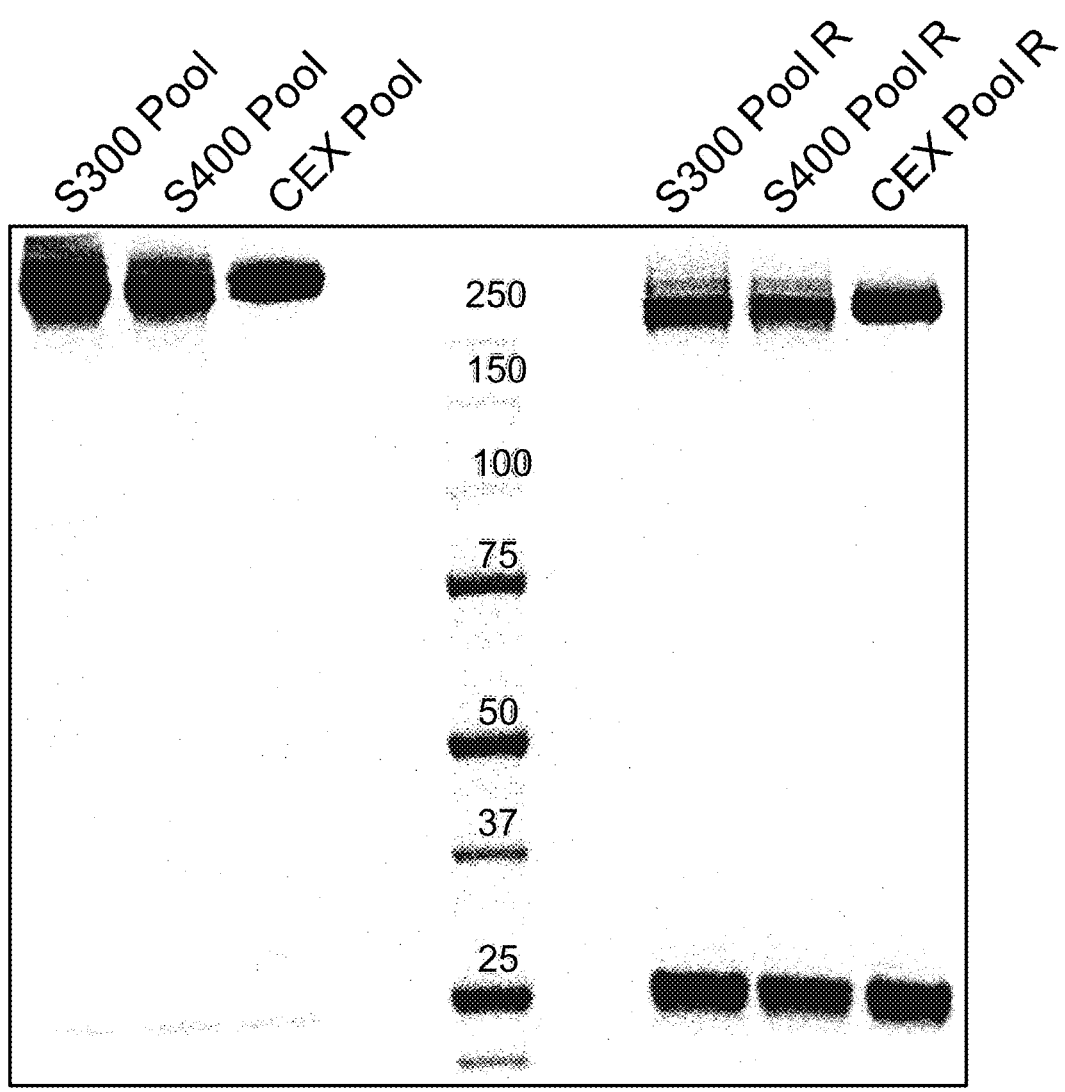

FIGS. 21A-21B compare the results of the purification methods for the AFD.v14.C+TP octamer after cation exchange chromatography (CEX), SEC chromatography on the SEC S-400 HR column, or SEC chromatography on the SEC S-300 HR column (21A: stacked display of the chromatograms of the three different purification columns; 21B: SEC gel comparing the samples from the three different purification columns).

Figure 22A:
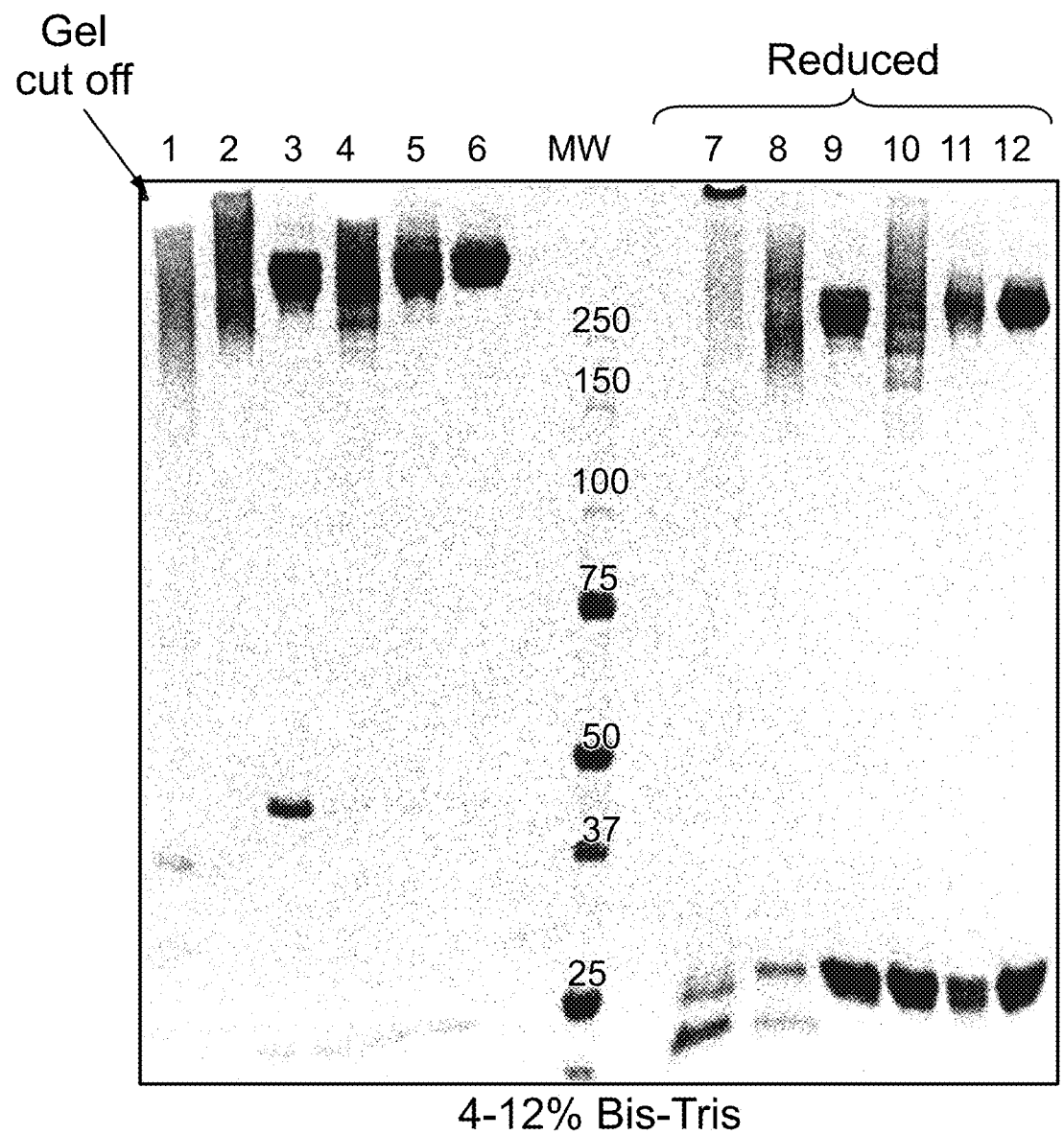
Figure 22B:
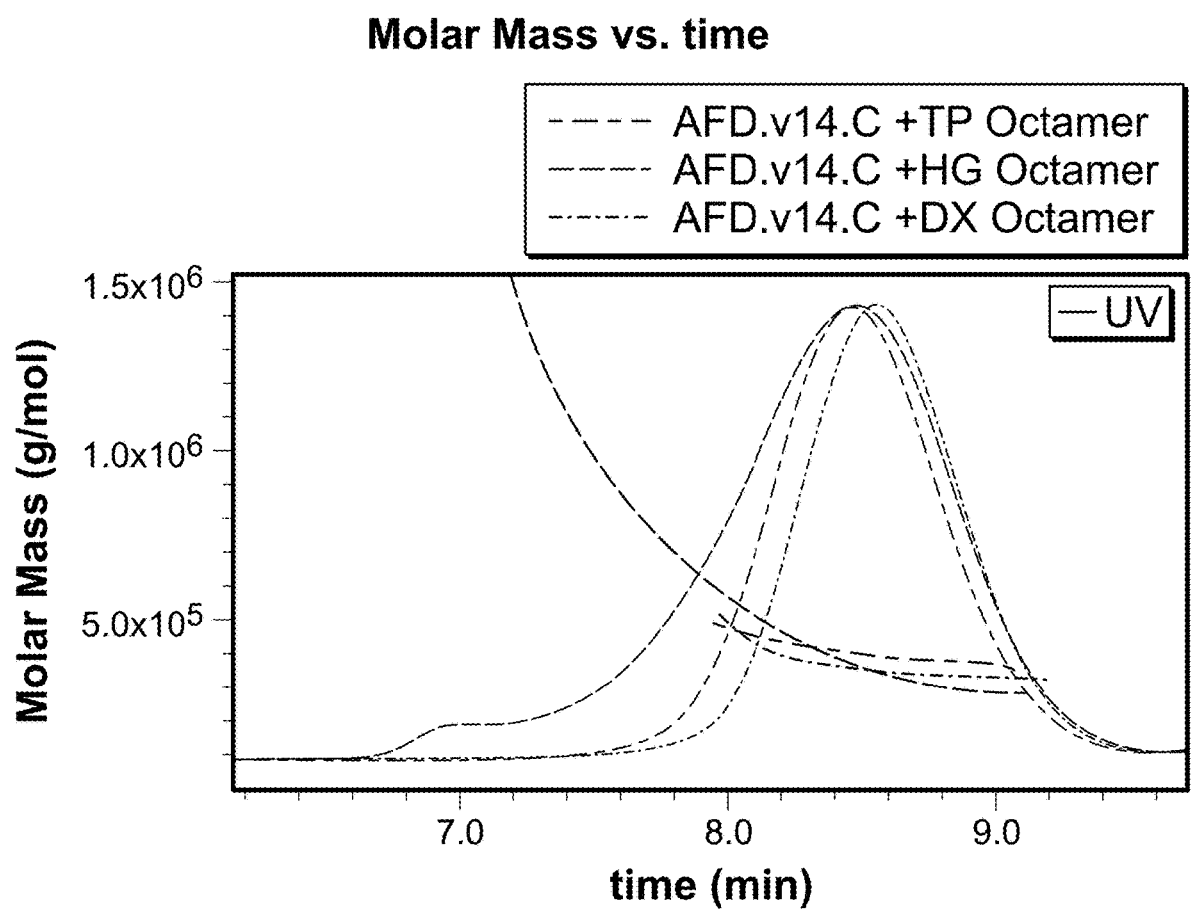

FIGS. 22A-22B compare PEG-Fab conjugates prepared with PEGs having different cores (22A: SEC gel comparing the purified samples of the conjugates with the different cores; 22B: MALS profile of the conjugates prepared with the different cores).

Figure 23:
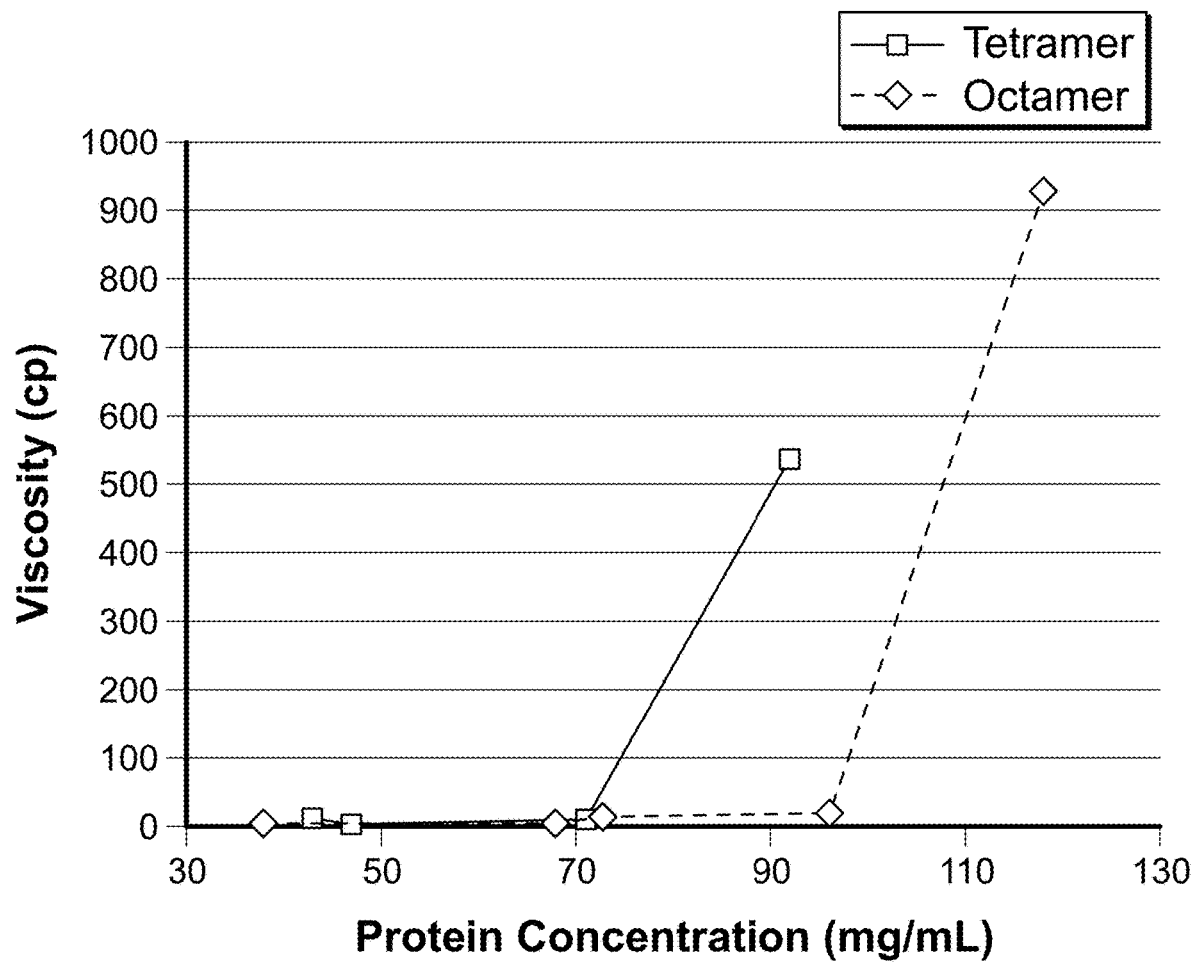

FIG. 23 shows the viscosity of the AFD.v14.C+HG octamer and a PEG-Fab conjugate prepared from Sunbright® PTE-400MA from NOF America Corp. (a tetramer) as a function of AFD.v14 concentration.

Figure 24:
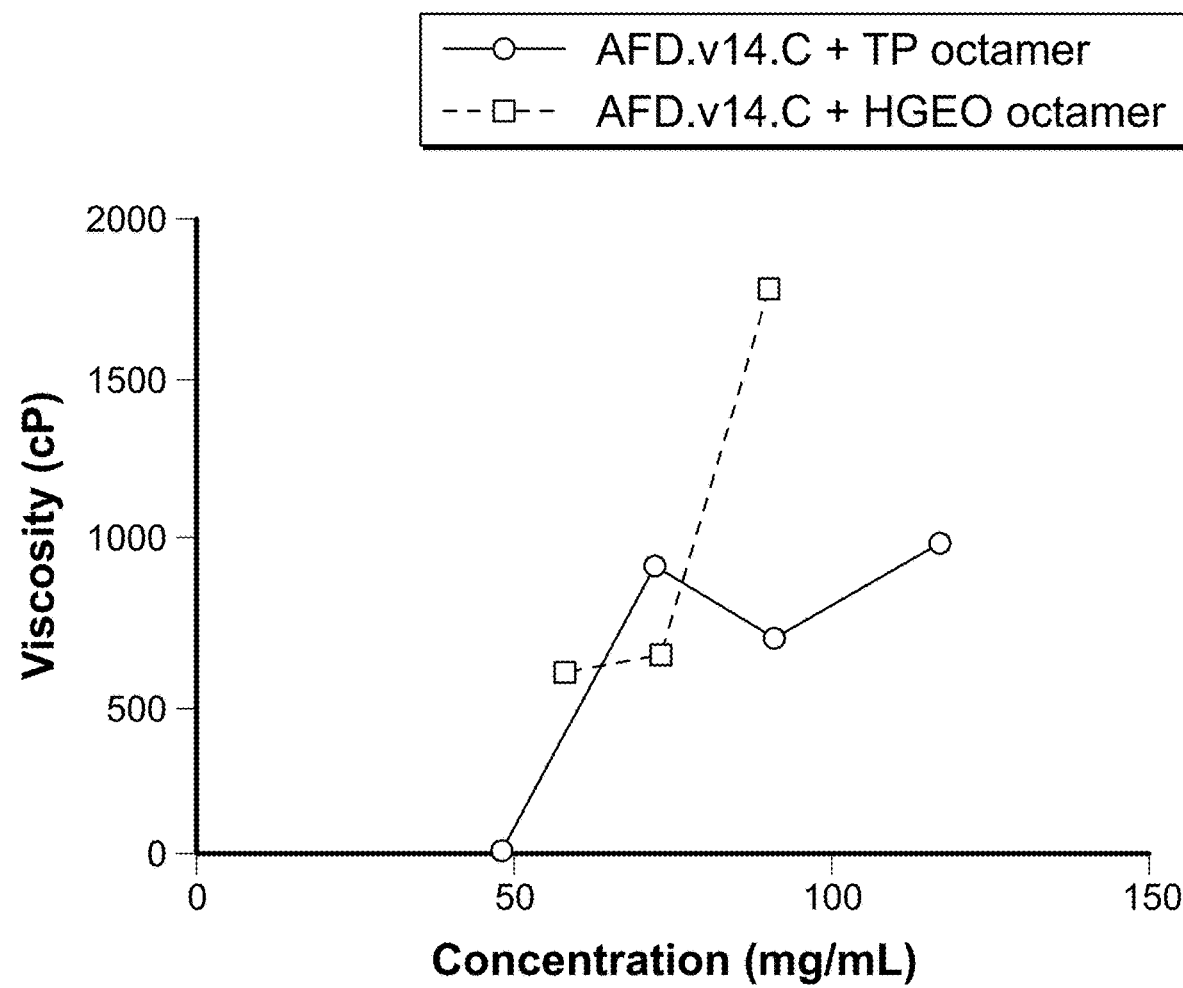

FIG. 24 shows the viscosity of the AFD.v14.C+TP octamer and the AFD.v14.C+HGEO octamer as a function of AFD.v14 concentration in 20 mL His-Ace, pH 6.5 and 50 mM NaCl at 20° C.

Figure 25A:
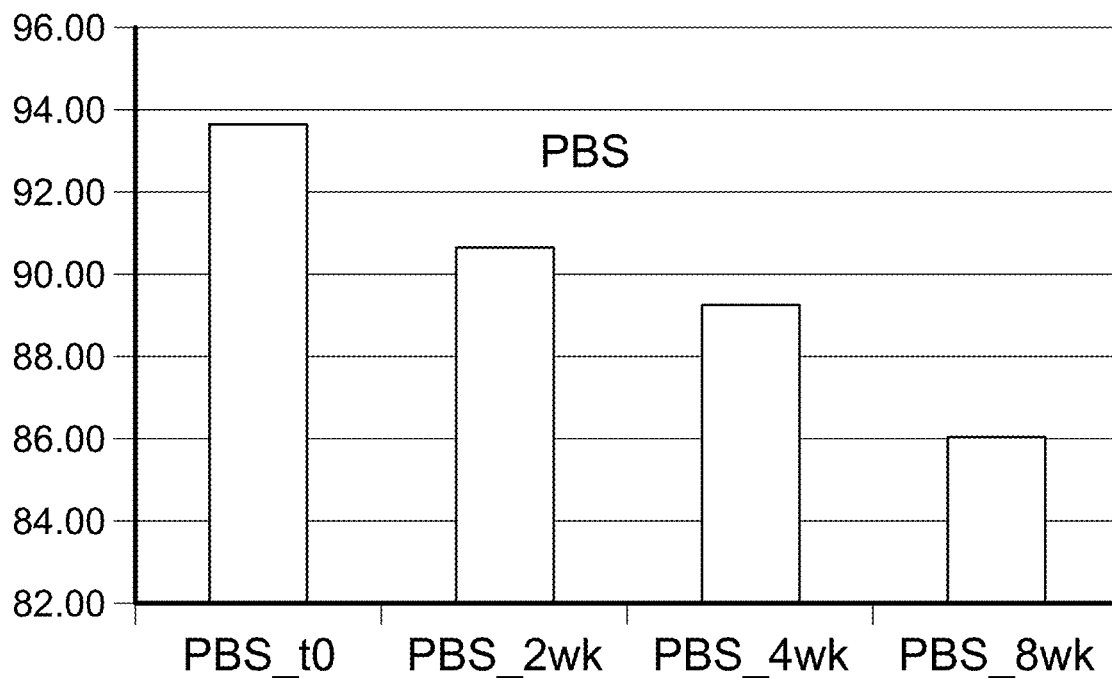
Figure 25B:
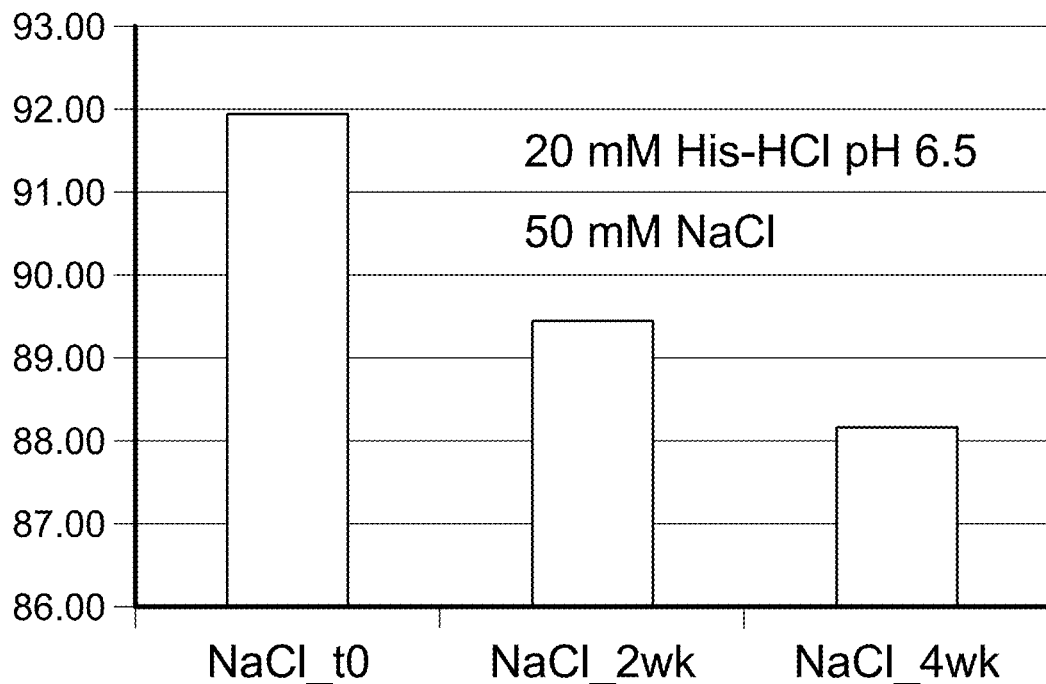

FIGS. 25A and 25B show the thermal stability of the AFD.v14.C+TP octamer in 10 mg/mL, PBS (25A) and 10 mg/mL of 20 mM histidine HCl, 50 mM NaCl, at pH 6.5 (25B) as a function of time.

Figure 26:
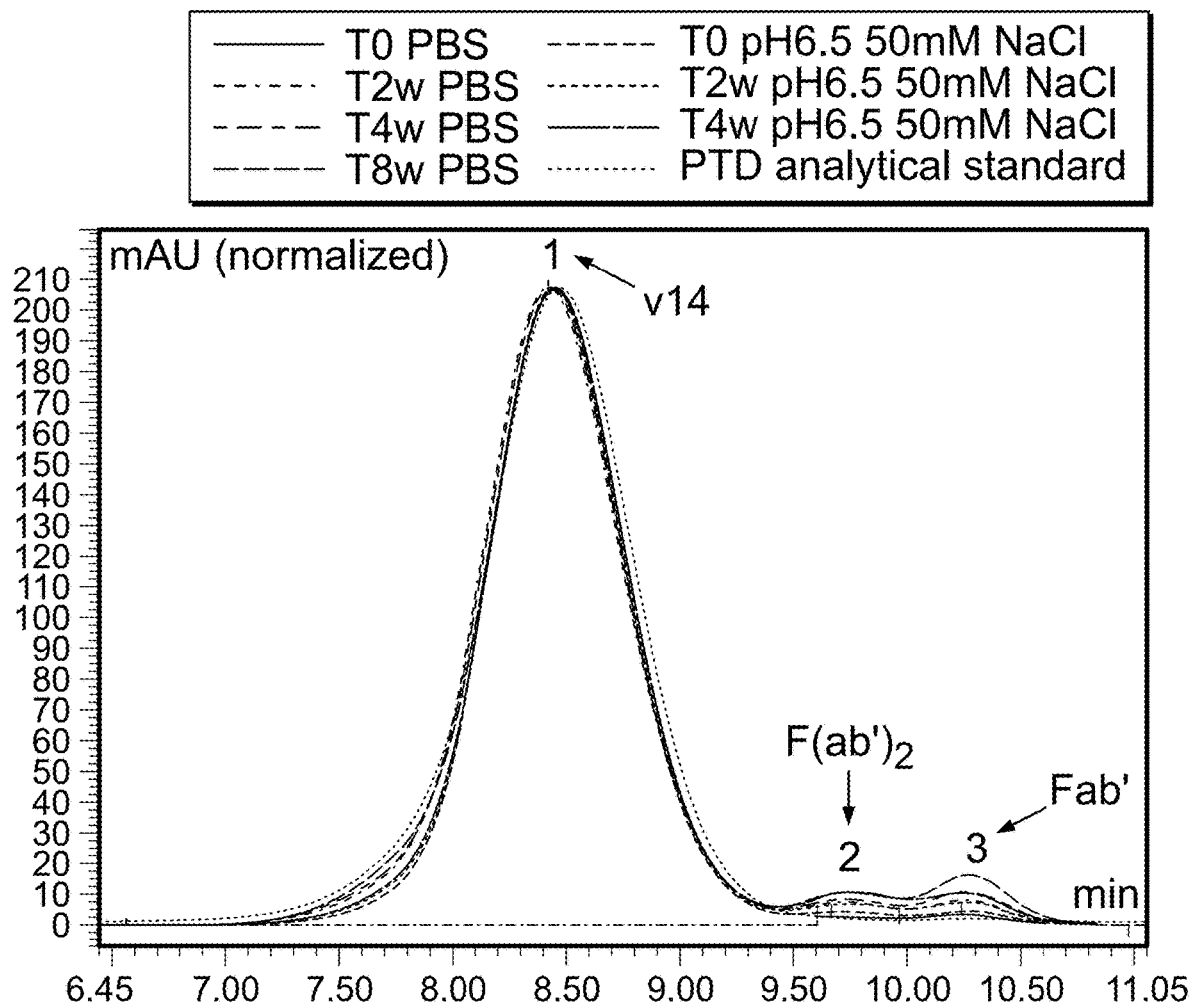
Figure 27:
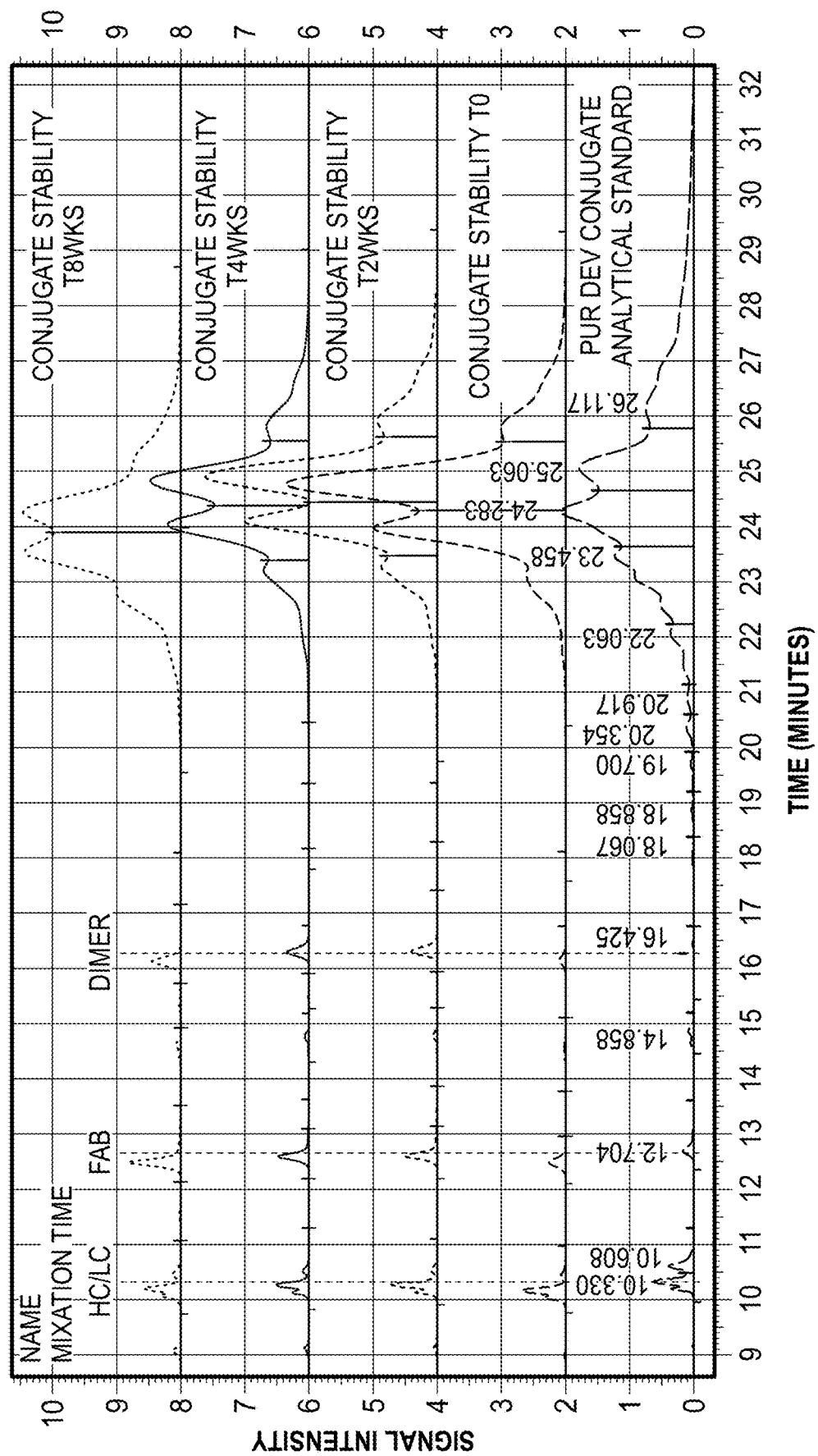

FIGS. 26 and 27 show the slow release of the Fab fragment and dimerization during the course of the thermal stability study (26: SEC-MALS analysis of the conjugate over time; 27: CE-SDS analysis of the conjugate over time).

Figure 28:
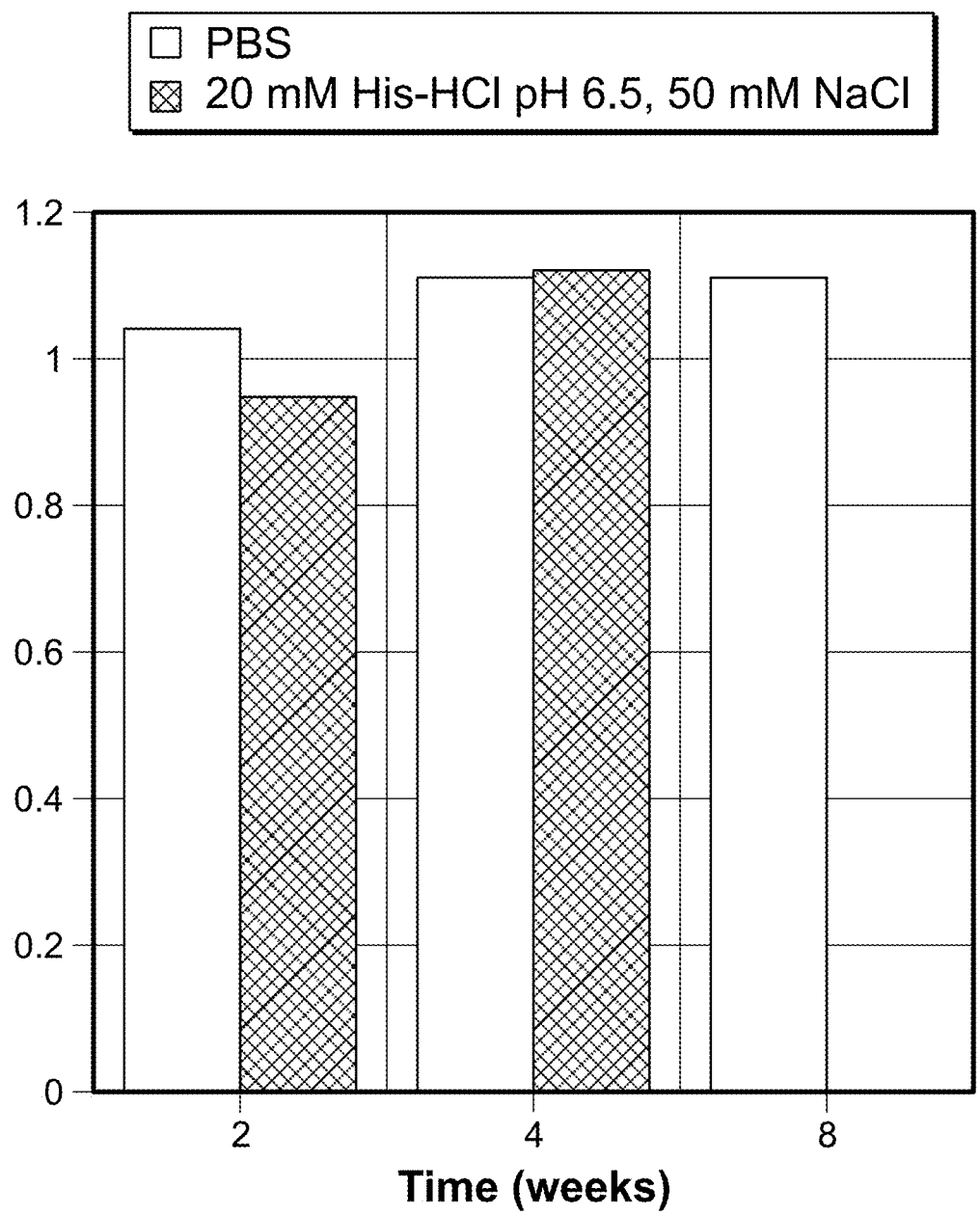

FIG. 28 shows the maintenance of binding capacity of the AFD.v14.C+TP octamer to Factor D during the thermal stability study as measured by surface plasmon resonance.

Figure 29A:
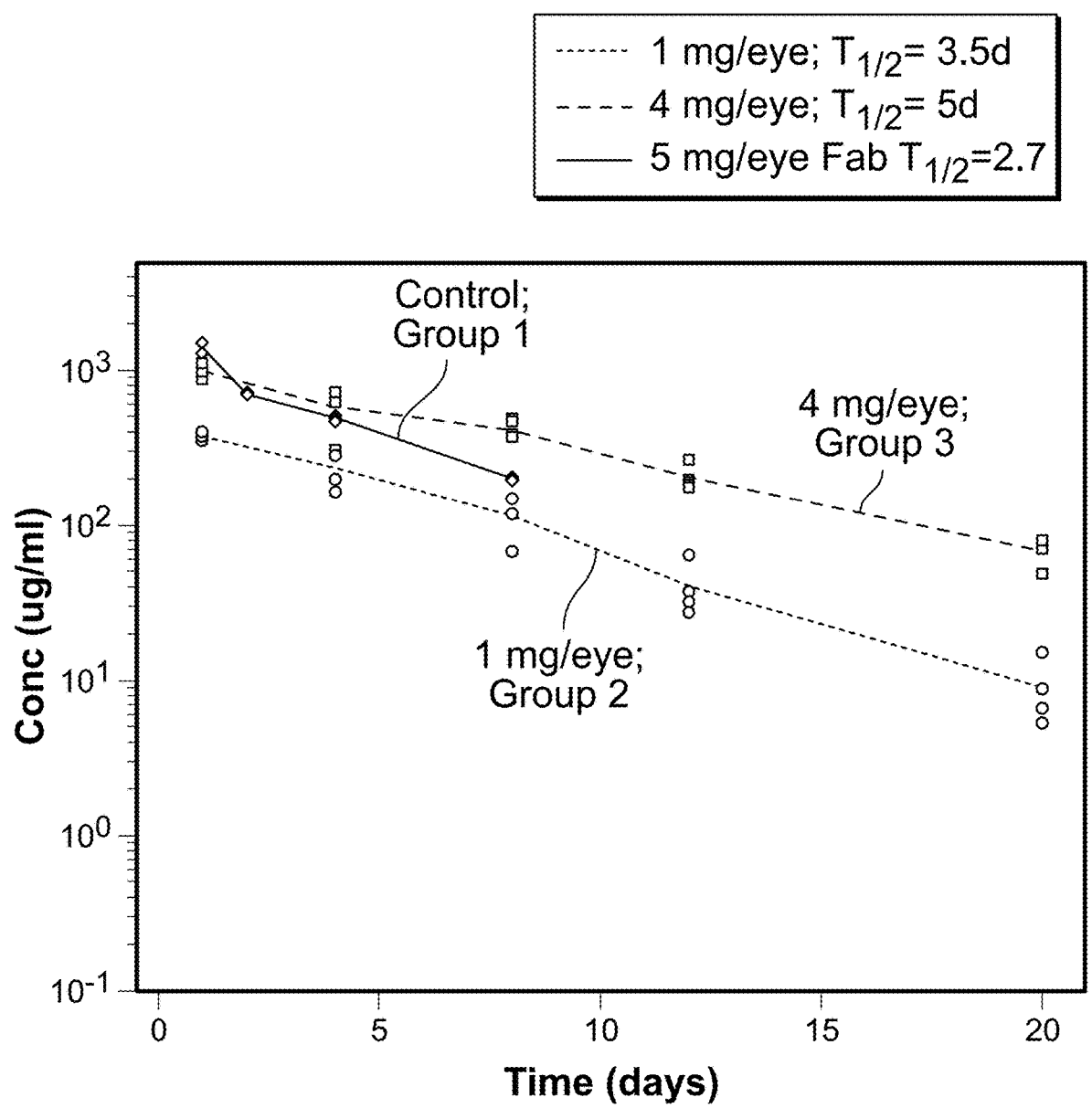
Figure 29B:
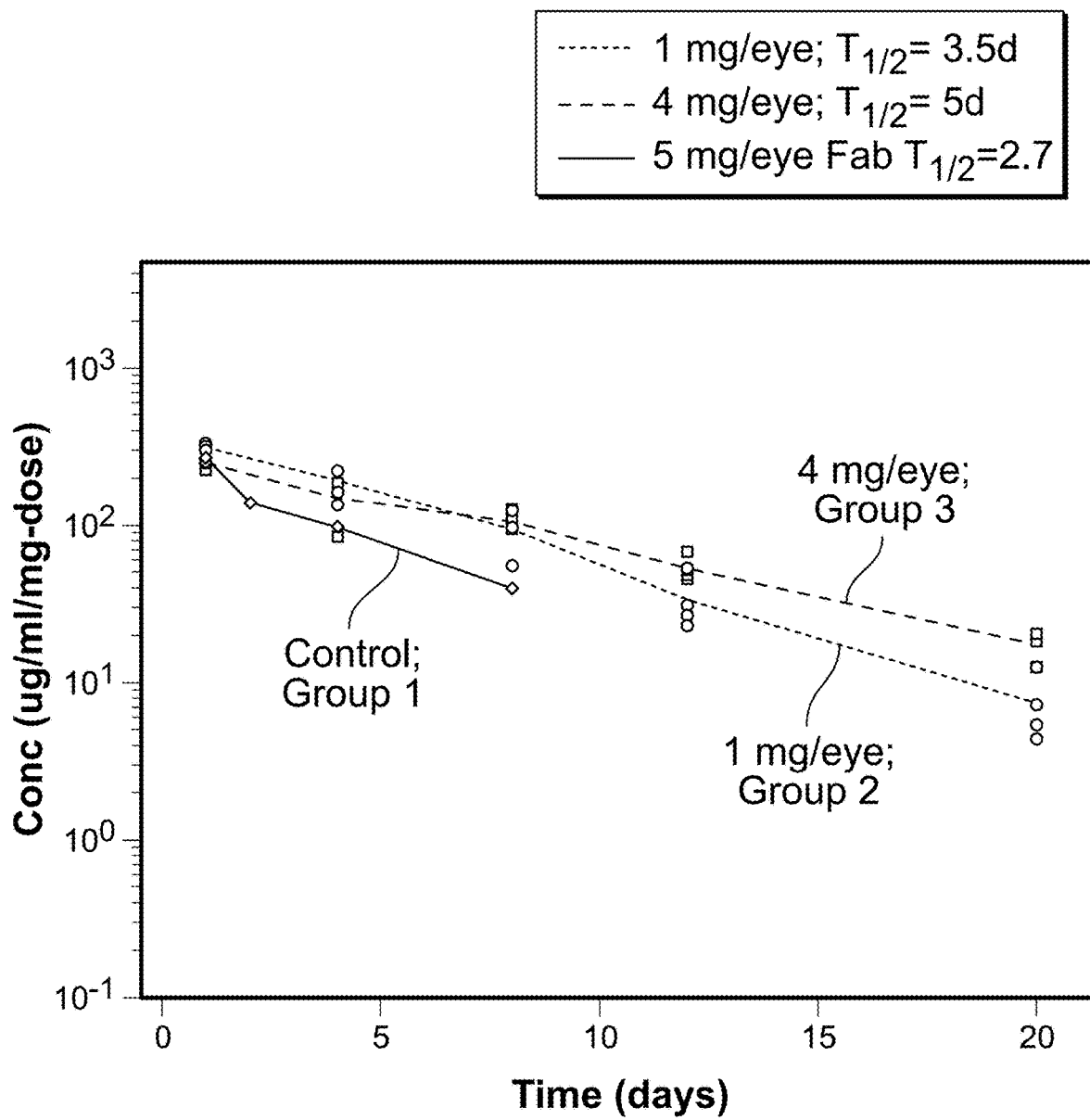

FIGS. 29A and 29B show the concentration versus time of AFD.v14 in cynomolgus monkey vitreous humor following administration of AFD.v14 or AFD.v14.C+TP octamer in a pharmacokinetic study (29A: vitreous humor concentration; 29B: vitreous humor concentration data normalized for dosing strength).

Figure 30A:
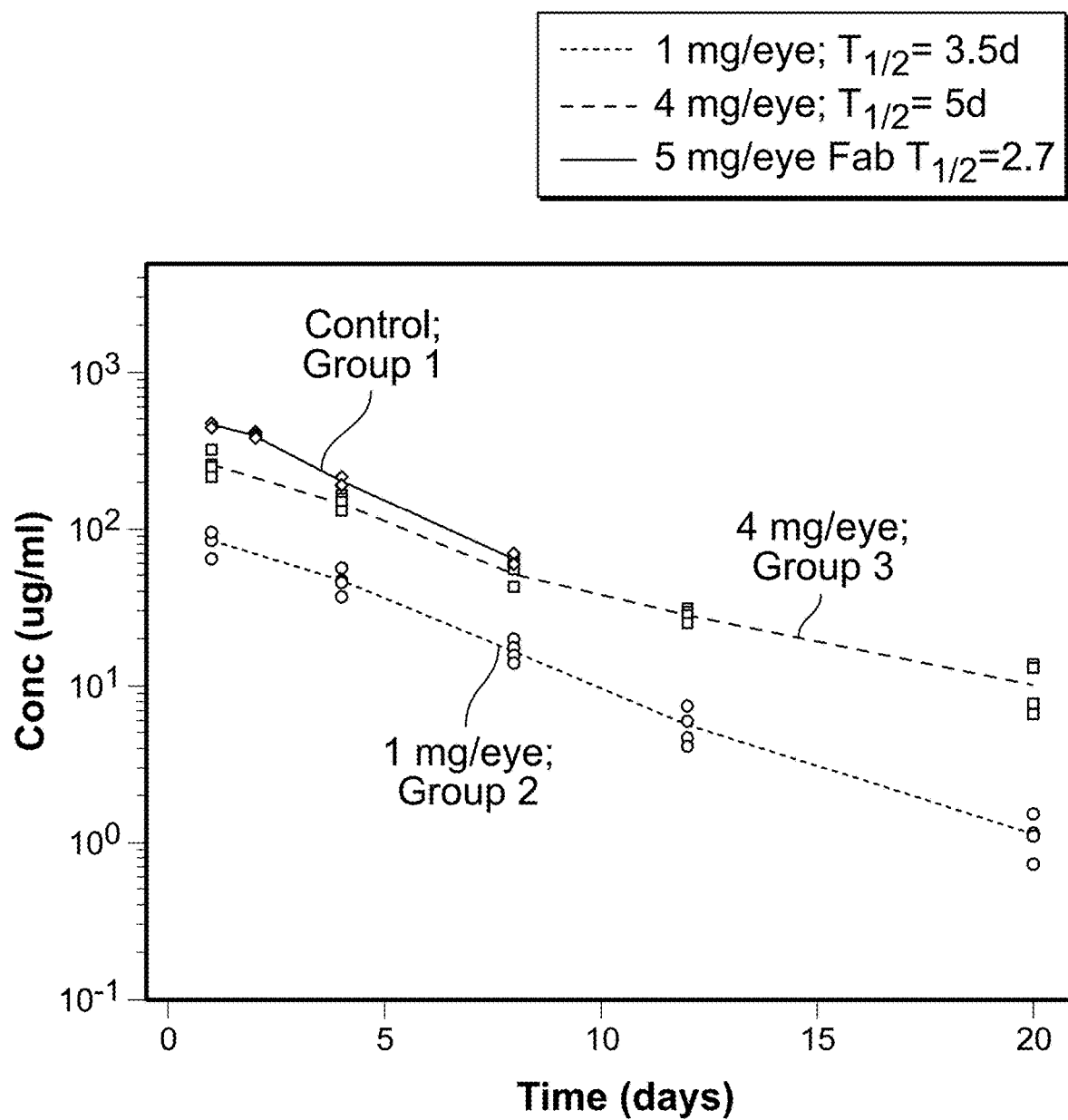
Figure 30B:
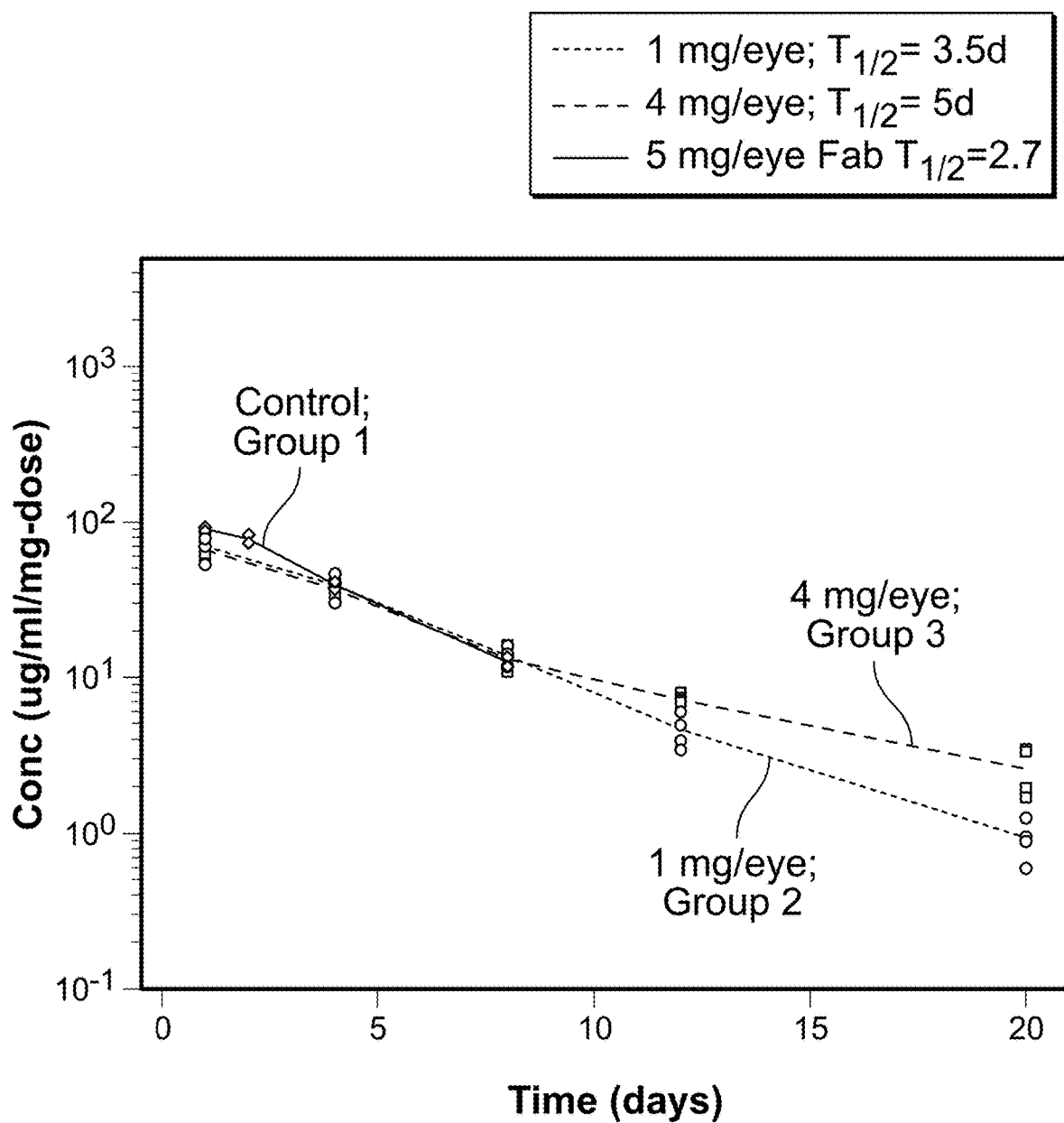

FIGS. 30A and 30B show the concentration versus time of AFD.v14 in cynomolgus monkey eye aqueous humor following administration of AFD.v14 or AFD.v14.C+TP octamer in a pharmacokinetic study (30A: eye aqueous humor concentration; 30B: eye aqueous humor concentration data normalize for dosing strength).

Figure 31A:
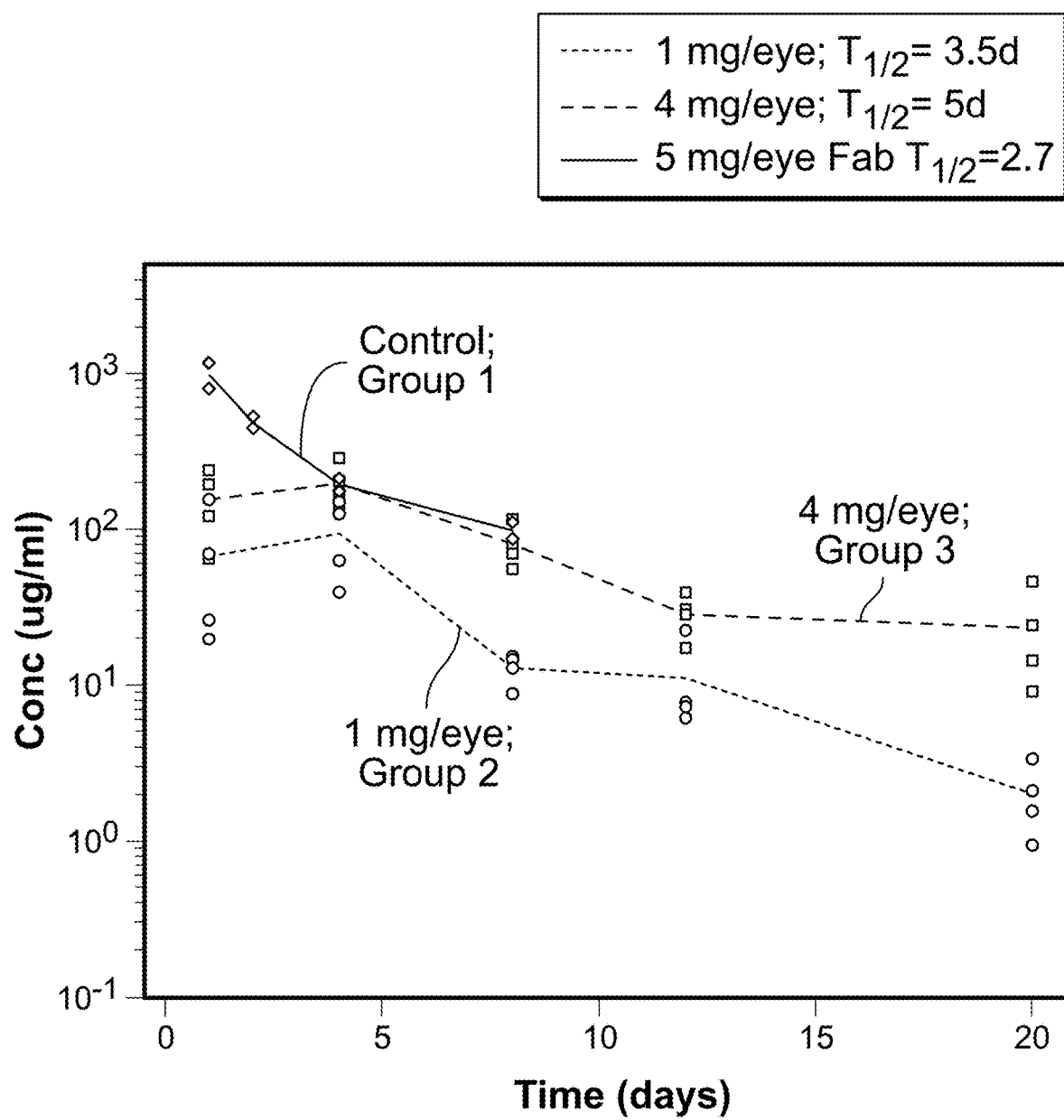
Figure 31B:
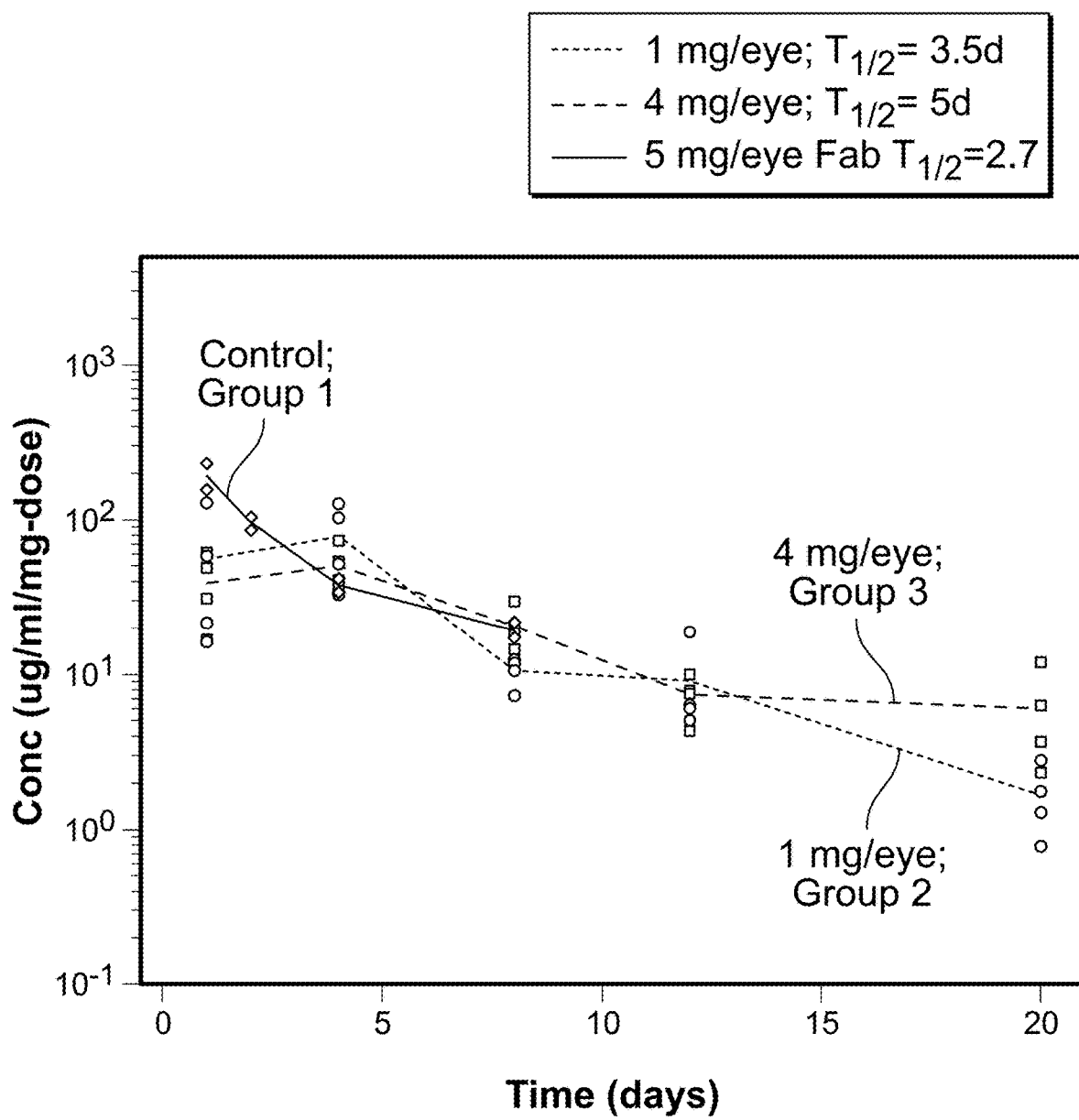

FIGS. 31A and 31B show the concentration versus time of AFD.v14 in cynomolgus monkey retinal homogenate following administration of AFD.v14 or AFD.v14.C+TP octamer in a pharmacokinetic study (31A: retinal concentration; 31B: retinal concentration data normalize for dosing strength).

Figure 32A:
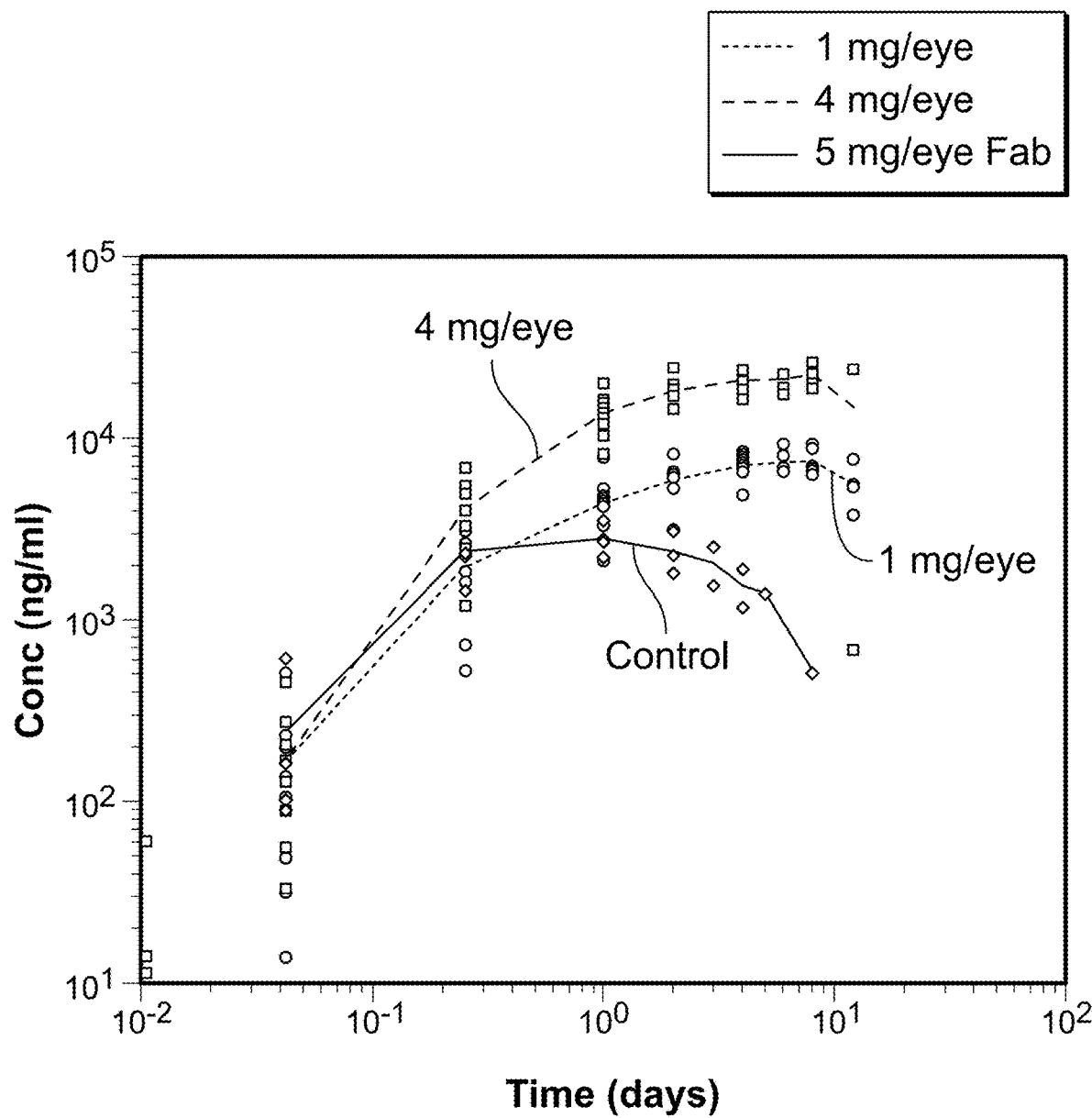
Figure 32B:
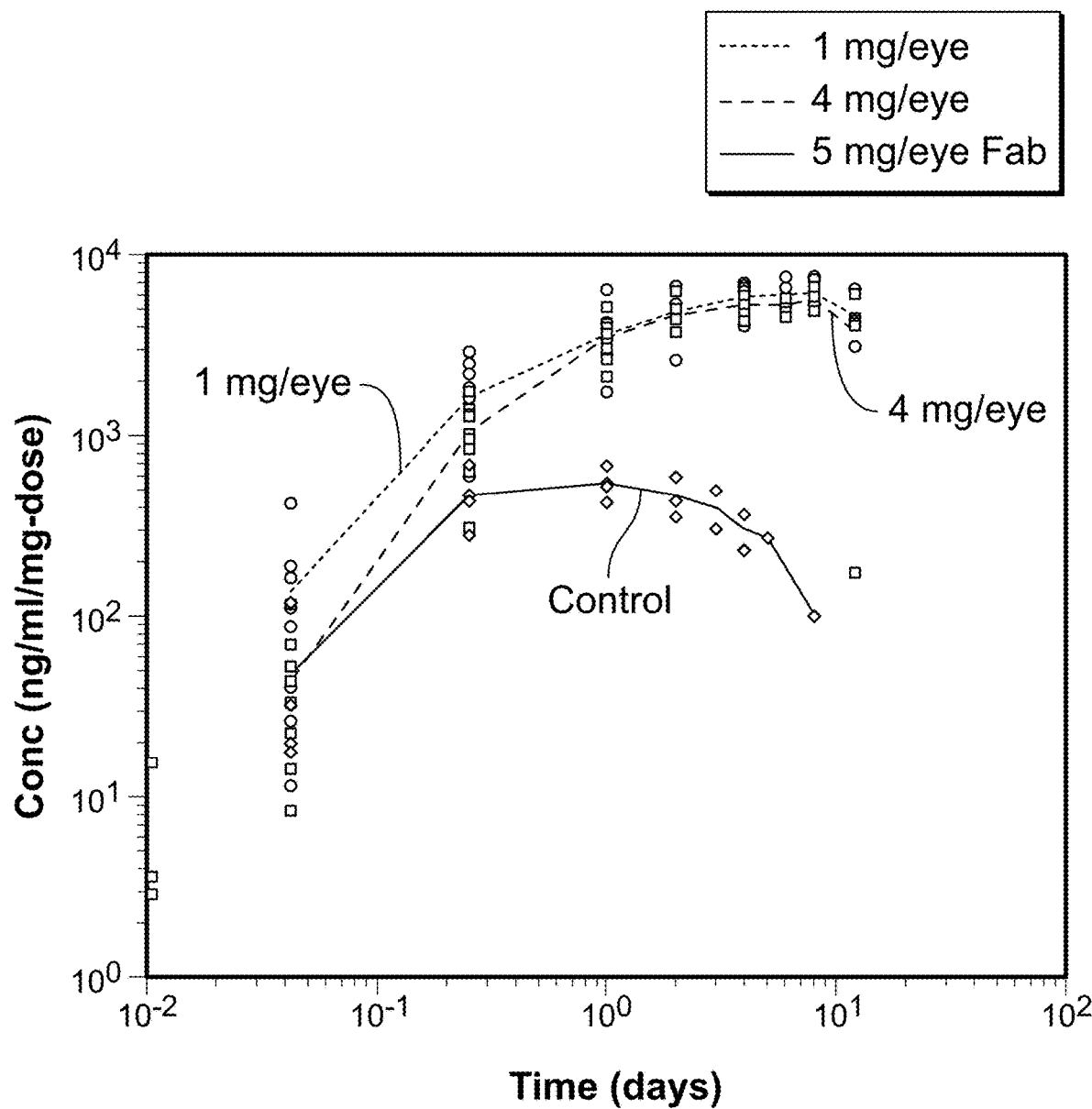
Figure 32C:
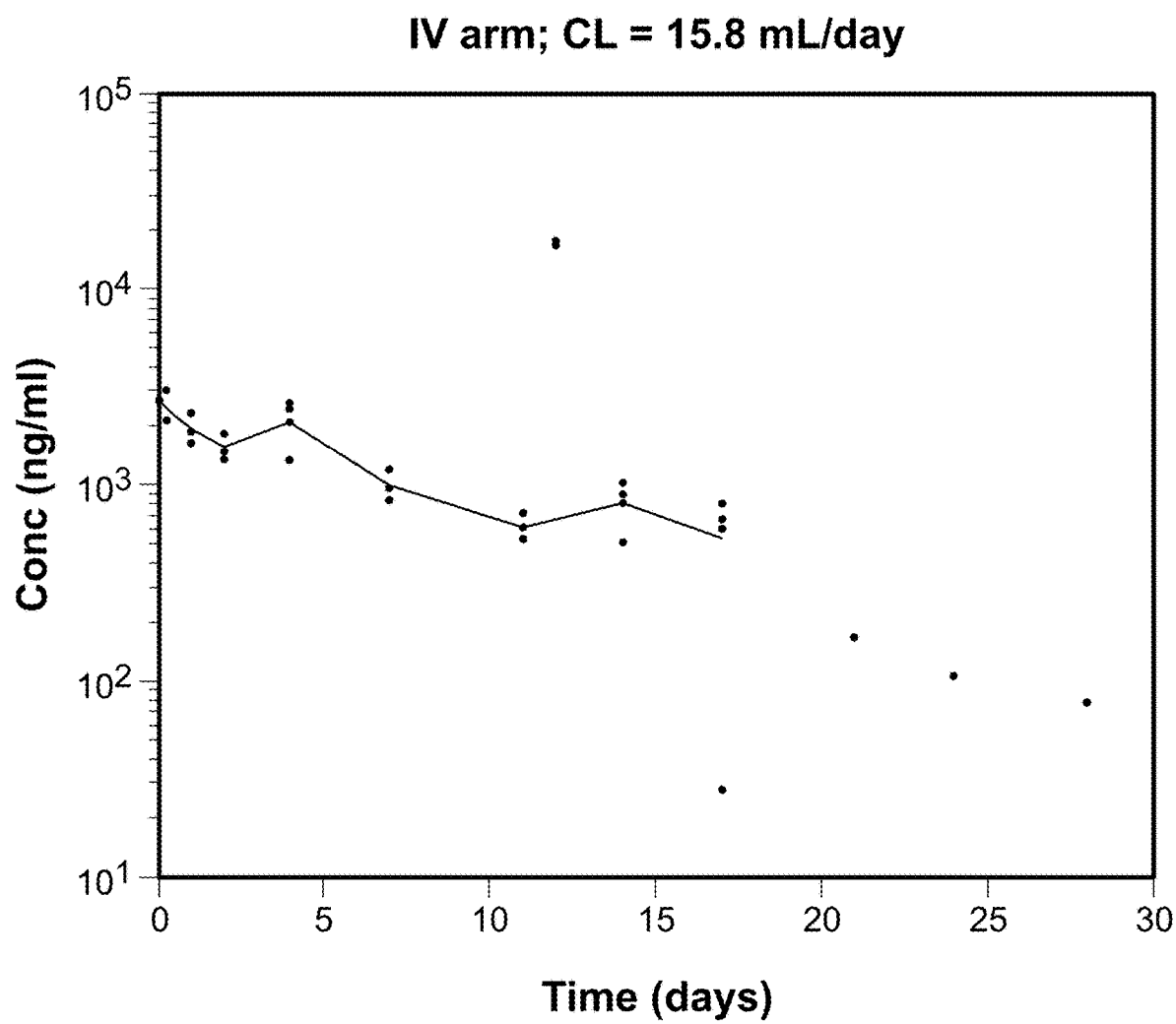

FIGS. 32A-32C show the concentration versus time of AFD.v14 in cynomolgus monkey serum following administration of AFD.v14 or AFD.v14.C+TP octamer in a pharmacokinetic study for both intravitreal and intravenous injection administration (32A: serum concentration for intravitreal injection; 32B: serum concentration for intravitreal injection normalize for dosing strength; 32C: serum concentration for intravenous administration).

Figure 33A:
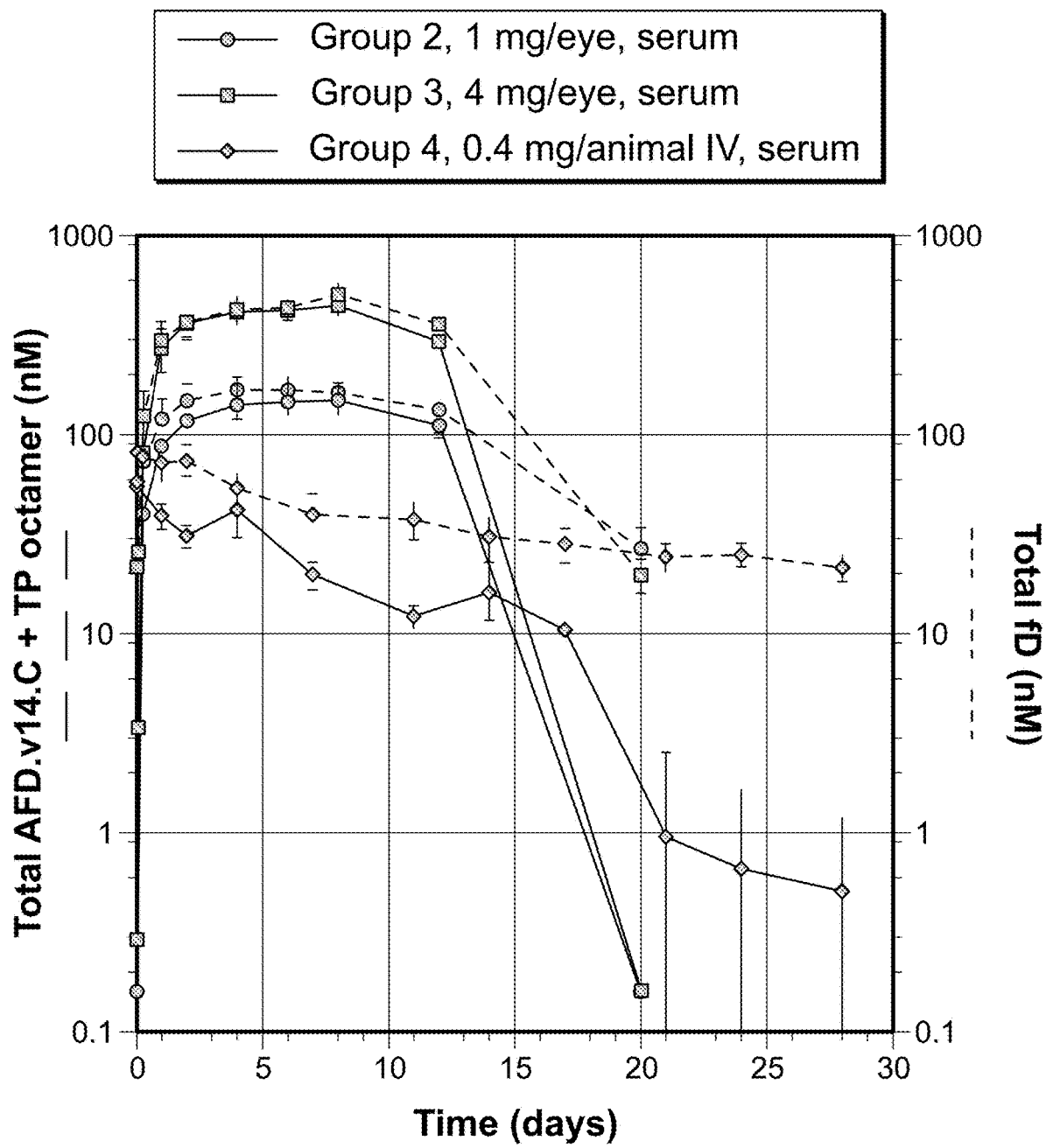
Figure 33B:
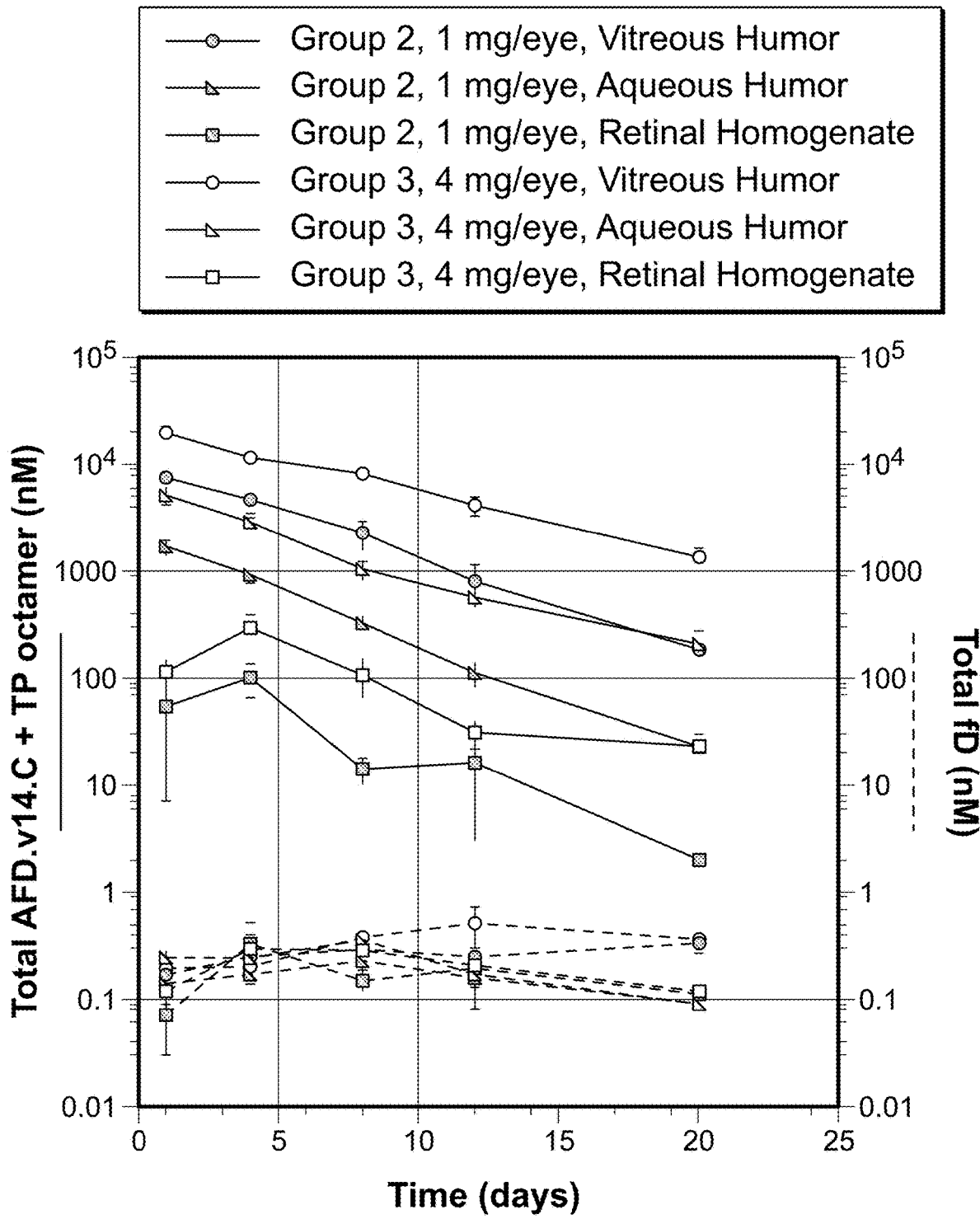

FIGS. 33A-33B shows a comparison of the Factor D concentration and AFD.v14.C+TP octamer in a pharmacokinetic study following the administration of the AFD.v14.C+TP octamer by either an intravenous or intravitreal injection (33A: serum concentrations; 33B: ocular concentrations).

Figure 34A:
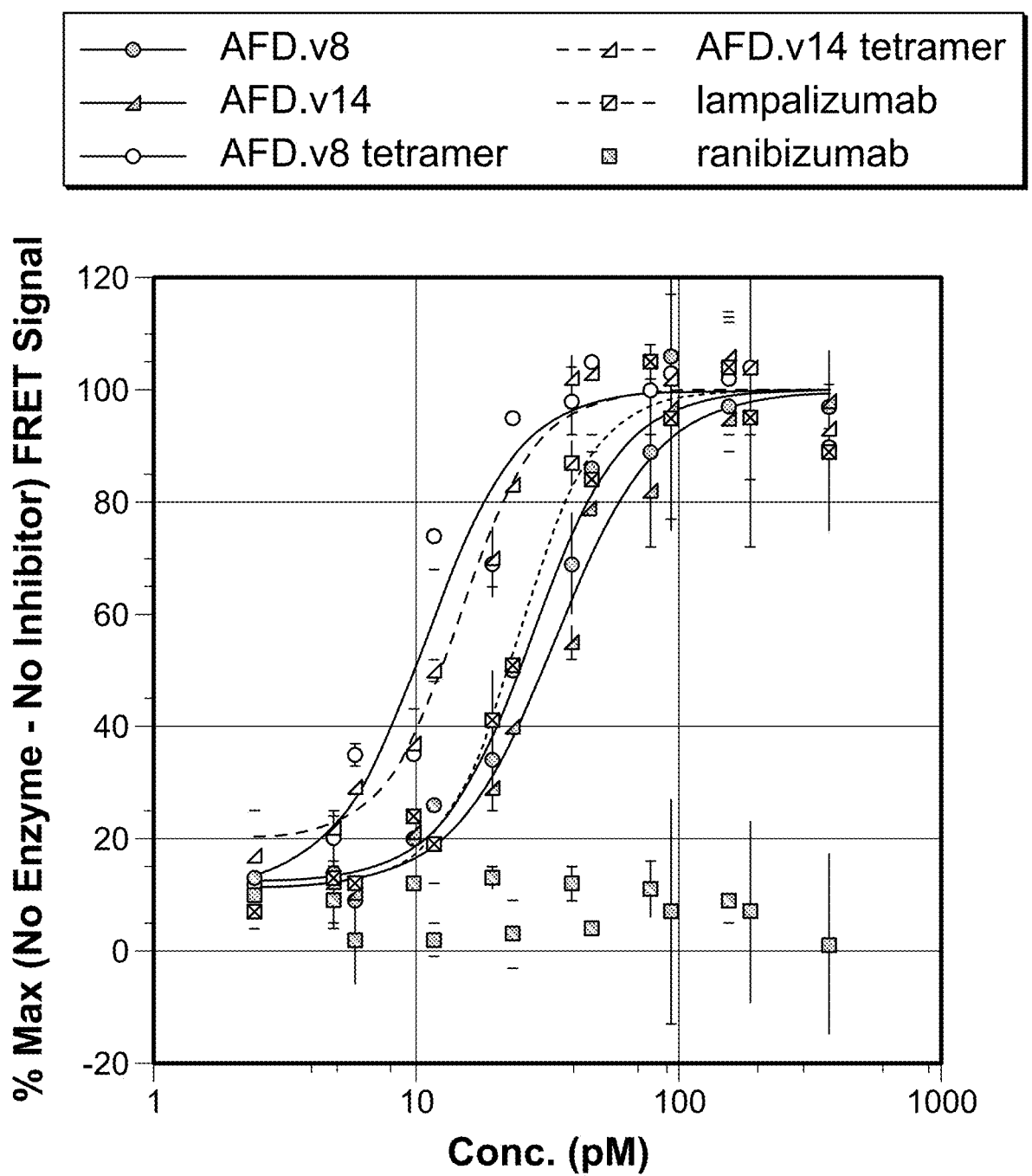
Figure 34B:
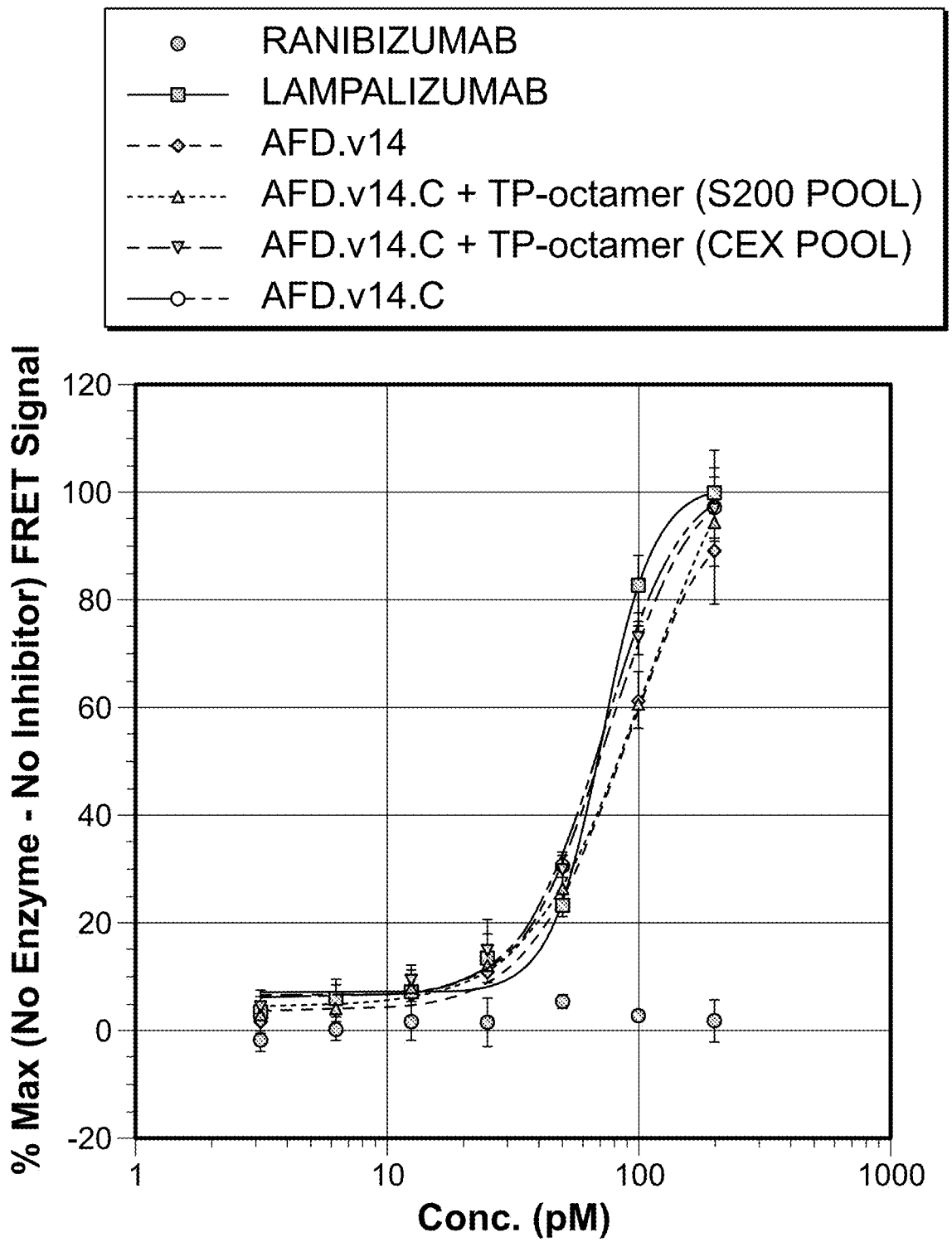

FIGS. 34A-34B show inhibition curves for a time-resolved fluorescence energy transfer (TR-FRET) assay of Factor D-dependent factor B activation (34A: Fab-tetramer conjugates as compared to unconjugated Fab; 34B: AFD.v14.C+TP octamer as compared to unconjugated Fab).

FIGS. 35A-35E show the systemic AP complement activity as compared to total Factor D and therapeutic agent concentration in cynomolgus monkey serum following intravitreal injection administration (35A: 10 mg/eye lampalizumab (comparative data); 35B: 25 mg/eye AFD.v14; 35C: 3.9 mg/eye AFD.v14.C+TP octamer; 35D: 7.1 mg/eye AFD.v14.C+HG octamer; 35E: 11.8 mg/eye AFD.v14.C+HG octamer).

DETAILED DESCRIPTION OF THE INVENTION

Definitions

Terms used throughout this application are to be construed with ordinary and typical meaning to those of ordinary skill in the art. However, Applicants desire that the following terms be given the particular definition as defined below.

The term "antibody" is used in the broadest sense, and specifically covers full length monoclonal antibodies, polyclonal antibodies, multispecific antibodies (e.g., bispecific antibodies) and antibody fragments so long as they exhibit the desired biological activity such as antigen-binding activity. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain (VH) followed by a number of constant domains. Each light chain has a variable domain at one end (VL) and a constant domain at its other end. The term "Antibody" as used herein expressly encompasses antibody fragments retaining antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab-SH, Fab'-SH, Fab', Fab-C, Fab'-C, Fab'-C-SH, Fab-C-SH, scFv, diabody, or F(ab')2; diabodies; linear antibodies; single-chain antibody molecules (e.g., scFv); and multispecific antibodies formed from antibody fragments.

As used herein, an "anti-factor D antibody" means an antibody which specifically binds to Factor D in such a manner so as to inhibit or substantially reduce complement activation.

The term "Factor D" is used herein to refer to native sequence and variant Factor D polypeptides.

As used herein, the term "AFD.Ab" refers to any anti-Factor D antibody.

As used herein, a "Fab" refers to an antibody that comprises a heavy chain constant region that comprises the CH1 domain, or a sufficient portion of the CH1 domain to form a disulfide bond with the light chain constant region, but does not contain a CH2 domain or a CH3 domain. As used herein, a Fab may comprise one or more amino acids of the hinge region. Thus, as used herein, the term "Fab" encompasses Fab' antibodies. A Fab may comprise additional non-native amino acids, such as a C-terminal cysteine, in which case it may be referred to as a Fab-C. As discussed below, the term Fab-C also encompasses Fabs comprising native amino acids of the hinge region, including a native cysteine at the C-terminus. In some embodiments, a Fab comprises an engineered cysteine (i.e., a Fab may be a THIOMAB).

A "Fab-C" refers to a Fab with a C-terminal cysteine, which may be a native cysteine that occurs at that residue position (such as a cysteine from the hinge region), or may be a cysteine added to the C-terminus that does not correspond to a native cysteine. The anti-Factor D antibodies include without limitation AFD.C antibodies, with "C" indicating that the antibody is a Fab with a C-terminal cysteine. Nonlimiting exemplary Fab-C heavy chain constant regions include the sequences of SEQ ID NOs: 56, 57, 59, 60, 61, 62, 68, and 74.

A "Fab-SH" refers to a Fab with a free thiol group. In some embodiments, the free thiol group is located in the last 10 amino acids of the C-terminus of the Fab. Fab-C antibodies are typically also Fab-SH antibodies. A further nonlimiting exemplary Fab-SH heavy chain constant region having the amino acid sequence of SEQ ID NO: 58. Typically, a Fab comprising an engineered cysteine (i.e., a Fab that is a THIOMAB) is a Fab-SH.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

The Fab fragment also contains the constant domain of the light chain and the first constant domain (CH1) of the heavy chain. Fab' fragments (including Fab-C) differ from Fab fragments by the addition of a few residues at the carboxy terminus of the heavy chain CH1 domain including one or more cysteines from the antibody hinge region. Antibody fragments with free thiol groups may be indicated with an "—SH." Fab'-SH (including Fab-C-SH) is the designation for Fab' in which at least one cysteine residue of the constant domains bears a free thiol group. F(ab')2 antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. HVR-H3 is believed to play a unique role in conferring fine specificity to antibodies. See, e.g., Xu et al. (2000) Immunity 13:37-45; Johnson and Wu (2003) in Methods in Molecular Biology 248:1-25 (Lo, ed., Human Press, Totowa, N.J.). "Framework Region" or "FR" residues are those variable domain residues other than the hypervariable region residues as herein defined. An HVR region as used herein comprise any number of residues located within positions 24-36 (for L1), 46-56 (for L2), 89-97 (for L3), 26-35B (for H1), 47-65 (for H2), and 93-102 (for H3). Therefore, an HVR includes residues in positions described previously:

A) 24-34 (L1), 50-52 (L2), 91-96 (L3), 26-32 (H1), 53-55 (H2), and 96-101 (H3) (Chothia and Lesk, J. Mol. Biol. 196:901-917 (1987);

B) 24-34 of L1, 50-56 of L2, 89-97 of L3, 31-35B of H1, 50-65 of H2, and 95-102 of H3 (Kabat et al., Sequences of Proteins of Immunological Interest, 5th Ed. Public Health Service, National Institutes of Health, Bethesda, Md. (1991).

C) 30-36 (L1), 46-55 (L2), 89-96 (L3), 30-35 (H1), 47-58 (H2), 93-100a-j (H3) (MacCallum et al. J. Mol. Biol. 262:732-745 (1996).

Hypervariable regions may comprise "extended hypervariable regions" as follows: 24-36 or 24-34 (L1), 46-56 or 50-56 (L2) and 89-97 (L3) in the VL and 26-35B (H1), 50-65, 47-65 or 49-65 (H2) and 93-102, 94-102 or 95-102 (H3) in the VH. The variable domain residues are numbered according to Kabat et al., supra for each of these definitions.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).)

An "antibody variant" or "modified antibody" of a reference antibody (also referred to as "starting antibody" or "parent antibody") is an antibody that comprises an amino acid sequence different from that of the reference/starting antibody, wherein one or more of the amino acid residues of the reference antibody have been modified. Generally, an antibody variant will possess at least 80% sequence identity, preferably at least 90% sequence identity, more preferably at least 95% sequence identity, and most preferably at least 98% sequence identity with the reference antibody. Percentage sequence identity is determined for example, by the Fitch et al., Proc. Natl. Acad. Sci. USA, 80: 1382-1386 (1983), version of the algorithm described by Needleman et al., J. Mol. Biol., 48: 443-453 (1970), after aligning the sequences of the reference antibody and the candidate antibody variant to provide for maximum homology. Identity or similarity is defined herein as the percentage of amino acid residues in the candidate variant sequence that are identical (i.e., same residue) or similar (i.e., amino acid residue from the same group based on common side-chain properties, see below) with the parent antibody residues, after aligning the sequences and introducing gaps, if necessary, to achieve the maximum percent sequence identity. Amino acid sequence variants of an antibody may be prepared by introducing appropriate nucleotide changes into DNA encoding the antibody, or by peptide synthesis. Such variants include, for example, deletions from, and/or insertions into and/or substitutions of, residues within the amino acid sequence of the antibody of interest. Any combination of deletion, insertion, and substitution is made to arrive at the final construct, provided that the final construct possesses the desired characteristics. The amino acid changes also may alter post-translational processes of the antibody, such as changing the number or position of glycosylation sites. Methods for generating antibody sequence variants of antibodies are similar to those for generating amino acid sequence variants of polypeptides described in U.S. Pat. No. 5,534,615, expressly incorporated herein by reference, for example.

A protein including an antibody is said to be "stable" if it essentially retains the intact conformational structure and biological activity. Various analytical techniques for measuring protein stability are available in the art and are reviewed in, e.g., Peptide and Protein Drug Delivery, 247-301, Vincent Lee Ed., Marcel Dekker, Inc., New York, N.Y., Pubs. (1991) and Jones (1993) Adv. Drug Delivery Rev. 10: 29-90. An antibody variant with "improved stability" refers to an antibody variant that is more stable comparing to the starting reference antibody. Preferably, antibody variants with improved stability are variants of the native (wild-type) antibodies in which specific amino acid residues are altered for the purpose of improving physical stability, and/or chemical stability, and/or biological activity, and/or reducing immunogenicity of the native antibodies. Walsh (2000) Nat. Biotech. 18:831-3.

The term "isomerization" refers generally to a chemical process by which a chemical compound is transformed into any of its isomeric forms, i.e., forms with the same chemical composition but with different structure or configuration and, hence, generally with different physical and chemical properties. Specifically used herein is aspartate isomerization, a process wherein one or more aspartic acid (D or Asp) residue(s) of a polypeptide have been transformed to isoaspartic acid residue(s). Geiger and Clarke (1987) J. Biol. Chem. 262:785-94.

The term "deamidation" refers generally to a chemical reaction wherein an amide functional group is removed from an organic compound. Specifically used herein is asparagine deamidation, a process wherein one or more asparagine (N or Asn) residue(s) of a polypeptide have been converted to aspartic acid (D or Asp), i.e., the neutral amide side chain has been converted to a residue with an overall acidic property. Xie and Schowen (1999) J. Pharm. Sci. 88:8-13.

Amino acid residues "prone" to certain identified physical or chemical processes (e.g., isomerization or deamidation) refer to those residues within a specific protein molecule that have been identified to have the propensity to undergo the identified processes such as isomerization or deamidation. Their propensities are often determined by their relative positions within the primary and/or conformational structure of the protein. For example, it has been shown that the first Asp in an Asp-XXX motif (wherein XXX can be Asp, Gly, His, Ser or Thr) is prone to Asp isomerization due to the involvement of its adjacent residue, where some other Asp within the same protein may not possess such propensity. Assays for identifying residues to certain process within a specific protein molecule are known in the art. See, e.g., Cacia et al (1996) Biochem. 35:1897-1903.

"Active" or "activity" or "biological activity" in the context of an anti-factor D antibody of the present disclosure is the ability to antagonize (partially or fully inhibit) a biological activity of Factor D. One example of a biological activity of a Factor D antagonist is the ability to achieve a measurable improvement in the state, e.g., pathology, of a Factor D-associated disease or condition, such as, for example, a complement-associated eye condition. The activity can be determined in in vitro or in vivo tests, including binding assays, alternative pathway hemolysis assays (e.g., assays measuring inhibition of the alternative pathway complement activity or activation), using a relevant animal model, or human clinical trials.

The term "complement-associated disorder" is used in the broadest sense and includes disorders associated with excessive or uncontrolled complement activation. They include complement activation during cardiopulmonary bypass operations; complement activation due to ischemia-reperfusion following acute myocardial infarction, aneurysm, stroke, hemorrhagic shock, crush injury, multiple organ failure, hypobolemic shock, intestinal ischemia or other events causing ischemia. Complement activation has also been shown to be associated with inflammatory conditions such as severe burns, endotoxemia, septic shock, adult respiratory distress syndrome, hemodialysis; anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. It also includes autoimmune disease such as systemic lupus erythematosus, myasthenia gravis, rheumatoid arthritis, Alzheimer's disease and multiple sclerosis. Complement activation is also associated with transplant rejection. Complement activation is also associated with ocular diseases such as age-related macular degeneration, diabetic retinopathy and other ischemia-related retinopathies, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization.

The term "complement-associated eye condition" is used in the broadest sense and includes all eye conditions the pathology of which involves complement, including the classical and the alternative pathways, and in particular the alternative pathway of complement. Complement-associated eye conditions include, without limitation, macular degenerative diseases, such as all stages of age-related macular degeneration (AMD), including dry and wet (non-exudative and exudative) forms, choroidal neovascularization (CNV), uveitis, diabetic and other ischemia-related retinopathies, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. In one example, complement-associated eye conditions includes age-related macular degeneration (AMD), including non-exudative (e.g., intermediate dry AMD or geographic atrophy (GA)) and exudative (e.g., wet AMD (choroidal neovascularization (CNV)) AMD, diabetic retinopathy (DR), endophthalmitis and uveitis. In a further example, nonexudative AMD may include the presence of hard drusen, soft drusen, geographic atrophy and/or pigment clumping. In one example, complement-associated eye conditions include age-related macular degeneration (AMD), including early AMD (e.g., includes multiple small to one or more non-extensive medium sized drusen), intermediate AMD (e.g., includes extensive medium drusen to one or more large drusen) and advanced AMD (e.g., includes geographic atrophy or advanced wet AMD (CNV). (Ferris et al., AREDS Report No. 18; Sallo et al., Eye Res., 34(3): 238-40 (2009); Jager et al., New Engl. J. Med., 359(1): 1735 (2008)). In a further example, intermediate dry AMD may include large confluent drusen. In a further example, geographic atrophy may include photoreceptor and/or Retinal Pigmented Epithelial (RPE) loss. In a further example, the area of geographic atrophy may be small or large and/or may be in the macula area or in the peripheral retina. In one example, complement-associated eye condition is intermediate dry AMD. In one example, complement-associated eye condition is geographic atrophy. In one example, complement-associated eye condition is wet AMD (choroidal neovascularization (CNV)).

"Treatment" (and grammatical variations thereof such as "treat" or "treating") is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, conjugates of the invention are used to delay development of a disease or to slow the progression of a disease. In treatment of an immune related disease, a therapeutic agent may directly alter the magnitude of response of a component of the immune response, or render the disease more susceptible to treatment by other therapeutic agents, e.g., antibiotics, antifungals, anti-inflammatory agents, chemotherapeutics, etc.

The "pathology" of a disease, such as a complement-associated eye condition, includes all phenomena that compromise the well-being of the patient. This includes, without limitation, abnormal or uncontrollable cell growth (neutrophilic, eosinophilic, monocytic, lymphocytic cells), antibody production, auto-antibody production, complement production, interference with the normal functioning of neighboring cells, release of cytokines or other secretory products at abnormal levels, suppression or aggravation of any inflammatory or immunological response, infiltration of inflammatory cells (neutrophilic, eosinophilic, monocytic, lymphocytic) into cellular spaces, etc.

The term "mammal" as used herein refers to any animal classified as a mammal, including, without limitation, humans, higher primates, domestic and farm animals, and zoo, sports or pet animals such horses, pigs, cattle, dogs, cats and ferrets, etc. In some embodiments of the disclosure, the mammal is a human.

Administration "in combination with" one or more further therapeutic agents includes simultaneous (concurrent) and consecutive administration in any order.

"Therapeutically effective amount" is the amount of a "Factor D antagonist" which is required to achieve a measurable improvement in the state, e.g., pathology, of the target disease or condition, such as, for example, a complement-associated eye condition.

An "amino acid substitution" refers to the replacement of at least one existing amino acid residue in a predetermined amino acid sequence with another different "replacement" amino acid residue. The replacement residue or residues may be "naturally occurring amino acid residues" (i.e., encoded by the genetic code) and selected from the group consisting of: alanine (ala); arginine (Arg); asparagine (Asn); aspartic acid (Asp); cysteine (Cys); glutamine (Gln); glutamic acid (Glu); glycine (Gly); histidine (His); isoleucine (Ile); leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residue(s) in a polypeptide chain. Examples of non-naturally occurring amino acid residues include norleucine, ornithine, norvaline, homoserine and other amino acid residue analogues such as those described in Ellman et al., Meth. Enzym, 202: 301-336 (1991). To generate such non-naturally occurring amino acid residues, the procedures of Noren et al., Science, 244: 182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g., insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

The terms "long-acting delivery", "sustained-release" and "controlled release" are used generally to describe a delivery mechanism using formulation, dosage form, device or other types of technologies to achieve the prolonged or extended release or bioavailability of a therapeutic drug. It may refer to technologies that provide prolonged or extended release or bioavailability of the drug to the general systemic circulation or a subject or to local sites of action in a subject including (but not limited to) cells, tissues, organs, joints, regions, and the like. Furthermore, these terms may refer to a technology that is used to prolong or extend the release of the drug from a formulation or dosage form or they may refer to a technology used to extend or prolong the bioavailability or the pharmacokinetics or the duration of action of the drug to a subject or they may refer to a technology that is used to extend or prolong the pharmacodynamic effect elicited by a formulation. A "long-acting formulation," a "sustained release formulation," or a "controlled release formulation" is a pharmaceutical formulation, dosage form, or other technology that is used to provide long-acting delivery. In some aspects, the controlled release is used to improve drug's local bioavailability, specifically ocular residence time in the context of ocular delivery. "Increased ocular residence time" refers to the post-delivery period during which the delivered ocular drug remains effective both in terms of quality (activity) and in terms of quantity (effective amount). In addition to or in lieu of high dose and controlled release, the drug can be modified post-translationally, such as via PEGylation, to achieve increased in vivo half-life.

The term "port delivery system" refers to an implantable device for the eye with a refillable reservoir that allows delivery of a therapeutic agent over an extended period of time. Exemplary port delivery systems are described, e.g., in U.S. Patent Application Serial No. 2010/0174272, and U.S. Pat. Nos. 8,277,830; 8,399,006; 8,795,712; and 8,808,727, all of which are herein incorporated by reference.

The term "polyol" when used herein refers broadly to polyhydric alcohol compounds. Polyols can be any water-soluble poly(alkylene oxide) polymer for example, and can have a linear or branched chain. Preferred polyols include those substituted at one or more hydroxyl positions with a chemical group, such as an alkyl group having between one and four carbons. Typically, the polyol is a poly(alkylene glycol), preferably polyethylene glycol (PEG). However, those skilled in the art recognize that other polyols, such as, for example, poly (propylene glycol) and polyethylene-polypropylene glycol copolymers, can be employed using the techniques for conjugation described herein for PEG. The polyols of the disclosure include those well known in the art and those publicly available, such as from commercially available sources.

The term "conjugate" is used herein according to its broadest definition to mean joined or linked together. Molecules are "conjugated" when they act or operate as if joined. In particular embodiments, "conjugate" refers to an antibody (e.g., an antibody fragment, as detailed herein) covalently bound to a multi-armed polyol.

A "small-bore needle" or a "narrow-bore needle" refers to a needle for injection of fluid composition of about 30, 29, 28, 27, 26, 25, 24, 23, or 22 gauge or higher, such as a 30 gauge needle. In some embodiments, the small-bore needle has standard sized walls. In another embodiment, the small-bore needle has thin walls, which may be preferred for viscous solutions.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

A drug that is administered "simultaneously" with one or more other drugs is administered during the same treatment cycle, on the same day of treatment as the one or more other drugs, and, optionally, at the same time as the one or more other drugs.

Anti-Factor D Antibodies and Variants Thereof

In some aspects, the present disclosure is directed to the production and use of conjugates comprising one or more anti-Factor D antibodies or variants thereof. Anti-Factor D antibodies and variants thereof that are suitable for use in forming the conjugates of the disclosure are described in U.S. patent application Ser. No. 14/700,853 (filed Apr. 30, 2015), which is herein incorporated by reference in its entirety.

In some aspects, the parent reference anti-Factor D antibody forming the base for creating the variants used in the conjugates of the disclosure is a humanized anti-Factor D antibody. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies can in some instances be important to reduce antigenicity and/or HAMA response (human anti-mouse antibody) when the antibody is intended for human therapeutic use. Reduction or elimination of a HAMA response is generally a significant aspect of clinical development of suitable therapeutic agents. See, e.g., Khaxzaeli et al. (1988) J. Natl. Cancer Inst 80:937; Jaffers et al. (1986) Transplantation 41:572; Shawler et al. (1985) J. Immunol. 135:1530; Sears et al. (1984) J. Biol. Response Mod. 3:138; Miller et al. (1983) Blood 62:988; Hakimi et al. (1991) J. Immunol. 147:1352; Reichmann et al. (1988) Nature 332:323; Junghans et al. (1990) Cancer Res. 50:1495. As described herein, in some aspects, the present disclosure provides conjugates comprising antibodies that are humanized such that HAMA response is reduced or eliminated. Variants of these antibodies can further be obtained using routine methods known in the art, some of which are further described below. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al. (1993) J. Immunol. 151:2296; Chothia et al. (1987) J. Mol. Biol. 196:901). Another method uses a particular framework region derived from the consensus sequence of all human antibodies of a particular subgroup of light or heavy chains. The same framework may be used for several different humanized antibodies (Carter et al. (1992) Proc. Natl. Acad. Sci. USA 89:4285; Presta et al. (1993) J. Immunol. 151: 2623).

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), the acceptor human frameworks may be from, or derived from, a human consensus framework sequence as such frameworks have been demonstrated to have minimal, or no, immunogenicity in human patients. An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. In some embodiments, the VH acceptor human framework is identical in sequence to the VH human immunoglobulin framework sequence or human consensus framework sequence. In some embodiments, the VL acceptor human framework is identical in sequence to the VL human immunoglobulin framework sequence or human consensus framework sequence. A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In some embodiments, for the VL, the subgroup is subgroup kappa I as in Kabat et al. In some embodiments, for the VH, the subgroup is subgroup III as in Kabat et al.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor. The acceptor human framework may be from or derived from human antibody germline sequences available in the public databases.

In some embodiments, human consensus frameworks herein are from, or derived from, VH subgroup VII and/or VL kappa subgroup I consensus framework sequences.

In some embodiments, the human framework template used for generation of an anti-Factor D antibody may comprise framework sequences from a template comprising a combination of VI-4.1b+ (VH7 family) and JH4d for VH chain and/or a combination of DPK4 (VκI family) and JK2 for VL chain.

While the acceptor may be identical in sequence to the human framework sequence selected, whether that be from a human immunoglobulin or a human consensus framework, the present disclosure contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

Hypervariable region residues of the non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-36 or 24-34 (L1), 46-56 or 50-56 (L2) and 89-97 (L3), 26-35B (H1), 50-65, 47-65 or 49-65 (H2) and 93-102, 94-102, or 95-102 (H3).

In some aspects, the anti-Factor D antibody or antibody variants used in the conjugates comprise a light chain domain and a heavy chain variable domain. In some aspects, the reference anti-Factor D antibody comprises a light chain variable domain of SEQ ID NO:3. In some aspects, the reference anti-Factor D antibody comprises a heavy chain variable domain of SEQ ID NO:4.

Further, an anti-Factor D antibody may comprise any suitable constant domain sequence, provided that the antibody retains the ability to bind Factor D. For example, in some embodiments, anti-Factor D antibodies used in the conjugates of the disclosure comprise at least a portion of a heavy chain constant domain. In some embodiments, anti-Factor D antibodies comprise a heavy chain constant domain of either one or a combination of an α, δ, ε, γ, or μ heavy chain. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in CH sequence and function, e.g., humans express the following subclasses: IgG1, IgG2, IgG3, IgG4, IgA1, and IgA2. In some embodiments, anti-Factor D antibodies used in the conjugates of the disclosure comprise a heavy chain constant domain comprising substitutions at amino acid positions that results in a desired effect on effector function (e.g., binding affinity). In some embodiments, anti-Factor D antibodies used in the conjugates of the disclosure comprise a heavy chain constant domain comprising substitutions at amino acid positions that do not result in an effect on effector function (e.g., binding affinity). In some embodiments, the anti-Factor D antibodies comprise a heavy chain constant domain of the IgG type (e.g., IgG1, IgG2, IgG3 or IgG4) and further comprise a substitution at position 114 (Kabat numbering; equivalent to 118 in EU numbering), 168 (Kabat numbering; equivalent to 172 in EU numbering), 172 (Kabat numbering; equivalent to 176 in EU numbering) and/or 228 (EU numbering). In some embodiments, the anti-Factor D antibodies comprise a heavy chain constant domain of the IgG (e.g., IgG1, IgG2, IgG3 or IgG4) type and further comprise a substitution at position 114 wherein position 114 is a cysteine (C) or alanine (A), position 168 is cysteine (C) or alanine (A), position 172 is a cysteine (C) or alanine (A) and/or position 228 is a proline (P), arginine (R) or serine (S).

Further, for example, in some embodiments, anti-Factor D antibodies used in the conjugates of the disclosure comprise at least a portion of a light chain constant domain. In some embodiments, the anti-Factor D antibodies comprise a light chain constant domain of either one or a combination of a kappa or a lambda light chain, as the light chain from any vertebrate species can be assigned to one of two clearly distinct types, called kappa and lambda, based on the amino acid sequences of their constant domains. In some embodiments, anti-Factor D antibodies used in the conjugates of the disclosure comprise a light chain constant domain comprising substitutions at amino acid positions that results in a desired effect on effector function (e.g., binding affinity). In some embodiments, anti-Factor D antibodies used in the conjugates of the disclosure comprise a light chain constant domain comprising substitutions at amino acid positions that do not result in an effect on effector function (e.g., binding affinity). In some embodiments, anti-Factor D antibodies used in the conjugates of the disclosure comprise a light chain constant domain of the kappa type and further comprise a substitution at position 110, 144, 146 and/or 168 (Kabat numbering). In some embodiments, anti-Factor D antibodies used in the conjugates of the disclosure comprise a light chain constant domain of the kappa type and further comprise a substitution at position 110 wherein 110 is a cysteine (C) or valine (V), at position 144 wherein 144 is a cysteine (C) or alanine (A), at position 146 wherein 146 is a isoleucine (I) or valine (V) and/or at position 168 wherein 168 is a cysteine (C) or serine (S).

A parent or reference anti-Factor D antibody, including a humanized anti-Factor D antibody, can be modified to generate modified anti-Factor D antibodies, or anti-Factor D antibody variants. In some embodiments, the modified anti-Factor D antibodies, and variants thereof, may have improved physical, chemical, biological or homogeneity properties over the parent antibody.

In some embodiments, an antibody used in the conjugates of the disclosure comprises one or more amino acid alterations (e.g., substitutions) into one or more of the hypervariable regions of the parent antibody. Alternatively, or in addition, one or more alterations (e.g., substitutions) of framework region residues may be introduced in the parent antibody. Examples of framework region residues to modify include those which non-covalently bind antigen directly (Amit et al., (1986) Science, 233: 747-753); interact with/effect the conformation of a CDR (Chothia et al. (1987) J. Mol. Biol., 196: 901-917), and/or participate in the VL-VH interface (EP 239 400B1). In certain embodiments, modification of one or more of such framework region residues results in an enhancement of the binding affinity of the antibody for the antigen. For example, from about one to about 5 framework residues may be altered in this embodiment of the disclosure. Examples of framework or HVR region residues to modify include sites, wherein modifications at such sites result in the generation of deamidated variants (for example, asparagine (N or Asn) residue(s) modified to aspartate (D or Asp), oxidation variants (for example, methionine (M or Met) residue(s) and/or tryptophan (W or Trp) residue(s) modified to sulfone or sulfoxide) or pyroglutamate variants (for example, glutamine (Q or Gln) residue(s) modified to pyroglutamate). Examples of framework region residues or HVR region residues to modify include possible deamidation sites (i.e., asparagine (N or Asn)), oxidation sites (i.e., methionine (M or Met) or tryptophan (W or Trp)) or pyroglutamate conversion sites (i.e., glutamine (Q or Gln)), wherein modification at such sites prevent deamidation and/or oxidation and/or pyroglutamate conversion, respectively.

To prevent the formation of deamidated variants, asparagine (N or Asn) may be mutated to alanine (A or Ala), glutamine (Q or Gln) or serine (S or Ser). To prevent the formation of oxidated variants, methionine (Met) or tryptophan (W or Trp) may be mutated to leucine (L) or isoleucine (I). To prevent the formation of pyroglutamate variants, glutamine (Q or Gln) may be mutated to glutamate (E or Glu). (Amphlett, G. et al., Pharm. Biotechnol., 9:1-140 (1996)). Alternatively, or in addition, one or more alterations (e.g., substitutions) of framework region residues may be in the Fc region in the parent antibody.

One useful procedure for generating such modified antibodies is called "alanine scanning mutagenesis" (Cunningham and Wells (1989) Science 244:1081-1085). Here, one or more of the hypervariable region residue(s) are replaced by alanine or polyalanine residue(s) to affect the interaction of the amino acids with the antigen. Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. The ala-mutants produced this way are screened for their biological activity (i.e., binding affinity or hemolysis assay) as described herein.

Even more substantial modifications in the antibodies or fragments thereof (e.g., antigen-binding fragments) biological properties are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
  (2) neutral hydrophilic: cys, ser, thr, asn, gln;
  (3) acidic: asp, glu;
  (4) basic: his, lys, arg;
  (5) residues that influence chain orientation: gly, pro; and
  (6) aromatic: trp, tyr, phe.

Non-conservative substitutions will entail exchanging a member of one of these classes for another class.

In another embodiment, the sites selected for modification are modified, and those modifications with improved binding affinity are selected by phage display.

Nucleic acid molecules encoding amino acid sequence mutants or modified amino acid sequences are prepared by a variety of methods known in the art. These methods include, but are not limited to, oligonucleotide-mediated (or site-directed) mutagenesis, PCR mutagenesis, and cassette mutagenesis of an earlier prepared variant or a non-variant version of the parent antibody. One method for making mutants or variants or modified amino acid sequences is site directed mutagenesis (see, e.g., Kunkel (1985) Proc. Natl. Acad. Sci. USA 82:488).

In certain embodiments, the modified antibody will only have a single hypervariable region residue substituted. In other embodiments, two or more of the hypervariable region residues of the parent antibody will have been substituted, e.g., from about two to about ten hypervariable region substitutions. Ordinarily, the modified antibody will have an amino acid sequence having at least 75% amino acid sequence identity or similarity (defined above in Definition section) with the amino acid sequence of either the heavy or light chain variable domain of the parent antibody, more preferably at least 80%, more preferably at least 85%, more preferably at least 90%, and most preferably at least 95%.

Following production of the modified antibody, the biological activity of that molecule relative to the parent antibody is determined. As noted above, this may involve determining the binding affinity and/or other biological activities of the antibody variant, or fragment thereof (e.g., antigen-binding fragment). In some embodiments of the disclosure, a panel of modified antibodies is prepared and screened for binding affinity for the antigen such as Factor D or a fragment thereof. One or more of the antibody mutants or modified antibodies selected from this initial screen are optionally subjected to one or more further biological activity assays to confirm that the antibody variant(s), or fragments thereof (e.g., antigen-binding fragments) are indeed useful, e.g., for preclinical studies.

The modified anti-Factor D antibodies described herein may be subjected to further modifications, oftentimes depending on the intended use of the modified antibody. Such modifications may involve further alteration of the amino acid sequence, fusion to heterologous polypeptide(s) and/or covalent modifications such as those elaborated below. With respect to amino acid sequence alterations, exemplary modifications are elaborated above. For example, any cysteine residue not involved in maintaining the proper conformation of the modified antibody also may be substituted, generally with serine, to improve the oxidative stability of the molecule and prevent aberrant cross linking. Conversely, cysteine bond(s) may be added to the antibody to improve its stability (particularly where the antibody is an antibody fragment such as an Fv fragment).

Another type of amino acid mutant has an altered glycosylation pattern. This may be achieved by deleting one or more carbohydrate moieties found in the antibody, and/or adding one or more glycosylation sites that are not present in the antibody. Glycosylation of antibodies, or antibody fragments (e.g., antigen-binding fragments) is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Affinity and Biological Activity of Anti-Factor D Antibodies and Variants Thereof Antibodies having characteristics identified herein as being desirable in an anti-Factor D antibody, may be screened for desirable properties such as factor D-binding affinity and factor D-inhibiting activity in vitro or in vivo.

a. Affinity

In some aspects, the anti-Factor D antibody variants used in the conjugates of the disclosure compete with the parent anti-Factor D antibody from which they are generated. Anti-Factor D antibody variants that bind to the same epitope as the parent anti-Factor D antibody are also provided.

To determine whether an anti-Factor D antibody variant bind to the same epitope on human Factor D bound by a reference anti-Factor D antibody, a cross-blocking assay may be performed (Antibodies, A Laboratory Manual, Cold Spring Harbor Laboratory, Ed Harlow and David Lane (1988)). Alternatively, epitope mapping may be performed to determine whether an anti-Factor D antibody binds an epitope of interest (Champe et al. (1995) J. Biol. Chem. 270: 1388-1394. Antibody affinities, for example for human Factor D, may be determined using standard methods, including the surface plasmon resonance (SPR) assay described in more details in the Examples.

In some aspects, the factor D binding affinity of the anti-Factor D antibody variant used in the conjugates of the disclosure is comparable to that of the parent anti-Factor D antibody from which it is generated. In some aspects, the factor D binding affinity of anti-Factor D antibody variant used in the conjugates of the disclosure is within 10-fold, 7-fold, 5-fold, 2-fold or 1-fold of that of the parent anti-Factor D antibody.

In some embodiments, the disclosure provides a conjugate comprising an anti-Factor D antibody, wherein the affinity of the antibody in its monovalent form to Factor D (e.g., affinity of the antibody as a Fab fragment to Factor D) is 20 nM ($20 \times 10^{-9}$ M) or better. In another embodiment, the disclosure provides a conjugate comprising an anti-Factor D antibody, wherein the affinity of the antibody in its monovalent form to Factor D (e.g., affinity of the antibody as a Fab fragment to Factor D) is 10 nM ($10 \times 10^{-9}$ M) or better. In another embodiment, the disclosure provides a conjugate comprising an anti-Factor D antibody, wherein the affinity of the antibody in its monovalent form to Factor D (e.g., affinity of the antibody as a Fab fragment to Factor D) is 1.0 nM ($1.0 \times 10^{-9}$ M) or better. In another embodiment, the disclosure provides a conjugate comprising an anti-Factor D antibody, wherein the affinity of the antibody in its monovalent form to Factor D (e.g., affinity of the antibody as a Fab fragment to Factor D) is 0.5 nM ($0.5 \times 10^{-9}$ M) or better. In another embodiment, the disclosure provides a conjugate comprising an anti-Factor D antibody, wherein the affinity of the antibody in its monovalent form to Factor D (e.g., affinity of the antibody as a Fab fragment to Factor D) is 1.0 pM (1.0×10-12 M) or better. In another embodiment, the disclosure provides a conjugate comprising an anti-Factor D antibody, wherein the affinity of the antibody in its monovalent form to Factor D (e.g., affinity of the antibody as a Fab fragment to Factor D) is 0.5 pM (0.5×10-12 M) or better.

In another embodiment, the disclosure provides a conjugate comprising an anti-Factor D antibody, wherein the affinity of the antibody in its bivalent form to Factor D (e.g., affinity of the antibody as an IgG to Factor D) is 10.0 nM (10.0×10-9 M) or better. In another embodiment, the disclosure provides a conjugate comprising an anti-Factor D antibody, wherein the affinity of the antibody in its bivalent form to Factor D (e.g., affinity of the antibody as an IgG to Factor D) is 5.0 nM (5.0×10-9 M) or better. In another embodiment, the disclosure provides a conjugate comprising an anti-Factor D antibody, wherein the affinity of the antibody in its bivalent form to Factor D (e.g., affinity of the antibody as an IgG to Factor D) is 1.0 nM (1.0×10-9 M) or better. In another embodiment, the disclosure provides a conjugate comprising an anti-Factor D antibody, wherein the affinity of the antibody in its bivalent form to Factor D (e.g., affinity of the antibody as an IgG to Factor D) is 0.5 nM (0.5×10-9 M) or better. In another embodiment, the disclosure provides a conjugate comprising an anti-Factor D antibody, wherein the affinity of the antibody in its bivalent form to Factor D (e.g., affinity of the antibody as an IgG to Factor D) is 5.0 pM (5.0×10-12 M) or better. In another embodiment, the disclosure provides a conjugate comprising an anti-Factor D antibody, wherein the affinity of the antibody in its bivalent form to Factor D (e.g., affinity of the antibody as an IgG to Factor D) is 2.0 pM (2.0×10-12 M) or better. In another embodiment, the disclosure provides a conjugate comprising an anti-Factor D antibody, wherein the affinity of the antibody in its bivalent form to Factor D (e.g., affinity of the antibody as an IgG to Factor D) is 1.0 pM (1.0×10-12 M) or better. In another embodiment, the disclosure provides a conjugate comprising an anti-Factor D antibody, wherein the affinity of the antibody in its bivalent form to Factor D (e.g., affinity of the antibody as an IgG to Factor D) is 0.5 pM (0.5×10-12 M) or better.

In another embodiment, the disclosure provides a conjugate comprising an anti-Factor D antibody, wherein the affinity of the antibody in its monovalent form to Factor D (e.g., affinity of the antibody as a Fab fragment to Factor D) is between 0.5 mM (0.5×10-6 M) and 0.5 pM (0.5×10-12 M). In another embodiment, the disclosure provides a conjugate comprising an anti-Factor D antibody, wherein the affinity of the antibody in its monovalent form to Factor D (e.g., affinity of the antibody as a Fab fragment to Factor D) is between 15 nM (15×10-9 M) and 0.1 nM (0.1×10-9 M). In another embodiment, the disclosure provides a conjugate comprising an anti-Factor D antibody, wherein the affinity of the antibody in its monovalent form to Factor D (e.g., affinity of the antibody as a Fab fragment to Factor D) is between 5.5 nM (5.5×10-9 M) and 1 nM (1×10-9 M). In another embodiment, the disclosure provides a conjugate comprising an anti-Factor D antibody, wherein the affinity of the antibody in its monovalent form to Factor D (e.g., affinity of the antibody as a Fab fragment to Factor D) is between 0.5 pM (0.5×10-12 M) and 50 pM (5×10-11 M).

In another embodiment, the disclosure provides a conjugate comprising an anti-Factor D antibody, wherein the affinity of the antibody in its bivalent form to Factor D (e.g., affinity of the antibody as an IgG to Factor D) is between 0.5 mM (0.5×10-6 M) and 0.5 pM (0.5×10-12 M). In another embodiment, the disclosure provides a conjugate comprising an anti-Factor D antibody, or antibody variants thereof, wherein the affinity of the antibody in its bivalent form to Factor D (e.g., affinity of the antibody as an IgG to Factor D) is between 10 nM (10×10-9 M) and 0.05 nM (0.05×10-9 M). In another embodiment, the disclosure provides a conjugate comprising an anti-Factor D antibody, wherein the affinity of the antibody in its bivalent form to Factor D (e.g., affinity of the antibody as an IgG to Factor D) is between 5.5 nM (5.5×10-9 M) and 1 nM (1×10-9 M). In another embodiment the disclosure provides a conjugate comprising an anti-Factor D antibody, wherein the affinity of the antibody in its bivalent form to Factor D (e.g., affinity of the antibody as an IgG to Factor D) is between 0.5 pM (0.5×10-12 M) and 50 pM (5×10-11 M).

In another embodiment, the disclosure provides a conjugate comprising an anti-Factor D antibody, wherein the affinity of the antibody in its monovalent form to Factor D (e.g., affinity of the antibody as a Fab fragment to Factor D) is about 1.4 pM (1.4×10-12 M). In another embodiment, the disclosure provides a conjugate comprising an anti-Factor D antibody, wherein the affinity of the antibody in its bivalent form to Factor D (e.g., affinity of the antibody as a IgG to Factor D) is about 1.1 pM (1.1×10-12 M). In another embodiment, the disclosure provides a conjugate comprising an anti-Factor D antibody, wherein the affinity of the antibody in its monovalent form to Factor D (e.g., affinity of the antibody as a Fab fragment to Factor D) is about 0.19 nM (0.19×10-9 M). In another embodiment, the disclosure provides a conjugate comprising an anti-Factor D antibody, wherein the affinity of the antibody in its bivalent form to Factor D (e.g., affinity of the antibody as a IgG to Factor D) is about 0.08 nM (0.08×10-9 M). In another embodiment, the disclosure provides a conjugate comprising an anti-Factor D antibody, wherein the affinity of the antibody in its monovalent form to Factor D (e.g., affinity of the antibody as a Fab fragment to Factor D) is about 12.3 nM (12.3×10-9 M). In another embodiment, the disclosure provides a conjugate comprising an anti-Factor D antibody, wherein the affinity of the antibody in its bivalent form to Factor D (e.g., affinity of the antibody as an IgG to Factor D) is about 9.0 nM (9.0×10-9 M).

In another embodiment, the disclosure provides a conjugate comprising an anti-Factor D antibody, wherein the affinity of the antibody in its monovalent form to Factor D (e.g., affinity of the antibody as a Fab fragment to Factor D) is about 1.4 pM (1.4×10-12 M)+/−0.5. In another embodiment, the disclosure provides a conjugate comprising an anti-Factor D antibody, wherein the affinity of the antibody in its bivalent form to Factor D (e.g., affinity of the antibody as an IgG to Factor D) is about 1.1 pM (1.1×10-12 M)+/−0.6. In another embodiment, the disclosure provides a conjugate comprising an anti-Factor D antibody, wherein the affinity of the antibody in its monovalent form to Factor D (e.g., affinity of the antibody as a Fab fragment to Factor D) is about 0.19 nM (0.19×10-9 M)+/−0.01. In another embodiment, the disclosure provides a conjugate comprising an anti-Factor D antibody, wherein the affinity of the antibody in its bivalent form to Factor D (e.g., affinity of the antibody as a IgG to Factor D) is about 0.08 nM (0.08×10-9 M)+/−0.01. In another embodiment, the disclosure provides a conjugate comprising an anti-Factor D antibody, wherein the affinity of the antibody in its monovalent form to Factor D (e.g., affinity of the antibody as a Fab fragment to Factor D) is about 12.3 nM (12.3×10-9 M)+/−2. In another embodiment, the disclosure provides a conjugate comprising an anti-Factor D antibody, wherein the affinity of the antibody in its bivalent form to Factor D (e.g., affinity of the antibody as a IgG to Factor D) is about 9.0 nM (9.0×10-9 M)+/−1.

In another embodiment, an anti-Factor D antibody used in the conjugates of the disclosure may have an affinity in its monovalent form to Factor D (e.g., affinity of the antibody as a Fab fragment to Factor D) of about 1.4 pM (1.4×10-12 M)+/−2. In another embodiment, an anti-Factor D antibody used in the conjugates of the disclosure may have an affinity in its bivalent form to Factor D (e.g., affinity of the antibody as a IgG to Factor D) of about 1.1 pM (1.1×10-12 M)+/−2. In another embodiment, an anti-Factor D antibody used in the conjugates of the disclosure may have an affinity in its monovalent form to Factor D (e.g., affinity of the antibody as a Fab fragment to Factor D) is about 0.19 nM (0.19×10-9 M)+/−2. In another embodiment, an anti-Factor D antibody, or antibody variant thereof, used in the conjugates of the disclosure may have an affinity in its bivalent form to Factor D (e.g., affinity of the antibody as a IgG to Factor D) is about 0.08 nM (0.08×10-9 M)+/−2. In another embodiment, an anti-Factor D antibody used in the conjugates of the disclosure may have an affinity in its monovalent form to Factor D (e.g., affinity of the antibody as a Fab fragment to Factor D) is about 12.3 nM (12.3×10-9 M)+/−2. In another embodiment, an anti-Factor D antibody used in the conjugates of the disclosure may have an affinity in its bivalent form to Factor D (e.g., affinity of the antibody as a IgG to Factor D) is about 9.0 nM (9.0×10-9 M)+/−2.

As is well-established in the art, binding affinity of a ligand to its receptor can be determined using any of a variety of assays, and expressed in terms of a variety of quantitative values. Accordingly, in some embodiments, the binding affinity is expressed as KD values and reflects intrinsic binding affinity (e.g., with minimized avidity effects). Generally and preferably, binding affinity is measured in vitro, whether in a cell-free or cell-associated setting. As described in greater detail herein, fold difference in binding affinity can be quantified in terms of the ratio of the monovalent binding affinity value of a humanized antibody (e.g., in Fab form) and the monovalent binding affinity value of a reference/comparator antibody (e.g., in Fab form) (e.g., a murine antibody having donor hypervariable region sequences), wherein the binding affinity values are determined under similar assay conditions. Thus, in some embodiments, the fold difference in binding affinity is determined as the ratio of the KD values of the humanized antibody in Fab form and said reference/comparator Fab antibody. For example, in some embodiments, if an antibody of the disclosure (A) has an affinity that is "3-fold lower" than the affinity of a reference antibody (M), then if the KD value for A is 3×, the KD value of M would be 1×, and the ratio of KD of A to KD of M would be 3:1. Conversely, in some embodiments, if an antibody of the disclosure (C) has an affinity that is "3-fold greater" than the affinity of a reference antibody (R), then if the KD value for C is 1×, the KD value of R would be 3×, and the ratio of KD of C to KD of R would be 1:3. Any of a number of assays known in the art, including those described herein, can be used to obtain binding affinity measurements, including, for example, Biacore, radioimmunoassay (MA) and ELISA.

Further, KD values for an antibody used in the conjugates of the disclosure may vary depending on conditions of the particular assay used. For example, in some embodiments, binding affinity measurements may be obtained in an assay wherein the Fab or antibody is immobilized and binding of the ligand, i.e., Factor D, is measured or alternatively, the ligand, i.e., Factor D, for the Fab or antibody is immobilized and binding of the Fab or antibody is measured. In some embodiments, the binding affinity measurements may be obtained in an assay wherein the regeneration conditions may comprise (1) 10 mM glycine or 4M MgCl2 at pH 1.5, and (2) pH between pH of 1.0 and pH of 7.5, including pH of 1.5, pH of 5.0, pH of 6.0 and pH of 7.2. In some embodiments, the binding affinity measurements may be obtained in an assay wherein the binding conditions may comprise (1) PBS or HEPES-buffered saline and (2) Tween-20, i.e., 0.1% Tween-20. In some embodiments, the binding affinity measurements may be obtained in an assay wherein the source of the ligand, i.e., Factor D, may be from commercially available sources. In some embodiments, binding affinity measurements may be obtained in an assay wherein (1) the Fab or antibody is immobilized and binding of the ligand, i.e., Factor D is measured, (2) the regeneration conditions comprise 4M MgCl2 at pH 7.2 and (3) the binding conditions comprise HEPES-buffered saline, pH 7.2 containing 0.1% Tween-20. In some embodiments, binding affinity measurements may be obtained in an assay wherein (1) the ligand, i.e., Factor D, is immobilized and binding of the Fab or antibody is measured, (2) the regeneration conditions comprise 10 mM glycine at pH 1.5 and (3) the binding conditions comprise PBS buffer.

b. Biological Activity

To determine whether an anti-Factor D antibody, or variant or fragment thereof (e.g. antigen-binding fragment) is capable of binding to Factor D and exerting a biological effect, for example, inhibition of alternative pathway hemolysis, hemolytic inhibition assays using rabbit RBCs may be used, including those described in Example 2. Such hemolytic inhibition may be determined using standard assays (Kostavasili et al. (1997) *J of Immunology* 158:1763-72; Wiesmann et al. (2006) *Nature* 444:159-60). Activation of complement in such assays may be initiated with serum or plasma. Appropriate concentrations of Factor D in serum or plasma (Pascual et al. (1998) *Kidney International* 34:529-536; Complement Facts Book, Bernard J. Morley and Mark J. Walport, editors, Academic Press (2000); Barnum et al. (1984) *J. Immunol. Methods*, 67: 303-309) can be routinely determined according to methods known in the art, including those that have been described in references such as Pascual et al. (1998) *Kidney International* 34:529-536 and Barnum et al. (1984) *J. Immunol. Methods* 67:303-309. The present disclosure relates generally to antibodies capable of inhibiting biological activities associated with Factor D. For example, at a concentration of 18 μg/ml (equivalent to about 1.5 times the molar concentration of human factor D in the blood; molar ratio of anti-Factor D antibody to Factor D of about 1.5:1), significant inhibition of the alternative complement activity by the antibody can be observed (see, e.g., U.S. Pat. No. 6,956,107)

In some embodiments, the present disclosure is directed to conjugates comprising anti-Factor D antibodies, wherein a Fab fragment of such antibodies inhibits alternative pathway hemolysis with $IC_{50}$ values less than 30 nM. In some embodiments, the disclosure is directed to conjugates comprising anti-Factor D antibodies, wherein a Fab fragment of such antibodies inhibits alternative pathway hemolysis with $IC_{50}$ values less than 15 nM. In some embodiments, the disclosure is directed to conjugates comprising anti-Factor D antibodies, wherein a Fab fragment of such antibodies inhibits alternative pathway hemolysis with $IC_{50}$ values less than 10 nM. In some embodiments, the disclosure is directed to conjugates comprising anti-Factor D antibodies, wherein a Fab fragment of such antibodies inhibits alternative pathway hemolysis with $IC_{50}$ values less than 5 nM.

In some embodiments, the disclosure is directed to conjugates comprising anti-Factor D antibodies, wherein a Fab fragment of such antibodies inhibits alternative pathway hemolysis with $IC_{50}$ values between 30 nM and 2 nM. In some embodiments, the disclosure is directed to conjugates comprising anti-Factor D antibodies, wherein a Fab fragment of such antibodies inhibits alternative pathway hemolysis with $IC_{50}$ values between 25 nM and 7 nM. In some embodiments, the disclosure is directed to conjugates comprising anti-Factor D antibodies, wherein a Fab fragment of such antibodies inhibits alternative pathway hemolysis with $IC_{50}$ values between 20 nM and 12 nM. In some embodiments, the disclosure is directed to conjugates comprising anti-Factor D antibodies, wherein a Fab fragment of such antibodies inhibits alternative pathway hemolysis with $IC_{50}$ values between 30 nM and 15 nM. In some embodiments, the disclosure is directed to conjugates comprising anti-Factor D antibodies, wherein a Fab fragment of such antibodies inhibits alternative pathway hemolysis with $IC_{50}$ values between 12 nM and 8 nM. In some embodiments, the disclosure is directed to conjugates comprising anti-Factor D antibodies, wherein a Fab fragment of such antibodies inhibits alternative pathway hemolysis with $IC_{50}$ values between 7 nM and 2 nM. In some embodiments, the disclosure is directed to conjugates comprising anti-Factor D antibodies, wherein a Fab fragment of such antibodies inhibits alternative pathway hemolysis with $IC_{50}$ values between 6 nM and 3 nM. In some embodiments, the disclosure is directed to conjugates comprising anti-Factor D antibodies, wherein a Fab fragment of such antibodies inhibits alternative pathway hemolysis with $IC_{50}$ values between 8 nM and 5 nM. In some embodiments, the disclosure is directed to conjugates comprising anti-Factor D antibodies, wherein a Fab fragment of such antibodies inhibits alternative pathway hemolysis with $IC_{50}$ values between 5 nM and 2 nM. In some embodiments, the disclosure is directed to conjugates comprising anti-Factor D antibodies, wherein a Fab fragment of such antibodies inhibits alternative pathway hemolysis with $IC_{50}$ values between 10 nM and 5 nM. In some embodiments, the disclosure is directed to conjugates comprising anti-Factor D antibodies, wherein a Fab fragment of such antibodies inhibits alternative pathway hemolysis with $IC5_{50}$ values between 8 nM and 2 nM. In some embodiments, the disclosure is directed to conjugates comprising anti-Factor D antibodies, wherein a Fab fragment of such antibodies inhibits alternative pathway hemolysis with $IC_{50}$ values between 7 nM and 3 nM. In some embodiments, the disclosure is directed to conjugates comprising anti-Factor D antibodies, wherein a Fab fragment of such antibodies inhibits alternative pathway hemolysis with $IC_{50}$ values between 6 nM and 4 nM. In another embodiment, the disclosure is directed to conjugates comprising anti-Factor D antibodies, wherein a Fab fragment of such antibodies inhibits alternative pathway hemolysis with an $IC_{50}$ value of about 4.7 nM±0.6 nM. In another embodiment, the disclosure is directed to anti-Factor D antibodies, wherein a Fab fragment of such antibodies inhibits alternative pathway hemolysis with an $IC_{50}$ value of about 6.4 nM±0.6 nM. In another embodiment, the disclosure is directed to conjugates comprising anti-Factor D antibodies, wherein a Fab fragment of such antibodies inhibits alternative pathway hemolysis with an $IC_{50}$ value of about 3.5 nM±0.5 nM. In another embodiment, the disclosure is directed to conjugates comprising anti-Factor D antibodies, wherein a Fab fragment of such antibodies inhibits alternative pathway hemolysis with an $IC_{50}$ value of about 4.4 nM±1.5 nM. In another embodiment, the disclosure is directed to conjugates comprising anti-Factor D antibodies, wherein a Fab fragment of such antibodies inhibits alternative pathway hemolysis with an $IC_{50}$ value of about 10.2 nM±0.8 nM. In another embodiment, the disclosure is directed to conjugates comprising anti-Factor D antibodies, wherein a Fab fragment of such antibodies inhibits alternative pathway hemolysis with an $IC_{50}$ value of about 23.9 nM±5.0 nM.

In some embodiments, the disclosure is directed to conjugates comprising anti-Factor D antibodies, wherein a Fab fragment of such antibodies inhibits alternative pathway hemolysis with $IC_{90}$ values less than 80 nM. In some embodiments, the disclosure is directed to conjugates comprising anti-Factor D antibodies, wherein a Fab fragment of such antibodies inhibits alternative pathway hemolysis with $IC_{90}$ values less than 50 nM. In some embodiments, the disclosure is directed to conjugates comprising anti-Factor D antibodies, wherein a Fab fragment of such antibodies inhibits alternative pathway hemolysis with $IC_{90}$ values less than 40 nM. In some embodiments, the disclosure is directed to conjugates comprising anti-Factor D antibodies, wherein a Fab fragment of such antibodies inhibits alternative pathway hemolysis with $IC_{90}$ values less than 20 nM. In some embodiments, the disclosure is directed to conjugates comprising anti-Factor D antibodies, wherein a Fab fragment of such antibodies inhibits alternative pathway hemolysis with $IC_{50}$ values less than 15 nM.

In some embodiments, the disclosure is directed to conjugates comprising anti-Factor D antibodies, wherein a Fab fragment of such antibodies inhibits alternative pathway hemolysis with $IC_{90}$ values between 80 nM and 10 nM. In some embodiments, the disclosure is directed to conjugates comprising anti-Factor D antibodies, wherein a Fab fragment of such antibodies inhibits alternative pathway hemolysis with $IC_{90}$ values between 75 nM and 15 nM. In some embodiments, the disclosure is directed to conjugates comprising anti-Factor D antibodies, wherein a Fab fragment of such antibodies inhibits alternative pathway hemolysis with $IC_{90}$ values between 70 nM and 20 nM. In some embodiments, the disclosure is directed to conjugates comprising anti-Factor D antibodies, wherein a Fab fragment of such antibodies inhibits alternative pathway hemolysis with $IC_{90}$ values between 65 nM and 25 nM. In some embodiments, the disclosure is directed to conjugates comprising anti-Factor D antibodies, wherein a Fab fragment of such antibodies inhibits alternative pathway hemolysis with $IC_{90}$ values between 60 nM and 30 nM. In some embodiments, the disclosure is directed to conjugates comprising anti-Factor D antibodies, wherein a Fab fragment of such antibodies inhibits alternative pathway hemolysis with $IC_{90}$ values between 55 nM and 35 nM. In some embodiments, the disclosure is directed to conjugates comprising anti-Factor D antibodies, wherein a Fab fragment of such antibodies inhibits alternative pathway hemolysis with $IC_{90}$ values between 50 nM and 40 nM. In some embodiments, the disclosure is directed to conjugates comprising anti-Factor D antibodies, wherein a Fab fragment of such antibodies inhibits alternative pathway hemolysis with $IC_{90}$ values between 80 nM and 70 nM. In some embodiments, the disclosure is directed to conjugates comprising anti-Factor D antibodies, wherein a Fab fragment of such antibodies inhibits alternative pathway hemolysis with $IC_{90}$ values between 55 nM and 25 nM. In some embodiments, the disclosure is directed to conjugates comprising anti-Factor D antibodies, wherein a Fab fragment of such antibodies inhibits alternative pathway hemolysis with $IC_{90}$ values between 16 nM and 12 nM. In another embodiment, the disclosure is directed to conjugates comprising anti-Factor D antibodies, wherein a Fab fragment of such antibodies inhibits alternative pathway hemolysis with an $IC_{90}$ value of about 14.0 nM±1.0 nM. In another embodiment, the disclosure is directed to conjugates comprising anti-Factor D antibodies, wherein a Fab fragment of such antibodies inhibits alternative pathway hemolysis with an $IC_{90}$ value of about 38.0 nM±11.0 nM. In another embodiment, the disclosure is directed to conjugates comprising anti-Factor D antibodies, wherein a Fab fragment of such antibodies inhibits alternative pathway hemolysis with an $IC_{90}$ value of about 72.6 nM±4.8 nM.

In some embodiments, the disclosure is directed to conjugates comprising an anti-Factor D antibody wherein a Fab fragment of such antibodies inhibits alternative pathway hemolysis in an antibody to Factor D molar ratio of about 0.05:1 (0.05) to about 10:1 (10), or about 0.09:1 (0.09) to about 8:1 (8), or about 0.1:1 (0.1) to about 6:1 (6), or about 0.15:1 (0.15) to about 5:1 (5), or about 0.19:1 (0.19) to about 4:1 (4), or about 0.2:1 (0.2) to about 3:1 (3), or about 0.3:1 (0.3) to about 2:1 (2), or about 0.4:1 (0.4) to about 1:1 (1), or about 0.5:1 (0.5) to about 1:2 (0.5), or about 0.6:1 (0.6) to about 1:3 (0.33), or about 0.7:1 (0.7) to about 1:4 (0.25), or about 0.8:1 (0.8) to about 1:5 (0.2) or about 0.9:1 (0.9) to about 1:6 (0.17).

In some embodiments, the disclosure is directed to conjugates comprising fragments of humanized anti-Factor D antibodies (e.g. antigen-binding fragments). The antibody fragments of the present disclosure may, for example, be Fv, Fab, Fab-SH, Fab'-SH, Fab', Fab-C, Fab'-C, Fab'-C-SH, Fab-C-SH, scFv, diabody, or F(ab')$_2$, dAb, complementarity determining region (CDR) fragments, linear antibodies, single-chain antibody molecules, minibodies, diabodies, or multispecific antibodies formed from antibody fragments. In a further embodiment, the disclosure is directed to conjugates comprising a humanized anti-Factor D antibody fragment (e.g. antigen-binding fragment) that is capable of penetrating substantially all of the retina. In an even further embodiment, the disclosure is directed to conjugates comprising a humanized anti-Factor D antibody fragment (e.g. antigen-binding fragment) that is capable of penetrating throughout the entire thickness of the retina.

In some embodiments, the disclosure is directed to conjugates comprising anti-Factor D antibodies, wherein an unconjugated Fab fragment of such antibodies has a half-life of at least 3, 5, 7, 10 or 12 days after administration into a mammalian eye (e.g. human) via a single intravitreal injection. In another embodiment, the disclosure is directed to conjugates comprising humanized anti-Factor D antibodies, wherein an unconjugated Fab fragment of such antibodies inhibits alternative pathway (AP) complement activation for at least 40, 45, 50, 55, 60, 65, 70, 75, 80, 85, 90, 95, 100, 105, 110 or 115 days after administration into a mammalian eye (e.g. human) via a single intravitreal injection. In another embodiment, the disclosure is directed to conjugates comprising humanized anti-Factor D antibodies, wherein the concentration of an unconjugated Fab fragment of such antibodies that inhibits alternative pathway (AP) complement activation is maintained in retinal tissue for at least 40, 45, 50, 55, 60, 65, 70, 75, 80 or 85 days after administration into a mammalian eye (e.g. human) via a single intravitreal injection. In another embodiment, the disclosure is directed to conjugates comprising humanized anti-Factor D antibodies, wherein the concentration of an unconjugated Fab fragment of such antibodies that inhibits alternative pathway (AP) complement activation is maintained in the vitreous humor for at least 80, 85, 90, 95, 100, 105, 110 or 115 days after administration into a mammalian eye (e.g. human) via a single intravitreal injection.

Construction of Anti-Factor D Antibody or Antibody Variant—Polymer Conjugates a. Multi-Armed Polymers In some aspects, the conjugates of the present disclosure can be made by derivatizing the anti-Factor D antibodies or antibody variants described herein by conjugating the antibodies or variants thereof with a multi-armed polymer. It will be appreciated that any multi-armed polymer that provides the conjugate with the desired size or that has the selected average molecular weight as described herein is suitable for use in constructing the antibody-polymer conjugates of the disclosure.

Many polymers are suitable for use in pharmaceuticals. See, e.g., Davis et al., Biomedical Polymers: Polymeric Materials and Pharmaceuticals for Biomedical Use, pp. 441-451 (1980). In all embodiments of the present disclosure, a non-proteinaceous polymer is used to form the conjugates of the disclosure. The non-proteinaceous polymer ordinarily is a hydrophilic synthetic polymer, i.e., a polymer not otherwise found in nature. However, polymers which exist in nature and are produced by recombinant or in vitro methods may also be useful, as are polymers which are isolated from native sources.

In some aspects, the anti-Factor D antibodies or antibody variants are derivatized by conjugating (e.g., covalently linking) the antibodies or variants thereof to a multi-armed polyol. Thus, in some embodiments, the disclosure is directed to a conjugate comprising one or more anti-Factor D antibody or antibody variant disclosed herein covalently linked to one or more multi-armed polyol. The polyol employed can be any water-soluble poly (alkylene oxide) polymer and can have a linear or branched chain. Suitable polyols include those substituted at one or more hydroxyl positions with a chemical group, such as an alkyl group having between one and four carbons. Typically, the polyol is a poly(alkylene glycol), such as polyethylene glycol (PEG), and thus, for ease of description, the remainder of the discussion relates to an exemplary embodiment wherein the polyol employed is PEG, and the process of conjugating the polyol to a polypeptide is termed "PEGylation." However, those skilled in the art will recognize that other polyols, such as, for example, poly(propylene glycol) and polyethylene-polypropylene glycol copolymers, can be employed using the techniques for conjugation described herein for PEG.

The polyols used to form the conjugates of the present disclosure are multi-armed polyols. As used herein, "multi-armed polyol" refers to a polyol comprising a core structure to which at least two arms are attached. The multi-armed polyol may be, for example, a dimer (two arms), a tetramer (four arms), a hexamer (six arms), an octamer (eight arms), etc. In some aspects, the multi-armed polyol is a multi-armed PEG.

The weight average molecular weight of the multi-armed PEG used in the PEGylation of the anti-Factor D antibodies and antibody variants can vary, and typically may range from about 500 to about 300,000 daltons (D). In some embodiments, the weight average molecular weight of the multi-armed PEG is from about 1,000 to about 100,000 D, and, in some embodiments, from about 20,000 to about 60,000 D. In some embodiments, PEGylation is carried out with a multi-armed PEG having a weight average molecular weight of about 40,000 D.

A variety of methods for PEGylating proteins are known in the art. Specific methods of producing proteins conjugated to PEG include the methods described in U.S. Pat. Nos. 4,179,337, 4,935,465, and 5,849,535, all of which are herein incorporated by reference in their entirety. Typically the protein is covalently bonded via one or more of the amino acid residues of the protein to a terminal reactive group on the polymer. The polymer with the reactive group(s) is designated herein as an activated or functionalized polymer (e.g., a functionalized PEG). The reactive group selectively reacts with free sulfhydryl or amino or other reactive groups on the antibody or antibody variant. The multi-armed PEG polymer can be coupled to the sulfhydryl or amino or other reactive group on the antibody or antibody variant in either a random or a site specific manner. It will be understood, however, that the type and amount of the reactive group chosen, as well as the type of polymer employed, to obtain optimum results, will depend on the particular antibody or antibody variant employed to limit, and preferably substantially prevent, having the reactive group react with too many active groups on the antibody. As it may not be possible to sufficiently limit or prevent this in some instances, typically from about 0.05 to about 1000 moles, or, in some embodiments, from about 0.05 to about 200 moles, of functionalized polymer per mole of antibody, depending on antibody concentration, may be employed. The final amount of functionalized polymer per mole of antibody is a balance to maintain optimum activity, while at the same time optimizing, if possible, the vitreous humor, retina, and/or aqueous humor half-life of the antibody.

While the residues may be any reactive amino acids on the antibody or antibody variant, such as the N-terminal amino acid group, in some embodiments, the reactive amino acid is cysteine, which is linked to the reactive group of the functionalized polymer through its free thiol group as shown, for example, in WO 99/03887, WO 94/12219, WO 94/22466, U.S. Pat. Nos. 5,206,344, 5,166,322, and 5,206,344, all of which are herein incorporated by reference in their entirety. In such embodiments, the polymer may comprise at least one terminal reactive group that is capable of reacting specifically with the free sulfhydryl or thiol group(s) on the parental antibody. Such groups include, but are not limited to, maleimide, a sulfhydryl, a thiol, trifluoromethanesulfonate, tosylate, aziridine, epoxide, a pyridyl disulfide, succinimidyl ester, —NH2, an aldehyde, a haloacetate, a haloacetamide, and a para-nitrophenyl carbonate, among others. The polymer can be coupled to the parental antibody using any protocol suitable for the chemistry of the coupling system selected, such as the protocols and systems described in U.S. Pat. Nos. 4,179,337, 7,122,636, and Jevsevar, et al., Biotech J., Vol. 5, pp. 113-128 (2010). Alternatively, the reactive amino acid may be lysine, which is linked to the reactive group of the functionalized polymer through its free epsilon-amino group (see, e.g., WO 93/00109, incorporated by reference herein), or glutamic or aspartic acid, which is linked to the polymer through an amide bond. The reactive group of the polymer can then react with, for example, the α (alpha) and ε (epsilon) amines or sulfhydryl groups of proteins to form a covalent bond. It will be appreciated that the present disclosure is not limited to conjugates utilizing any particular type of linkage between an antibody or antibody fragment and a polymer.

Suitable functionalized multi-armed PEGs for use in preparing the conjugates of the disclosure can be produced by a number of conventional reactions. For example, a N-hydroxysuccinimide ester of a PEG (M-NHS-PEG) can be prepared from a PEG-monomethyl ether by reaction with N,N'-dicyclohexylcarbodiimide (DCC) and N-hydroxysuccinimide (NETS), according to the method of Buckmann and Merr, Makromol. Chem., Vol. 182, pp. 1379-1384 (1981). In addition, a PEG terminal hydroxy group can be converted to an amino group, for example, by reaction with thionyl bromide to form PEG-Br, followed by aminolysis with excess ammonia to form PEG-NH2. The PEG-NH2 can then be conjugated to the antibody or antibody variant of interest using standard coupling reagents, such as Woodward's Reagent K. Furthermore, a PEG terminal-CH2OH group can be converted to an aldehyde group, for example, by oxidation with MnO2. The aldehyde group can be conjugated to the antibody or antibody variant by reductive alkylation with a reagent such as cyanoborohydride.

In some embodiments, the multi-armed PEG used to prepare the conjugates of the present disclosure has the structure of general formula (I):

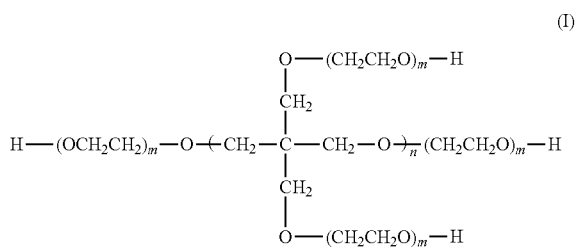

(I)

wherein each m denotes the length or size of the particular arm of the polyol (PEG) and is independently an integer of from about 45 to about 1000, or from about 3 to about 250, or from about 50 to about 200, or from about 100 to about 150; and n is an integer from about 1 to about 10.

In some embodiments, the multi-armed PEG has the structure of general formula (I), wherein n is 1, and the multi-armed PEG is a tetramer. In another embodiment, the multi-armed PEG has the structure of general formula (I), wherein n is 2, and the multi-armed PEG is a hexamer. In another embodiment, the multi-armed PEG has the structure of general formula (I), wherein n is 3, and the multi-armed PEG is an octamer.

In another aspect, the multi-armed PEG used to prepare the conjugates of the present disclosure has the structure of general formula (II):

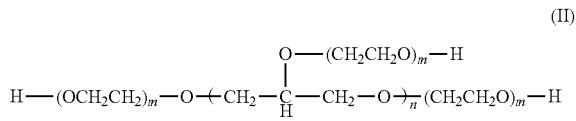

(II)

wherein each m denotes the length or size of the particular arm of the polyol (PEG) and is independently an integer of from about 45 to about 1000, or from about 3 to about 250, or from about 50 to about 200, or from about 100 to about 150; and n is an integer from about 1 to about 10.

In some embodiments, the multi-armed PEG has the structure of general formula (II), wherein n is 2, and the multi-armed PEG is a tetramer. In another embodiment, the multi-armed PEG has the structure of general formula (II), wherein n is 4, and the multi-armed PEG is a hexamer. In another embodiment, the multi-armed PEG has the structure of general formula (II), wherein n is 6, and the multi-armed PEG is an octamer.

In another aspect, the multi-armed PEG used to prepare the conjugates of the present disclosure has the structure of general formula (III):

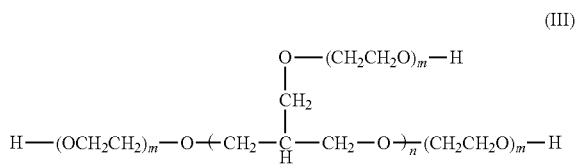

(III)

wherein each m denotes the length or size of the particular arm of the polyol (PEG) and is independently an integer of from about 45 to about 1000, or from about 3 to about 250, or from about 50 to about 200, or from about 100 to about 150; and n is an integer from about 1 to about 10.

In some embodiments, the multi-armed PEG has the structure of general formula (III), wherein n is 2, and the multi-armed PEG is a tetramer. In another embodiment, the multi-armed PEG has the structure of general formula (III), wherein n is 4, and the multi-armed PEG is a hexamer. In another embodiment, the multi-armed PEG has the structure of general formula (III), wherein n is 6, and the multi-armed PEG is an octamer.

In another aspect, the multi-armed PEG used to prepare the conjugates of the present disclosure has the structure of general formula (IV):

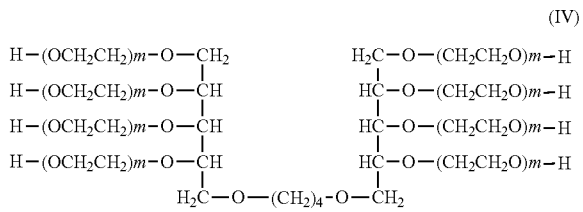

(IV)

wherein each m denotes the length or size of the particular arm of the polyol (PEG) and is independently an integer of from about 45 to about 1000, or from about 3 to about 250, or from about 50 to about 200, or from about 100 to about 150.

The multi-armed PEG having the structure of any of general formulas (I) to (IV) may be functionalized to, for example, attach a terminal reactive group suitable for reacting with or conjugating to the antibody (e.g., antibody fragment) using any of the techniques described above to produce a functionalized multi-armed PEG. In other embodiments, however, the multi-armed PEG can be covalently linked to the anti-Factor D antibodies or antibody variants through a multifunctional crosslinking agent which reacts with the PEG and one or more amino acid residues of the antibody or antibody variant to be linked, as described in, for example, U.S. Pat. No. 7,122,636, which is herein incorporated by reference in its entirety.

In other aspects, the multi-armed PEG used to prepare the conjugates of the present disclosure is a functionalized multi-armed PEG comprising at least one terminal reactive group. The terminal reactive group can conjugate directly to the anti-Factor D antibodies or antibody variants to form the conjugates of the present disclosure. In some embodiments, the functionalized multi-armed PEG has the structure of general formula (Ia):

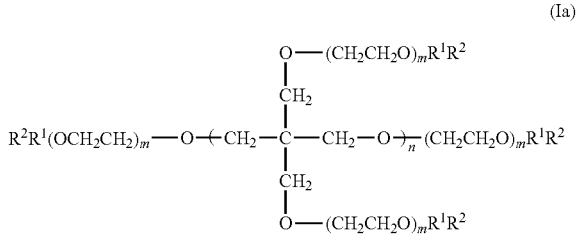

(Ia)

wherein each m denotes the length or size of the particular arm of the polyol (PEG) and is independently an integer of from about 45 to about 1000, or from about 3 to about 250, or from about 50 to about 200, or from about 100 to about 150; and n is an integer from about 1 to about 10; each $R^1$ is independently either absent, or is a linking group; and each $R^2$ is independently either hydrogen or a terminal reactive group; wherein at least one $R^2$ is a terminal reactive group. In some embodiments, $R^2$ is independently selected form the group consisting of a thiol reactive group, an amino reactive group, and combinations thereof.

In some embodiments, the functionalized multi-armed PEG has the structure of general formula (Ia), wherein n is an integer from 1 to 3. In some embodiments, the functionalized multi-armed PEG has the structure of general formula (Ia), wherein n is 1, and the multi-armed PEG is a tetramer. In another embodiment, the functionalized multi-armed PEG has the structure of general formula (Ia), wherein n is 2, and the multi-armed PEG is a hexamer. In another embodiment, the functionalized multi-armed PEG has the structure of general formula (Ia), wherein n is 3, and the multi-armed PEG is an octamer. In such embodiments, the octamer has the structure of general formula (Ib):

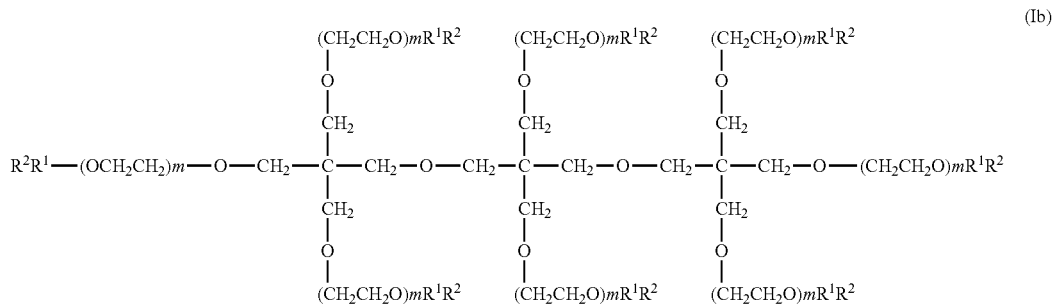

(Ib)

wherein m, $R^1$, and $R^2$ are as defined above. In particular, in one embodiment, each m denotes the length or size of the particular arm of the polyol (PEG) and is independently an integer of from about 45 to about 1000, or from about 3 to about 250, or from about 50 to about 200, or from about 100 to about 150; each $R^1$ is independently either absent, or is a linking group; and each $R^2$ is independently either hydrogen or a terminal reactive group; wherein at least one $R^2$ is a terminal reactive group. In some embodiments, $R^2$ is independently selected form the group consisting of a thiol reactive group, an amino reactive group, and combinations thereof.

Multi-armed PEGs having the structure of general formula (Ib) have a tripentaerythritol (TP) core structure, and are also referred to herein as TP octamers.

In some embodiments, the functionalized multi-armed PEG has the structure of general formula (Ia) or (Ib), wherein each R', when present, is the same or different, and $R^1$ and $R^2$ when taken together are selected from the group consisting of

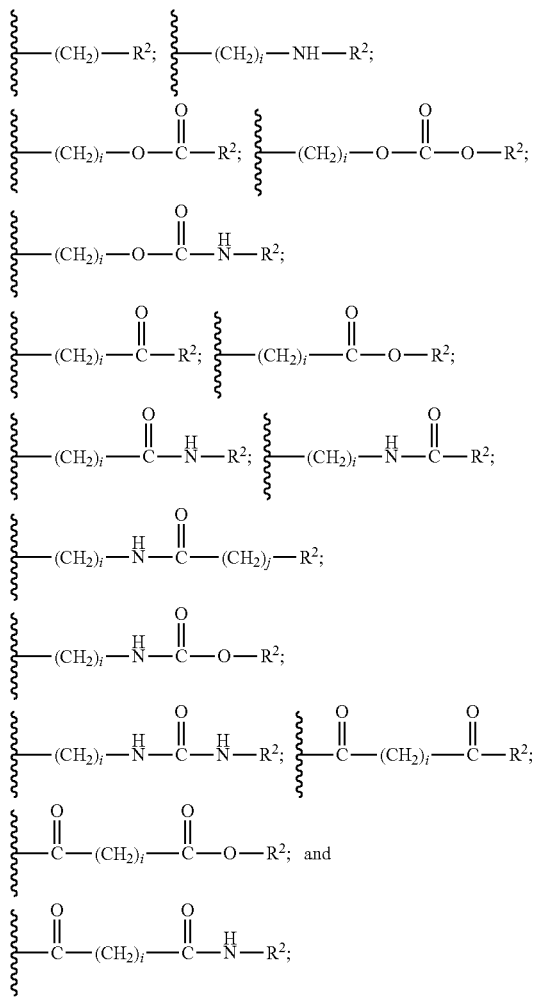

and combinations thereof; wherein each i is independently an integer of 0-10; j is an integer of 0-10; and $R^2$ is as defined herein. In some embodiments, each $R^1$ is a linking group.

In some embodiments, the functionalized multi-armed PEG has the structure of general formula (Ia) or (Ib), wherein $R^1$ and $R^2$, when taken together, are

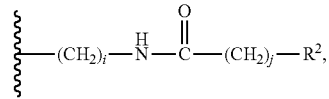

wherein i, j, and $R^2$ are as defined herein. In some embodiments, $R^1$ and $R^2$, when taken together, are

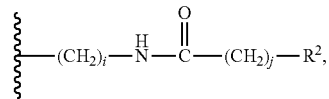

wherein i is 2; j is 2 or 3, and $R^2$ is as defined herein.

In some aspects, the functionalized multi-armed PEG has the structure of general formula (Ia) or (Ib), wherein each $R^2$ is independently selected from the group consisting of a maleimide, a sulfhydryl, a thiol, trifluoromethanesulfonate, tosylate, aziridine, epoxide, a pyridyl disulfide, succinimidyl ester, $-NH_2$, an aldehyde, a haloacetate, a haloacetamide, and a para-nitrophenyl carbonate. In some embodiments, each $R^2$ is independently a haloacetate selected from the group consisting of bromoacetate, iodoacetate, chloroacetate, and combinations thereof. In some embodiments, each $R^2$ is independently a haloacetamide selected from the group consisting of bromoacetamide, iodoacetamide, chloroacetamide, and combinations thereof. In some embodiments, $R^2$ is a maleimide.

In some embodiments, the functionalized multi-armed PEG has the structure of general formula (Ia) or (Ib), wherein each $R^2$ is a maleimide. In some embodiments, the functionalized multi-armed PEG has the structure of general formula (Ia) or (Ib), wherein $R^1$ and $R^2$, when taken together, are

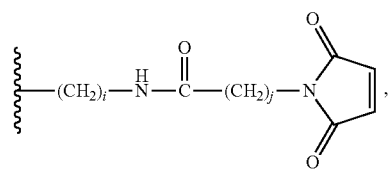

wherein i and j are as defined above. In one embodiment, the functionalized multi-armed PEG has the structure of general formula (Ia) or (Ib), wherein $R^1$ and $R^2$, when taken together, are

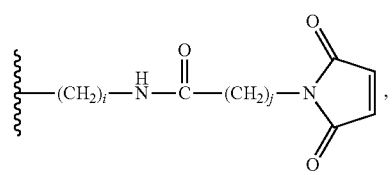

wherein i is 2 and j is 2.

In another aspect, the functionalized multi-armed PEG used to prepare the conjugates of the present disclosure has the structure of general formula (IIa):

(IIa)

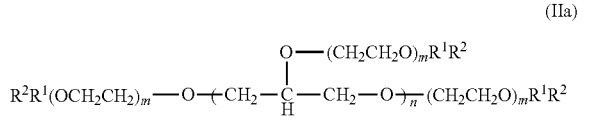

wherein each m denotes the length or size of the particular arm of the polyol (PEG) and is independently an integer of about 45 to about 1000, or from about 3 to about 250, or from about 50 to about 200, or from about 100 to about 150; and n is an integer from about 1 to about 10; each $R^1$ is independently either absent, or is a linking group; and each $R^2$ is independently either hydrogen or a terminal reactive group; wherein at least one $R^2$ is a terminal reactive group. In some embodiments, $R^2$ is independently selected form the group consisting of a thiol reactive group, an amino reactive group, and combinations thereof.

In some embodiments, the functionalized multi-armed PEG has the structure of general formula (IIa), wherein n is an integer from 2 to 6. In some embodiments, the functionalized multi-armed PEG has the structure of general formula (IIa), wherein n is 3. In another embodiment, the functionalized multi-armed PEG has the structure of general formula (IIa), wherein n is 2, and the multi-armed PEG is a tetramer. In another embodiment, the functionalized multi-armed PEG has the structure of general formula (IIa), wherein n is 4, and the multi-armed PEG is a hexamer. In another embodiment, the functionalized multi-armed PEG has the structure of general formula (IIa), wherein n is 6, and the multi-armed PEG is an octamer. Octamers having the structure of general formula (IIa) have a hexaglycerin (HG) core structure, and are also referred to herein as HG octamers.

In some embodiments, the functionalized multi-armed PEG has the structure of general formula (IIa), wherein each R', when present, is the same or different, and $R^1$ and $R^2$ when taken together are selected from the group consisting of

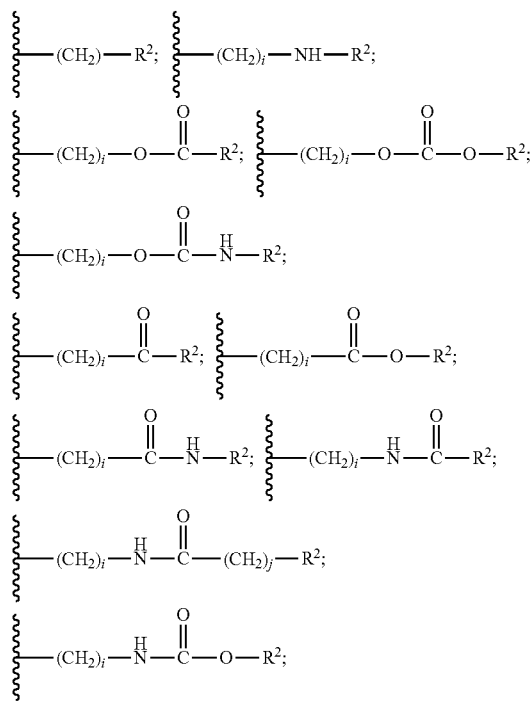

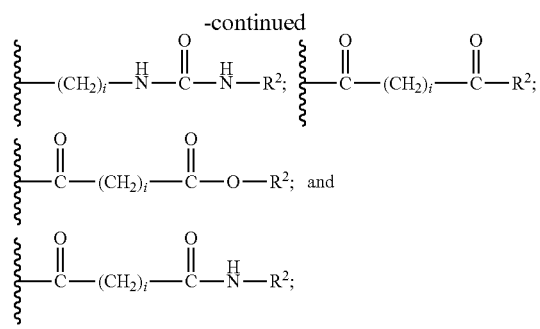

and combinations thereof wherein each i is independently an integer of 0-10; j is an integer of 0-10; and $R^2$ is as defined herein. In some embodiments, each $R^1$ is a linking group.

In some embodiments, the functionalized multi-armed PEG has the structure of general formula (IIa), wherein $R^1$ and $R^2$, when taken together, are

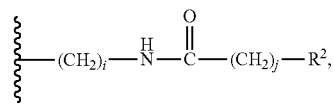

wherein i, j, and $R^2$ are as defined herein. In some embodiments, $R^1$ and $R^2$, when taken together, are

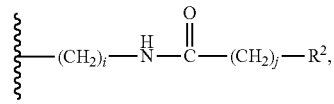

wherein i is 2; j is 2 or 3, and $R^2$ is as defined herein.

In some aspects, the functionalized multi-armed PEG has the structure of general formula (IIa), wherein each $R^2$ is independently selected from the group consisting of a maleimide, a sulfhydryl, a thiol, trifluoromethanesulfonate, tosylate, aziridine, epoxide, a pyridyl disulfide, succinimidyl ester, —NH$_2$, an aldehyde, a haloacetate, a haloacetamide, and a para-nitrophenyl carbonate. In some embodiments, each $R^2$ is independently a haloacetate selected from the group consisting of bromoacetate, iodoacetate, chloroacetate, and combinations thereof. In some embodiments, each $R^2$ is independently a haloacetamide selected from the group consisting of bromoacetamide, iodoacetamide, chloroacetamide, and combinations thereof. In some embodiments, $R^2$ is a maleimide.

In some embodiments, the functionalized multi-armed PEG has the structure of general formula (IIa), wherein each $R^2$ is a maleimide. In some embodiments, the functionalized multi-armed PEG has the structure of general formula (IIa), wherein $R^1$ and $R^2$, when taken together, are

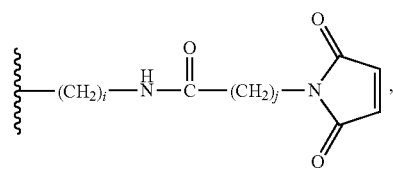

wherein i and j are as defined above. In some embodiments, the functionalized multi-armed PEG has the structure of general formula (IIa), wherein $R^1$ and $R^2$, when taken together, are

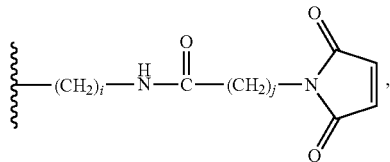

wherein i is 2 and j is 2.

In another aspect, the functionalized multi-armed PEG has the structure of general formula (IIIa):

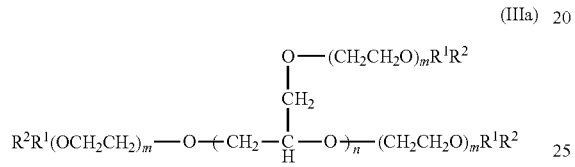
(IIIa)

wherein each m denotes the length or size of the particular arm of the polyol (PEG) and is independently an integer of from about 45 to about 1000, or from about 3 to about 250, or from about 50 to about 200, or from about 100 to about 150; and n is an integer from about 1 to about 10; each $R^1$ is independently either absent, or is a linking group; and each $R^2$ is independently either hydrogen or a terminal reactive group; wherein at least one $R^2$ is a terminal reactive group. In some embodiments, $R^2$ is independently selected form the group consisting of a thiol reactive group, an amino reactive group, and combinations thereof.

In some embodiments, the functionalized multi-armed PEG has the structure of general formula (IIIa), wherein n is an integer from 2 to 6. In some embodiments, the functionalized multi-armed PEG has the structure of general formula (IIIa), wherein n is 2, and the multi-armed PEG is a tetramer. In another embodiment, the functionalized multi-armed PEG has the structure of general formula (IIIa), wherein n is 4, and the multi-armed PEG is a hexamer. In another embodiment, the functionalized multi-armed PEG has the structure of general formula (IIIa), wherein n is 6, and the multi-armed PEG is an octamer. Octamers having the structure of general formula (IIIa) have a hexaglycerol (HGEO) core structure, and are also referred to herein as HGEO octamers.

In some embodiments, the functionalized multi-armed PEG has the structure of general formula (IIIa), wherein each R', when present, is the same or different, and $R^1$ and $R^2$ when taken together are selected from the group consisting of

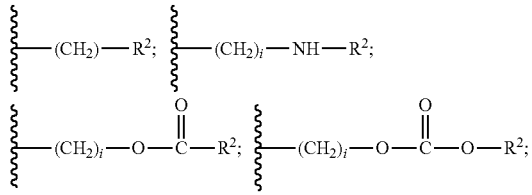

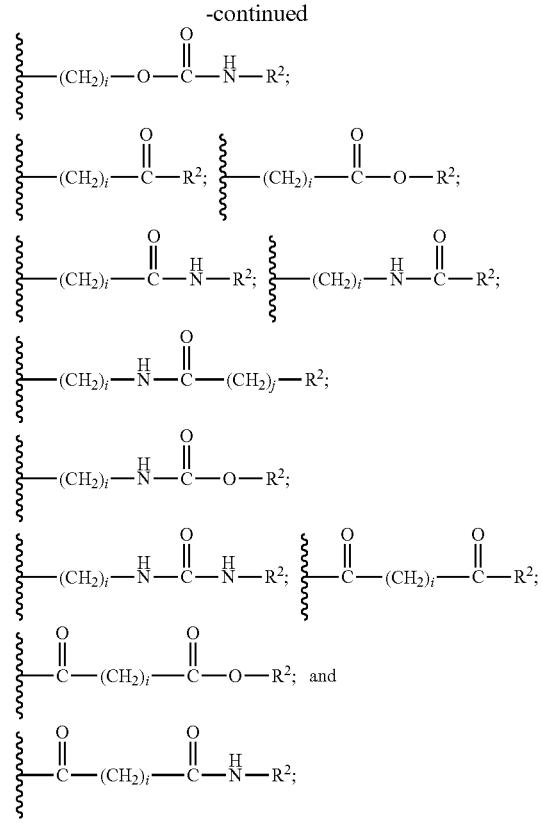

and combinations thereof wherein each i is independently an integer of 0-10; j is an integer of 0-10; and $R^2$ is as defined herein. In some embodiments, each $R^1$ is a linking group.

In some embodiments, the functionalized multi-armed PEG has the structure of general formula (IIIa), wherein $R^1$ and $R^2$, when taken together, are

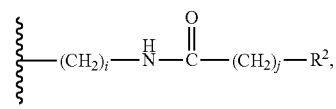

wherein i, j, and $R^2$ are as defined herein. In some embodiments, $R^1$ and $R^2$, when taken together, are

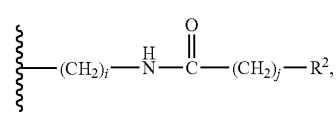

wherein i is 2; j is 2 or 3, and $R^2$ is as defined herein.

In some aspects, the functionalized multi-armed PEG has the structure of general formula (IIIa), wherein each $R^2$ is independently selected from the group consisting of a maleimide, a sulfhydryl, a thiol, trifluoromethanesulfonate, tosylate, aziridine, epoxide, a pyridyl disulfide, succinimidyl ester, —NH$_2$, an aldehyde, a haloacetate, a haloacetamide, and a para-nitrophenyl carbonate. In some embodiments, each $R^2$ is independently a haloacetate selected from the group consisting of bromoacetate, iodoacetate, chloroacetate, and combinations thereof. In some embodiments, each $R^2$ is independently a haloacetamide selected from the group consisting of bromoacetamide, iodoacetamide, chloroacetamide, and combinations thereof. In some embodiments, $R^2$ is a maleimide.

In some embodiments, the functionalized multi-armed PEG has the structure of general formula (IIIa), wherein each $R^2$ is a maleimide. In some embodiments, the functionalized multi-armed PEG has the structure of general formula (IIIa), wherein $R^1$ and $R^2$, when taken together, are

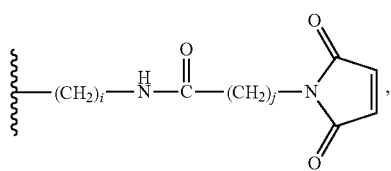

wherein i and j are as defined above. In some embodiments, the functionalized multi-armed PEG has the structure of general formula (IIIa), wherein $R^1$ and $R^2$, when taken together, are

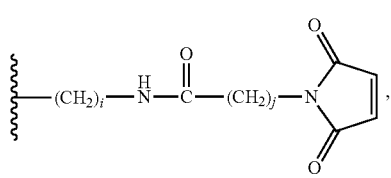

wherein i is 3 and j is 2.

In another aspect, the functionalized multi-armed PEG has the structure of general formula (IVa):

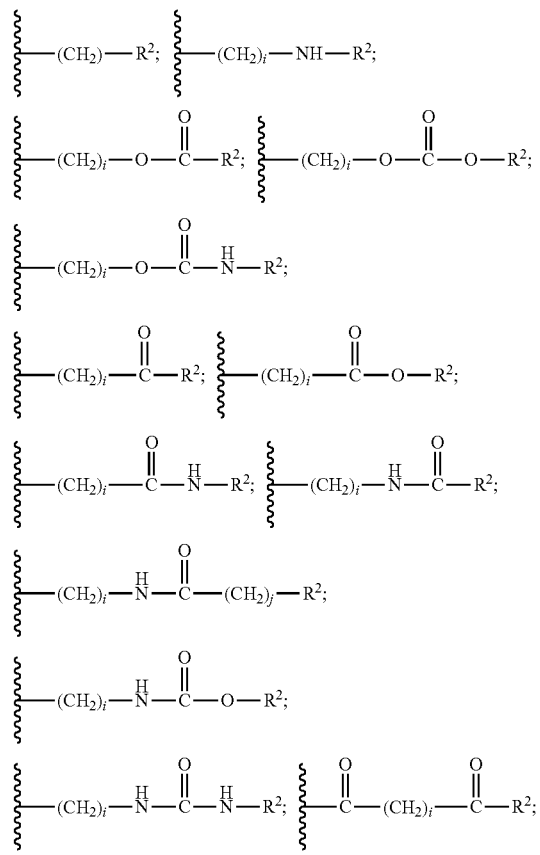

(IVa)

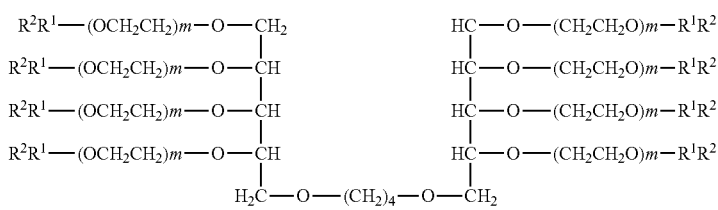

wherein each m denotes the length or size of the particular arm of the polyol (PEG) and is independently an integer of from about 45 to about 1000, or from about 3 to about 250, or from about 50 to about 200, or from about 100 to about 150; each $R^1$ is independently either absent, or is a linking group; and each $R^2$ is independently either hydrogen or a terminal reactive group; wherein at least one $R^2$ is a terminal reactive group. In some embodiments, $R^2$ is independently selected form the group consisting of a thiol reactive group, an amino reactive group, and combinations thereof.

Multi-armed PEGs having the structure of general formula (IVa) have a butanediol core structure, and are also referred to herein as DX octamers.

In some embodiments, the functionalized multi-armed PEG has the structure of general formula (IVa), wherein each $R^1$, when present, is the same or different, and $R^1$ and $R^2$ when taken together are selected from the group consisting of -continued

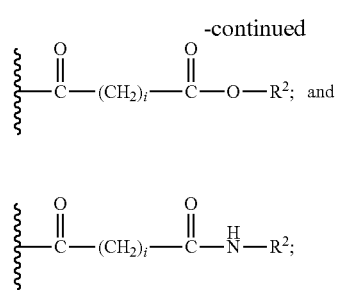

and combinations thereof; wherein each i is independently an integer of 0-10; j is an integer of 0-10; and $R^2$ is as defined herein. In some embodiments, each $R^1$ is a linking group.

In some embodiments, the functionalized multi-armed PEG has the structure of general formula (IVa), wherein $R^1$ and $R^2$, when taken together, are

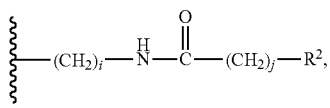

wherein i, j, and $R^2$ are as defined herein. In some embodiments, $R^1$ and $R^2$, when taken together, are

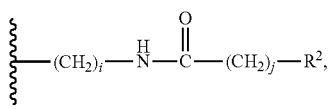

wherein i is 2; j is 2 or 3, and $R^2$ is as defined herein.

In some aspects, each $R^2$ is independently selected from the group consisting of a maleimide, a sulfhydryl, a thiol, trifluoromethanesulfonate, tosylate, aziridine, epoxide, a pyridyl disulfide, succinimidyl ester, —$NH_2$, an aldehyde, a haloacetate, a haloacetamide, and a para-nitrophenyl carbonate. In some embodiments, each $R^2$ is independently a haloacetate selected from the group consisting of bromoacetate, iodoacetate, chloroacetate, and combinations thereof. In some embodiments, each $R^2$ is independently a haloacetamide selected from the group consisting of bromoacetamide, iodoacetamide, chloroacetamide, and combinations thereof. In some embodiments, $R^2$ is a maleimide.

In some embodiments, the functionalized multi-armed PEG has the structure of general formula (IVa), wherein each $R^2$ is a maleimide. In some embodiments, the functionalized multi-armed PEG has the structure of general formula (IVa), wherein $R^1$ and $R^2$, when taken together, are

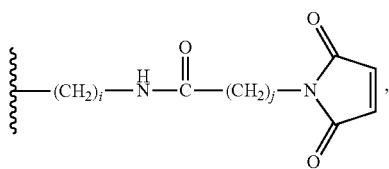

wherein i and j are as defined above. In some embodiments, the functionalized multi-armed PEG has the structure of general formula (IVa), wherein $R^1$ and $R^2$, when taken together, are

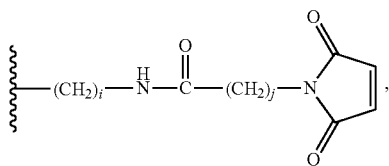

wherein i is 3 and j is 2.

The multi-armed PEGs used to prepare the conjugates of the disclosure preferably will have a low polydispersity of PEG chain (arm) length. In particular, a high polydispersity of the multi-armed PEG used to prepare the conjugate may in some instances complicate the analysis of the final conjugate, in particular making an accurate determination of the number of antibodies (e.g., Fabs) per PEG more difficult and uncertain. Accordingly, the PEG used to form the conjugate will typically have a polydispersity (determined using methods known in the art) within a range of about 1 to about 1.35, and in various embodiments will have a polydispersity of about 1 to about 1.25, about 1 to about 1.2, about 1 to about 1.15, about 1 to about 1.1, about 1.05, or even about 1.

Other functionalized multi-armed PEGs suitable for use in the present disclosure are described in U.S. Pat. App. Publ. No. 2011/0286956, and U.S. Pat. App. Publ. No. 2015/0073155, both of which are herein incorporated by reference in their entirety.

Functionalized multi-armed PEGs suitable for use in the present disclosure can also be purchased from a number of vendors. For example, JenKem Technology, USA sells maleimide-functionalized PEG octamers (e.g., 8ARM (TP)-PEG-MAL and 8ARM (HG)-PEG-MAL) and tetramers. NOF America Corp. also sells maleimide functionalized PEG octamers (e.g., Sunbright® HGEO-400MA; Sunbright® DX-400MA) and tetramers (e.g., Sunbright® PTE-400MA). Such octamers and tetramers are available in a variety of molecular weights, including an average molecular weight of 40,000 D.

b. Conjugates

In some embodiments, the disclosure is directed to a conjugate comprising one or more anti-Factor D antibody or antibody variant disclosed herein and one or more multi-armed polyol, wherein the conjugate is prepared by covalently linking at least one anti-Factor D antibody or antibody variant to the polyol. In some embodiments, the multi-armed polyol is a PEG. In some embodiments, the PEG is an octamer. In some embodiments, the PEG has the structure of general formula (Ia), (Ib), (IIa), (IIIa), or (IVa).

The conjugates of the present disclosure may be characterized by the number of anti-Factor D antibodies or antibody variants conjugated to each multi-armed PEG. This is referred to herein as "fabylation" or "degree of fabylation". The number of anti-Factor D antibodies or antibody variants conjugated to each PEG may vary depending on a variety of factors, including: 1) the number of arms in the PEG; 2) the number and/or reactivity of the terminal reactive groups on the PEG; 3) the core structure of the PEG; and/or, 4) PEGylation reaction conditions.

In one preferred embodiment, the conjugate of the disclosure comprises an eight-armed PEG, wherein at least one anti-Factor D antibody or antibody variant is covalently linked to the PEG. In another embodiment, the conjugate of the disclosure comprises an eight-armed PEG, wherein at least two anti-Factor D antibodies or antibody variants are covalently linked to the PEG. In another embodiment, the conjugate of the disclosure comprises an eight-armed PEG, wherein at least three anti-Factor D antibodies or antibody variants are covalently linked to the PEG. In another embodiment, the conjugate of the disclosure comprises an eight-armed PEG, wherein at least four anti-Factor D antibodies or antibody variants are covalently linked to the PEG. In another embodiment, the conjugate of the disclosure comprises an eight-armed PEG, wherein at least five anti-Factor D antibodies or antibody variants are covalently linked to the PEG. In another embodiment, the conjugate of the disclosure comprises an eight-armed PEG, wherein at least six anti-Factor D antibodies or antibody variants are covalently linked to the PEG. In another embodiment, the conjugate comprises an eight-armed PEG, wherein at least seven anti-Factor D antibodies or antibody variants are covalently linked to the PEG. In another embodiment, the conjugate of the disclosure comprises an eight-armed PEG, wherein eight anti-Factor D antibodies or antibody variants are covalently linked to the PEG. In some embodiments, the conjugate of the disclosure comprises an eight-armed PEG, wherein from 5-8 anti-Factor D antibodies or antibody variants are covalently linked to the PEG. In another embodiment, the conjugate of the disclosure comprises an eight-armed PEG, wherein from 6-8 anti-Factor D antibodies or antibody variants are covalently linked to the PEG. In another embodiment, the conjugate of the disclosure comprises an eight-armed PEG, wherein from 7-8 anti-Factor D antibodies or antibody variants are covalently linked to the PEG.

In some embodiments, the conjugate of the disclosure comprises a multi-armed PEG having the structure of any one of general formulas (Ia), (Ib), (IIa), (IIIa), or (IVa). In such embodiments, at least one R2 is covalently linked to an anti-Factor D antibody or antibody variant described herein. In some embodiments, the multi-armed PEG having the structure of any one of general formulas (Ia), (Ib), (IIa), (IIIa), or (IVa) is an octamer, and at least two, at least three, at least four, at least five, at least six, at least seven, or all eight R2 groups are covalently linked to an anti-Factor D antibody or antibody variant described herein.

In some aspects, the conjugates of the present disclosure include species wherein the multi-armed polyol is covalently attached to a specific site or specific sites on the parental antibody; i.e., polymer attachment is targeted to a particular region or a particular amino acid residue or residues in the parental antibody or antibody fragments. Standard mutagenesis techniques can be used to alter the number and/or location of potential PEGylation sites in the parental antibody or antibody fragments. Thus, to the extent that amino acid substitutions introduce or replace amino acids such as cysteine and lysine, the anti-Factor D antibodies and variants thereof of the present disclosure can contain a greater or lesser number of potential PEGylation sites than a native sequence anti-Factor D (shown in FIG. 1).

As discussed above, site specific conjugation of polymers is most commonly achieved by attachment to cysteine residues in the parental antibody or antibody fragment. In such embodiments, the coupling chemistry can, for example, utilize the free sulfhydryl group of a cysteine residue not in a disulfide bridge in the parental antibody.

In some embodiments, one or more cysteine residue(s) naturally present in the parental antibody is (are) used as attachment site(s) for polymer conjugation. In other embodiments, free amino groups on the antibody or antibody variant can be thiolated with 2-imino-thiolane (Traut's reagent) and then coupled to, e.g., a maleimide-functionalized PEG, as described in Pedley, et al., Br. J. Cancer, Vol. 70, pp. 1126-1130 (1994). In another embodiment, one or more cysteine residue(s) is (are) engineered into a selected site or sites in the parental antibody for the purpose of providing a specific attachment site or sites for polymer.

Cysteine engineered antibodies have been described previously (U.S. Pat. Pub. No. 2007/0092940 and Junutula, J. R., et al, J. Immunol Methods, Vol. 332(1-2), pp. 41-52 (2008), all herein incorporated by reference in their entirety). In some embodiments, cysteine engineered antibodies can be parental antibodies. These are useful for generating antibody fragments having a free cysteine in a particular location, typically in a constant domain, e.g., CL or CH1. A parent antibody engineered to contain a cysteine is referred to herein as a "ThioMab" and Fab fragments produced from such cysteine engineered antibodies, regardless of the method of production, are referred to herein as "ThioFabs." As described previously (see, e.g., U.S. Pat. Pub. No. 2007/0092940 and Junutula, J. R., et al, J. Immunol Methods, Vol. 332(1-2), pp. 41-52 (2008)), mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. In addition to having a reactive thiol group, ThioMabs should be selected such that they retain antigen binding capability. The design, selection, and preparation of cysteine engineered antibodies were described in detail previously (see, e.g., WO 2011/069104, which is herein incorporated by reference). In some embodiments, engineered cysteines are introduced into the constant domains of heavy or light chains. As such, the cysteine engineered antibodies retain the antigen binding capability of their wild type, parent antibody counterparts and, as such, are capable of binding specifically, to antigens.

In some aspects, the present disclosure relates to antibody fragment-polymer conjugates, wherein the antibody fragment is a Fab, and the polymer is attached to one or more cysteine residue in the light or heavy chain of the Fab fragment that would ordinarily form the inter-chain disulfide bond linking the light and heavy chains.

In another aspect, the present disclosure relates to antibody fragment-polymer conjugates, wherein the antibody fragment is a Fab-C, and the polymer attachment is targeted to the hinge region of the Fab-C fragment. In some embodiments, one or more cysteine residue(s) naturally present in the hinge region of the antibody fragment is (are) used to attach the polymer. In another embodiment, one or more cysteine residues is (are) engineered into the hinge region of the Fab-C fragment for the purpose of providing a specific attachment site or sites for polymer. In some embodiments, an anti-Factor D antibody variant Fab fragment disclosed herein is modified by adding one cysteine at the C'-terminal end for the purpose of providing one attachment site for polymer conjugation. In another embodiment, an anti-Factor D antibody variant Fab fragment described herein is modified by adding four additional residues, Cys-Pro-Pro-Cys (SEQ ID NO: 21), at the C'-terminal end for the purpose of providing two attachment sites for polymer conjugation. In still another embodiment, an anti-Factor D antibody variant Fab fragment described herein is modified by adding four additional residues, Ser-Pro-Pro-Cys (SEQ ID NO:111, at the C'-terminal end for the purpose of providing one attachment site for polymer conjugation. In still another embodiment, an anti-Factor D antibody variant Fab fragment described herein is modified by adding four additional residues, Cys-Pro-Pro-Ser (SEQ ID NO: 112), at the C'-terminal end for the purpose of providing one attachment site for polymer conjugation. In still another embodiment, an anti-Factor D antibody variant Fab fragment described herein is modified by adding four additional residues, Ala-Pro-Pro-Cys (SEQ ID NO:113), at the C'-terminal end for the purpose of providing one attachment site for polymer conjugation. In still another embodiment, an anti-Factor D antibody variant Fab fragment described herein is modified by adding four additional residues, Ser-Gly-Gly-Cys (SEQ ID NO:114), at the C'-terminal end for the purpose of providing one attachment site for polymer conjugation. In still another embodiment, an anti-Factor D antibody variant Fab fragment described herein has a C'-terminal end that has been modified to end in "CYGPPC", providing one attachment site for polymer conjugation.

The degree and sites of PEGylation can also be manipulated by adjusting reaction conditions, such as the relative concentrations of the functionalized PEG and the protein as well as the pH. Suitable conditions for a desired degree of PEGylation can be determined empirically by varying the parameters of standard PEGylation reactions.

PEGylation of anti-Factor D antibodies and antibody variants is carried out by any convenient method. Suitable PEGylation conditions are set forth in WO 2011/069104 and WO 03/029420, both of which are herein incorporated by reference in their entirety.

c. Characterization and Activity

The PEGylated proteins can be characterized by SDS-PAGE, gel filtration, NMR, peptide mapping, liquid chromatography-mass spectrophotometry, and in vitro biological assays. The extent of fabylation is typically first shown by SDS-PAGE. Polyacrylamide gel electrophoresis in 10% SDS is typically run in 10 mM Tris-HCl pH 8.0, 100 mM NaCl as elution buffer. To demonstrate which residue is PEGylated, peptide mapping using proteases such as trypsin and Lys-C protease can be performed. Thus, samples of PEGylated and non-PEGylated antibodies can be digested with a protease such as Lys-C protease and the resulting peptides separated by a technique such as reverse phase HPLC. The chromatographic pattern of peptides produced can be compared to a peptide map previously determined for the anti-Factor D polypeptide.

Each peak can then be analyzed by mass spectrometry to verify the size of the conjugate in the peak. Depending on the PEG used in the conjugation, and the size of the conjugate in the peak, the number of antibodies or variants thereof conjugated to the PEG can be estimated. The fragment(s) that conjugated to PEG groups are usually not retained on the HPLC column after injection and disappear from the chromatograph. Such disappearance from the chromatograph is an indication of PEGylation on that particular fragment that should contain at least one PEGylatable amino acid residue. PEGylated anti-Factor D antibodies and antibody variants may further be assayed for ability to interact with Factor D and other biological activities using known methods in the art.

PEGylation changes the physical and chemical properties of the antibody drug, and may results in improved pharmacokinetic behaviors, including but not limited to: improved stability; decreased immunogenicity; increased hydrodynamic radius (RH); and/or extended circulating life, as well as increased ocular residence time.

In some embodiments, the conjugates of the present disclosure have an increased half-life after administration into a mammalian eye (e.g. human) via a single intravitreal injection, as compared to the corresponding unconjugated anti-Factor D antibody or antibody variant. In some embodiments, the increase in half-life is at least 1.4 times, or at least 1.5 times, or at least 1.8 times, or at least 2 times the half-life of the corresponding unconjugated anti-Factor D antibody or antibody variant.

In some embodiments, the conjugates of the present disclosure may have a hydrodynamic radius (RH), as determined using methods known in the art, of from about 3 nm to about 30 nm or more, or alternatively from about 5 nm to about 25 nm, and in some embodiments may be about 5 nm, about 10 nm, about 15 nm, about 20 nm, about 25 nm, or more.

In some embodiments, the conjugates of the present disclosure may exhibit a stability, characterized by the % loss of binding capacity (e.g., fD-binding capacity) per month measured using methods known in the art (e.g., when exposed to physiological conditions), of about 15%, about 12%, about 10%, about 8%, or even less.

In some embodiments, the conjugates of the present disclosure may exhibit an IC50 potency value, as determined using a time-resolved fluorescence energy transfer (TR-FRET) assay of Factor D-dependent Factor B activation, as detailed in the examples. In some embodiments, the conjugates inhibit Factor D-dependent Factor B activation with IC50 values of from about 25 pM to about 10 nM, or from about 25 pM to about 5 nM, or from about 25 pM to about 1 nM, or from about 25 pM to about 750 pM, or from about 25 pM to about 500 pM.

In some embodiments, the conjugate has a viscosity that makes it suitable for administration through a narrow bore needle. In some embodiments, the viscosity of the conjugate is less than 800 cP, less than 700 cP, less than 600 cP, less than 500 cP, less than 400 cP, less than 300 cP, less than 200 cP, less than 100 cP, less than 50 cP, or less than 30 cP at a concentration of 150-250 mg/ml. In some embodiments, the viscosity of the conjugate is less than 300 cP at a concentration of 200 mg/ml.

Pharmaceutical Formulations

Therapeutic formulations of the conjugates of the present disclosure thereof may be prepared for storage as lyophilized formulations or aqueous solutions by mixing the conjugate having the desired degree of purity with optional "pharmaceutically-acceptable" carriers, excipients or stabilizers typically employed in the art (all of which are termed "excipients"). For example, buffering agents, stabilizing agents, preservatives, isotonifiers, non-ionic detergents, antioxidants and other miscellaneous additives. (See Remington's Pharmaceutical Sciences, 16th edition, A. Osol, Ed. (1980)). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives may be added to retard microbial growth, and may be added in amounts ranging from 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

Isotonicifiers sometimes known as "stabilizers" may be added to ensure isotonicity of liquid compositions of the present disclosure and include polyhydric sugar alcohols, preferably trihydric or higher sugar alcohols, such as glycerin, erythritol, arabitol, xylitol, sorbitol and mannitol.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, .alpha.-monothioglycerol and sodium thio sulfate; low molecular weight polypeptides (i.e., <10 residues); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; polysaccharides such as dextran. Stabilizers may be present in the range from 0.1 to 10,000 weights per part of weight active protein.

Non-ionic surfactants or detergents (also known as "wetting agents") may be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.). Non-ionic surfactants may be present in a range of about 0.05 mg/ml to about 1.0 mg/ml, preferably about 0.07 mg/ml to about 0.2 mg/ml.

Additional miscellaneous excipients include bulking agents, (e.g. starch), chelating agents (e.g. EDTA), antioxidants (e.g., ascorbic acid, methionine, vitamin E), and cosolvents. The formulation herein may also contain more than one active ingredient as necessary for the particular indication being treated. In some embodiments, the active ingredients have complementary activities that do not adversely affect each other. For example, it may be desirable to further provide an immunosuppressive agent. Such molecules are suitably present in combination in amounts that are effective for the purpose intended. The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin micropheres, microemulsions, nano-particles and nanocapsules) or in macroemulsions. Such techniques are disclosed in Remington's Pharmaceutical Sciences, 16th edition, A. Osal, Ed. (1980).

The formulations to be used for in vivo administration must be sterile. This is readily accomplished, for example, by filtration through sterile filtration membranes. Sustained-release preparations may be prepared. Suitable examples of sustained-release preparations include semi-permeable matrices of solid hydrophobic polymers containing the antibody, or antibody variant or fragment (e.g. antigen-binding fragment) thereof, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C. resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The conjugates of the disclosure for prevention or treatment of an ocular disease or condition are typically administered by ocular, intraocular, and/or intravitreal injection, and/or juxtascleral injection, and/or subtenon injection, and/or superchoroidal injection and/or topical administration in the form of eye drops and/or ointment. Such conjugates of the disclosure may be delivered by a variety of methods, e.g. intravitreally as a device and/or a depot that allows for slow release of the compound into the vitreous, including those described in references such as Intraocular Drug Delivery, Jaffe, Jaffe, Ashton, and Pearson, editors, Taylor & Francis (March 2006). In one example, a device may be in the form of a min pump and/or a matrix and/or a passive diffusion system and/or encapsulated cells that release the compound for a prolonged period of time (Intraocular Drug Delivery, Jaffe, Jaffe, Ashton, and Pearson, editors, Taylor & Francis (March 2006). Other methods of administration may also be used, which includes but is not limited to, topical, parenteral, subcutaneous, intraperitoneal, intrapulmonary, intranasal, and intralesional administration. Parenteral infusions include intramuscular, intravenous, intraarterial, intraperitoneal, or subcutaneous administration.

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as AMD and CNV, is direct intravitreal injection. Intravitrial injections are usually repeated at intervals which depend on the patient's condition, and the properties and half-life of the drug delivered. For intraocular (e.g. intravitreal) penetration, usually molecules of smaller size are preferred. In one embodiment, administration is intravitreal using a narrow bore needle. In one embodiment, the narrow bore needle is 30, 29, 28, 27, 26, 25, 24, 23, or 22 gauge.

The efficacy of the treatment of complement-associated eye conditions, such as AMD or CNV, can be measured by various endpoints commonly used in evaluating intraocular diseases. For example, vision loss can be assessed. Vision loss can be evaluated by, but not limited to, e.g., measuring by the mean change in best correction visual acuity (BCVA) from baseline to a desired time point (e.g., where the BCVA is based on Early Treatment Diabetic Retinopathy Study (ETDRS) visual acuity chart and assessment at a test distance of 4 meters), measuring the proportion of subjects who lose fewer than 15 letters in visual acuity at a desired time point compared to baseline, measuring the proportion of subjects who gain greater than or equal to 15 letters in visual acuity at a desired time point compared to baseline, measuring the proportion of subjects with a visual-acuity Snellen equivalent of 20/2000 or worse at a desired time point, measuring the NEI Visual Functioning Questionnaire, measuring the size of CNV and amount of leakage of CNV at a desired time point, e.g., by fluorescein angiography, etc. Ocular assessments can be done, e.g., which include, but are not limited to, e.g., performing eye exam, measuring intraocular pressure, assessing visual acuity, measuring slit-lamp pressure, assessing intraocular inflammation, etc.

The amount of antibody or antibody variant thereof which will be effective in the treatment of a particular disorder or condition will depend on the nature of the disorder or condition, and can be determined by standard clinical techniques. Where possible, it is desirable to determine the dose-response curve and the pharmaceutical compositions of the disclosure first in vitro, and then in useful animal model systems prior to testing in humans.

In some embodiments, the antibodies and conjugates described herein may be formulated to provide a concentration of antibody in the formulations of at least 50 mg/mL, at least 75 mg/mL, at least 100 mg/mL, at least 125 mg/mL, at least 150 mg/mL, at least 175 mg/mL, at least 200 mg/mL, at least 225 mg/mL, at least 250 mg/mL, at least 275 mg/mL, at least 300 mg/mL, at least 325 mg/mL, at least 350 mg/mL, at least 375 mg/mL, at least 400 mg/mL, at least 425 mg/mL, at least 450 mg/mL, at least 475 mg/mL, or at least 500 mg/mL. In some embodiments, the antibody in the formulation is in an amount of at least 100 mg/mL. In some embodiments, the antibody in the formulation is in an amount of at least 200 mg/mL. In some embodiments, the antibody in the formulation is in an amount of at least 300 mg/mL. In some embodiments, the antibodies and conjugates described herein may be formulated to provide a concentration of antibody in the formulations of from about 50 mg/mL to about 500 mg/mL, about 50 mg/mL to about 300 mg/mL, about 100 mg/mL to about 500 mg/mL, about 100 mg/mL to about 300 mg/mL, about 200 mg/mL to about 500 mg/mL, about 200 mg/mL to about 400 mg/mL, about 200 mg/mL to about 300 mg/mL, or about 250 mg/mL to about 375 mg/mL.

In some embodiments, an aqueous solution of conjugate comprising therapeutic polypeptide, antibody, or antibody variant thereof, or fragment thereof (e.g. antigen-binding fragment), is administered by subcutaneous injection. In another embodiment, an aqueous solution of conjugate comprising therapeutic polypeptide, antibody, or antibody variant thereof, or fragment thereof (e.g. antigen-binding fragment) is administered by intravitreal injection. Each dose may range from about 0.3 mg to about 30 mg per eye.

The dosing schedule for subcutaneous administration may vary form once a month to daily depending on a number of clinical factors, including the type of disease, severity of disease, and the subject's sensitivity to the therapeutic agent.

Articles of Manufacture and Kits

Another embodiment of the disclosure is an article of manufacture containing materials useful for the treatment, prevention and/or diagnosis of conditions targeted by the antibodies of the disclosure, or variants thereof or fragments thereof (e.g. antigen-binding fragments). For example, the disclosure concerns an article of manufacture containing materials useful for the treatment, prevention and/or diagnosis of complement-associated disorders. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating, preventing and/or diagnosis of the complement-associated condition and may have a sterile access port (for example the container may be an intravenous solution bag or a vial having a stopper pierceable by a hypodermic injection needle). At least one active agent in the composition is an anti-Factor D antibody conjugate of the disclosure. The label or package insert indicates that the composition is useful for treatment, prevention and/or diagnosis of a particular condition.

Package insert refers to instructions customarily included in commercial packages of therapeutic products that contain information about the indications, usage, dosage, administration, contraindications and/or warnings concerning the use of such therapeutic products. In some embodiments, the label or package insert indicates that the composition is used for treating complement-associated disorders, such as, for example, any of the conditions listed before, including eye disorders, e.g. age-related macular degeneration (AMD). The label or package insert will further comprise instructions for administering the antibody composition to the patient.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, kits are also provided that are useful for various purposes, e.g., for treatment, prevention and/or diagnosis of complement-associated disorders, for complement-associated hemolysis assays, for purification or immunoprecipitation of Factor D polypeptide from cells. For isolation and purification of Factor D polypeptide, the kit can contain an anti-Factor D antibody coupled to beads (e.g., sepharose beads). Kits can be provided which contain the antibodies for detection and quantitation of Factor D polypeptide in vitro, e.g., in an ELISA or a Western blot. As with the article of manufacture, the kit comprises a container and a label or package insert on or associated with the container. The container holds a composition comprising a conjugate of the disclosure comprising at least one anti-Factor antibody. Additional containers may be included that contain, e.g., diluents and buffers, control antibodies. The label or package insert may provide a description of the composition as well as instructions for the intended in vitro or detection use. The label or package insert may provide instructions for the administration (e.g. the antibody, or antibody fragment thereof (e.g. antigen-binding fragment) to a subject.

Therapeutic Uses

The conjugates of the present disclosure may be used to treat a mammal. In some embodiments, the conjugate is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody, or may be used to study toxicity of the antibody of interest. In each of these embodiments, dose escalation studies may be performed on the mammal.

The conjugate is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the conjugate is suitably administered by pulse infusion, particularly with declining doses of the antibody, or antibody variant thereof or fragment thereof (e.g. antigen-binding fragment). In some embodiments, the dosing is given by injections, such as intravenous or subcutaneous injections, depending in part on whether the administration is brief or chronic. In one embodiment, administration is intravitreal using a narrow bore needle. In one embodiment, the narrow bore needle is 30, 29, 28, 27, 26, 25, 24, 23, or 22 gauge. In one embodiment, the dosing is administered using an implantable port delivery system.

For the prevention or treatment of disease, the appropriate dosage of the conjugate will depend on the type of disease to be treated, the severity and course of the disease, whether the antibody is administered for preventive or therapeutic purposes, previous therapy, the patient's clinical history and response to the antibody and the discretion of the attending physician.

Depending on the type and severity of the disease, a sufficient amount of conjugate may be administered to provide from about 1 to about 25 mg/eye (i.e., from about 0.015 mg/kg to about 0.36 mg/kg, assuming one eye is treated) of the antibody to the patient, whether, for example, by one or more separate administrations, or by continuous infusion. A typical daily dosage of the conjugate might be sufficient to provide the antibody in a range from about 1 to about 20 mg/eye or more, or from about 1 to about 15 mg/eye or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188.

The conjugate compositions may be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the conjugate to be administered will be governed by such considerations, and is the minimum amount necessary to prevent, ameliorate, or treat a disease or disorder. The conjugate need not be, but is optionally formulated with one or more agents currently used to prevent or treat the disorder in question. The effective amount of such other agents depends on the amount of antibody, or antibody variant thereof or fragment thereof (e.g. antigen-binding fragment), present in the formulation, the type of disorder or treatment, and other factors discussed above. These are generally used in the same dosages and with administration routes as used hereinbefore or about from 1 to 99% of the heretofore employed dosages.

The antibodies disclosed herein which recognize Factor D as their target and the conjugates comprising these antibodies may be used to treat complement-mediated (complement-associated) disorders in a subject. These disorders are associated with excessive or uncontrolled complement activation. They include: complement activation during cardiopulmonary bypass operations; complement activation due to ischemia-reperfusion following acute myocardial infarction, aneurysm, stroke, hemorrhagic shock, crush injury, multiple organ failure, hypobolemic shock and intestinal ischemia. These disorders can also include disease or condition is an inflammatory condition such as severe burns, endotoxemia, septic shock, adult respiratory distress syndrome, hemodialysis, anaphylactic shock, severe asthma, angioedema, Crohn's disease, sickle cell anemia, poststreptococcal glomerulonephritis and pancreatitis. The disorder may be the result of an adverse drug reaction, drug allergy, IL-2 induced vascular leakage syndrome or radiographic contrast media allergy. The disorder may be systemic. It may also include autoimmune disease such as systemic lupus erythematosus, myasthenia gravis, rheumatoid arthritis, Alzheimer's disease and multiple sclerosis. Complement activation is also associated with transplant rejection. Recently there has been a strong correlation shown between complement activation and ocular diseases such as age-related macular degeneration, diabetic retinopathy and other ischemia-related retinopathies, choroidal neovascularization (CNV), uveitis, diabetic macular edema, pathological myopia, von Hippel-Lindau disease, histoplasmosis of the eye, Central Retinal Vein Occlusion (CRVO), corneal neovascularization, and retinal neovascularization. In one embodiment, the complement-associated disorder is a complement-associated eye condition. In one embodiment, the complement-associated eye condition is selected from the group consisting of age-related macular degeneration (AMD), including dry and wet (non-exudative and exudative) forms, choroidal neovascularization (CNV), uveitis, diabetic retinopathy, ischemia-related retinopathy, diabetic macular edema, pathological myopia, von Hippel-Lindau disease, histoplasmosis of the eye, Central Retinal Vein Occlusion (CRVO), corneal neovascularization, and retinal neovascularization. In one embodiment, the complement-associated eye condition is selected from intermediate dry form AMD or geographic atrophy (GA).

A conjugate comprising Factor D antagonist can be administered alone or in combination with at least a second therapeutic compound. Administration of the conjugate and any second therapeutic compound can be done simultaneously, e.g., as a single composition or as two or more distinct compositions using the same or different administration routes. Alternatively, or additionally the administration can be done sequentially, in any order. In certain embodiments, intervals ranging from minutes to days, to weeks to months, can be present between the administrations of the two or more compositions. For example, the conjugate comprising the Factor D antagonist may be administered first, followed by the second therapeutic compound. However, simultaneous administration or administration of the second therapeutic compound prior to the conjugate is also contemplated. In one example, the Factor D antagonist is an anti-Factor D antibody. In a further example, the anti-Factor D antibody is an anti-Factor D antibody variant described herein. In some embodiments, the second therapeutic compound is selected from an HTRA1 antagonist, an ANG2 antagonist (such as anti-ANG2 antibodies as disclosed, for example, in US20090304694 A1), a TIE2 antagonist (such as anti-TIE2 antibodies as disclosed, for example, in U.S. Pat. No. 6,376,653), a VEGF antagonist (such as VEGF antagonists as disclosed, for example, in U.S. Pat. No. 6,884,879 issued Feb. 26, 2015 and WO98/45331 (bevacizumab and other humanized anti-VEGF antibodies); WO2005/012359 and WO2005/044853 (G6 or B20 series antibodies (e.g. G6-31, B20-4.1), and a second complement component antagonist. In one example, the second therapeutic compound is a HTRA1 antagonist, an ANG2 antagonist, a TIE2 antagonist, or a VEGF antagonist. In a further example, the HTRA1 antagonist is an anti-HTRA1 antibody. In another embodiment, the ANG2 antagonist is an anti-ANG2 antibody. In another embodiment, the TIE2 antagonist is an anti-TIE2 antibody. In some embodiments, the VEGF antagonist is selected from a VEGF trap (such as aflibercept (Eylea®) and an anti-VEGF antibody (such as bevacizumab (Avastin®) or ranabizumab (Lucentis®)).

Other therapeutic agents suitable for combined administration with the conjugates comprising an anti-Factor D antibody as disclosed herein are antagonists of various members of the classical or alternative complement pathway (complement inhibitors). Thus, the conjugates disclosed herein may be administered in combination with antagonists of one or more of the C1, C2, C3, C4, C5, C6, C7, C8, and C9 complement components. In some embodiments, the conjugates comprising anti-Factor D disclosed herein are combined with antagonists of the C2 and/or C4 and/or C5 complement components, such as anti-C2 and/or anti-C4 and/or anti-C5 antibodies. Such antibodies are known in the art and/or are commercially available. An anti-C5 antibody eculizumab (Alexion, Cheshire, Conn., USA), has been approved for the treatment of Paroxysmal nocturnal hemoglobinuria (PNH) and atypical hemolytic uremic syndrome (aHUS). Other complement inhibitors are disclosed, for example, in US Publication No. 20050036991 A1. Thus, the conjugates comprising anti-Factor D antibody as disclosed herein may be administered in combination with an effective amount of one or more complement inhibitors, including, without limitation, anti-C2 and anti-C5 antibodies, optionally in combination with at least one additional Factor D antagonist/antibody.

In some embodiments, the treatment of the present disclosure for complement-mediated disorders in a human subject with a complement-mediated disorder comprises administering to the subject an effective amount of a therapeutic compound, such as a Factor D antagonist or a conjugate comprising the Factor D antagonist, and further comprising administering to the subject an effective amount of a second therapeutic compound, that is a HTRA1 antagonist, an ANG2 antagonist, a TIE2 antagonist, a VEGF antagonist, and/or an antagonist of one or more of the C1, C2, C3, C4, C5, C6, C7, C8, and C9 complement components. In one example, the Factor D antagonist is an anti-Factor D antibody, and the conjugate comprises one or more anti-factor D antibodies. In a further example, the anti-Factor D antibody is an anti-Factor D antibody variant described herein, and the conjugate comprises one or more anti-Factor D antibody variant. In one example, the HTRA antagonist is an anti-HTRA1 antibody. In another example, the ANG2 antagonist is an anti-ANG2 antibody. In another example, the TIE2 antagonist is an anti-TIE2 antibody. In another example, the VEGF antagonist is an anti-VEGF antibody. In another embodiment, the antagonist of the C2 and/or C4 and/or C5 complement components is as anti-C2 and/or anti-C4 and/or anti-C5 antibody. In one example, the complement-mediated disorder is an complement-associated eye condition. In one example, the ocular disorder is age-related macular degeneration (AMD), including non-exudative (e.g. intermediate dry AMD or geographic atrophy (GA)) and exudative (e.g. wet AMD (choroidal neovascularization (CNV)) AMD, diabetic retinopathy (DR), endophthalmitis and uveitis. In one example, the complement-associated eye condition is intermediate dry AMD. In one example, the complement-associated eye condition is geographic atrophy. In one example, the complement-associated eye condition is wet AMD (choroidal neovascularization (CNV)).

Combined administration herein includes co-administration, using separate formulations or a single pharmaceutical formulation, and consecutive administration in either order, wherein generally there is a time period while both (or all) active agents simultaneously exert their biological activities.

EXAMPLES

The following examples are offered by way of illustration and not by way of limitation. Commercially available reagents referred to in the examples were used according to manufacturer's instructions unless otherwise indicated. The source of those cells identified in the following examples, and throughout the specification, by ATCC accession numbers is the American Type Culture Collection, 10801 University Boulevard, Manassas, Va. 20110-2209.

Example 1: Generation of Anti-Factor D Antibody Variants

Lampalizumab, a humanized anti-Factor D Fab fragment that potently inhibits Factor D and the alternative complement pathway, through binding to an exosite on factor D is currently in clinical development for the treatment of geographic atrophy (GA), an advanced form of dry AMD. Lampalizumab (FCFD4515S; hereinafter "aFD") is an antibody Fab fragment comprised of a 214 residue light chain (SEQ ID NO:1) and a 223 residue heavy chain (SEQ ID NO:2).

While results of a phase II human clinical trial in GA indicate that a treatment effect is obtained with monthly intravitreal injection of aFD, there exist incentives to use higher drug doses to achieve even better efficacy. Meanwhile, less frequent dosing would provide improved convenience to the patient, have potential benefits of decreased infection rate and increased clinical efficacy, and could facilitate treatment of patients with less advanced forms of dry AMD.

Efforts were made to further improve the wild type aFD (WT)'s physical and chemical stabilities, especially under low pH conditions and/or at high concentrations under neutral pH. Aspartic acid residues Asp-30 on the light chain and Asp-62 on the heavy chain (FIG. 1A) have been identified as prone to isomerization. Asp isomerization involves dehydration to form a cyclic imide intermediate (Asu) that is normally long-lived at pH<8 and detected as a basic peak upon ion exchange chromatography (IEC). Formation of the cyclic intermediate is accelerated at lower pH.

Hydrolysis of the cyclic intermediate to form Asp or Iso-Asp, yielding the same charge state as the starting material and thus not detectable by IEC, is faster at higher pH. Isomerization of Asp-62 (Asp-61 according to Kabat numbering) does not appear to affect potency since it is not in contact with factor D in the crystal structure of the Fab:fD complex. Katschke et al. (2012) J. Biol. Chem. 287:12886. Asp-30, together with light chain residues Asp-32 and Asp-92, make an electrostatic contact with basic residues on factor D. Isomerization of Asp-30 is quite rapid and presumed to account for an observed loss in potency of the antibody. Isomerization of Asp residues 32 and 92 could also have an effect on fD-binding but the rates are known to be very slow. Formation of the cyclic imide, or its subsequent hydrolysis to iso-aspartic acid, at position 30 could negatively impact antigen binding through perturbation of the electrostatic interaction. Antigen-binding measurements on the isolated basic fraction suggest that the cyclic intermediate form is fully active, consistent with iso-asp formation as the cause of loss in binding.

Asn-103 (Asn-101 according to Kabat numbering) on the heavy chain is susceptible to deamidation, a reaction that proceeds with higher rate at neutral as compared with slightly acidic pH (6-7). Deamidation can be detected as the appearance of an acidic peak upon IEC. Asn deamidation, like Asp isomerization, proceeds through a cyclic Asu intermediate. However, since formation of Asu from Asn only occurs at higher pH where Asu is hydrolyzed to form Asp or Iso-Asp, usually only the acidic peak is detected. The side chain of Asn-103 forms a hydrogen bond with factor D residue Arg-172. The effect of deamidation at this site, or formation of the cyclic imide intermediate, Asu, on antigen binding is unknown.

The aFD.WT has a lower pI (7.1) than a typical humanized Fab (pI 8-9). The composition of CDR-L1 (FIG. 1A) results in a negative charge cluster on the VL domain. These features may affect solubility of the molecule, especially at low pH and low ionic strength. In addition, high concentration formulations of aFD.WT, even at neutral pH and physiological ionic strength, may have the tendency to form non-covalent dimers at a faster rate at 37° C.

Several variants of aFD.WT were produced for the purpose of improving stabilities. Point mutations were introduced by site-directed mutagenesis using the QuikChangeII® (Agilent) mutagenesis kit following the protocol supplied with the kit. Oligonucleotide primers specifying the required codon changes were synthesized. Plasmids with designed changes were identified and confirmed by DNA sequencing. For small scale expression and purification, DNA was transformed into E. coli strain 64B4. Single colonies were picked into 5 mL LB media (media prep code A2008) containing 50 µg/mL carbenecillin (media prep code A3232) and grown overnight in 14 mL culture tubes with shaking at 200 RPM in an Innova incubator at 37° C. These cultures were used to inoculate 250 mLs of complete soy crap media (media prep code A4564), 50 µg/mL carbenecillin, in a 1 L baffled shake flask. Cultures were grown overnight at 30° C. with shaking at 200 RPM and then harvested by centrifugation. The cell pellet was lysed using PopCulture media (Invitrogen), and Fabs purified on Gravitrap Protein G columns (GE Healthcare), following protocols supplied by the manufacturers. For larger scale production of Fabs, cell paste from 10 L fermentation of transformed cells was suspended in extraction buffer and homogenized using a microfluidizer. Fabs were captured by immunoaffinity chromatography on Protein G-Sepharose or kappa-select and eluted with a low pH buffer. The low pH eluate was adjusted to pH 5 and further purified by cation exchange chromatography on an S-Sepharose column. Identities of the purified proteins were confirmed by mass spectroscopy and the pooled fractions were concentrated to about 10 mg/mL, and exchanged into PBS buffer (pH 7.3) (also referred to herein as "PBS"; 8 mM dibasic sodium phosphate (Na2HPO4), 2 mM monobasic potassium phosphate (KH2PO4), 140 mM NaCl, 2.7 mM KCl), via diafiltration.

Example 2: Bioactivities of the Anti-Factor D Antibody Variants

Promising single and combination mutants were tested for factor D (fD) binding affinity and ability to inhibit factor D activities.

a. Factor D Binding Affinity by Surface Plasmon Resonance (SPR) Measurements

Kinetics and binding constant $K_D$ for factor D binding to immobilized aFD.WT and variants thereof was determined by surface plasmon resonance (SPR) measurements on a Biacore® T200 instrument. Antibody Fab fragments were immobilized on a Series S CM5 sensor chip using the anti-huFab capture kit (GE healthcare Cat. #28-9583-25) following a protocol described by the manufacturer. Kinetics of binding were calculated from sensorgrams recorded for injection of 60 µL aliquots of solutions of human factor D varied in concentration from 0.39 nM to 25 nM in 2-fold increments. The flow rate was 30 µL/minute, the running buffer was HBS-P+, the temperature of analysis was 25° C., real-time reference cell subtraction was employed, and dissociation following factor D injection was followed for 10 minutes. After subtraction of the sensorgram observed for injection of running buffer, data were analyzed according to a 1:1 model using BiaEval software v4.1 (GE Healthcare) to extract the kinetics and affinity constants.

TABLE 1

Effect of mutations on affinity for factor D

| Mutant | SPR $K_D$ (pM) | Variant # |
|---|---|---|
| aFD.WT | ≤10 | |
| VL-D28S | ≤10 | AFD.v1 |
| VL-D30E | ≤10 | AFD.v2 |
| VL-D31S | ≤10 | AFD.v3 |
| VL-D32S | 26 | AFD.v4 |
| VL-D28S:D31S:D32S | 280 | AFD.v5 |
| VL-D30E:D31S VH-D62E ("TM") | ≤10 | AFD.v6 |
| VL-D30E:D31S VH-D62E VL-D92E ("TM.D92E") | ≤10 | AFD.v7 |
| VL-D28S:D30E:D31S VH-D62E ("SIESD") | 16.7 ± 4.4 | AFD.v8 |
| VL-D28S:D30E:D31S VH-D62E VL-N34S | 30 | AFD.v9 |
| VL-D28S:D30E:D31S VH-D62E VL-D92E | 70 | AFD.v10 |
| VL-D28S:D30E:D31S:D92E VH-D62E:N103S | 102 | AFD.v15 |
| VL-D28S:D30E:D31S VH-D62E VH-N52S | 70 | AFD.v11 |
| VL-D28S:D30E:D31S VH-D62E VH-N103D | 23 | AFD.v12 |
| VL-D28S:D30E:D31S VH-D62E VH-N103Q | 60 | AFD.v13 |
| VL-D28S:D30E:D31S VH-D62E VH-N103S ("SIESD.N103S") | 25.6 ± 6.3 | AFD.v14 |

Mutants are named and numbered based on location in aFD.WT's light chain variable domain (VL; SEQ ID NO:3) and heavy chain variable domain (VH; SEQ ID NO:4). Single letter code for the wild-type residue followed by sequence position followed by single letter code for the substituted amino acid. Multiple changes on the same domain are separated by a colon.

As shown in Table 1, aFD.WT has a high affinity for fD, at the limit (~10 pM KD) that can be determined with SPR technology. Aspartic acid residues 28, 30, and 31 in CDR-L1 could be individually substituted with Ser, Glu, and Ser, respectively, without apparent effect on affinity for fD (Table 1). In contrast, replacement of CDR-L1 Asp32 with Ser resulted in a significant loss in fD-binding whether tested individually (AFD.v4) or in combination with D28S and D31S mutants (AFD.v5). fD affinities equivalent to the wild-type molecule were determined for a triple mutant ("TM" (AFD.v6)) combining VL-D30E, D31S and VH-D62E and for a quad mutant (TM.D92E (AFD.v7)) which adds VL-D92E to TM (AFD.v6). The VH-D62E is a replacement at a site that undergoes isomerization without apparent effect on fD-binding; VL-Asp92 is an antigen contact residue with a slow rate of isomerization. The quad mutant "SIESD" (AFD.v8) combining VL-D28S, D30E, D31S and VH-D62E shows a small (~2-fold) loss in affinity for fD. In the context of SIESD (AFD.v8), the VL-D92E replacement resulted in a further loss in affinity for fD (see AFD.v10 (SIESD.D92E in Table 1)).

Potential sites of deamidation were tested for replacement with other residues. Both VL-N34 and VH-N52 are in contact with fD in the co-crystal structure but neither of these sites show significant rates of deamidation under neutral pH conditions. Ser substitution at these sites resulted in a loss in affinity (Table 1; AFD.v9 and AFD.v11). VH residue Asn-103 does contact fD and has a measurable rate of deamidation in PBS. Substitution of Asn-103 with Asp or Ser in the context of SIESD (AFD.v8) resulted in small, acceptable losses in affinity for fD (see AFD.v12 (SIESD.N103D) and AFD.v14 (SIESD.N103S)) (Table 1). A Gln substitution for Asn-103 resulted in a larger decrease in binding affinity (see AFD.v13 (SIESD.N103Q) (Table 1). Similar to SIESD (AFD.v8), SIESD.N103S.D92E (AFD.v15) which added VL-D92E to the penta mutant SIESD.N103S (AFD.v14) resulted in a further 4-fold decrease in affinity for fD.

b. Factor D Inhibition Assays aFD.WT and variants were tested for their abilities to inhibit Factor D-induced complement activation, using an alternative pathway (AP) hemolysis assay. The AP hemolysis assay using rabbit erythrocytes (Er) has been previously described. Pangburn (1998), *Methods. Enzymol.* 162:639; Katschke et al. (2009) *J. Biol. Chem.* 284:10473. Er (Colorado Serum) were washed three times with 0.5% bovine skin gelatin in veronal buffer (GVB) and re-suspended. Dilutions of aFDs were prepared at a 2× concentration and added to 96-well polypropylene plates. Er suspension were mixed with GVB/0.1M EGTA/0.1M $MgCl_2$ and added to the plates. Complement activation was initiated by the addition of C1q-depleted human serum to avoid any complement activation through the classical pathway (CompTech; diluted 1:3 in GVB). After a 30 minute incubation at room temperature, the reaction stopped by adding 10 mM EDTA in GVB. The plates were centrifuged and the supernatants transferred. The absorbance of the supernatant was read at 412 nm. The AFD.Ab concentrations causing half-maximal inhibition (IC50) were determined by a nonlinear regression analysis.

TABLE 2

Inhibitory potency of AFD.Ab variants

| Sample | IC50 (nM)* AP Hemolysis |
|---|---|
| WT (aFD.WT) | 3.4 |
| SIESD (AFD.v8) | 4.2 |
| SIESD.N103S (AFD.v14) | 4.1 |
| TM.D92E (AFD.v7) | 3.8 |

*RSE = ±30%

As shown in Table 2, variants SIESD (AFD.v8), SIESD.N103S (AFD.v14), and TM.D92E (AFD.v7) have potencies for inhibiting fD-dependent complement activation activities that are equivalent to aFD.WT, given the standard error in IC50 measurement of ±30%.

c. Binding Capacity Over Prolonged Time

SPR was also used to measure total binding of AFD.Ab variants to fD over time under defined conditions. The standard error in these measurements is ±10%. FIG. 2A shows that at pH 5.5, loss in binding was about 40% in one month for aFD.WT and AFD.Ab variants, D30E (AFD.v2) and TM (AFD.v6), whereas loss of binding for SIESD (AFD.v8) and SIESD.N103S (AFD.v14) was smaller at about 15%, even for prolonged period of time (70 days). As a comparison, an anti-VEGF antibody Fab fragment (aVEGF) showed no loss in binding over 70 days. Addition of salt to the pH 7.4 condition seemed to enhance the rate of loss in binding for aFD.WT and aVEGF (data not shown). As shown in FIG. 2B, in the presence of PBS (with Fab protein concentration at 100 mg/ml), D30E (AFD.v2) and TM (AFD.v6) had equivalent rates of loss in binding that was slower than observed for aFD.WT. The loss in binding after 10 weeks at 37° C. was about 30% for aFD.WT, and 20% for D30E (AFD.v2) and TM (AFD.v6) variants of anti-factor D. Loss in binding after 10 weeks at 37° C. was only 10% for SIESD.N103S (AFD.14; FIG. 2B), no greater than the experimental error, and equivalent to that observed for aVEGF under the same conditions. The thermal stress in PBS experiment at 100 mg/mL Fab concentration was repeated for SIESD (AFD.v8) in order to collect data out to 70 days. As shown in FIG. 2C, loss in binding at 70 days was less than 10% for SIESD (AFD.v8).

Example 3. Anti-Factor D Antibody Variants with Improved Stability

Based on the affinity assays above, several single and combination anti-Factor D antibody variants were selected for further stability analysis.

a. Solubility

Samples were initially tested for solubility at low ionic strength and pH 6. Samples were first prepared in 20 mM His-HCl pH 5 buffer by concentration to ~100 mg/mL using Amicon Centriprep YM-10 centrifugal filter units. These solutions at pH 5 and low ionic strength did not show turbidity upon visual inspection. Samples were centrifuged at 14,000×g for 10 minutes to pellet any insoluble material. No pellet was observed, and the protein concentration of the solution was determined by UV absorbance measurements. Samples (~1 mL) were placed in Slide-A-Lyzer cassettes of 10 K MWCO (Pierce) and dialyzed overnight at 4° C. versus 1 L of 20 mM His buffer, pH 6, followed by visual inspection for turbidity. Photographs of the solutions were taken and are provided in FIG. 6. At pH 6 and low ionic strength conditions (~100 mg/ml in 20 mM His-HCl, pH 6), aFD.WT and D30E (AFD.v2) solutions were noticeably turbid, TM (AFD.v6) solution was less turbid and the solution of SIESD (AFD.v8) was clear (FIG. 6). After centrifugation as above, whereby large pellets were visually observed for aFD.WT and AFD.v2, a smaller pellet for TM (AFD.v6), and no pellet for SIESD (AFD.v8), protein concentrations of the supernatants were determined by UV absorbance measurements (Table 3). aFD.WT and D30E (AFD.v2) showed solubilities of less than 50 mg/ml, TM (AFD.v6) showed solubility approaching 100 mg/mL and SIESD (AFD.v8) was fully soluble under these conditions. The small reduction in protein concentration for SIESD (AFD.v8) after pH 6 dialysis relative to the pH 5 starting concentration reflects a dilution effect upon dialysis rather than precipitation of AFD.v8 since no pellet was observed upon centrifugation.

TABLE 3

Solubility of AFD.Ab Variants (~100 mg/ml in 20 mM His-HCl, pH 6)

| AFD.Ab Variant # | Concentration at pH 5, before pH 6 dialysis (mg/ml) | Concentration after pH 6 dialysis at 4° C. and centrifugation (mg/ml) |
|---|---|---|
| aFD.WT | 102 | 40 |
| AFD.v2 (D30E) | 102 | 14 |
| AFD.v6 (TM) | 102 | 92 |
| AFD.v8 (SIESD) | 100 | 94 |

Further variants AFD.v3, AFD.v12, AFD.v13 and AFD.v14 were tested in no salt solubility tests. After dialysis into pH 6 buffer at 4° C. and incubation overnight at 37° C., all of the protein solutions except aFD.WT were clear (FIG. 7). Measurements of protein concentration after 37° C. incubation and centrifugation (Table 4) indicate that all the variants were more soluble than aFD.WT. The turbid solution of aFD.WT (FIG. 7, top row) became clear when subsequently dialyzed versus PBS (pH 7.3), a salt (NaCl) containing buffer, which suggests that the precipitation was reversible with salt addition and/or increase in pH (FIG. 7, bottom row). The solubility data on AFD.v3 indicates that the single amino acid change D31S, removal of 1 negatively charged residue, can result in increased solubility. The further amino acid changes in AFD.v8, AFD.v12, AFD.v13 and AFD.v14 also result in increased solubility.

TABLE 4

Solubility of AFD.Ab Variants at pH 6, no salt

| Condition | aFD.WT | AFD.v3 (D31S) | AFD.v8 (SIESD) | AFD.v12 (SIESD.N103D) | AFD.v13 (SIESD.N103Q) | AFD.v14 (SIESD.N103S) |
|---|---|---|---|---|---|---|
| Concentration at pH 5, before pH 6 dialysis (mg/ml) | 112 | 106 | 120 | 118 | 109 | 103 |
| Concentration after pH 6 dialysis at 4° C., incubation at 37° C. overnight and centrifugation (mg/ml) | 63 | 97 | 99 | 94 | 96 | 80 | aFD.WT, SIESD (AFD.v8) and SIESD.N103S (AFD.v14) were also tested for solubility under conditions of physiological pH (pH 7.3) and ionic strength. For solubility testing under physiological pH and ionic strength, samples were dialyzed overnight versus PBS, and then concentrated to 227-372 mg/mL using Amicon Centriprep YM-10 centrifugal filter units. After overnight incubation at 4° C., samples were visually inspected for turbidity, a portion was centrifuged to remove precipitated protein and the concentration of protein was determined by UV absorbance measurements and reported in Table 5. Prior to centrifugation, the aFD.WT sample was turbid whereas the solutions of SIESD (AFD.v8) and SIESD.N103S (AFD.v14) were clear (aFD.WT, AFD.v8 and AFD.v14 shown in FIG. 8). The concentration of AFD.v14 was 344 mg/mL for the solution in the photograph (FIG. 8) which was then further concentrated to 372 mg/mL. The concentration of AFD.v8 was 269 mg/ml for the solution in FIG. 8. The concentration of aFD.WT was 227 mg/mL for the solution in FIG. 8. After centrifugation, a pellet was observed with the aFD.WT solution, but no pellet was observed for the solutions of SIESD (AFD.v8) and SIESD.N103S (AFD.v14). The protein concentration data (Table 5) indicated that aFD.WT can only be concentrated to 227 mg/mL in PBS before precipitation is observed, whereas the solubility limits are higher for SIESD (AFD.v8) (≥269 mg/mL) and SIESD.N103S (AFD.v14) (≥372 mg/mL). Since no precipitate was observed for SIESD (AFD.v8) at 269 mg/mL, and no attempt was made to further concentrate the solution, this is the lower limit of solubility for this variant in PBS. Similarly, the lower limit of solubility for SIESD.N103S (AFD.v14) in PBS is 372 mg/mL. The 269 mg/mL solution of SIESD (AFD.v8) in PBS remained clear after 4 weeks of incubation at 2-8° C. Similarly, there was not any apparent increase in turbidity for the 372 mg/mL solution of SIESD.N103S (AFD.v14) in PBS after 3 weeks of incubation at 2-8° C. At this concentration, there was a very small change in % aggregate as measured using size-exclusion chromatography (SEC) (FIG. 9), increasing from 0.9% to 2.1% in 3 weeks at 2-8° C. (SEC data prior to 3 week incubation (0.9% aggregate) is shown in FIG. 9; SEC data after 3 week incubation is data not shown).

TABLE 5

Solubility of AFD.Ab Variants (in PBS (pH 7.3))

| AFD.Ab Variant # | Isoelectric point (pI)* | Concentration after centrifugation (mg/ml) |
|---|---|---|
| aFD.WT | 7.1 | 227 |
| SIESD (AFD.v8) | 7.3 | 269 |
| SIESD.N103S (AFD.v14) | 7.4 | 372 |

*pI values were determined by imaged capillary isoelectric focusing (icIEF)

Solubilities of variants SIESD (AFD.v8) and SIESD.N103S (AFD.v14) were also compared in a buffer of pH 5.5 (20 mM HCl pH 5.5), and varied NaCl concentration, that may be representative of formulations used for drugs administered via intravitreal injection. Solutions of about 100 mg/mL protein concentration were prepared and dialyzed against a test buffer. These solutions were then concentrated using Amicon Centriprep YM-10 centrifugal filter units. The concentrations obtained whereby the solutions remained visibly clear at ambient temperature are reported in Table 6. SIESD (AFD.v8) has high solubility, up to 314 mg/mL, at pH 5.5 and low NaCl concentration. High concentrations of SIESD.N103S (AFD.v14) were also achievable, up to 278 mg/mL with addition of 100 mM NaCl.

TABLE 6

Solubility of AFD.Ab variants at pH 5.5
(20 mM His-HCl pH 5.5) and varied NaCl concentration

| NaCl Concentration, mM | SIESD (AFD.v8) mg/mL | SIESD.N103S (AFD.v14) mg/mL |
|---|---|---|
| 0 | 314 | NT |
| 50 | 290 | 200 |
| 100 | NT | 278 |

NT = not tested

Although SIESD.N103S (AFD.v14) has two (2) fewer negatively charged residues in comparison to aFD.WT, these changes in charge do not result in a significant change in pI (Table 5), as measured by imaged capillary isoelectric focusing (iCIEF) (Salas-Solano et al, *J. Sep Sci,* 35(22): 3124 (2012)). Proteins are expected to have minimum solubility at pH values close to the pI (Green, A. A., *J. Biol. Chem.,* 93: 517-542 (1931)). For SIESD.N103S (AFD.v14) the increased solubility in PBS (pH 7.3) is not correlated with change in pI. Rather, the Asp to Ser amino acid changes in LC-CDR-L1 (VL-D28S and D31S) appear to alter the charge distribution on the surface of the molecule.

b. Isomerization and Deamidation

To simulate the exposure of variants to a variety of conditions that may be found in long-acting delivery systems, antibodies were stressed under varied pH and salt conditions for several weeks at 37° C. Specifically, antibodies were evaluated in the following five different formulations:

Formulation 1: 10 mg/mL, 10 mM phosphate buffer at pH 2.5,

Formulation 2: 10 mg/mL, 10 mM histidine HCl at pH 5.5,

Formulation 3: 10 mg/mL, 10 mM phosphate buffer at pH 7.4 ("low salt"),

Formulation 4: 10 mg/mL, pH 7.4 PBS ("high salt"; 10 mM phosphate, 137 mM NaCl); and, Formulation 5: 100 mg/mL, pH 7.4 PBS.

All solutions had 0.02% PS20, were incubated at 37° C. and were sampled every 2 weeks. The low salt conditions (pH 2.5, 5.5, and 7.4) were to evaluate the effect of chemical degradation in liquid formulations. PBS was used as a mimic of the pH and ionic strength of human vitreous. In addition, comparing the 10 mM phosphate, pH 7.4, to PBS condition should reveal ionic strength effects on chemical and physical stability. The PBS samples were buffer exchanged regularly during incubation to simulate the exchange of vitreous. The wild type AFD ("WT" or "aFD.WT") and aVEGF were evaluated in all 5 conditions. D30E (AFD.v2) and TM (AFD.v6) variants were tested in all formulations except number 4. SIESD (AFD.v8) and SIESD.N103S (AFD.v14) were tested in formulations 2 and 5.

The chemical degradation being quantified were deamidation, which is characterized by the formation of acidic peaks, and the dehydration step of isomerization, which is characterized by the formation of a long-lived succinimide (Asu) intermediate detected as basic peaks. Anionic exchange chromatography (Dionex ProPac SAX-10 columns) (IEC) was used to quantify the appearance of Asn deamidated and Asp dehydrated species within antibody samples in different formulations.

For all conditions tested, aFD.WT shows the greatest rate in loss of main peak and increase in basic peak amongst the tested antibodies. This is most noticeable at pH 5.5 where aVEGF, D30E (AFD.v2), TM (AFD.v6), SIESD (AFD.v8), and SIESD.N103S (AFD.v14) all show significantly lower rates of main peak loss than aFD.WT, see FIG. 3A. SIESD.N103S (AFD.v14) shows the slowest rate of main peak loss with the rate similar to aVEGF at pH 5.5 (FIG. 3A) and even slower than aVEGF in PBS (FIG. 3B). As shown in FIG. 4B (100 mg/ml of Fab in PBS (pH 7.3), D30E (AFD.v2) shows approximately half the rate of basic peak formation as aFD.WT whereas TM (AFD.v6), SIESD (AFD.v8), and SIESD.N103S (AFD.14) show negligible basic peak formation. In contrast, as shown in FIG. 4B (100 mg/ml of Fab in PBS (pH 7.3), the rate of acidic peak generation for aFD.WT and D30E (AFD.v2) are equivalent for PBS condition and about 2-fold slower than determined for TM (AFD.v6) and SIESD (AFD.v8). Acidic peak formation for SIESD.N103S (AFD.v14) in PBS is essentially negligible.

c. Aggregation

Size exclusion chromatography (SEC) was utilized to quantify the formation of aggregates and monomers for tested antibodies. Column used was TSK-GEL Super SW2000 (Tosoh Biosci.). Materials and conditions were used based on the manufacturer's instructions (www.tskgel.com).

The % monomers over time based on SEC data for tested antibodies at 100 mg/ml of Fab formulated in PBS at 37° C. are shown in FIG. 5. aFD.WT shows a decrease in monomer peak fraction by 3-4% per month. AFD.v2 (D30E) which has no change in negative charge compared to aFD.WT shows a similar rate of monomer loss. AFD.v6, AFD.v8 and AFD.v14 show a decreased rate of monomer loss. The differences in monomer content at day zero reflect minor variations in the homogeneity of the purified preparations. The aggregation rate for D30E (AFD.v2) and TM (AFD.v6) is comparable at pH 5.5 and 7.4 (no salt) at 10 mg/ml protein concentration. The addition of salt at pH 7.4 does not affect the rate of aggregation for AFD.Ab variants but it doubles the rate of aggregation for aVEGF. Aggregation is protein concentration dependent since increasing the concentration from 10 mg/mL to 100 mg/mL in PBS increases the rate of aggregation for all samples tested (Table 7). Aggregation at 10 mg/mL concentration in 10 mM phosphate buffer pH 7.4 and no NaCl, and at 10 mg/mL concentration in PBS was minimal (Table 7). At 100 mg/mL concentration in PBS, the loss in monomer is much greater for aFD.WT and D30E (AFD.v2) (5.8% and 7.3% in 40 days, respectively) than for aVEGF, TM (AFD.v6), SIESD (AFD.v8), and SIESD.N103S (AFD.v14) (1.8%, 1.5%, 0.7%, and 1.5% in 40 days, respectively) at 100 mg/mL in PBS at 37° C. These data suggest that AFD.v6, AFD.v8 and AFD.v14 have less aggregation than aFD.WT and AFD.v2 and may be more suitable as therapeutics as they may be less prone to in vivo immunogenicity.

TABLE 7

Effect of salt and protein concentration on aggregation of AFD.Ab variants and aVEGF as determined by SEC at 40 days

| Formulation Conditions | Decrease in % Monomer after 40 Days | | | | | |
|---|---|---|---|---|---|---|
| | aFD.WT | D30E (AFD.v2) | TM (AFD.v6) | SIESD (AFD.v8) | SIESD.N103S (AFD.v14) | aVEGF |
| 10 mg/mL in 10 mM sodium phosphate pH 7.4 | 1.6 | 2.1 | .9 | | | .36 |
| 10 mg/mL in PBS | 1.5 | | .8 | | | .63 |
| 100 mg/mL in PBS | 5.8 | 7.3 | 1.5 | 0.7 | 1.5 | 1.78 |

To detect fragmentation formed as a function of pH, capillary electrophoresis sodium dodecyl sulfate (CE-SDS) was performed using a Beckman PA800 System with an uncoated fused-silica capillary with a 50 μm internal diameter (Polymicro Technologies, Inc.). Samples were prepared by a Beckman Coulter NXp Liquid Handling Robot with automation equivalent to Q12695. Samples were injected into the capillary at a voltage of 5 kV for 15 seconds and then mobilized at a voltage of 15 kV for 30 minutes. All samples were run at ambient temperature. The electropherograms of all tested antibodies are similar to that of aFD.WT. Only at pH 2.5 was significant fragmentation observed. At no condition were higher molecular weight species observed, indicating that any aggregates formed are SDS-dissociable and not covalently linked.

The above stability results show that the triple (TM (AFD.v6)) and quad (SIESD (AFD.v8)) mutant variants of anti-Factor D have chemical stability that is significantly improved over aFD.WT or D30E (AFD.v2). In this series, SIESD.N103S (AFD.14) has the highest chemical stability at pH 5.5 and in PBS, similar to the stability of aVEGF. Both isomerization and deamidation sites have been removed and solubility at neutral pH has been increased while maintaining the fD binding affinity. Based on the above findings, the selected anti-Factor D variants described herein, particularly the SIESD (AFD.v8) and SIESD.N103S (AFD.v14) variants, are suitable for both high concentration formulation and for long acting delivery via, e.g., a port delivery system (PDS) device. For example, long acting delivery using a permanent, refillable device, such as a port delivery system may require high concentration formulation and low tendency to aggregate under physiological conditions of pH (~7.3) and ionic strength (~150 mM NaCl).

List of HVR Sequences (substitutions in variants are underlined)

| SEQ ID NO: | Description | Sequence |
|---|---|---|
| 5 | HVR-L1 of WT | ITSTDIDDDMN |
| 6 | HVR-L2 of WT/TM (AFD.v6)/TM.92E (AFD.v7)/SIESD (AFD.v8)/SIESD.N103S (AFD.v14) | GGNTLRP |
| 7 | HVR-L3 of WT/TM (AFD.v6)/SIESD (AFD.v8)/SIESD.N103S (AFD.v14) | LQSDSLPYT |
| 8 | HVR-H1 of WT/TM (AFD.v6)/TM.92E (AFD.v7)/SIESD (AFD.v8)/SIESD.N103S (AFD.v14) | GYTFTNYGMN |
| 9 | HVR-H2 of WT | WINTYTGETTYADDFKG |
| 10 | HVR-H3 of WT/TM (AFD.v6)/TM.92E (AFD.v7)/SIESD (AFD.v8) | EGGVNN |
| 11 | HVR-L1 of TM (AFD.v6)/TM.92E (AFD.v7) | ITSTDIESDMN |
| 12 | HVR-H2 of TM (AFD.v6)/TM.92E (AFD.v7)/SIESD (AFD.v8)/SIESD.N103S (AFD.v14) | WINTYTGETTYAEDFKG |
| 13 | HVR-L3 of TM.D92E (AFD.v7) | LQSESLPYT |
| 14 | HVR-L1 of SIESD (AFD.v8)/SIESD.N103S (AFD.v14) | ITSTSIESDMN |
| 15 | HVR-H3 of SIESD.N103S (AFD.v14) | EGGVSN |

Example 4: Stability of High Concentration Formulation of SIESD (AFD.v8)

Based on the stability studies above, AFD.v8 was assessed for suitability for high concentration formulations in low ionic strength, pH 5.5 buffer by performing a thermal (37° C.) stress test. A solution of about 100 mg/mL AFD.v8 was prepared and dialyzed versus 20 mM histidine hydrochloride (His-HCl), pH 5.5, then concentrated using Amicon YM-10 centrifugal filter units. Protein concentration upon removal from the filter units was determined to be 272 mg/mL using absorbance measurements at 280 nm. Aliquots of 100 μL were filtered through 0.22 μm cellulose acetate filters using sterilized Spin-X (Costar) centrifuge tube filters. The filtered solutions contained in snap-cap eppendorf tubes were sealed with parafilm and placed in a warm room maintained at 37° C. At pre-determined times of 0, 1, 2, 4, and 8 months a tube was removed, diluted 10-fold by addition of 900 μL storage buffer (10 mM His-HCl, pH 5.5, 10% trehalose, 0.01% polysorbate 20) and stored frozen at −70° C. until analysis could be performed. Samples were analyzed for generation of charge variants by ion-exchange chromatography (IEC), presence of aggregates by size-exclusion chromatography (SEC), retention of antigen-binding capacity by surface plasmon resonance (SPR) measurements, and specific chemical changes in the variable domains by peptide mapping. IEC was performed as described in Example 3 (paragraph 00292), with SEC done as described in Example 3 (paragraph 00294). SPR and peptide mapping was done as described below.

a. Peptide Mapping

Samples of AFD.v8 were diluted with RCM buffer (6M guanidine HCl, 360 mM Tris, 2 mM EDTA, pH 8.6) to 1 mg/mL in a 1.5 mL eppendorf tube. The reduction reaction was initiated by adding 1M dithiothreitol (DTT) to a final concentration of 20 mM and then incubating at 37° C. for 1 hour. Following reduction, the alkylation reaction was carried out by adding 1M iodo acetic acid (IAA) to a final concentration of 50 mM and incubating in the dark at room temperature for 15 minutes. The reduced and alkylated samples were buffer exchanged into the digest buffer (25 mM Tris, 2.0M $CaCl_2$, pH 8.2) using G-25 Minitrap columns. Trypsin was added in a 1:40 trypsin to protein ratio (by mass) and the digestion was allowed to go to completion by incubating at 37° C. for 4 hours.

LC/MS-MS

A Waters H-Class Acquity connected to a Thermo Orbitrap Q Exactive mass spectrometer were used for LC/MS-MS analysis. 10 μg of trypsin digested samples were loaded onto the Waters Acquity UPLC CSH column and run using the following LC conditions:

Mobile phase A—0.1% FA in $H_2O$
Mobile phase B—0.1% FA in ACN
Column temperature: 77 C
Flow rate: 0.2 mL/min

| Time (minutes) | % B |
|---|---|
| 0 | 1.0 |
| 2 | 1.0 |
| 7 | 13.0 |
| 42 | 35.0 |
| 44.1 | 95.0 |
| 46.0 | 95.0 |
| 46.1 | 1.0 |
| 64 | 1.0 |

For the mass spectral analysis, full MS1 scans were detected at 35K resolution using the FTMS (Fourier transform MS, Orbitrap). The top eight ions detected (dynamic exclusion off) in the full MS1 scans were selected for HCD fragmentation in data dependent MS2 scans, which were detected using the FTMS. Downstream data analysis including extracted ion chromatographs and quantification of native and post-translationally modified peptides were performed using Thermo Scientific's XCalibur software.

b. Binding Capacity by SPR Measurements

Functional activity for binding to immobilized human factor D was assessed by SPR measurements. A Series S, CM5 sensor chip was docked into a Biacore® T200 instrument[1] (GE Healthcare), primed with 1× running buffer and normalized with 70% glycerol following a protocol supplied by the manufacturer. The sensor chip surface was activated for amine-coupling of antigens using the amine coupling kit with the materials provided and the protocol suggested by the manufacturer. On a flow cell of the sensor chip human factor D (fD) was covalently immobilized by injecting a solution containing 100 μg/mL fD prepared by dilution of fD (2.4 mg/mL) with 10 mM sodium acetate pH 5. The flow rate was 10 μL/minute and an injection volume of 70 μL was used. This yielded a typical coupling density across multiple experiments of about 5000 Resonance Units (RU) for fD. Unreacted amine coupling sites were blocked by injection of 70 μL 1 M ethanolamine.

Antigen-binding active concentrations of AFD were determined using the calibration-dependent concentration analysis routine of the Biacore® T200 evaluation software. A standard curve of unstressed AFD was prepared through gravimetric dilution of standards to 5 μg/mL followed by serial 2-fold dilutions to produce samples of 2.5, 1.25, 0.625, 0.313, 0.156, and 0.078 μg/mL. Test samples were prepared by gravimetric dilution to obtain protein concentrations of about 0.5, 1.0, or 1.5 μg/mL. All samples (200 μL volume) were prepared using 1× running buffer (10 mM HEPES pH 7.4, 150 mM NaCl, 0.01% PS20). 60 μL aliquots were injected over the specific antigen surface using a flow rate of 10 μL/minute with the sensor chip maintained at 25° C. and primed with 1× running buffer. Antibody bound to specific antigen was determined from the SPR signal near the end of the sample injection. Bound antibody was eluted at the end of each binding cycle through injection of 30 μL of 10 mM Gly-HCl pH 2.1 to cause dissociation of the antibody-antigen complex. The standard curve of starting material was used to determine the relationship of SPR signal to antibody concentration using a four-parameter function to analyze the data. Parameters calculated from the standard curve were used to calculate the antigen-binding concentration of test samples based on the observed SPR signal. The ratio of this concentration to the protein concentration determined by absorbance measurements gives the fraction or percent binding.

c. Results

Results of this thermal stress test indicate that AFD.v8 is a stable molecule in high concentration formulation. Greater than 80% of antigen-binding capacity (FIG. 10A) was maintained after 4 months at 37° C. Very little aggregate formation occurred at 4 months and the protein was nearly 100% monomer by SEC (FIG. 10B). Some chemical changes took place by 4 months as indicated by the increase in acidic species (FIG. 10B, % Acidic—IEC) to approximately 15% and basic species to approximately 20% (FIG. 10B, % Basic—IEC). After 8 months at 37° C. there was an additional increase in acidic and basic species, a loss in monomer content, and a decrease in factor D-binding capacity. Peptide mapping suggests that the acidic species primarily arose from deamidation of CDR-H3 Asn-103 (Asn-101 according to Kabat numbering) (FIG. 10B, CDR-H3 N101% deamindation) whereas basic variants were contributed by pyroglutamic acid formation at the N-terminus of the heavy chain (FIG. 10B, HC-E1% succinimide) and isomerization of CDR-H3 residue Glu-99 (Glu-95 according to Kabat numbering) (FIG. 10B, CDR-H3 E97% isomerization). Since Asn-103 and Glu-99 (Asn-101 and Glu-95, respectively, according to Kabat numbering) are in contact with factor D in the co-crystal structure of lamaplizumab and factor D (Katschke K J, Jr., Wu P, Ganesan R, Kelley R F, Mathieu M A, Hass P E, Murray J, Kirchhofer D, Weismann C, van Lookeren Campange M, "Inhibiting alternative pathway complement activation by targeting the factor D exosite", *J. Biol. Chem.* (2012) 287:12886-92), but the N-terminus of the heavy chain is not, it is likely that Asn-103 deamidation and Glu-99 isomerization, as well as the decrease in monomer content, directly contribute to the loss in factor D-binding at 8 months. Nonetheless, given the slow rate of these chemical and physical changes, coupled with the expected further decrease in rate at lower temperature, a high concentration liquid formulation of AFD.v8 stored at 2-8° C. or frozen at −20° C. would appear to give acceptable shelf-life.

Example 5: Rabbit pK for AFD.v8/v14

In vivo pK studies for AFD.v8 and AFD.v14 were performed in rabbits. pK parameters were determined from single dose experiments because humanized antibodies are immunogenic in rabbits upon repeat dosing or when exposure is increased through sustained delivery formulations.

The animals' care was in accordance with Genentech Institutional Animal Care and Use Committee guidelines. Naïve New Zealand White (NZW) rabbits (41 male animals; 3.1 kg to 4.1 kg and approximately 4 months of age at the time of dosing) were assigned to dose groups and dosed with the test items at Charles River Laboratories.

SIESD(AFD.v8), SIESD.N103S(AFD.v14) or ranibizumab were administered via a single bilateral intravitreal injection to rabbits and observed for up to 27 days. Topical antibiotic (tobramicin ophthalmic ointment) was applied to both eyes twice on the day before treatment, immediately following the injection, and twice on the day following the injection, with the exception of animals sent to necropsy on Days 1 and 2. Prior to dosing, mydriatic drops (1% tropicamide) were applied to each eye for full pupil dilation. Animals were sedated with isoflurane/oxygen gas prior to and during the procedure. Alcaine (0.5%) was also applied to each eye prior to injection. The conjunctivae was flushed with benzalkonium chloride (Zephiran™) diluted in sterile water, U.S.P. to 1:10,000 (v/v)

Syringes were filled under a laminar flow hood immediately prior to dosing. Fabs were administered by a single 30 μL intravitreal injection (0.3 mg dose) to both eyes in all animals. Doses were administered by a board-certified veterinary ophthalmologist using sterilized 100 μL Hamilton Luer Lock syringes with a 30-gauge×½" needle. In order to mimic clinical dosing, eyes were dosed in the infero-temporal quadrants, i.e., in 5 o'clock and 7 o'clock positions for the left and right eyes, respectively (when facing the animal). The eyes were examined by slit-lamp biomicroscopy and/or indirect ophthalmoscopy immediately following treatment.

All animals underwent exsanguination by incision of the axillary or femoral arteries following anesthesia by intravenous injection of sodium pentobarbital. Aqueous humor, vitreous humor and retina tissue were collected, snap frozen in liquid nitrogen and stored at −80° C. Antibody Fab in retina was extracted by homogenization in 50 mM Tris-HCl pH 8.0, 1 M NaCl. Determination of vitreous and retinal concentrations of test articles was by GRIP ELISA as described below. Values below the LLOQ were not used in pharmacokinetic analysis or for graphical or summary purposes. Pharmacokinetic parameters were determined by non-compartmental analysis with nominal time and dose (Phoenix WinNonlin, Pharsight Corp, Mountain View, Calif.).

Analyses of SIESD (AFD.v8), SIESD.N103S (AFD.v14) and ranibizumab were done in the generic immunoglobulin pharmacokinetic (GRIP) ELISA, with the exceptions noted herein. Sheep anti-human-IgG (The Binding Site; San Diego, Calif.) was diluted to 1000 ng/mL in 0.5 M carbonate/bicarbonate, pH 9.6, and coated onto 384-well ELISA plates (Nunc; Neptune, N.J.) during an overnight incubation at 4° C. Plates were washed with PBS plus 0.05% Tween-20 and blocked during a 1- to 2-hour incubation with PBS plus 0.5% bovine serum albumin (BSA). This and all subsequent incubations were performed at room temperature with gentle agitation. The standard curves were prepared by serially diluting AFD.v8, AFD.v14 or ranibizumab from 40-0.625 ng/mL in assay buffer (PBS, 0.5% BSA, 15 ppm Proclin, 0.05% Tween 20, 0.25% CHAPS, 5 mM EDTA, 0.35M NaCl, (pH 7.4)). The rabbit vitreous or retinal homogenate samples were diluted a minimum of 1:100 or 1:50, respectively, in assay buffer. The diluted standards, controls, and samples were then incubated on the washed plates for 1-2 hours. Following a wash step, plate-bound AFD.v8, AFD.v14 or ranibizumab was detected during a 1.5 hour incubation with HRP-conjugated sheep anti-human IgG mAb (Bethyl Laboratories Inc; Montgomery, Tex.) diluted to 83.3 ng/mL in assay diluent (PBS+0.5% BSA+0.05% Tween 20+10 ppm Proclin). After a final wash, tetramethyl benzidine peroxidase substrate (Moss, Inc., Pasadena, Md.) was added, color was developed for 10-15 minutes, and the reaction was stopped with 1 M phosphoric acid. The plates were read at 450 nm with a 620 nm reference using a microplate reader (Multiscan Ascent, Thermo Fischer; Waltham, Mass.). The concentrations of AFD.v8, AFD.v14 or ranibizumab were calculated from a four-parameter fit of the respective standard curve using in-house Excel-based software. Taking into account the minimum dilution in vitreous or retinal homogenate, the minimum quantifiable concentration of AFD.v8, AFD.v14 or ranibizumab in rabbit vitreous or retinal homogenate was 62.5 ng/mL or 31.25 ng/mL, respectively.

Time-dependent concentration curves observed for intravitreal injection of 0.3 mg SIESD (AFD.v8), SIESD.N103S (AFD.v14), or a comparator dose of ranibizumab (anti-VEGF), are shown in FIG. 11.

Analysis of the vitreal data using a non-compartmental model indicated that both SIESD (AFD.v8) and SIESD.N103S (AFD.v14) have clearance properties very similar to ranibizumab. All three proteins gave very similar exposure, as reflected in the AUC parameter, in the three ocular compartments: vitreous humor, aqueous humor, and retina. PK parameters calculated for ranibizumab were consistent with results of earlier studies in rabbits (Gaudrealt et al, *Retina,* 27:1260-6 (2007)). Both SIESD (AFD.v8) and SIESD.N103S (AFD.v14) show target-independent ocular clearance properties that render these molecules suitable for development.

Example 6: Viscosity for AFD.v8/v14

As low viscosity is important for intravitreal administration, viscosity for SIESD (AFD.v8) and SIESD.N103S (AFD.v14) was measured at different protein concentrations in a pH 5.5, low salt buffer. Viscosity measurements were performed on a TA Instruments cone and plate rheometer thermostatted at 25° C. using a shear rate of 1000 $s^{-1}$.

aFD.WT, SIESD (AFD.v8) and SIESD.N103S (AFD.v14) gave similar profiles of viscosity dependence on protein concentration with viscosities acceptable for intravitreal injection (<30 cP) even at concentrations exceeding 200 mg/mL (FIG. 12).

Example 7. Anti-Factor D Antibody Variants Further Modified for Polymer Conjugation The aFD.WT and variants described in the above Examples are Fab fragments. While the variable domains of their light and heavy chains (VL and VH) vary in sequences as shown in FIG. 1B, their constant domains CL and CH1 remain the same. In particular, the CH1 domain of the heavy chain ends at the Threonine residue as shown in FIG. 1A (SEQ ID NO:2) FIG. 1C (SEQ ID NO: 27) and FIG. 1D (SEQ ID NO: 29). In order to prepare the AFD.Ab variants for polymer conjugation such as PEGylation, the heavy chains of the Fab fragments were further modified by adding the first cysteine residue from the hinge region of the Fab' counterpart (e.g., Cys-modified HC (Fab-C) for AFD.v8 (SEQ ID NO: 30) and Cys-modified HC (Fab-C) for AFD.v14 (SEQ ID NO: 32)), so that the added cysteine serves as the attachment site of PEG polymer. The resulting fragment can therefore be conjugated with one arm of the multi-arm PEG. The heavy chains of the Fab fragments were also modified by adding the first four residues from the hinge region of the Fab' counterpart, namely Cys-Pro-Pro-Cys (SEQ ID NO: 21) (e.g., Cys-Pro-Pro-Cys-modified HC for AFD.v8 (SEQ ID NO: 31) and Cys-Pro-Pro-Cys-modified HC for AFD.v14 (SEQ ID NO: 33)), so that the two added Cys both serve as attachment sites for PEG, resulting in a modified AFD.Ab Fab fragment capable of attaching two PEG molecules.

The Cys-modified and Cys-Pro-Pro-Cys-modified variants were prepared using the QuikChangeII® (Agilent) mutagenesis kit following the protocol supplied with the kit. Oligonucleotide primers specifying the required codon changes were synthesized. Plasmids with designed changes were identified and confirmed by DNA sequencing. For small scale expression, DNA was transformed into *E. coli* strain 64B4. Single colonies were picked into 5 mL LB media (media prep code A2008) containing 50 µg/mL carbenecillin (media prep code A3232) and grown overnight in 14 mL culture tubes with shaking at 200 RPM in an Innova incubator at 37° C. These cultures were used to inoculate 250 mLs of complete soy crap media (media prep code A4564), 50 µg/mL carbenecillin, in a 1 L baffled shake flask. Cultures were grown overnight at 30° C. with shaking at 200 RPM and then harvested by centrifugation. The cell pellet was lysed using PopCulture media (Invitrogen), and Fab-C purified as described in Example 1. For larger scale production of Fab-C, cell paste from 10 L fermentation of transformed cells was suspended in extraction buffer and homogenized using a microfluidizer, and the Fab-C was purified as described in Example 8.

Example 8: Preparation of AFD.v14 Conjugates

The AFD.v14 variant containing the Cys-modified HC (SEQ ID NO: 32) prepared in Example 7 (referred to herein as the "Cys-modified AFD.v14 variant" or "AFD.v14.C") was conjugated with commercially available maleimide-functionalized multi-armed PEGs having varying core structures.

a. Maleimide-Functionalized Multi Armed PEGs

The maleimide-functionalized multi-armed PEGs detailed in Table 8, below, were used in the conjugation reactions:

TABLE 8

Maleimide-functionalized multi-armed PEGs

| PEG | Vendor | Core structure | | Functional Group (X) | *Poly-Dispersity | Average MW |
|---|---|---|---|---|---|---|
| 8ARM (TP)-PEG-MAL | JenKem Technology, U.S.A. | Tripentaerythritol (TP) $X-(OCH_2CH_2)m-O$ $CH_2$ $X-(OCH_2CH_2)m-O-CH_2-C-CH_2-O-CH_2-C-CH_2-O-(CH_2CH_2O)m-X$ $CH_2$ $CH_2$ $O-(CH_2CH_2)m-X$ $O-(CH_2CH_2O)m-X$ | | $-CH_2CH_2-NH-\overset{O}{\underset{\|}{C}}-CH_2CH_2-$ [maleimide] | ~1.04 | 40,000 |
| 8ARM-PEG-MAL | JenKem Technology, U.S.A. | Hexaglycerin (HG) $X-(OCH_2CH_2)m-$ $[O(CH_2CH_2O)m-X\ O(CH_2CH_2O)m-X\ O(CH_2CH_2O)m-X]_4$ | | $-CH_2CH_2-NH-\overset{O}{\underset{\|}{C}}-CH_2CH_2-$ [maleimide] | ~1.08 | 40,000 |
| Sunbright® HGEO-400MA | NOF America Corp. | Hexaglycerol (HGEO) $X-O(CH_2CH_2O)-(CH_2CHO)_6-(CH_2CH_2O)m-X$ with $CH_2O(CH_2CH_2O)m-X$ branches | | $-(CH_2)_3-NH-\overset{O}{\underset{\|}{C}}-CH_2CH_2-$ [maleimide] | ~1.33 | 40,000 |
| Sunbright® DX-400MA | NOF America Corp. | Butanediol $X-(OCH_2CH_2)m-O-CH_2$ $X-(OCH_2CH_2)m-O-CH$ $X-(OCH_2CH_2)m-O-CH$ $X-(OCH_2CH_2)m-O-CH$ $H_2C-O-(CH_2)_4-O-CH_2$ $H_2C-O-(CH_2CH_2O)m-X$ $HC-O-(CH_2CH_2O)m-X$ $HC-O-(CH_2CH_2O)m-X$ $HC-O-(CH_2CH_2O)m-X$ | | $-(CH_2)_3-NH-\overset{O}{\underset{\|}{C}}-CH_2CH_2-$ [maleimide] | ~1.01 | 40,000 |

TABLE 8-continued

Maleimide-functionalized multi-armed PEGs

| PEG | Vendor | Core structure | Functional Group (X) | *Poly-Dispersity | Average MW |
|---|---|---|---|---|---|
| Sunbright ® PTE-400MA | NOF America Corp. | X—(OCH$_2$CH$_2$)m—O—CH$_2$—C(CH$_2$—O(CH$_2$CH$_2$O)m—X)(CH$_2$—O(CH$_2$CH$_2$O)m—X)—CH$_2$—O(CH$_2$CH$_2$O)m—X | —(CH$_2$)$_3$—NH—C(=O)—CH$_2$CH$_2$—N(maleimide) | — | 40,000 |

*As provided by vendor. Note that this refers to the PEG chain length.

The 8ARM (TP)-PEG-MAL (JenKem Technology, USA) and Sunbright® HGEO-400MA (NOF America, Corp.) were analyzed using MALDI to compare the homogeneity of PEG octamers containing either the TP core or the HGEO core. The results are set forth in FIGS. 13A and 13B.

As can be seen from FIGS. 13A and 13B, the 8ARM (TP)-PEG-MAL containing the TP core was more homogeneous than the Sunbright® HGEO-400MA containing the HGEO core.

b. Conjugation of Cys Modified AFD. v14 Variant and Maleimide-Functionalized Multi Armed PEGs The Cys-modified AFD.v14 variant prepared in Example 7 was captured using Gamma Plus resin, with 6.5 mM GSH pH 8.5 wash for 5 column volumes to deblock c-terminal cysteine and disrupt Fab-C dimer formation, followed by elution into 0.1M acetic acid pH 2.9. The Cys-modified AFD.v14 monomer was further isolated using SP Sepharose High Performance strong cation exchange resin (from GE Healthcare) in 25 mM sodium acetate pH 5.0, with 0.05% Triton X-100+0.05% Triton X-114 for 19 hours for endotoxin removal. Elution was performed with gradient between 0-20% 25 mM sodium acetate pH 5.0+1 M NaCl over 20 column volumes. The monomeric Fab-C with deblocked c-terminal cysteine was then prepared for PEGylation by titrating to pH 6.5 using 1 M HEPES pH 7.2. The Cys-modified AFD.v14 Fab-C was then conjugated to the maleimide-functionalized multi-armed PEG in 25 mM sodium acetate pH 6.5, 150 mM NaCl, 4 mM EDTA, at a concentration around 5 mg/mL. The Cys-modified AFD.v14 variant was not further concentrated in order to minimize cysteine reactivity loss due to Fab-C dimerization. After equilibrating to room temperature, the maleimide-functionalized multi-armed PEG was resuspended in 25 mM sodium acetate pH 5.0 to a concentration of 10 mg/mL. The pH was kept below pH 6 to avoid maleimide ring opening. Once the PEG was solubilized, it was added to the Fab-C pool at a molar ratio of 0.1125:1 PEG to Fab-C. The mixture was then left at room temperature with gentle shaking overnight. The following day, the conjugation efficiency (# Fab/PEG) was checked by SEC-MALS.

Example 9: Purification and Characterization of AFD.v14 Conjugates

The conjugates prepared in Example 8 were purified and analyzed using SEC-MALS to confirm PEGylation and determine conjugation efficiency for different PEG core structures. Unless otherwise indicated, conjugation efficiency was determined by Size Exclusion Chromatography (SEC) using a 300×8 mm Shodex OH pak SB-804 HQ run at 0.8 mL/minute using phosphate buffered saline (PBS) pH 7.2, 150 mM NaCl under isocratic conditions. Molar mass was determined using in-line static Multi-Angle laser Light Scattering (MALS) by Wyatt Technology. Photon correlation spectroscopy was used to determine hydrodynamic radii (RH), using Quasi-Elastic Light Scattering (QELS), a single photon counting module with detection at a 99.0°, also by Wyatt Technology. Raw data was worked up using Wyatt's proprietary Astra software, where molar mass and RH constants were set using a rituximab standard.

a. Cys Modified AFD. v14-8ARM (TP)-PEG-MAL Conjugate

The Cys-modified AFD.v14-8ARM (TP)-PEG-MAL conjugate (containing the TP core structure) (hereinafter the "AFD.v14 TP conjugate" or "AFD.v14.C+TP octamer") prepared in Example 8 was purified using SEC on a Sephacryl S-300 HR (GE Healthcare) column in 20 mM His-acetate, pH 5.5, 50 mM NaCl (isocratic gradient). Molar mass and conjugation efficiency were determined using in-line static Multi-Angle laser Light Scattering (MALS) by Wyatt Technology and Shodex OH pak SB-804 (FIG. 14C). Raw data was analyzed using Wyatt's proprietary Astra software, where molar mass constants were set using a rituximab standard. Molar mass was used to estimate the average number of AFD.v14 variants attached to each PEG. The results are shown in FIGS. 14A, 14B, and 14C and in Table 9.

TABLE 9

| Fraction # | Molar Mass (g/mol) | Estimated Fabylation* |
|---|---|---|
| B2 | 502,000 | agg |
| B3 | 470,200 | n/d |
| B4 | 453,200 | n/d |
| B5 | 444,300 | 8 Fabs/PEG |
| B6 | 430,400 | 8 Fabs/PEG |
| B7 | 410,900 | 8 Fabs/PEG |
| C1 | 388,100 | 7 Fabs/PEG |
| C2 | 349,100 | 6-7 Fabs/PEG | agg = aggregates; n/d = not determined
*B5-B7 are deemed to be 8 Fabs/PEG based on % error in the MALS measurements.

As can be seen from Table 9, conjugation of the Cys-modified AFD.v14 variant (AFD.v14.C) with a multi-armed PEG octamer having the TP core produced conjugates comprising 8 Fabs/PEG, demonstrating that good conjugation efficiency can be achieved with PEG octamers comprising a TP core (e.g., approximately 45% recovery of 8 Fabs/PEG from conjugation).

b. Cys Modified AFD.v14-8ARM-PEG-MAL Conjugate

The Cys-modified AFD.v14-8ARM-PEG-MAL conjugate (containing the HG core structure (JenKem)) (hereinafter the "AFD.v14 HG conjugate" or the "AFD.v14.C+HG octamer") prepared in Example 8 was purified using SEC on a Sephacryl S-300 HR (GE Healthcare) column in 20 mM His-acetate, pH 5.5, 50 mM NaCl (isocratic gradient). Molar mass and conjugation efficiency was determined using Tosoh G3000PW column and in-line static MALS by Wyatt Technology. Photon correlation spectroscopy was used to determine hydrodynamic radii (RH), using Quasi-Elastic Light Scattering (QELS), a single photon counting module with detection at a 99°, also by Wyatt Technology. Raw data was analyzed using Wyatt's proprietary Astra software, where molar mass and RH constants were set using a rituximab standard. Molar mass was used to estimate the number of AFD.v14 variants attached to each PEG. The results are shown in FIGS. 15A, 15B, and 15C and in Table 10.

TABLE 10

| Fraction # | Mw (kDa) | Estimated Fabylation | $R_H$ (nm) |
|---|---|---|---|
| A6 | 1146.6 (±0.1%) | agg | 16.0 (±4.9%) |
| B3 | 861.6 (±0.1%) | agg | 14.5 (±4.0%) |
| B6 | 758.3 (±0.1%) | agg | 13.7 (±3.8%) |
| C1 | 649.3 (±3.8%) | n/d | 13.5 (±3.8%) |
| C6 | 562.6 (±0.1%) | n/d | 12.8 (±3.6%) |
| D2 | 546.7 (±0.1%) | n/d | 12.8 (±3.7%) |
| D4 | 536.6 (±0.1%) | n/d | 12.6 (±3.6%) |
| E2 | 525.4 (±0.1%) | n/d | 12.5 (±3.5%) |
| E5 | 489.2 (±0.2%) | 8 Fab/PEG | 12.3 (±3.7%) |
| F1 | 409.2 (±0.2%) | 7-8 Fab/PEG | 10.8 (±3.7%) |
| F4 | 342.2 (±0.1%) | 6-7 Fab/PEG | 9.7 (±2.9%) |
| F6 | 325.5 (±0.2%) | 6 Fab/PEG | 9.5 (±0.3%) |
| G2 | 302.4 (±0.2%) | 5-6 Fab/PEG | 9.3 (±3.1%) | agg = aggregates; n/d = not determined

As can be seen from Table 10, conjugation of the Cys-modified AFD.v14 variant (AFD.v14.C) with a PEG octamer comprising the HG core produced conjugates comprising 8 Fabs/PEG. The recovery of conjugates comprising 8 Fabs/PEG (approximately 20% recovery), however, was about half the amount of conjugates comprising 8 Fabs/PEG that was recovered when using the conjugate with the TP core. Conjugation with the HG core also produced more conjugates comprising 5-7 Fabs/PEG, than was observed with the TP core, and significantly more aggregates.

In an effort to improve Fabylation estimate and RH measurement, the product containing fractions obtained following the S-300 purification were pooled and alternately analyzed using SEC-MALS on a 10/300 Sephacryl S-400 HR (GE Healthcare) column in PBS, pH 7.4, run at 0.25 mL/minute. Molar mass and RH were determined as described above. The SEC and MALS results are set forth in FIGS. 16A and 16B.

The conjugates prepared using the 8ARM-PEG-MAL (HG core) and analyzed using Sephacryl S-400 HR had an average RH of 12.2 nm (±4.5%), an average molar mass of 340.3 kDa (±8.9%), and an average of 6.4 Fabs/PEG.

c. Cys Modified AFD. v14-HGEO-400MA Conjugate

The Cys-modified AFD.v14-HGEO-400MA conjugate (containing the Sunbright® HGEO-400MA PEG) (hereinafter the "AFD.v14 HGEO conjugate" or "AFD.v14.C+ HGEO octamer") prepared in Example 8 was purified using SEC on a Sephacryl S-300 HR (GE Healthcare) column in 20 mM His-acetate, pH 5.5, 50 mM NaCl (isocratic gradient). Molar mass, conjugation efficiency, and RH were determined as described above using Sephacryl S-400 HR, run at 0.25 mL/minute in PBS, pH 7.4.

The results are set forth in FIGS. 17A and 17B. The conjugates prepared using the Sunbright® HGEO-400MA PEG (HGEO core) had an average RH of 15.2 nm (±4.5%), an average molar mass of 423.8 kDa (±10.6%), and an average of 8.2 Fabs/PEG.

Following purification of the AFD.v14 HGEO conjugates using SEC on the Sephacryl S-300 HR column, conjugation efficiency and molar mass were alternately determined using Tosoh G3000PW column and in-line static MALS by Wyatt Technology, as described above. Molar mass was used to estimate the number of AFD.v14 variants attached to each PEG. The results from this analysis are set forth in FIGS. 18A and 18B, and in Table 11.

TABLE 11

| Fraction # | Molar Mass (g/mol) | Estimated Fabylation |
|---|---|---|
| B1 | 2,145,000 (±0.8%) | agg |
| B2 | 665,800 (±0.7%) | agg |
| B3 | 426,400 (±0.8%) | 8 Fabs/PEG |
| B4 | 296,400 (±0.8%) | 6 Fabs/PEG |
| B5 | 246,200 (±0.8%) | 5 Fabs/PEG |
| B6 | 215,000 (±0.8%) | n/d | agg = aggregates; n/d = not determined

As can be seen from Table 11, conjugation of the Cys-modified AFD.v14 variant (AFD.v14.C) with a PEG octamer comprising the HGEO core produced conjugates comprising 8 Fabs/PEG. Conjugation with the HGEO core also produced more conjugates comprising 5-6 Fabs/PEG, than was observed with the TP core. Finally, conjugation with the HEGO core resulted in more aggregates, and a lower conjugation efficiency, as compared to the TP core.

Example 10: Enrichment of AFD.v14 Conjugates

One way to increase the Fab concentration in an intravitreal formulation without significantly increasing formulation viscosity is to increase the percentage of highly fabylated conjugates in the formulation. In this example, cation exchange chromatography was used to enrich for highly fabylated conjugates.

Fractions B4-B7 (estimated fabylation of 8 Fab/PEG) from the SEC purification of the AFD.v14.C+TP octamer described in Example 9a were pooled (about 45% recovery), and subjected to cation exchange chromatography (CEX) using SP Sepharose High Performance strong cation exchange resin (GE Healthcare) in 25 mM sodium acetate pH 5.0, with 0.05% Triton X-100+0.05% Triton X-114 wash for 19 hours to remove endotoxin, followed by gradient elution between 10-20% using 25 mM sodium acetate pH 5.0 plus 1 M NaCl over 50 column volumes (CV). Fractions were analyzed using SEC-MALS+QELS using Shodex OH pak SB-804 HQ, as described above. The results are set forth in FIGS. 19A, 19B, 19C, and Table 12.

TABLE 12

| Fraction # | Molar mass (g/mol) | Estimated Fabylation | GEL Lane # |
|---|---|---|---|
| 3B11 | 335,000 | 6 Fabs/PEG | 1, 8 |
| 3E12 | 367,100 | 7 Fabs/PEG | 2, 9 |
| 4A7 | 414,200 | 8 Fabs/PEG | 3, 10 |
| 4C5 | 430,000 | 8 Fabs/PEG | 4, 11 |
| 4F3 | 483,900 | n/d | 5, 12 |
| 4H9 | 567,400 | n/d | 6, 13 |

The conjugate containing fractions obtained following CEX on SP Sepharose resin were pooled and analyzed using a 300×8 mm Shodex OH pak SB-804 HQ, run at 0.8 mL/minute using phosphate buffered saline (PBS), pH 7.4, 150 mM NaCl, under isocratic conditions. Molar mass and RH were determined as described above. The MALS results are set forth in FIG. 20.

Following enrichment, conjugates prepared using the 8ARM (TP)-PEG-MAL (TP core) were obtained that had an average RH of 10.5 nm (±2.5%), an average molar mass of 407.1 kDa (±0.2%), and an average of 7.8 Fabs/PEG.

The conjugate containing fractions obtained following cation exchange chromatography purification of the TP conjugate described above were pooled (CEX pool) and compared to pooled fractions obtained following SEC using Sephacryl S-300 HR (GE Healthcare) (see Example 9a) (S300 pool), and pooled fractions obtained following SEC using Sephacryl S-400 HR (GE Healthcare) in 20 mM His-acetate, pH 5.5, 50 mM NaCl (isocratic gradient) (data not shown) (S400 pool). The pooled fractions were subject to capillary SDS gel electrophoresis (CE-SDS), and the results are set forth in FIGS. 21A and 21B.

As can be seen from FIGS. 21A and 21B, purification on S-300 and S-400 resin gave similar results. Enrichment of the conjugates using CEX, however, visibly enriched the amount of conjugates comprising 8 Fabs/PEG, while removing lower and higher molecular weight contaminants.

Example 11: Comparison of PEG Cores

The properties of conjugates prepared in Example 8, comprising either the 8ARM-(TP)-PEG-MAL (containing the TP core structure), the 8ARM-PEG-MAL (containing the HG core structure (JenKem)), or the Sunbright®-DX-400MA PEG (containing the butanediol core structure, referred to herein as the "AFD.v14 DX conjugate" or the "AFD.v14.C+DX octamer"), were compared using SEC-MALS. The HG and DX conjugates were purified using SEC on a Sephacryl S-300 HR (GE Healthcare) column in 20 mM His-acetate, pH 5.5, 50 mM NaCl (isocratic gradient). For the TP conjugate, pooled fractions obtained following purification on Sephacryl S-300 HR as described in Example 9a ("CEX load") and pooled fractions obtained following the CEX enrichment as described in Example 10 ("TP final") were used. Molar mass and conjugation efficiency was determined using MALS by Wyatt Technology and a 300×8 mm Shodex OH pak SB-804 HQ run at 0.8 mL/minute using phosphate buffered saline (PBS) pH 7.2, 150 mM NaCl under isocratic conditions. RH was determined as described above. The results are set forth in FIGS. 22A, 22B, and Table 13.

TABLE 13

| Conjugate | PEG Core Structure | Mw (kDa) | Polydispersity (Mw/Mn) | $R_H$ (nm) | Gel Lane # |
|---|---|---|---|---|---|
| AFD.v14.C + TP octamer* | Tripentaerythritol (TP) | 407.1 | 1.004 | 10.5 | 6, 12 |
| AFD.v14.C + HG octamer | Hexaglycerol (HG, JenKem) | 539.1 | 1.289 | 12.8 | 4, 10 |
| AFD.v14.C + DX octamer | Butanediol (DX) | 355.6 | 1.005 | 9.2 | 3, 9 |

*Data is for TP final. Gel lanes 5 and 11 (FIG. 22A) were CEX load.

Polydispersity was determined using methods known in the art, and in particular was determined using Astra software commercially available from Wyatt Technology.

As can be observed from these results, although the AFD.v14 DX conjugate had a low polydispersity, it did not provide as high a conjugation efficiency as the AFD.v14.C+ TP octamer.

Example 12: Viscosity of AFD.v14 Conjugates

As low viscosity is important for intravitreal administration, viscosity of the Cys-modified AFD.v14 variant (AFD.v14.C) conjugated to either a PEG octamer (8ARM (HG)-PEG-MAL from JenKem Technology, USA; the AFD.v14.C+HG octamer) or a PEG tetramer (Sunbright® PTE-400MA from NOF America Corp.), prepared in Example 8, was measured at different protein concentrations in a pH 7.4 phosphate buffered saline (PBS) solution. Viscosity measurements were performed on a TA Instruments cone and plate rheometer thermostatted at 40° C. using a shear rate of 1000 $s^{-1}$. The results are shown in FIG. 23.

As can be seen from FIG. 23, conjugation of the AFD.v14 variant to the HGEO octamer allowed for a greater protein concentration, as compared to conjugation to the tetramer, at comparable viscosity.

The viscosity of the AFD.v14 HGEO conjugate (AFD.v14.C+HGEO octamer) at different protein concentrations was compared to that of the AFD.v14.C+TP octamer. Viscosity was measured at different protein concentrations at pH 6.5 in 20 mM His-Ace, 50 mM NaCl formulation. Viscosity measurements were performed on a TA Instruments cone and plate rheometer thermostatted at 20° C. using a shear rate of 1000 $s^{-1}$. The results are set forth in FIG. 24.

As can be seen from FIG. 24, the AFD.v14.C+TP octamer had a lower viscosity than the AFD.v14.C+HGEO octamer, at comparable protein concentrations.

Example 13: Thermal Stability of AFD.v14 Conjugates

To simulate the exposure of the AFD.v14 conjugates to conditions that may be found in long-acting delivery systems, samples of the AFD.v14.C+TP octamer (prepared in Example 8) were stressed under two different pH and salt conditions for several weeks at 37° C. Specifically, conjugates were evaluated in the following formulations:
Formulation 1: 10 mg/mL, PBS; and,
Formulation 2: 10 mg/mL, 20 mM histidine HCl, 50 mM NaCl, at pH 6.5.

PBS was used as a mimic of the pH and ionic strength of human vitreous. Aliquots (100 µL) of solutions of AFD.v14- TP conjugate, formulated at 10 mg/mL in PBS or 20 mM His-acetate pH 6.5, 50 mM NaCl, were sterile filtered by centrifugal filtration using 0.22 µm Costar® Spin-X centrifuge tubes (Corning) and then incubated at 37° C. for 0, 2, 4, or 8 weeks (T0, T2w, T4w, or T8w, respectively). Incubations were terminated by freezing at −70° C. After thawing, samples were analyzed by SEC-MALS using a Shodex OH pak SB-804 HQ as described above, CE-SDS and by biacore to assess fD-binding capacity, as described below. The relative peak area for the conjugate determined by CE-SDS as a function of incubation time is shown in FIGS. 25A and 25B, suggesting a 1%/week decrease in conjugate at 37° C. A similar change in conjugate, with increase in free Fab and dimer species, is observed by SEC-MALS (FIG. 26). No change in binding capacity greater than the standard error in the measurements (±10%) was determined for incubation of the conjugate at 37° C. (FIG. 28). The binding capacity remained steady even after 8 weeks at 37° C. in phosphate buffered saline (PBS) and after 4 weeks at pH 6.5.

a. CE-SDS Analysis
Material and Reagents:
AFD.v14.C+TP octamer samples were thawed from −70° C. before use. Potassium cyanide (KCN) and 3-(2-furoyl) quinoline-2-carboxaldeyde (FQ) reagents were purchased from Molecular Probes (Eugene, Oreg., USA). Monobasic and dibasic sodium phosphate, dimethyl sulfoxide (DMSO), dithiothreitol (DTT) and N-ethylmaleimide were purchased from Sigma-Aldrich (St. Louis, Mo., USA). Sodium dodecyl sulfate (SDS), 0.1 M sodium hydroxide (NaOH) and 0.1 M hydrochloric acid (HCl) reagents were purchased from J. T. Baker (Phillipsburg, N.J., USA). Replaceable sieving gel was purchased from Beckman Coulter, Inc. (Fullerton, Calif., USA).
Solutions:
Aqueous solutions were prepared with deionized 18.2 MS2 water from a Millipore purification system (Billerica, Mass., USA). Solutions of 0.1M sodium phosphate, pH 6.7 reaction buffer and 4% SDS were filtered through a 0.2 µm membrane filter (Millipore, Bedford, Mass., USA) and diluted before use. Stock solutions of 20 mM fluorogenic FQ were prepared in Dimethyl sulfoxide (DMSO) and stored in the dark at −20° C. Aliquots were thawed and diluted with water before use.
FQ Labeling Procedure:
Solutions of AFD.v14.C+TP octamer (300 µg) were exchanged into 0.5 mL sodium phosphate reaction buffer using NAP-5 gel filtration columns (GE Healthcare, Piscataway, N.J., USA) to remove potentially competing formulation constituents. A 250 µL aliquot of the desalted conjugate was mixed with 30 µL of 150 mM N-ethylmaleimide dissolved in 4% SDS and incubated for 5 minutes at 70° C. to control disulfide reshuffling under denaturing conditions (see, e.g., Michels, D. A., Brady, L. J., Guo, A., Balland, A., *Anal Chem* 2007, 79, 5963-5971). Ten microliters of each 2.5 mM FQ and 30 mM KCN reagents were added to the SDS-AFD.v14 solution, and the final solution was incubated for 10 minutes at 50° C. before diluted threefold with 1% SDS to quench the reaction. For reducing analysis, aliquots of the diluted samples were incubated with 50 mM DTT for 10 minutes at 70° C.

CE-SDS Analysis:

Separation of AFD.v14.C+TP octamer samples was performed with 31.2 cm (21 cm effective length) fused-silica capillaries of 50 μm ID (Polymicro technologies, Phoenix, Ariz., USA) encased in 40° C. thermal controlled cartridges. Fully automated Beckman PA800+ systems (Beckman Coulter, Brea, Calif., USA) were equipped with LIF detection and used 32 Karat version 9.1 to control the instrument. The LIF detector used a 3.5 mW argon-ion laser having an excitation at 488 nm; emission was collected through a 600±20 nm bandpass filter (Edmund Optics, Barrington, N.J., USA). Voltage was applied in the negative mode (reverse polarity). Sample solutions were introduced electrokinetically at 5 kV for 25 s and separated at 17 kV. Between runs, the capillary was washed with 0.1 M NaOH, 0.1 M HCl and Beckman gel buffer for 5 minutes, 1 minute, 1 minute and 10 minutes, respectively. (see, e.g., Michels, et al., *Anal Chem* 2007, 79, 5963-5971; Michels, et al., *Electrophoresis* 2012, 33, 815-826.)

b. Binding Capacity

The following materials were purchased from GE Healthcare: Series S CM5 Sensor Chips (cat # BR-1005-30); 10× Biacore® running buffer (cat # BR-1006-71): 0.1 M Hepes pH 7.4, 1.5 M NaCl, 0.5% Polysorbate® 20; regeneration solution (cat # BR-1003-55): 10 mM Gly-HCl pH 2.1; and, amine coupling kit (cat # BR-1000-50). A Series S, CM5 sensor chip was docked into a Biacore® T200 instrument (GE Healthcare), primed with 1× running buffer and normalized with 70% glycerol following a protocol supplied by the manufacturer. The sensor chip surface was activated for amine-coupling of antigens using the amine coupling kit with the materials provided and the protocol suggested by the manufacturer. Human factor D (fD) was covalently immobilized by injecting a solution containing 100 μg/mL antigen prepared by dilution of fD (PUR #20491, 2.4 mg/mL) with 10 mM sodium acetate pH 5. The flow rate was 10 μL/minute and an injection volume of 70 μL was used. This yielded a typical coupling density across multiple experiments of about 5000 Resonance Units (RU) for fD. Unreacted amine coupling sites were blocked by injection of 70 μL 1 M ethanolamine. Antigen-binding active concentrations of antibody Fab were determined using the calibration-dependent concentration analysis routine of the Biacore® T200 evaluation software. A standard curve of AFD.v14.C+TP octamer was prepared through gravimetric dilution of a stock solution to 5 μg/mL followed by serial 2-fold dilutions to produce samples of 2.5, 1.25, 0.625, 0.313, 0.156, and 0.078 μg/mL. Test samples were prepared by gravimetric dilution to obtain protein concentrations of about 0.5, 1.0, or 1.5 μg/mL. All samples (200 μL volume) were prepared using 1× running buffer. 60 μL aliquots were injected over the specific antigen surface using a flow rate of 10 μL/minute with the sensor chip maintained at 25° C. and primed with 1× running buffer. Antibody bound to specific antigen was determined from the SPR signal near the end of the sample injection. Bound antibody was eluted at the end of each binding cycle through injection of 30 μL of 10 mM Gly-HCl pH 2.1 to cause dissociation of the antibody-antigen complex. The standard curve of AFD.v14.C+TP octamer was used to determine the relationship of SPR signal to antibody concentration using a four-parameter function to analyze the data. Parameters calculated from the standard curve were used to calculate the antigen-binding concentration of test samples based on the observed SPR signal. The ratio of this concentration to the protein concentration determined by absorbance measurements gives the fraction or percent binding.

Example 14: Cynomolgus Monkey PK for AFD.v14 Conjugate

In vivo pK studies for the AFD.v14.C+TP octamer, prepared in Example 8, and purified as described in Examples 9a and 10, were performed in Cynomolgus monkey. PK parameters were determined from single dose experiments. Unconjugated, unmodified AFD.v14 (SIESD.N103S) was used as a control. The animals' care was in accordance with Genentech Institutional Animal Care and Use Committee guidelines.

a. Study Parameters

Cynomolgus monkeys (28 male animals; 2 kg to 4 kg and approximately 2-7 years in age at the time of dosing) were assigned to one of four dosing groups. Group 1 (control) animals (4 animals) received a single bilateral intravitreal dose of 5 mg/eye (10 mg/animal) of AFD.v14, through a 30 gauge needle (100 μl dose volume). Group 2 and 3 animals (10 animals in each group) received a bilateral intravitreal dose of 1 or 4 mg/eye (2 or 8 mg/animal), respectively based on Fab weight, of the AFD.v14.C+TP octamer through a 30-gauge needle (2 injections in each eye of 50 μl; 100 μl total dose volume). Animals were sedated (10 mg/kg ketamine HCl, 0.5 mg/kg diazepam) and treated with topical proparacaine prior to injection. The AFD.v14 or AFD.v14.C+TP octamer was then administered through the sclera and pars plana, 4 mm posterior to the limbus, with the needle directed posterior to the lens into the midvitreous. The Group 4 animals (4 animals) received a single IV bolus (1 mL) of the AFD.v14.C+TP octamer at 0.4 mg/animal. For IV administration, the AFD.v14.C+TP octamer was formulated as 10 mM sodium succinate, 10% trehalose, and 0.05% Tween-20 (pH 5.0).

Ocular tissues were collected from Groups 1, 2, and 3. One animal (2 eyes) from Group 1 and two animals (4 eyes) from each of Groups 2 and 3 were euthanized at the following times after dosing: Group 1—days 1 (24 hours), 2, 4, and 8; Groups 2 and 3—days 1 (24 hours), 4, 8, 12, and 20. After euthanasia, both eyes were enucleated, and vitreous humor, aqueous humor, and retinal tissue were collected from both eyes. The entire retinal layer was collected using filter paper days after flash freezing of the eyes. The AFD.v14 and AFD.v14.C+TP octamer concentrations were determined in the vitreous and aqueous humor and retinal tissues.

All blood samples (approximately 1 mL) were collected via a femoral or cephalic vein. Samples were drawn at the following times after IVT or IV dosing: Group 1-1 hour, 6 hours, and days 1 (24 hours), 2, 3, 4, 5, and 7; Groups 2 and 3-1 hour, 6 hours, and days 1 (24 hours), 2, 4, 6, 8, 12, and 20; Group 4-1 hour, 6 hours, and days 1 (24 hours), 2, 4, 7, 11, 14, 17, 21, 24, and 28. Within one hour of blood collection, samples were clotted at room temperature, and serum was separated by centrifugation and stored at −60° C. to −80° C.

Details of the study protocol are set forth in Table 14.

TABLE 14

Cynomolgus Monkey pK Study Parameters

| Group | Dose | Route | Number of Animals | Ocular time points (days) | Serum time points |
|---|---|---|---|---|---|
| 1 | 5 mg/eye | IVT (bilateral) | 4 | 1, 2, 4, 8 | 1 and 6 hr; 1, 2, 3, 4, 5, 7 days |
| 2 | 1 mg/eye | IVT (bilateral) | 10 | 1, 4, 8, 12, 20 | 6 hr; 1, 2, 4, 5, 8, 12, 20 days |
| 3 | 4 mg/eye | IVT (bilateral) | 10 | 1, 4, 8, 12, 20 | 6 hr; 1, 2, 4, 6, 8, 12, 20 days |
| 4 | 0.4 mg/ animal | IV | 4 | n/a | 6 hr; 1, 2, 4, 7, 11, 14, 17, 21, 24, 28 days | b. Pharmacokinetics Assay for AFD. v14 and AFD. v14. C+TP Octamer

A Gyrolab XP assay was used to quantify AFD.v14 and AFD.v14.C+TP octamer in cynomolgus monkey serum, vitreous humor, aqueous humor, and retinal homogenate. Samples were diluted 1:4-1:3000 in sample buffer (phosphate buffered saline (PBS), 0.5% bovine serum albumin (BSA), 15 ppm Proclin (Sigma-Aldrich), 0.05% Tween 20, 0.25% CHAPS, 50 µg/mL muIgG (Equitech Bio, Cat. # SLM66), 5 mM EDTA (pH 7.4)). The AFD.v14 and AFD.v14.C+TP octamer standard curves were prepared by serially diluting AFD.v14 or AFD.v14.C+TP octamer from 2.06-1500 ng/mL in sample buffer. Capture and detection reagents were applied at 100 µg/mL of biotin-conjugated goat anti-human IgG (HC+LC, Bethyl, Cat # A80-319B) in PBS/0.01% Tween 20/0.02% NaN$_3$ and Alexa-anti-CDR (clone 234, Genentech) at 25 nM in Rexxip F (Gyrolab). The assay was run on a Gyrolab Bioaffy 200 CD, and wash steps used PBS/0.01% Tween 20/0.02% NaN$_3$ followed by Gyros pH 11 wash buffer. The instrument was run and data analyzed as described by the manufacturer with a 1% PMT setting. The concentrations of AFD.v14 and AFD.v14.C+TP octamer were determined from a five-parameter fit of its standard curve. The minimum quantifiable concentration was 8.24 ng/mL (0.16 nM) for AFD.v14 and AFD.v14.C+TP octamer in cynomolgus monkey serum, vitreous humor, aqueous humor and retinal homogenate.

The vitreous humor, aqueous humor, and retinal pK results are set forth in FIGS. 29A (vitreous) and 29B (vitreous, normalized), FIGS. 30A (aqueous) and 30B (aqueous, normalized), and FIGS. 31A (retina) and 31B (retina, normalized) and in Tables 15-17 below.

TABLE 15

Vitreous PK for AFD.v14 control (Group 1) and AFD.v14.C + TP octamer (Groups 2 and 3)

| Group | Dose (µg/eye) | T$_{1/2}$ (days) | AUC (Day * µg/mL) | AUC/dose (Day * µg/mL/ mg dose) | T$_{1/2}$ ext* | Vss (mL) | Cl (mL/ day) |
|---|---|---|---|---|---|---|---|
| 1 | 5000 | 2.7 | — | — | — | 3 | 0.79 |
| 2 | 1000 | 3.5 | 2530 | 2100 | 1.3 | 2.3 | 0.47 |
| 3 | 4000 | 5 | 7730 | 1980 | 1.9 | 3.4 | 0.46 |

*increase compared to control

TABLE 16

Aqueous PK for AFD.v14.C + TP octamer

| Group | Dose (µg/eye) | T$_{1/2}$ (days) | AUC$_{last}$ (Day* µg/mL) | V$_Z$ (mL) | Cl/F (mL/Day) |
|---|---|---|---|---|---|
| 2 | 1000 | 3 | 434 | 12 | 2.73 |
| 3 | 4000 | 5.2 | 1430 | 20 | 2.58 |

TABLE 17

Retinal PK for AFD.v14.C + TP octamer

| Group | Dose (µg/eye) | T$_{1/2}$ (days) | AUC$_{last}$ (Day* µg/mL) | V$_Z$ (mL) | Cl/F (mL/Day) |
|---|---|---|---|---|---|
| 2 | 1000 | 3.6 | 31 | 196 | 38 |
| 3 | 4000 | 5.9 | 98 | 309 | 36 |

As can be seen from Table 15, the vitreal terminal half-life for both Group 2 (3.5 days) and Group 3 (5 days) was longer than that of the unconjugated AFD.v14 control (Group 1), and longer than the average half-life of unconjugated lampalizumab and ranibizumab Fabs (about 2.34 days). The average AUC/mg-dose for conjugated AFD.v14 Groups 2 and 3 (about 2040) was higher than the average AUC/mg-dose for the unconjugated lampalizumab Fab (about 1733). Based on vitreal terminal half-life, the 4.0 mg/eye dose cleared more slowly than the 1.0 mg/eye dose. As can be seen from Tables 16 and 17, and FIGS. 30 and 31, a longer terminal half-life was also observed in aqueous humor and retina for Groups 2 and 3 (conjugated AFD.v14), as compared to unconjugated Fab.

The serum pK results for Groups 1-3 are set forth in FIGS. 32A and 32B (normalized), and the serum pK results for Group 4 are set forth in FIG. 32C.

As can be seen from FIGS. 32A and 32B, the serum pK curves for Groups 2 and 3 (AFD.v14.C+TP octamer) are parallel to each other (FIG. 32A), and overlap after dose normalization (FIG. 32B). The serum AUC for Groups 2 and 3 is dose proportional, up until the last measured time point.

The terminal half-life for Group 4 (AFD.v14.C+TP octamer; IV dose) was 7.5 days, and the clearance was 15.8 mL/day (5.64 mL/kg/day (average weight of Group 4 monkeys was 2.8 kg)). On measurement days 21, 24, and 28, the serum concentration dropped below the limit of detection for 3 out of the 4 Group 4 monkeys.

c. Pharmacodynamics Assay for Factor D in Cynomolgus Monkey Serum

A sandwich ELISA was used to quantify factor D (fD) in cynomolgus monkey serum, vitreous humor, aqueous humor and retinal homogenate. Mouse anti-human factor D clone 4676 (Genentech) was diluted to 1 µg/mL in coating buffer (0.05M Sodium Carbonate, pH 9.6) and incubated overnight at 4° C. on 384-well Maxisorp plates (Thermo Scientific, Cat #. 464718). Plates were washed with PBS plus 0.05% Tween 20 and blocked during a 2 hour incubation with PBS plus 0.5% bovine serum albumin (BSA). This and all subsequent incubations were performed at room temperature with gentle agitation. The cynomolgus monkey fD standard curve was prepared by serially diluting fD from 0.04-5 ng/mL in sample buffer (assay buffer supplemented with 500 ng/mL of the AFD.v14 therapeutic and 50 µg/mL mouse IgG). The serum samples and controls were diluted to a minimum of 1:100 in sample buffer. The vitreous humor, aqueous humor, and retinal homogenate samples and controls were diluted to a minimum of 1:10 in sample buffer. The diluted standards, controls, and samples were then incubated on the plates for 2 hours, and plate-bound fD/AFD.Ab complex was detected using biotin-conjugated mouse-anti-CDR mAb to AFD.Ab (clone 242, 1 µg/mL) for one hour followed by High Sensitivity SA-HRP (3 ng/mL, Pierce Cat.#21130) also for one hour. After a final wash, tetramethyl benzidine (Moss, Cat.# TMBE-1000) was added and color was developed for 10-15 minutes, and the reaction was stopped with 1 M phosphoric acid. The plates were read at 450 nm with a 620 nm reference using a microplate reader. The concentrations of fD were determined from a four parameter fit of the standard curve. The minimum quantifiable concentration in cynomolgus monkey serum was 3.9 ng/mL (0.16 nM). The minimum quantifiable concentration in cynomolgus monkey vitreous humor, aqueous humor and retinal homogenate was 0.39 ng/ml (0.016 nM).

The average serum fD and AFD.v14.C+TP octamer concentrations for Groups 2, 3, and 4 are set forth in FIG. 33A. As can be seen from FIG. 33A, the serum fD concentration was higher than the AFD.Ab concentration at all time points tested. These results indicate that systemic AP complement activity is maintained in all groups.

The average ocular fD and AFD.v14.C+TP octamer concentrations for Groups 2 and 3 are set forth in FIG. 33B. As can be seen from FIG. 33B, the AFD.Ab concentration in the vitreous humor, aqueous humor, and retinal homogenate exceeded the fD concentration at all time points tested.

Example 15: Potency of Anti-Factor D Antibody Variants and Conjugates for Inhibition of Factor D The potency of AFD.Ab variants or conjugates comprising a Cys-modified Fab variant for inhibition of Factor D are determined in a time-resolved fluorescence energy transfer (TR-FRET) assay of Factor D-dependent factor B activation.

The Cys-modified AFD.v14 variant (AFD.v14.C), and the AFD.v8 variant containing the Cys-modified HC (SEQ ID NO: 30) prepared in Example 7 (the "Cys-modified AFD.v8 variant" or "AFD.v8.C") were each conjugated with a maleimide-functionalized multi-armed PEG tetramer (Sunbright® PTE-400MA from NOF America Corp.) according to the procedure set forth in Example 8, to form conjugates (referred to hereinafter as the "AFD.v14 tetramer" or the "AFD.v8 tetramer", respectively).

Dilutions of the AFD.Ab Fab variant, conjugate, or Fab control were prepared in enzymatic reaction buffer (ERB; 75 mM NaCl, 1 mM MgCl2, 25 mM Tris, 0.005% polysorbate 20, pH 7.3) at a 4× concentration and combined in equal volumes with 0.5 nM or 0.2 nM factor D (125 pM or 50 pM, respectively) (fD, Complement Technology; Tyler, Tex.) or ERB (no enzyme control). Ranibizumab (anti-VEGF) was used as the negative control. The Factor D/AFD.Ab or Factor D/conjugate mixtures (7 µl/well) were added to 364-well Proxiplate F plus black plates (Perkin Elmer Health Sciences; Waltham, Mass.) followed by 7 µl/well of substrate. The substrate consisted of a mixture of C3b (Complement Technology) at 7 µg/mL (40 nM) and factor B (Complement Technology) at 1 µg/mL (15 nM). The AFD.Ab Fab or conjugate, enzyme, cofactor, and substrate were incubated for 45 minutes at room temperature with gentle agitation. The reaction was stopped with 7 µl/well of a detection reagent cocktail mixture consisting of biotinylated anti-factor Bb (2F12, GNE PRO282909) at 8 nM, Europium-conjugated anti-factor Ba (custom conjugation of 1C3, GNE PRO282908 by Life Technologies; Madison, Wis.) at 4 nM, and streptavidin-Alexa 647 at 25 nM. The plate was incubated at room temperature in the dark for 30 minutes. Time-resolved fluorescence energy transfer was detected with a PHERAstar FS microplate reader (BMG LabTech; Cary, N.C.) by exciting at 337 nm and detecting Europium emission at 620 nm and Alexa fluor emission at 665 nm. The AFD.Ab or conjugate concentrations causing half-maximal inhibition (IC50) were determined by nonlinear regression analysis using a four-parameter fit model (KaleidaGraph Synergy Software; Reading, Pa.).

Inhibition curves for the TR-FRET assay are shown in FIG. 34A (Table 18). Lampalizumab has an IC50 for inhibition of Factor D-dependent fB activation of 24 pM, and the standard error in IC50 is ±25%. The IC50 for AFD.v8 and AFD.v14 is comparable to that measured for lampalizumab. See FIG. 34A (Table 18). The difference in IC50 for the conjugated Cys-modified AFD.Ab versions (AFD.v8 tetramer and AFD.v14 tetramer) compared to the unconjugated Fab is likely due to difficulty in handling more viscous PEGylated molecules (FIG. 34A, Table 18).

TABLE 18

| IC50 of Factor D-dependent Factor B Activation (50 pM fD) | |
|---|---|
| Molecule | Average IC50 fB Activation (pM) |
| AFD.v8 | 27.65 |
| AFD.v14 | 34.03 |
| AFD.v8 tetramer | 11.03 |
| AFD.v14 tetramer | 14.77 |
| Ranibizumab | n/a |
| Lampalizumab | 24.38 |

The potency of the AFD.v14.C+TP octamer for inhibition of Factor D was also determined in a TR-FRET assay of Factor D-dependent factor B activation using the procedure described above, with addition of 125 pM fD. The IC50 for the AFD.v14.C+TP octamer (AFD.v14.C+TP octamer) was compared to AFD.v14, Cys-modified AFD.v14 ("AFD.v14.C"), and lampalizumab. Ranibizumab was used as the negative control. The results are set forth in FIG. 34B and Table 19.

TABLE 19

| IC50 of Factor D-dependent Factor B Activation (125 pM fD) | |
|---|---|
| Molecule | Average IC50 fB Activation (pM) |
| Lampalizumab | 72 |
| AFD.v14 | 87 |
| AFD.v14 TP octamer (S200 pool)* | 104 |
| AFD.v14 TP octamer (CEX pool)^ | 77 |
| AFD.v14.C | 72 |
| Ranibizumab (GE Healthcare) column. | n/a |

*Obtained following purification using SEC on a Sephacryl S-200 HR (GE Healthcare) column.
^Obtained following CEX enrichment (Example 10).

The IC50 of the AFD.v14 TP octamer (both S300 pool and CEX pool) is potent, and is comparable to that measured for unconjugated Fab (lampalizumab, AFD.v14, AFD.v14.C). Enrichment of the AFD.v14 TP octamer using cation exchange chromatography resulted in a more potent product.

Example 16: Effect of Anti-Factor D Antibody Variants and Conjugates on Systemic Alternative Complement Pathway Activity Lampalizumab has previously been shown to transiently inhibit systemic complement function in cynomolgus monkeys (see Loyet, et al., *J. Pharmacol. Exp. Ther.,* 2014, Vol. 351, pp. 527-537). In the current example, the effect of intravitreal administration of an anti-Factor D antibody variant or an AFD.Ab conjugate on systemic alternative complement pathway (AP) activity was evaluated in cynomolgus monkeys.

a. Pharmacokinetic/Pharmacodynamic Studies in Cynomolgus Monkeys

The AFD.Ab variant and conjugate were administered by a single-dose IVT or intravenous injection to male cynomolgus monkeys (*M. fascicularis*) of Chinese origin to assess the pharmacokinetics (PK) and pharmacodynamics (PD) of the molecules. These studies were conducted at Covance Laboratories (Madison, Wis.). All procedures were conducted in compliance with the US Department of Agriculture Animal Welfare Act Regulations (9 CFR 3), Guide for the Care and Use of Laboratory Animals, and the Office of Laboratory Animal Welfare.

Four studies were performed. In the first (control) study (Study 1, n=10), lampalizumab was administered to both eyes, in two 50 µL IVT doses, separated by 15 minutes. These animals received 10 mg/eye for a total of 20 mg/animal. Blood was collected predose (day −2) and post dose at the following time points: 45 minutes, and 2, 6, 10, 24, 34, 48, 96, 120, 154, 192, 288, and 384 hours. After blood collections at 24, 48, 120, 192, and 384 hours, two animals per group were removed from the study and euthanized to collect ocular matrix. The lampalizumab control Study has previously been described in Loyet, et al., *J. Pharmacol. Exp. Ther.,* 2014, 351:527-537.

In Study 2 (n=3), AFD.v14 was administered to both eyes, in two 50 µL IVT doses, separated by 15 minutes. These animals received 25 mg/eye for a total of 50 mg/animal. Blood was collected predose (day −1 and −3) and post dose at the following time points: 30 minutes, and 2, 8, 24, 48, and 96 hours.

In Study 3 (n=10), the AFD.v14.C+TP octamer was administered to both eyes, in two 50 µL IVT doses, separated by 15 minutes, to provide 3.9 mg/eye of AFD.v14, for a total of 7.8 mg/animal of AFD.v14. Blood was collected predose (week −1 and week −2) and post dose at the following time points: 1, 6, 24, 48, 72, 96, 144, 192, 288, and 480 hours. Two animals per group at each time point (at 24, 96, 192, 288, and 480 hours) were removed from the study and euthanized to collect ocular matrix.

In Study 4, the AFD.v14.C+HG octamer was administered to both eyes in two 50 IVT doses, separated by 15 minutes, to provide either 7.1 mg/eye of AFD.v14 (n=2) or 11.8 mg/eye of AFD.v14 (n=1), for a total of 14.2 mg/animal or 23.6 mg/animal of AFD.v14. Blood was collected predose (day −7 and −1) and post dose at the following time points: 1, 6, 24, 96, and 168 hours.

For all studies, predose and postdose serum samples were collected from each animal via the femoral vein for PK and PD analyses. At each time point, whole blood was collected into serum separator tubes, allowed to clot at ambient temperature for at least 20 minutes, then centrifuged in a refrigerated centrifuge set at a temperature range of 2° C.-8° C. The serum was harvested within 20 minutes of centrifugation and stored between −60° C. and −80° C. until analysis.

b. Total AFD. v14/Conjugate Analysis

A Gyrolab XP assay was used to quantify AFD.v14, AFD.v14.C+TP octamer, and AFD.v14.C+HG octamer in cynomolgus monkey serum. Samples were diluted 1:4-1:3000 in sample buffer (phosphate buffered saline (PBS), 0.5% bovine serum albumin (BSA), 15 ppm Proclin (Sigma-Aldrich), 0.05% Tween 20, 0.25% CHAPS, 50 µg/mL muIgG (Equitech Bio, Cat. # SLM66), 5 mM EDTA (pH 7.4)). The AFD.v14 and AFD.v14 TP and HG conjugate standard curves were prepared by serially diluting AFD.v14, AFD.v14.C+TP octamer, or AFD.v14.C+HG octamer from 2.06-1500 ng/mL in sample buffer. Capture and detection reagents were applied at 100 µg/mL of biotin-conjugated goat anti-human IgG (HC+LC, Bethyl, Cat # A80-319B) in PBS/0.01% Tween 20/0.02% NaN3 and Alexa-anti-CDR (clone 234, Genentech) at 25 nM in Rexxip F (Gyrolab). The assay was run on a Gyrolab Bioaffy 200 CD, and wash steps used PBS/0.01% Tween 20/0.02% NaN3 followed by Gyros pH 11 wash buffer. The instrument was run and data analyzed as described by the manufacturer with a 1% PMT setting. The concentrations of AFD.v14, AFD.v14.C+TP octamer, and AFD.v14.C+HG octamer were determined from a five-parameter fit of its standard curve. The minimum quantifiable concentration was 8.24 ng/mL (0.16 nM) for AFD.v14, AFD.v14.C+TP octamer, and AFD.v14.C+HG octamer in cynomolgus monkey serum.

c. Pharmacodynamics Assay for Factor D in Cynomolgus Monkey Serum

A sandwich ELISA was used to quantify factor D (fD) in cynomolgus monkey serum. Mouse anti-human factor D clone 4676 (Genentech) was diluted to 1 µg/mL in coating buffer (0.05M Sodium Carbonate, pH 9.6) and incubated overnight at 4° C. on 384-well Maxisorp plates (Thermo Scientific, Cat #. 464718). Plates were washed with PBS plus 0.05% Tween 20 and blocked during a 2 hour incubation with PBS plus 0.5% bovine serum albumin (BSA). This and all subsequent incubations were performed at room temperature with gentle agitation. The cynomolgus monkey fD standard curve was prepared by serially diluting fD from 0.04-5 ng/mL in sample buffer (assay buffer supplemented with 500 ng/mL of the AFD.v14 therapeutic and 50 µg/mL mouse IgG). The serum samples and controls were diluted to a minimum of 1:100 in sample buffer. The diluted standards, controls, and samples were then incubated on the plates for 2 hours, and plate-bound fD/AFD.Ab complex was detected using biotin-conjugated mouse-anti-CDR mAb to AFD.Ab (clone 242, 1 µg/mL) for one hour followed by High Sensitivity SA-HRP (3 ng/mL, Pierce Cat.#21130) also for one hour. After a final wash, tetramethyl benzidine (Moss, Cat.# TMBE-1000) was added and color was developed for 10-15 minutes, and the reaction was stopped with 1 M phosphoric acid. The plates were read at 450 nm with a 620 nm reference using a microplate reader. The concentrations of fD were determined from a four parameter fit of the standard curve. The minimum quantifiable concentration in cynomolgus monkey serum was 3.9 ng/mL (0.16 nM).

d. AP Hemolysis Assay

The ability of AFD.v14 and AFD.v14.C+TP octamer to inhibit AP activity was evaluated in a hemolytic assay in which serum (either human or monkey) was combined with rabbit erythrocytes, as designed and described by Pangburn (*Methods Enzymol*, 1988, 162:639-653) and Katschke et al. (*J. Biol. Chem.,* 2009, 284:10473-10479). To ensure complement activation did not occur through the classic complement pathway (CP), C1q-depleted human serum (Complement Technologies, Tyler, Tex.) was used, and the buffer included EGTA to chelate calcium, a cation essential for CP activity.

C1q-depleted human serum was used to activate the AP. The concentration of fD present in 10% C1q-depleted human serum was 9.6 nM in-well, a value in agreement with previously reported fD levels in serum (Barnum, et al., *J. Immunol. Methods*, 1984, 67:303-309; Loyet et al., *Invest. Ophthalmol. Vis. Sci.,* 2012, 53:6628-6637).

e. Determination of Inhibition of Systemic AP Activity in AFD. v14. C+HG Octamer-Treated Cynomolgus Monkey Serum To evaluate the time course and dose dependency of any potential inhibition of systemic AP activity subsequent to dosing with AFD.v14.C+HG octamer or AFD.v14.C+TP octamer, either a plate-based WIESLAB Complement System AP ELISA (the data from this assay are referred to in FIG. 35 as "% AP complement activity") or an ex vivo assay similar to the in vitro AP hemolysis assay described above was performed (the data from this assay are referred to in FIG. 35 as "% relative hemolysis."). In this assay, however, instead of adding a dilution curve of exogenous AFD.v14.C+HG octamer or AFD.v14.C+TP octamer to the serum samples, the samples themselves were serially diluted, with any inhibition of hemolytic activity attributed to the injected dose of AFD.v14.C+HG octamer or AFD.v14.C+TP octamer.

Erythrocytes were prepared, and the assay was performed, as described above, for the AP hemolysis assay with the following modifications. To determine the absorbance corresponding to maximum lysis, total lysis controls were prepared with sterile water (80 µl/well), whereas GVB was added to all other wells (50 µl). Cynomolgus monkey serum samples were serially diluted 1:1.5 over six points and added along with a negative control (buffer only) to 96-well U-bottom polypropylene plates (30 µl/well). The total lysis controls represented maximum (100%) hemolysis. Data points were collected in triplicate, and the mean percent maximum hemolysis was plotted against the reciprocal of the final serum dilution in the assay. The 50% maximal hemolysis (AH50) values, defined as 50% maximal hemolysis, were determined by nonlinear regression analysis using a four-parameter fit model. For those curves that did not reach saturation, the AH50 was estimated using a curve fit in which the upper asymptote was fixed at 100%. The percent relative hemolysis was calculated for each individual time point as [(postdose AH50 for the individual time point)/(predose AH50)]×100. The AH50 value for serum from each individual normal cynomolgus monkey can vary as much as 2-fold from the overall average of AH50 values. Therefore, the predose and postdose samples from each study animal were run on the same assay plate to ensure that postdose changes in AP activity were directly compared with the individual animal's baseline complement activity.

f. Results

Figure 35A:
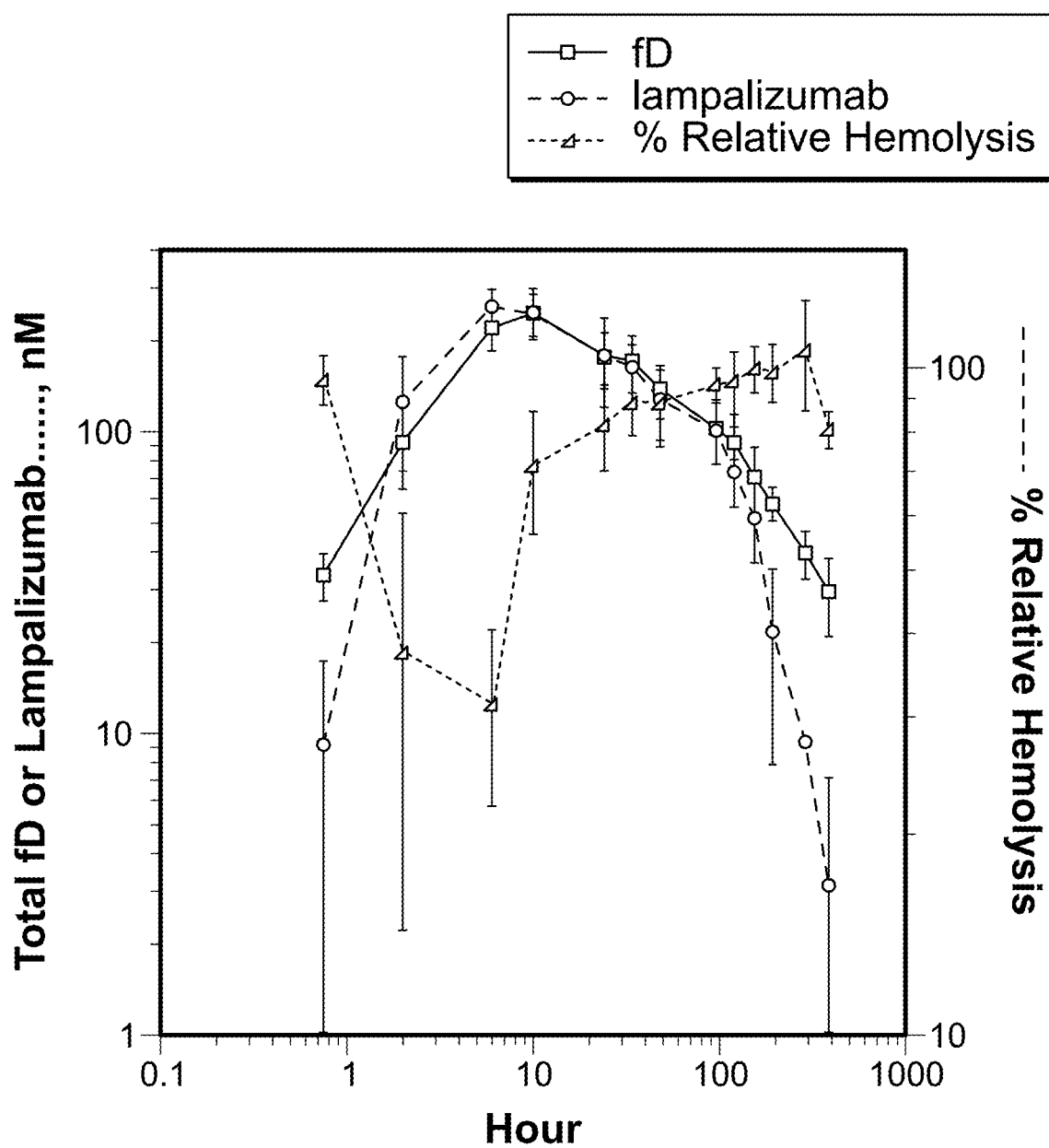
Figure 35B:
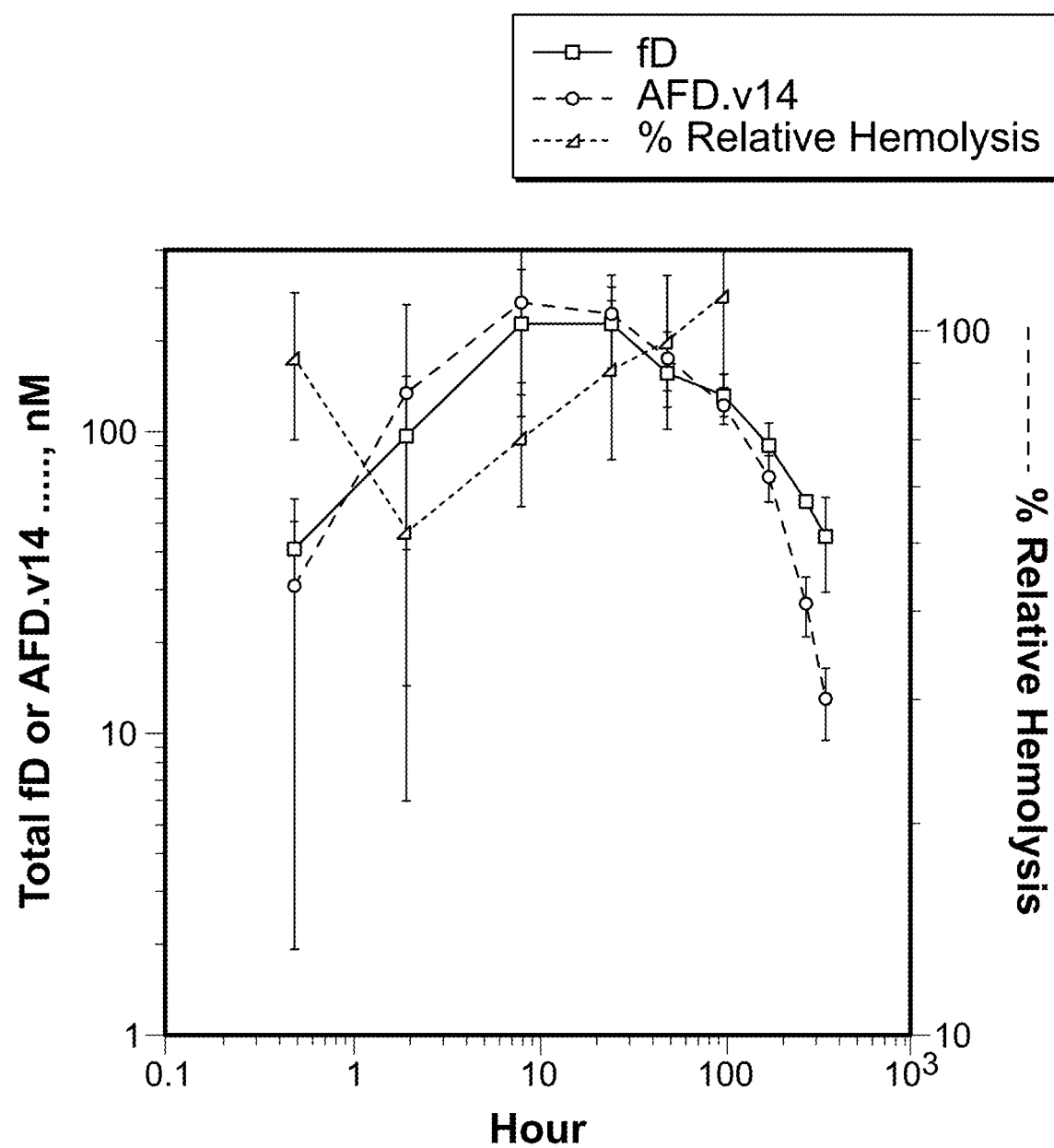
Figure 35C:
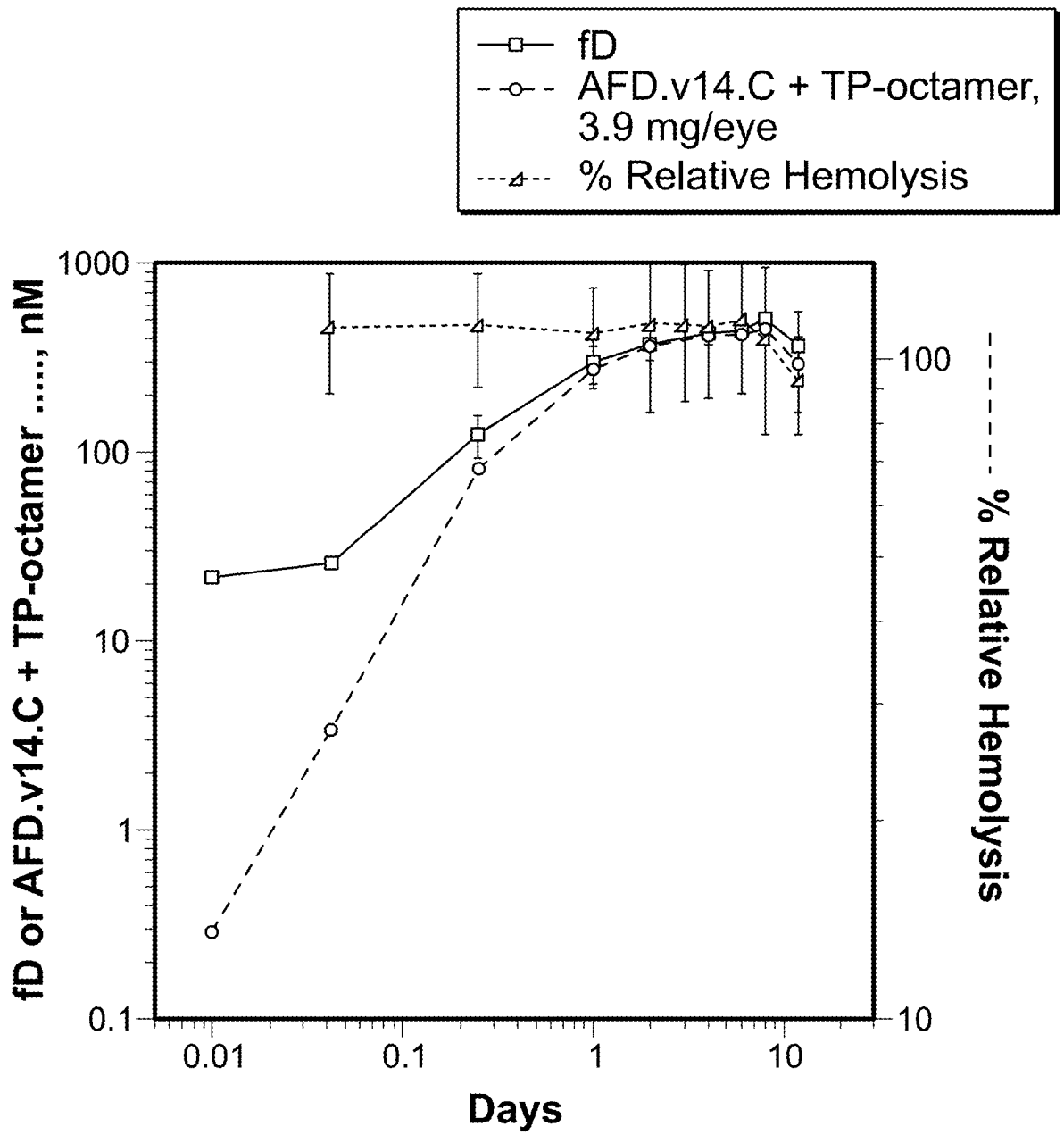

The percent relative hemolysis in comparison to total fD and the therapeutic active is shown in FIGS. 35A (lampalizumab, 10 mg/eye), 35B (AFD.v14, 25 mg/eye), and 35C (AFD.v14.C+TP octamer, 3.9 mg/eye). The lampalizumab data (FIG. 35A) is comparative data obtained following IVT administration of 10 mg/eye of lampalizumab, as described in Loyet, et al., *J. Pharmacol. Exp. Ther.,* 2014, 351:527-537). As can be seen from FIG. 35B, administration of 25 mg/eye of AFD.v14 transiently inhibited systemic AP activity, with activity returning to baseline by 24 hours post administration, similar to results previously observed for lampalizumab (FIG. 35A). In comparison, no systemic AP inhibition was observed following administration of 3.9 mg/eye of the AFD.v14.C+TP octamer (FIG. 35C). Without wishing to be bound to any particular theory, it is believed that the slower clearance from the eye obtained with the conjugate compared to Fab (e.g., lampalizumab and AFD.v14) allows fD to saturate the AFD.Ab at earlier time points, preventing systemic complement inhibition.

Figure 35D:
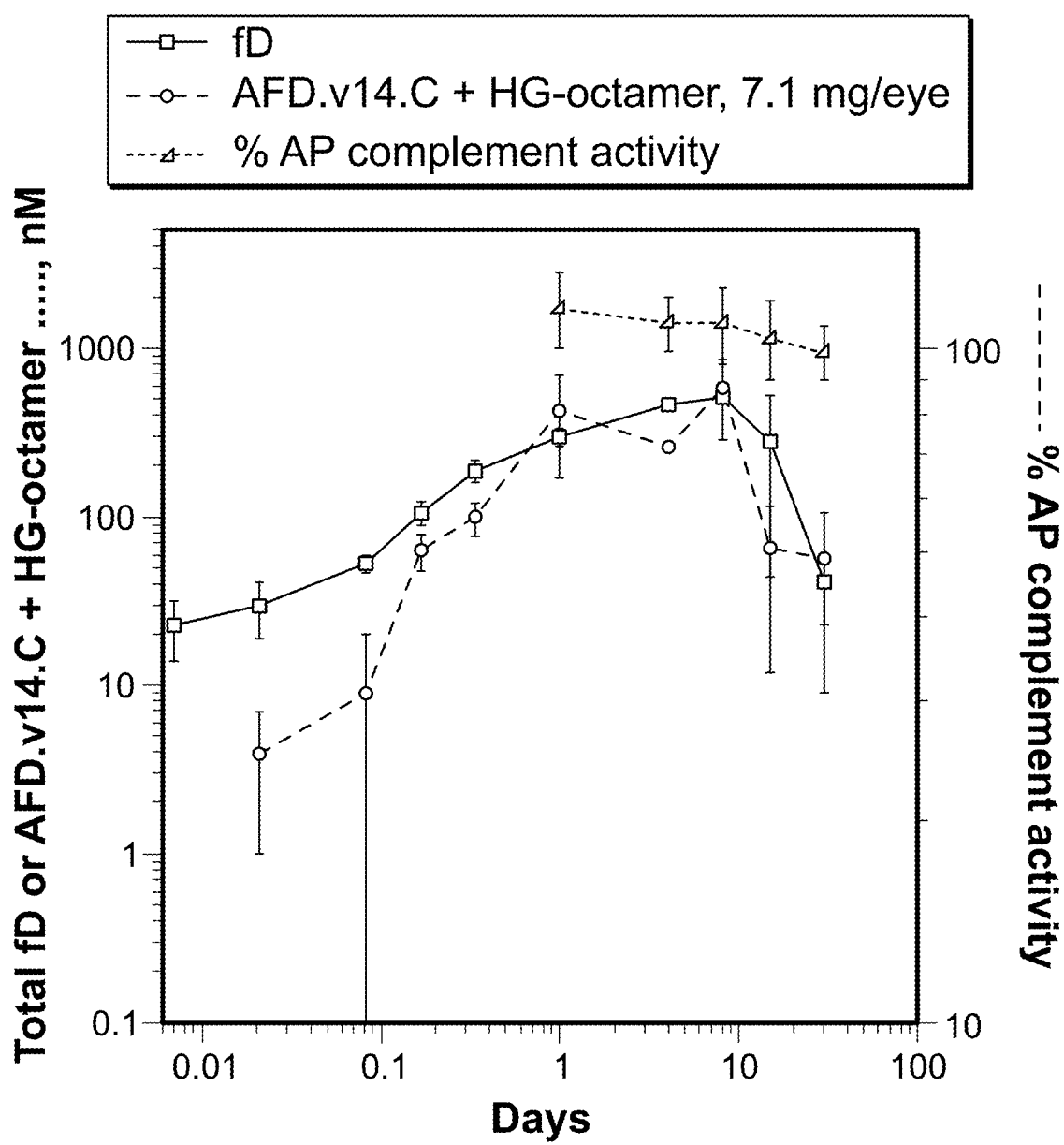
Figure 35E:
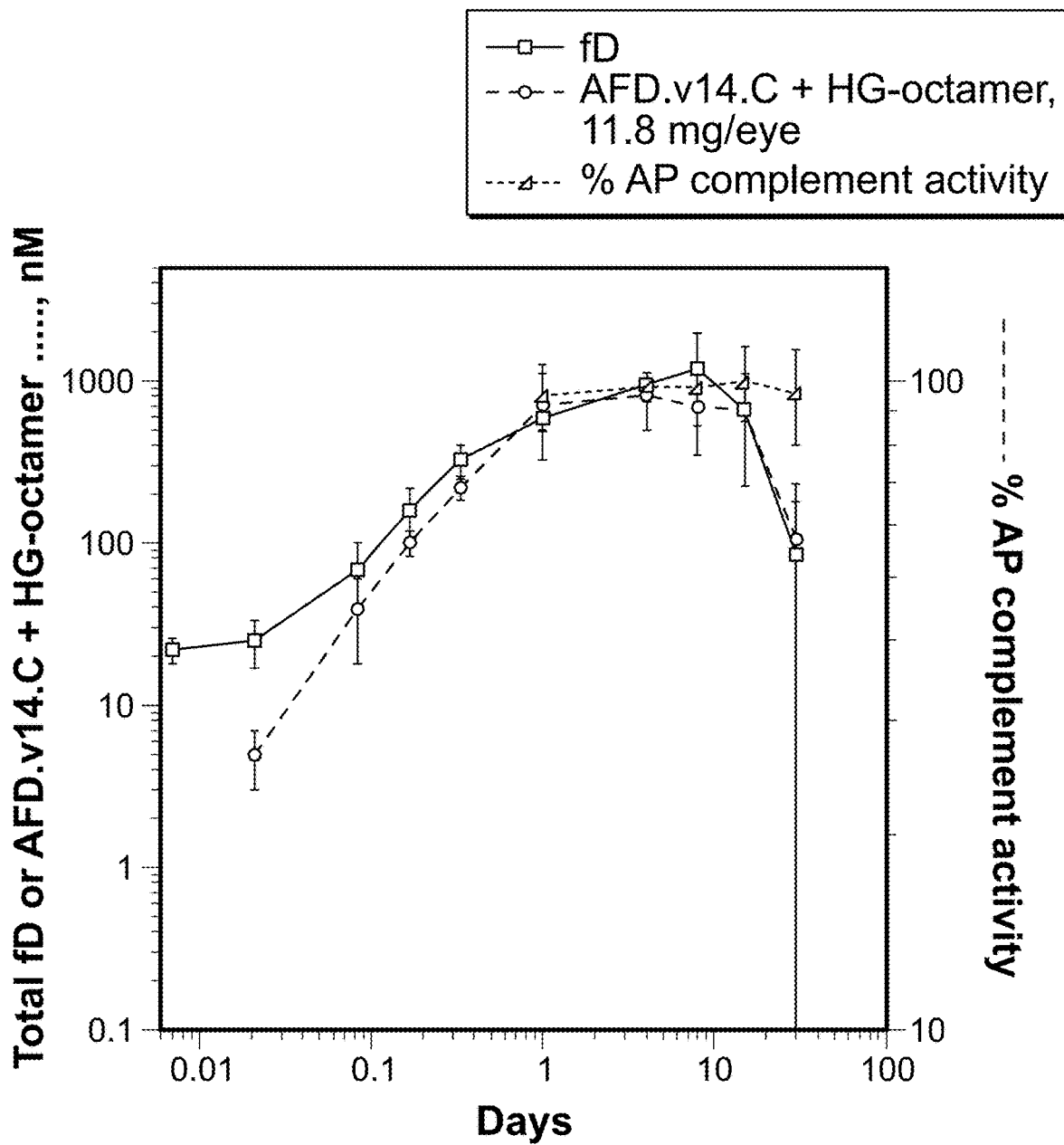

The percent relative AP complement activity in comparison to total fD and total conjugate is shown in FIGS. 35D (AFD.v14.C+HG octamer, 7.1 mg/eye) and 35E (AFD.v14.C+HG octamer, 11.8 mg/eye). As can be seen from these figures, negligible systemic complement inhibition was observed for the AFD.v14.C+HG octamer for IVT dosage up to 11.8 mg/eye. Due to the slower clearance from the eye, the conjugate concentration remains below the molar concentration of fD, in particular at time points earlier than 10 hours. This is in contrast to similar eye-dosed concentrations of the AFD.Ab Fab in which at these early time points the molar concentration exceeds the molar fD concentration and leads to systemic AP inhibition.

Those skilled in the art will recognize, or be able to ascertain using no more than routine experimentation, many equivalents to the specific embodiments of the disclosure described herein. Such equivalents are intended to be encompassed by the following claims.

Although the foregoing disclosure has been described in some detail by way of illustration and example for purposes of clarity of understanding, the descriptions and examples should not be construed as limiting the scope of the disclosure. The disclosures of all patent and scientific literatures cited herein are expressly incorporated in their entirety by reference.

The foregoing written specification is considered to be sufficient to enable one skilled in the art to practice the disclosure. The present disclosure is not to be limited in scope by the construct deposited, since the deposited embodiment is intended as a single illustration of certain aspects of the disclosure and any constructs that are functionally equivalent are within the scope of this disclosure. Indeed, various modifications of the disclosure in addition to those shown and described herein will become apparent to those skilled in the art from the foregoing description and fall within the scope of the appended claims.

We claim:

1. A conjugate comprising one or more anti-Factor D antibody covalently linked to one or more polyols, wherein at least one anti-Factor D antibody in the conjugate is an anti-Factor D antibody having a light chain having the amino acid sequence of SEQ ID NO: 28 and a heavy chain having the amino acid-sequence of SEQ ID NO: 32; and the polyol is a multi-armed polyol.

2. The conjugate according to claim 1, wherein the polyol is covalently linked to at least one of the anti-Factor D antibodies at a free sulfhydryl group of a cysteine residue.

3. The conjugate of claim 2, wherein the cysteine residue is an engineered cysteine.

4. The conjugate according to claim 2, wherein the cysteine residue is in a constant domain of the anti-Factor D antibody.

5. The conjugate according to claim 2, wherein the cysteine residue is at the C'-terminal end of the anti-Factor D antibody.

6. The conjugate according to claim 2, wherein the conjugate comprises at least two anti-Factor D antibodies, and the polyol is covalently linked to each anti-Factor D antibody at a free sulfhydryl group of a cysteine residue.

7. The conjugate according to claim 1, wherein the polyol is covalently linked to at least one of the anti-Factor D antibodies at a free amino group of a lysine residue.

8. The conjugate according to claim 7, wherein the lysine residue is within a constant domain of the anti-Factor D antibody.

9. The conjugate according to claim 1, wherein at least two anti-Factor D antibodies are covalently linked to the polyol.

10. The conjugate according to claim 1, wherein the multi-armed polyol is selected from the group consisting of a dimer, a tetramer, a hexamer, and an octamer.

11. The conjugate according to claim 10, wherein the multi-armed polyol is an octamer.

12. The conjugate according to claim 1, wherein the polyol is polyethylene glycol.

13. The conjugate according to claim 12, wherein the polyethylene glycol has a weight average molecular weight of from about 500 D to about 300,000 D.

14. The conjugate according to claim 13, wherein the polyethylene glycol has a weight average molecular weight of from about 20,000 D to about 60,000 D.

15. The conjugate according to claim 14, wherein the polyethylene glycol has a weight average molecular weight of about 40,000 D.

16. The conjugate according to claim 12, wherein the polyethylene glycol has the structure of general formula (Ia):

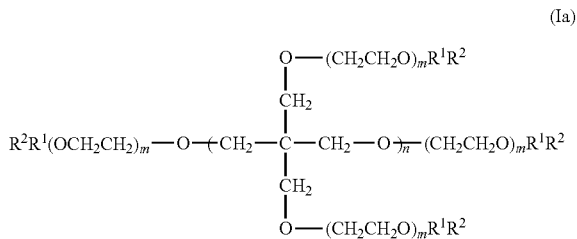

wherein each m is independently an integer from 3-250; n is an integer from 1-10; each $R^1$ is independently either absent, or is a linking group; and each $R^2$ is independently either hydrogen or a terminal reactive group; wherein at least one $R^2$ is a terminal reactive group and is covalently linked to the anti-Factor D antibody.

17. The conjugate according to claim 12, wherein the polyethylene glycol has the structure of general formula (Ib):

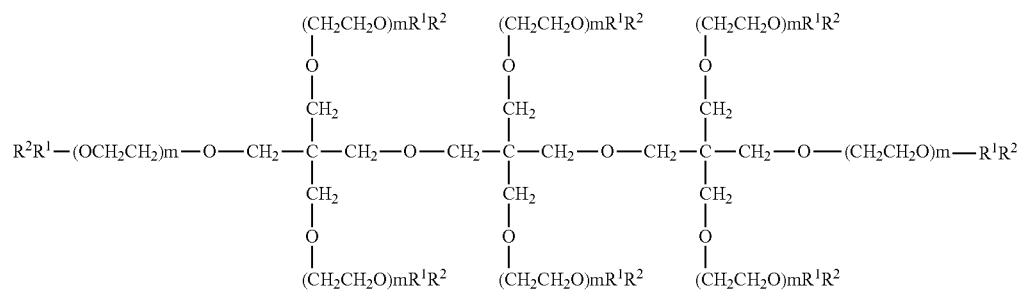

wherein each m is independently an integer from 3-250; each $R^1$ is independently either absent, or is a linking group; and each $R^2$ is independently either hydrogen or a terminal reactive group; wherein at least one $R^2$ is a terminal reactive group and is covalently linked to the anti-Factor D antibody.

18. The conjugate according to claim 12, wherein the polyethylene glycol has the structure of general formula (IIa):

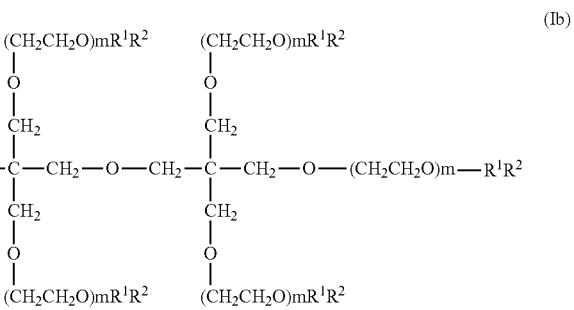

wherein each m is independently an integer of from 3-250; n is an integer from 1-10;
each $R^1$ is independently either absent, or is a linking group; and each $R^2$ is independently either hydrogen or a terminal reactive group; wherein at least one $R^2$ is a terminal reactive group and is covalently linked to the anti-Factor D antibody.

19. The conjugate according to claim 18, wherein n is 6.

20. The conjugate according to claim 12, wherein the polyethylene glycol has the structure of general formula (IIIa):

(IIIa)

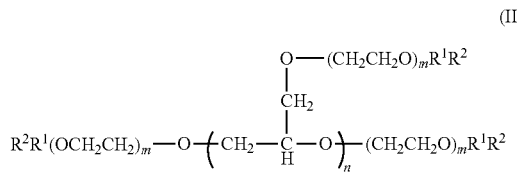

wherein each m is independently an integer of from 3-250; n is an integer from 1-10; each $R^1$ is independently either absent, or is a linking group; and each $R^2$ is independently either hydrogen or a terminal reactive group; wherein at least one $R^2$ is a terminal reactive group and is covalently linked to the anti-Factor D antibody.

21. The conjugate according to claim 20, wherein n is 4.

22. The conjugate according to claim 12, wherein the polyethylene glycol has the structure of general formula (IVa):

(IVa)

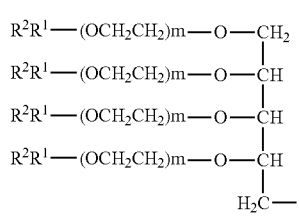 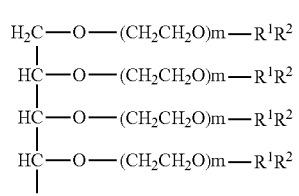

wherein each m is independently an integer of from 3-250; each $R^1$ is independently either absent, or is a linking group; and each $R^2$ is independently either hydrogen or a terminal reactive group; wherein at least one $R^2$ is a terminal reactive group and is covalently linked to the anti-Factor D antibody.

23. The conjugate according to claim 17, wherein m is an integer of 50-200.

24. The conjugate according to claim 23, wherein m is an integer of 100-150.

25. The conjugate according to claim 17, wherein at least one $R^1$ is a linking group, wherein $R^1$ and $R^2$ when taken together are selected from the group consisting of

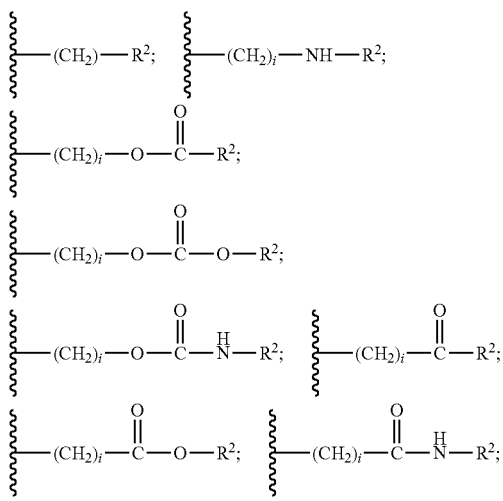

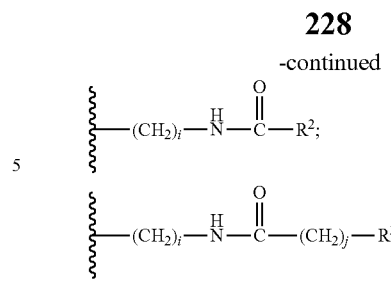

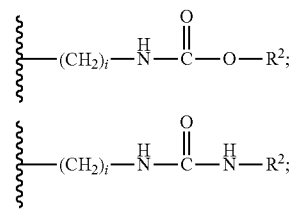

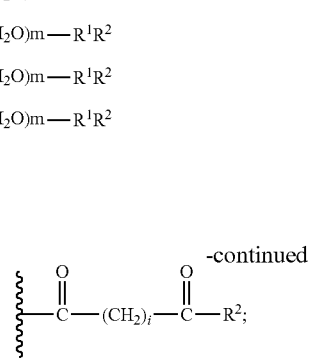

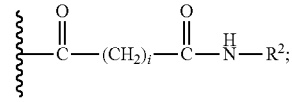

and combinations thereof; wherein each i is independently an integer of 0-10; and j is an integer of 0-10.

26. The conjugate according to claim 17, wherein each $R^2$ is independently selected from the group consisting of a thiol reactive group, an amino reactive group, and combinations thereof.

27. The conjugate according to claim 26, wherein each $R^2$ is independently selected from the group consisting of a maleimide, a sulfhydryl, a thiol, trifluoromethanesulfonate, tosylate, aziridine, epoxide, a pyridyl disulfide, succinimidyl ester, —$NH_2$, an aldehyde, a haloacetate, a haloacetamide, and a para-nitrophenyl carbonate.

28. The conjugate according to claim 17, wherein $R^2$ is a maleimide.

29. The conjugate according to claim 17, wherein $R^1$ and $R^2$, when taken together, are

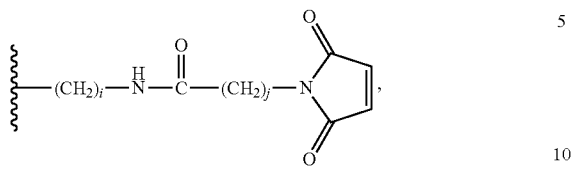

i is an integer of 0-10; and j is an integer of 0-10.

30. The conjugate according to claim 17, wherein at least seven of the $R^2$ groups are covalently linked to one of the anti-Factor D antibodies.

31. The conjugate according to claim 30, wherein eight of the $R^2$ groups are covalently linked to one of the anti-Factor D antibodies.

32. A conjugate comprising at least one anti-Factor D antibody covalently linked to a polyethylene glycol, wherein the polyethylene glycol has the structure of general formula (Ib):

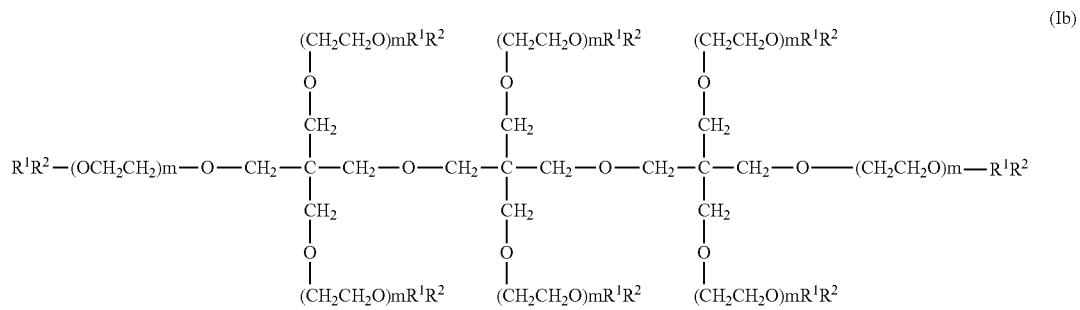

wherein each m is independently an integer from 3-250; each $R^1$ is independently either absent, or is a linking group; and each $R^2$ is independently either hydrogen or a terminal reactive group; wherein at least one $R^2$ is a terminal reactive group and is covalently linked to the anti-Factor D antibody; wherein each anti-Factor D antibody comprises a light chain having the amino acid sequence of SEQ ID NO: 28 and a heavy chain having the amino acid sequence of SEQ ID NO: 32.

33. The conjugate according to claim 32, wherein $R^1$ and $R^2$, when taken together, are

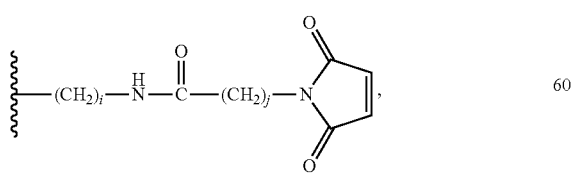

i is an integer of 0-10; and j is an integer of 0-10.

34. The conjugate according to claim 33, wherein i is 2 and j is 2.

35. A conjugate according to claim 1, wherein the conjugate is prepared by covalently linking at least one anti-Factor D antibody to the multi-armed polyol.

36. The conjugate of claim 35, wherein the multi-armed polyol is selected from the group consisting of a dimer, a tetramer, a hexamer, and an octamer.

37. The conjugate according to claim 35, wherein the polyol is a polyethylene glycol.

38. A pharmaceutical formulation comprising the conjugate according to claim 1.

39. The pharmaceutical formulation according to claim 38, wherein the concentration of the anti-Factor D antibody is at least 100 mg/ml.

40. The pharmaceutical formulation according to claim 38, wherein the concentration of the antibody is from about 50 mg/mL to about 300 mg/ml.

41. A long acting delivery device for ocular delivery comprising the pharmaceutical formulation according to claim 38 and a means for delivering the formulation intravitreally to a patient, whereby the formulation remains effective on site for a prolonged period of time.

* * * * *